United States Patent
Ban et al.

(10) Patent No.: US 12,018,093 B2
(45) Date of Patent: Jun. 25, 2024

(54) HEMIASTERLIN DERIVATIVES AND ANTIBODY-DRUG CONJUGATES INCLUDING SAME

(71) Applicant: Sumitomo Pharma Co., Ltd., Osaka (JP)

(72) Inventors: Hitoshi Ban, Osaka (JP); Yukihiro Nishio, Osaka (JP); Atsushi Suwa, Osaka (JP)

(73) Assignee: SUMITOMO PHARMA CO., LTD., Osaka (JP)

( * ) Notice: Subject to any disclaimer, the term of this patent is extended or adjusted under 35 U.S.C. 154(b) by 343 days.

(21) Appl. No.: 16/637,097

(22) PCT Filed: Aug. 10, 2018

(86) PCT No.: PCT/JP2018/030144
§ 371 (c)(1),
(2) Date: Feb. 6, 2020

(87) PCT Pub. No.: WO2019/031615
PCT Pub. Date: Feb. 14, 2019

(65) Prior Publication Data
US 2020/0247845 A1  Aug. 6, 2020

(30) Foreign Application Priority Data
Aug. 10, 2017  (JP) .................... 2017-155988

(51) Int. Cl.
| C07K 5/02 | (2006.01) |
| A61K 38/08 | (2019.01) |
| A61K 47/65 | (2017.01) |
| A61K 47/68 | (2017.01) |

(52) U.S. Cl.
CPC ............ C07K 5/0205 (2013.01); A61K 38/08 (2013.01); A61K 47/65 (2017.08); A61K 47/68 (2017.08)

(58) Field of Classification Search
None
See application file for complete search history.

(56) References Cited

U.S. PATENT DOCUMENTS

| 6,154,590 | A | * | 11/2000 | Jin ........................ G02B 6/022 398/1 |
| 7,579,323 | B1 | | 8/2009 | Andersen et al. |
| 11,795,195 | B2 | * | 10/2023 | Ban .................... A61K 47/6867 |
| 2005/0171014 | A1 | | 8/2005 | Tarasova et al. |
| 2008/0293951 | A1 | | 11/2008 | Iwama et al. |
| 2009/0136526 | A1 | | 5/2009 | McDonagh et al. |
| 2011/0171125 | A1 | | 7/2011 | Elkins et al. |
| 2017/0007714 | A1 | | 1/2017 | Kontermann et al. |

FOREIGN PATENT DOCUMENTS

| JP | 11-505211 | * | 5/1999 |
| JP | 11-505211 | A * | 5/1999 |
| JP | H11-505211 | A | 5/1999 |
| JP | 2011-500725 | A | 1/2011 |
| JP | 2012-522513 | A | 9/2012 |
| JP | 2016-516063 | A | 6/2016 |
| JP | 2017-506234 | A | 3/2017 |
| WO | 96/033211 | A1 | 10/1996 |
| WO | 03/082268 | A2 | 10/2003 |
| WO | 2004/026293 | A2 | 4/2004 |
| WO | 2006/063135 | A2 | 6/2006 |
| WO | 2013/173393 | A1 | 11/2013 |
| WO | 2014/057436 | A2 | 4/2014 |

(Continued)

OTHER PUBLICATIONS

Extended European Search Report issued in counterpart European Patent Application No. 18845109.0 dated Apr. 9, 2021.
Talpir et al., "Hemiasterlin and geodiamolide TA: Two New Cytotoxic Peptides from the Marine Sponge Hemiasterella Minor (Kirkpatrick)," Tetrahedron Letters, 35 (25): 4453-4456 (1994).
Zask et al., "D-pience modifications of the hemiasterlin analog HTI-286 produce potent tubulin inhibitors," Bioorganic & Medicinal Chemistry Letters, 14: 4353-4358 (2004).

(Continued)

*Primary Examiner* — Maury A Audet
(74) *Attorney, Agent, or Firm* — Morgan, Lewis & Bockius LLP

(57) ABSTRACT

A compound represented by formula (1):

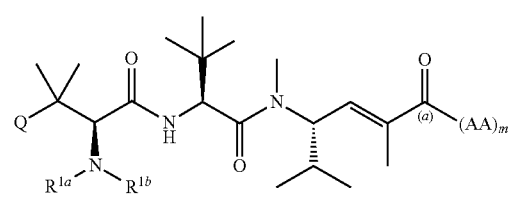

(1)

wherein
AA represents a particular amino acid residue or a $C_{1-6}$ alkyl ester thereof, and when there is a plurality of AAs, each AA may be the same as or different from each other and AAs are bonded to each other via an amide bond;
an N-terminal nitrogen atom of $(AA)_m$ forms an amide bond together with carbonyl (a);
Q represents an unsubstituted phenyl group, or a group represented by formula (Q-1), formula (Qa-2), formula (Qa-3), formula (Qa-4), formula (Qa-5), formula (Qa-6) or formula (Qa-7);
$R^{1a}$ and $R^{1b}$ each independently represent a hydrogen atom or a $C_{1-6}$ alkyl group; and
m represents an integer of 1 to 10,
or a salt thereof.

25 Claims, 3 Drawing Sheets

(56) References Cited

FOREIGN PATENT DOCUMENTS

| WO | 2014/144871 A1 | 9/2014 |
|----|----------------|--------|
| WO | 2015/095952 A1 | 7/2015 |
| WO | 2015/095953 A1 | 7/2015 |
| WO | 2015/151079 A2 | 10/2015 |
| WO | 2016/123582 A1 | 8/2016 |

OTHER PUBLICATIONS

Zask et al., "Synthesis and Biological Activity of Analogues of the Antimicrotubule Agent N,beta,beta-Trimethyl-L- phenylalanyl-N1-[(1S,2E)-3-carboxy-1-isopropylbut-2-enyl]-N1,3-dimethyl-L-valinamide (HTI-286)," Journal of Medicinal Chemistry, 47: 4774-4786 (2004).

Yamashita et al., "Synthesis and activity of novel analogs of hemiasterlin as inhibitors of tubulin polymerization: modification of the A segment," Bioorganic & Medicinal Chemistry Letters, 14: 5317-5322 (2004).

Nieman et al., "Synthesis and Antimitotic/Cytotoxic Activity of Hemiasterlin Analogues," Journal of Natural Products, 66: 183-199 (2003).

Rocha-Lima et al., "A phase 1 trial of E7974 administered on day 1 of a 21-day cycle in patients with advanced solid tumors," Cancer, 4262-4270 (2012).

Toki et al., "Protease-Mediated Fragmentation of p-Amidobenzyl Ethers: A New Strategy for the Activation of Anticancer Prodrugs," Journal of Organic Chemistry, 67: 1866-1872 (2002).

International Search Report issued in corresponding International Patent Application No. PCT/JP2018/030144 dated Nov. 13, 2018.

International Preliminary Report on Patentability and Written Opinion issued in corresponding International Patent Application No. PCT/JP2018/030144 dated Feb. 20, 2020.

* cited by examiner

HEMIASTERLIN DERIVATIVES AND ANTIBODY-DRUG CONJUGATES INCLUDING SAME

TECHNICAL FIELD

The present invention relates to hemiasterlin derivatives, antibody-drug conjugates thereof, and synthetic intermediates of the antibody-drug conjugates.

BACKGROUND ART

Hemiasterlin is a naturally occurring compound having a tripeptide structure, isolated from marine sponges, and is involved in microtubule depolymerization and mitotic arrest in cells (Non Patent Literature 1).

Several groups have so far conducted structural modification of hemiasterlin derivatives, and have reported structure-activity relationship (Patent Literatures 1 to 5 and Non Patent Literatures 2 to 5). As such, hemiasterlin derivatives exhibiting strong cytotoxicity (cellular toxicity) based on antimitotic effects have been found for treatment for diseases such as cancer. However, these hemiasterlin derivatives have been reported to exhibit cytotoxicity not only to target cells, but also to normal cells, and show side effects (Non Patent Literature 6).

In addition, antibody-drug conjugates containing hemiasterlin derivatives, exhibiting cytotoxic activity in antigen-expressing cells, have also been reported (Patent Literatures 4 and 6 to 9).

CITATION LIST

Patent Literature

Patent Literature 1: International Publication No. WO 2004/026293
Patent Literature 2: International Publication No. WO 96/33211
Patent Literature 3: U.S. Pat. No. 7,579,323
Patent Literature 4: International Publication No. WO 2014/144871
Patent Literature 5: International Publication No. WO 2003/082268
Patent Literature 6: International Publication No. WO 2016/123582
Patent Literature 7: International Publication No. WO 2015/095952
Patent Literature 8: International Publication No. WO 2015/095953
Patent Literature 9: International Publication No. WO 2013/173393

Non Patent Literature

Non Patent Literature 1: Talpir, R. et al., Tetrahedron Lett., 1994, 35, 4453-4456.
Non Patent Literature 2: Zask, A. et. al., Bioorg. Med. Chem. Lett., 2004, 14, 4353-4358.
Non Patent Literature 3: Zask, A. et. al., J. Med. Chem., 2004, 47, 4774-4786.
Non Patent Literature 4: Yamashita, A. et. al., Bioorg. Med. Chem. Lett., 2004, 14, 5317-5322.
Non Patent Literature 5: Nieman, J. A. et. al., J, Nat. Prod., 2003, 66, 183-199.
Non Patent Literature 6: Rocha-Lima, C. M. et. al., Cancer, 2012, 118, 4262-4270.
Non Patent Literature 7: Toki et. al., 2002, J. Org. Chem. 67, 1866-1872.

SUMMARY OF INVENTION

Technical Problem

An object of the present invention is to provide a hemiasterlin derivative that, when conjugated with an antibody to form an antibody-drug conjugate, provide cell damage specifically to target cells while suppressing cytotoxicity to normal cells, as well as antibody-drug conjugates thereof and synthetic intermediates of the antibody-drug conjugates.

Solution to Problem

As a result of diligent studies, the present inventors have found that an antibody-drug conjugate formed of a hemiasterlin derivative represented by formula (1) or formula (1a) and an antibody exhibits strong antitumor activity while having low cytotoxicity to normal cells, thereby completing the present invention.

That is, the present invention is as follows:

[Item 1]

A compound represented by formula (1):

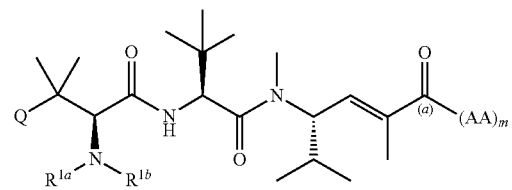

(1)

wherein
AA represents a glutamic acid residue (Glu), an aspartic acid residue (Asp), a lysine residue (Lys), a cysteine residue (Cys), a phosphotyrosine residue, a phosphoserine residue or a cysteic acid residue, or a $C_{1-6}$ alkyl ester thereof, and when there is a plurality of AAs, each AA may be the same as or different from each other and AAs are bonded to each other via an amide bond;
an N-terminal nitrogen atom of $(AA)_m$ forms an amide bond together with carbonyl (a);
Q represents a group represented by formula (Q-1), formula (Qa-2), formula (Qa-3), formula (Qa-4), formula (Qa-5), formula (Qa-6) or formula (Qa-7):

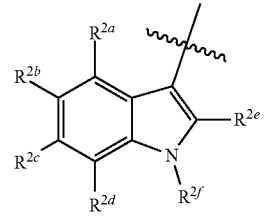

(Q-1)

-continued (Qa-2)
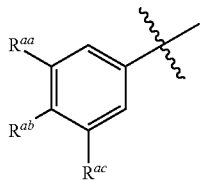

(Qa-3)
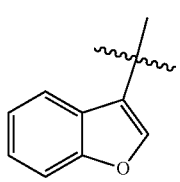

(Qa-4)
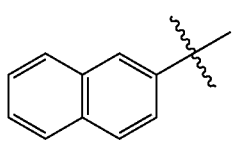

(Qa-5)
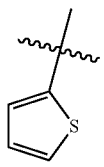

(Qa-6)
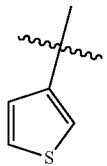

(Qa-7)
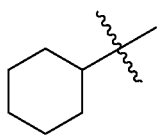

where
$R^{2a}, R^{2b}, R^{2c}, R^{2d}$ and $R^{2e}$ each independently represent a hydrogen atom, a halogen atom, a $C_{1-6}$ alkyl group optionally substituted with 1 to 5 fluorine atoms or a $C_{1-6}$ alkoxy group optionally substituted with 1 to 5 fluorine atoms;

$R^{2f}$ represents a hydrogen atom or a $C_{1-6}$ alkyl group; and $R^{aa}, R^{ab}$ and $R^{ac}$ each independently represent a hydrogen atom, a halogen atom, a hydroxy group, a cyano group, an amino group, a carboxyl group, a phenyl group, or a $C_{1-6}$ alkyl group, $C_{1-6}$ alkoxy group or $C_{1-6}$ alkyl ester group optionally substituted with 1 to 3 fluorine atoms;

$R^{1a}$ and $R^{1b}$ each independently represent a hydrogen atom or a $C_{1-6}$ alkyl group; and m represents an integer of 1 to 10, or a salt thereof.

[Item 2]
The compound according to item 1, represented by formula (1):

(1)
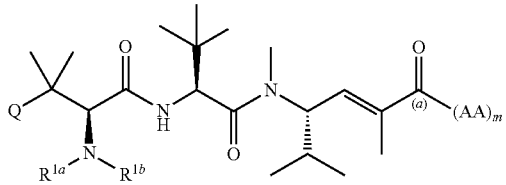

wherein
AA represents a glutamic acid residue (Glu), an aspartic acid residue (Asp), a lysine residue (Lys) or a cysteine residue (Cys), or a $C_{1-6}$ alkyl ester thereof, and when there is a plurality of AAs, each AA may be the same as or different from each other and AAs are bonded to each other via an amide bond;

an N-terminal nitrogen atom of $(AA)_m$ forms an amide bond together with carbonyl (a);

Q represents an unsubstituted phenyl group or a group represented by formula (Q-1):

(Q-1)
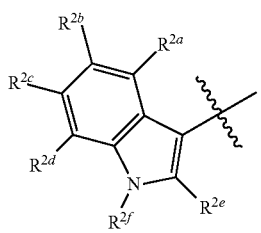

where
$R^{2a}, R^{2b}, R^{2c}, R^{2d}$ and $R^{2e}$ each independently represent a hydrogen atom, a halogen atom, a $C_{1-6}$ alkyl group optionally substituted with 1 to 5 fluorine atoms or a $C_{1-6}$ alkoxy group optionally substituted with 1 to 5 fluorine atoms; and $R^{2f}$ represents a hydrogen atom or a $C_{1-6}$ alkyl group;

$R^{1a}$ and $R^{1b}$ each independently represent a hydrogen atom or a $C_{1-6}$ alkyl group; and m represents an integer of 1 to 10, or a salt thereof.

[Item 3]
The compound according to item 1 or 2, wherein Q is a group represented by formula (Q-2):

(Q-2)
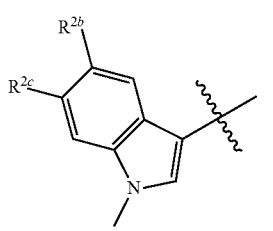

where $R^{2b}$ and $R^{2c}$ each independently represent a hydrogen atom, a halogen atom, a $C_{1-6}$ alkyl group or a $C_{1-6}$ alkoxy group, or a salt thereof.

[Item 4]
The compound according to any one of items 1 to 3, wherein Q is a group represented by formula (Q-2):

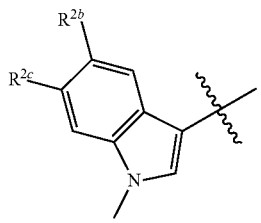

(Q-2)

where $R^{2b}$ and $R^{2c}$ each independently represent a hydrogen atom, a fluorine atom or a methoxy group, or a salt thereof.

[Item 5]
The compound according to item 3 or 4, wherein $R^{2b}$ and $R^{2c}$ are each a hydrogen atom,
or a salt thereof.

[Item 6]
The compound according to any one of items 1 to 5, wherein $R^{1a}$ is a methyl group and $R^{1b}$ is a hydrogen atom, or a salt thereof.

[Item 7]
A compound represented by formula (1a):

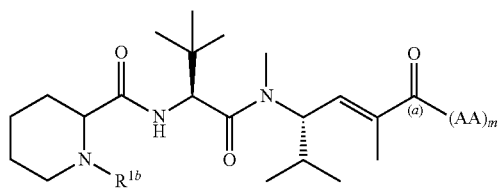

(1a)

wherein
AA represents a glutamic acid residue (Glu), an aspartic acid residue (Asp), a lysine residue (Lys), a cysteine residue (Cys), a phosphotyrosine residue, a phosphoserine residue or a cysteic acid residue, or a $C_{1-6}$ alkyl ester thereof, and when there is a plurality of AAs, each AA may be the same as or different from each other and AAs are bonded to each other via an amide bond;
an N-terminal nitrogen atom of $(AA)_m$ forms an amide bond together with carbonyl (a);
$R^{ad}$ represents a hydrogen atom or a $C_{1-6}$ alkyl group; and
m represents an integer of 1 to 10,
or a salt thereof.

[Item 8]
The compound according to any one of items 1 to 7, wherein m is an integer of 1 to 5, or a salt thereof.

[Item 9]
The compound according to any one of items 1 to 7, wherein m is an integer of 2 to 10; and
$(AA)_m$ is a linear peptide residue, or a salt thereof.

[Item 10]
The compound according to any one of items 1 to 7, wherein m is an integer of 3 to 10; and
$(AA)_m$ is a branched peptide residue having 1 or 2 branching points, or a salt thereof.

[Item 11]
The compound according to any one of items 1 to 7, wherein $(AA)_m$ is a group represented by formula (A-1):

(A-1)

where $AA_1$, $AA_2$ and $AA_3$ each independently represent Glu, Asp or Lys, or a salt thereof.

[Item 12]
The compound according to any one of items 1 to 10, wherein AA is D-Glu, L-Glu, D-Asp or L-Asp, and when there is a plurality of AAs, each AA may be the same as or different from each other, or a salt thereof.

[Item 13]
The compound according to item 1 or 2, selected from the following compounds:

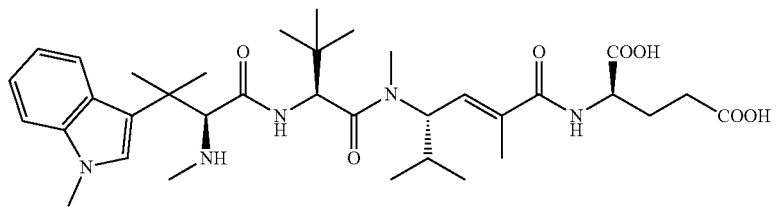

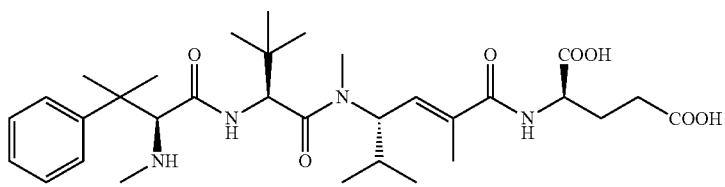

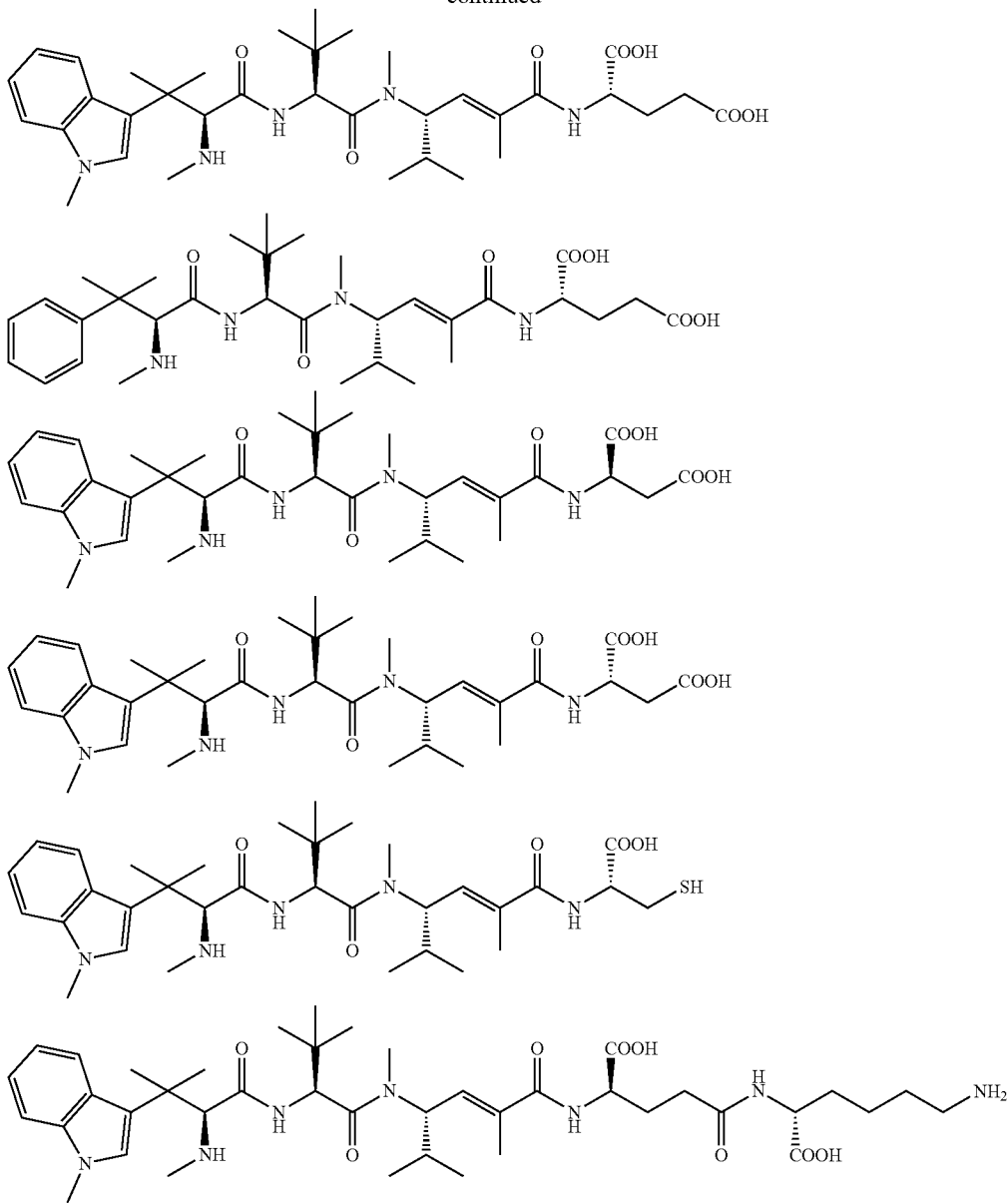

or a salt thereof.

[Item 14]

An antibody-drug conjugate represented by formula (2):

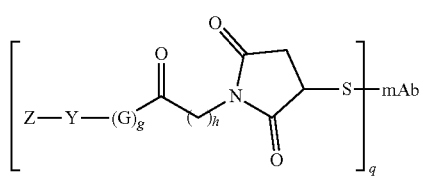

(2)

wherein
mAb represents an antibody;
q represents an integer of 1 to 8;
h represents an integer of 1 to 5;
G represents an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr), a valine residue (Val) or a citrulline residue (Cit), and when there is a plurality of Gs, each G may be the same as or different from each other and Gs are bonded to each other via an amide bond;

g represents an integer of 1 to 4;

Y is a single bond or a group represented by formula (Y-1):

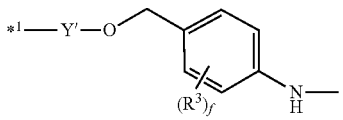

(Y-1)

where

Y' represents a single bond or a carbonyl group;

$R^3$ represents a halogen atom, a cyano group, a $C_{1-6}$ alkyl group optionally substituted with 1 to 5 fluorine atoms or a $C_{1-6}$ alkoxy group optionally substituted with 1 to 5 fluorine atoms, and when there is a plurality of $R^3$s, each $R^3$ may be the same as or different from each other; and f represents an integer of 0 to 2;

terminus*1 of the group represented by formula (Y-1) is bonded to Z; and

Z is a group represented by formula (Z-1), formula (Z-2), formula (Z-3), formula (Z-4), formula (Z-5), formula (Z-6), formula (Za-1), formula (Za-2), formula (Za-3), formula (Za-4), formula (Za-5), formula (Za-6), formula (Za-7), formula (Za-8), formula (Za-9) or formula (Za-10):

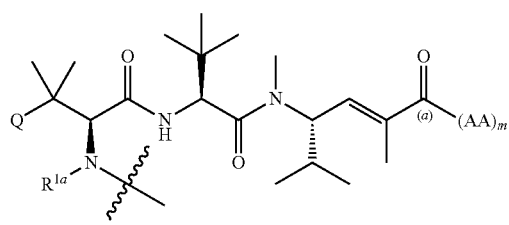

(Z-1)

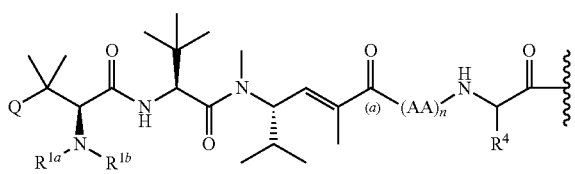

(Z-2)

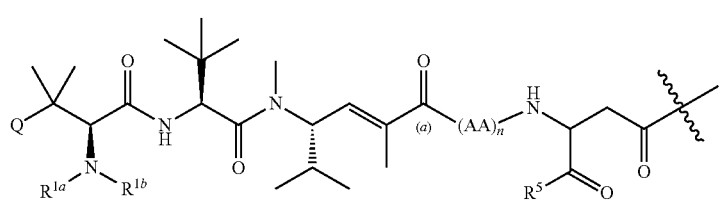

(Z-3)

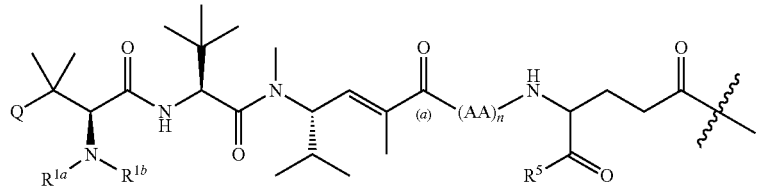

(Z-4)

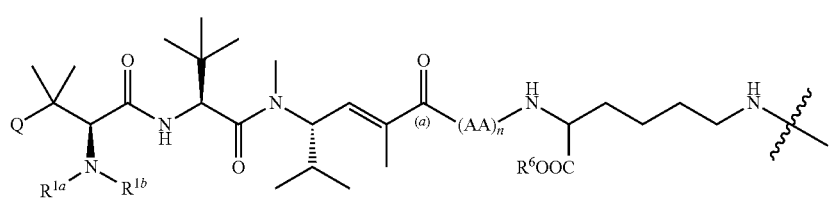

(Z-5)

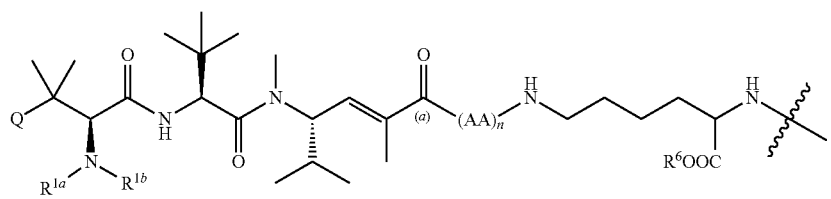

(Z-6)

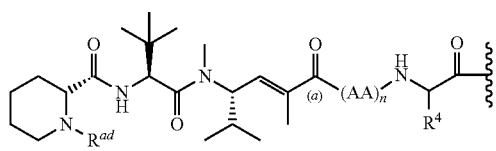

(Za-1)

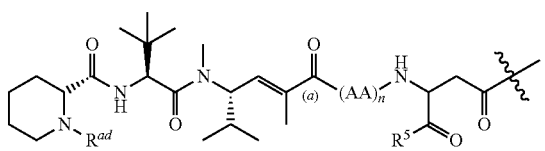

(Za-2)

-continued
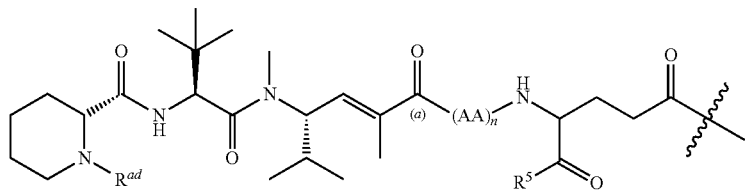
(Za-3)
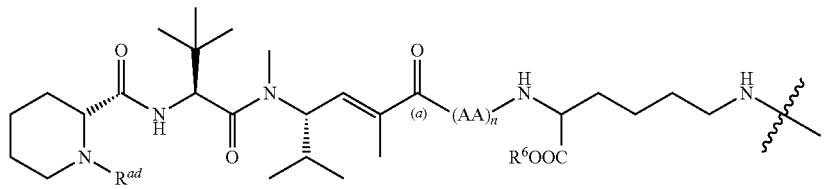
(Za-4)
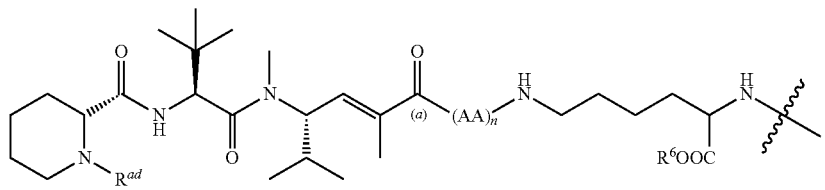
(Za-5)
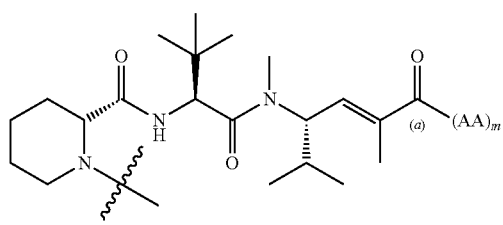
(Za-6)
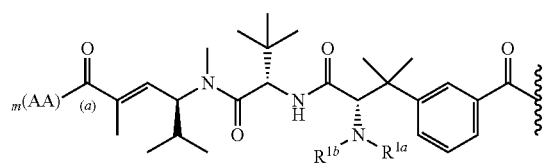
(Za-7)
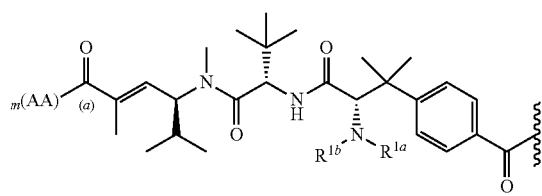
(Za-8)
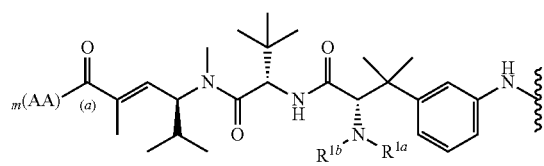
(Za-9)
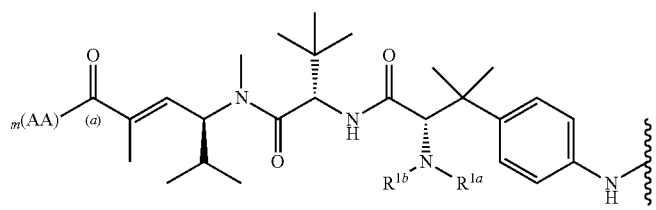
(Za-10)

where
AA represents Glu, Asp, Lys, Cys, a phosphotyrosine residue, a phosphoserine residue or a cysteic acid residue, or a $C_{1-6}$ alkyl ester thereof, and when there is a plurality of AAs, each AA may be the same as or different from each other and AAs are bonded to each other via an amide bond;

an N-terminal nitrogen atom of $(AA)_m$ forms an amide bond together with carbonyl group (a);

an N-terminal nitrogen atom of $(AA)_n$ forms an amide bond together with carbonyl group (a);

Q represents a group represented by formula (Q-1), formula (Qa-2), formula (Qa-3), formula (Qa-4), formula (Qa-5), formula (Qa-6) or formula (Qa-7):

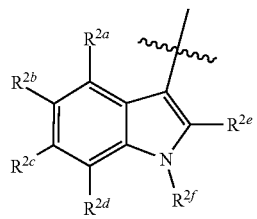
(Q-1)

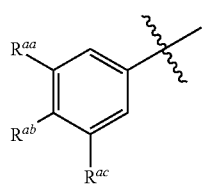
(Qa-2)

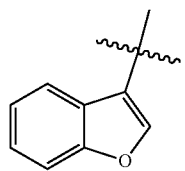
(Qa-3)

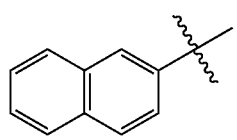
(Qa-4)

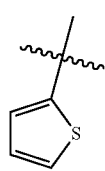
(Qa-5)

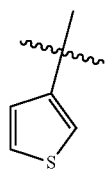
(Qa-6)

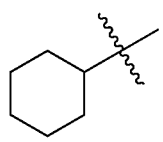
(Qa-7)

where
$R^{2a}$, $R^{2b}$, $R^{2c}$, $R^{2d}$ and $R^{2e}$ each independently represent a hydrogen atom, a halogen atom, a $C_{1-6}$ alkyl group optionally substituted with 1 to 5 fluorine atoms or a $C_{1-6}$ alkoxy group optionally substituted with 1 to 5 fluorine atoms;

$R^{2f}$ represents a hydrogen atom or a $C_{1-6}$ alkyl group; and $R^{aa}$, $R^{ab}$ and $R^{ac}$ each independently represent a hydrogen atom, a halogen atom, a hydroxy group, a cyano group, an amino group, a carboxyl group, a phenyl group, or a $C_{1-6}$ alkyl group, $C_{1-6}$ alkoxy group or $C_{1-6}$ alkyl ester group optionally substituted with 1 to 3 fluorine atoms;

$R^{1a}$ and $R^{1b}$ each independently represent a hydrogen atom or a $C_{1-6}$ alkyl group;

$R^{ad}$ represents a hydrogen atom or a $C_{1-6}$ alkyl group;

m represents an integer of 1 to 10;

n represents an integer of 0 to 4;

$R^4$ represents $-(CH_2)_u-COR^7$;

u represents 1 or 2;

$R^5$ and $R^7$ each independently represent $-OR^8$ or $-(AB)_p$;

$R^6$ and $R^8$ each independently represent a hydrogen atom or a $C_{1-6}$ alkyl group;

AB represents Glu, Asp or Lys, and when there is a plurality of ABs, each AB may be the same as or different from each other and ABs are bonded to each other via an amide bond; and p represents an integer of 1 to 4;

with a proviso that when $R^5$ or $R^7$ is $-(AB)_p$, a sum of n and p is an integer of 1 to 5;

with a proviso that when Y' is a single bond, Z is a group represented by formula (Z-2), formula (Z-3), formula (Z-4), formula (Za-1), formula (Za-2), formula (Za-3), formula (Za-7) or formula (Za-8), or a pharmaceutically acceptable salt thereof.

[Item 15]

The antibody-drug conjugate according to item 14, represented by formula (2):

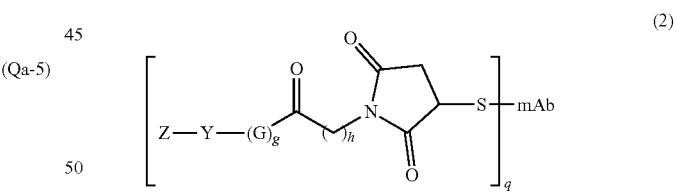
(2)

wherein
mAb represents an antibody;
q represents an integer of 1 to 8;
h represents an integer of 1 to 5;
G represents an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr), a valine residue (Val) or a citrulline residue (Cit), and when there is a plurality of Gs, each G may be the same as or different from each other and Gs are bonded to each other via an amide bond;

g represents an integer of 1 to 4;

Y is a single bond or a group represented by formula (Y-1):

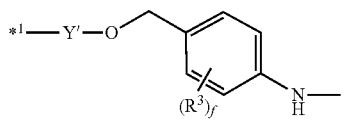

where

Y' represents a single bond or a carbonyl group;

$R^3$ represents a halogen atom, a cyano group, a $C_{1-6}$ alkyl group optionally substituted with 1 to 5 fluorine atoms or a $C_{1-6}$ alkoxy group optionally substituted with 1 to 5 fluorine atoms, and when there is a plurality of $R^3$s, each $R^3$ may be the same as or different from each other; and f represents an integer of 0 to 2;

terminus*¹ of the group represented by formula (Y-1) is bonded to Z; and

Z is a group represented by formula (Z-1), formula (Z-2), formula (Z-3), formula (Z-4), formula (Z-5) or formula (Z-6):

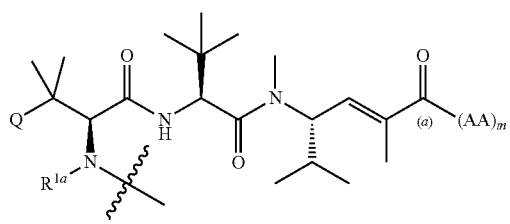

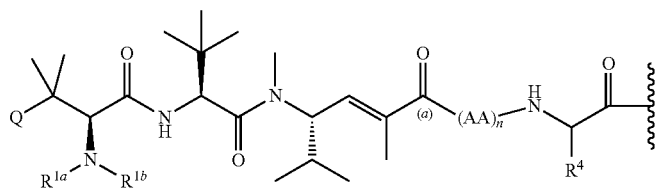

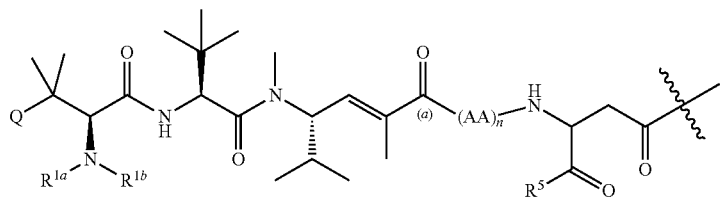

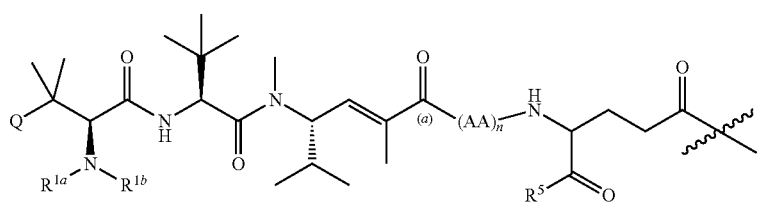

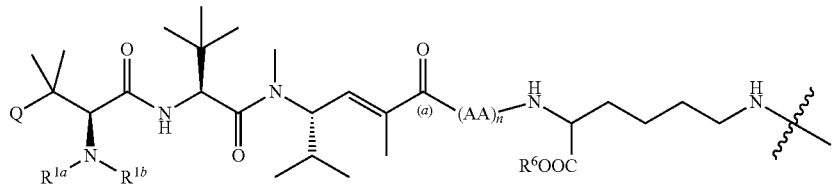

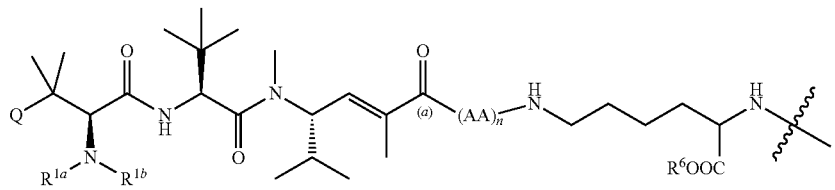

where
- AA represents Glu, Asp, Lys or Cys, or a $C_{1-6}$ alkyl ester thereof, and when there is a plurality of AAs, each AA may be the same as or different from each other and AAs are bonded to each other via an amide bond;
- an N-terminal nitrogen atom of $(AA)_m$ forms an amide bond together with carbonyl group (a);
- an N-terminal nitrogen atom of $(AA)_n$ forms an amide bond together with carbonyl group (a);
- Q represents an unsubstituted phenyl group or a group represented by formula (Q-1):

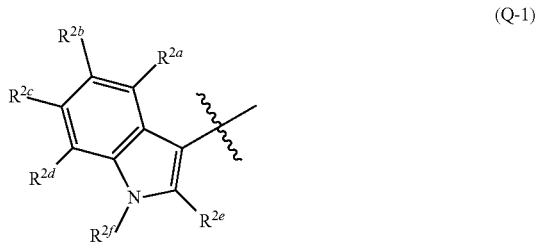

(Q-1)

where $R^{2a}$, $R^{2b}$, $R^{2c}$, $R^{2d}$ and $R^{2e}$ each independently represent a hydrogen atom, a halogen atom, a $C_{1-6}$ alkyl group optionally substituted with 1 to 5 fluorine atoms or a $C_{1-6}$ alkoxy group optionally substituted with 1 to 5 fluorine atoms, and $R^{2f}$ represents a hydrogen atom or a $C_{1-6}$ alkyl group;

$R^{1a}$ and $R^{1b}$ each independently represent a hydrogen atom or a $C_{1-6}$ alkyl group;

m represents an integer of 1 to 10;
n represents an integer of 0 to 4;
$R^4$ represents $-(CH_2)_u-COR^7$;
u represents 1 or 2;
$R^5$ and $R^7$ each independently represent $-OR^8$ or $-(AB)_p$;
$R^6$ and $R^8$ each independently represent a hydrogen atom or a $C_{1-6}$ alkyl group;
AB represents Glu, Asp or Lys, and when there is a plurality of ABs, each AB may be the same as or different from each other and ABs are bonded to each other via an amide bond; and
p represents an integer of 1 to 4;
with a proviso that when $R^5$ or $R^7$ is $-(AB)_p$, a sum of n and p is an integer of 1 to 5;
with a proviso that when Y' is a single bond, Z is a group represented by formula (Z-2), formula (Z-3) or formula (Z-4), or a pharmaceutically acceptable salt thereof.

[Item 16]

The antibody-drug conjugate according to item 14 or 15, wherein mAb is brentuximab, trastuzumab, inotuzumab, gemtuzumab, glembatumumab, labetuzumab, sacituzumab, lifastuzumab, indusatumab, polatuzumab, pinatuzumab, coltuximab, indatuximab, milatuzumab, rovalpituzumab, anetumab, tisotumab, mirvetuximab, lorvotuzumab, rituximab, depatuxizumab, denintuzumab, telisotuzumab, enfortumab, vandortuzumab, sofituzumab, vorsetuzumab, mirvetuximab, naratuximab, cantuzumab, lapriruximab, bivatuzumab, vadastuximab, lupartumab, aprutumab, abagovomab, abciximab, abituzumab, abrilumab, actoxumab, adalimumab, adecatumumab, aducanumab, afasevikumab, afelimomab, alacizumab, alemtuzumab, alirocumab, altumomab, amatuximab, anatumomab, anifrolumab, anrukinzumab, apolizumab, arcitumomab, ascrinvacumab, aselizumab, atezolizumab, atinumab, atorolimumab, avelumab, azintuxizumab, bapineuzumab, basiliximab, bavituximab, bectumomab, begelomab, belimumab, benralizumab, bertilimumab, besilesomab, bevacizumab, bezlotoxumab, biciromab, bimagrumab, bimekizumab, bleselumab, blinatumomab, blontuvetmab, blosozumab, bococizumab, brazikumab, briakinumab, brodalumab, brolucizumab, brontictuzumab, burosumab, cabiralizumab, camrelizumab, caplacizumab, capromab, carlumab, carotuximab, catumaxomab, cedelizumab, certolizumab, cetuximab, citatuzumab, cixutumumab, clenoliximab, clivatuzumab, codrituzumab, conatumumab, concizumab, cosfroviximab, crenezumab, crizanlizumab, crotedumab, dacetuzumab, daclizumab, dalotuzumab, dapirolizumab, daratumumab, dectrekumab, demcizumab, denosumab, detumomab, dezamizumab, dinutuximab, diridavumab, domagrozumab, dorlimomab, drozitumab, duligotuzumab, dupilumab, durvalumab, dusigitumab, duvortuxizumab, ecromeximab, eculizumab, edobacomab, edrecolomab, efalizumab, efungumab, eldelumab, elezanumab, elotuzumab, elsilimomab, emactuzumab, emapalumab, emibetuzumab, emicizumab, enavatuzumab, enlimomab, enoblituzumab, enokizumab, enoticumab, ensituximab, epitumomab, epratuzumab, eptinezumab, erenumab, erlizumab, ertumaxomab, etaracizumab, etrolizumab, evinacumab, evolocumab, exbivirumab, faralimomab, farletuzumab, fasinumab, felvizumab, fezakinumab, ficlatuzumab, figitumumab, firivumab, flanvotumab, fletikumab, fontolizumab, foralumab, foravirumab, fremanezumab, fresolimumab, frunevetmab, fulranumab, futuximab, galcanezumab, galiximab, ganitumab, gantenerumab, gatipotuzumab, gavilimomab, gedivumab, gevokizumab, gilvetmab, girentuximab, golimumab, guselkumab, ibalizumab, ibritumomab, icrucumab, idarucizumab, ifabotuzumab, igovomab, imalumab, imciromab, imgatuzumab, inclacumab, inebilizumab, infliximab, inolimomab, intetumumab, ipilimumab, iratumumab, isatuximab, itolizumab, ixekizumab, keliximab, lacnotuzumab, lampalizumab, lanadelumab, landogrozumab, larcaviximab, lebrikizumab, lemalesomab, lenzilumab, lerdelimumab, lesofavumab, letolizumab, lexatumumab, libivirumab, lifatuzumab, ligelizumab, lilotomab, lintuzumab, lirilumab, lodelcizumab, lokivetmab, lorvotuzumab, losatuximab, lucatumumab, lulizumab, lumretuzumab, lutikizumab, mapatumumab, margetuximab, maslimomab, matuzumab, mavrilimumab, mepolizumab, metelimumab, minretumomab, mitumomab, modotuximab, mogamulizumab, monalizumab, morolimumab, motavizumab, moxetumumab, muromonab, nacolomab, namilumab, naptumomab, narnatumab, natalizumab, navicixizumab, navivumab, nebacumab, necitumumab, nemolizumab, nerelimomab, nesvacumab, nimotuzumab, nivolumab, obiltoxaximab, obinutuzumab, ocaratuzumab, ocrelizumab, odulimomab, ofatumumab, olaratumab, oleclumab, olendalizumab, olokizumab, omalizumab, onartuzumab, ontuxizumab, opicinumab, oportuzumab, oregovomab, oreticumab, orticumab, otelixizumab, otlertuzumab, oxelumab, ozanezumab, ozoralizumab, pagibaximab, palivizumab, pamrevlumab, panitumumab, panobacumab, parsatuzumab, pascolizumab, pasotuxizumab, pateclizumab, patritumab, pembrolizumab, perakizumab, pertuzumab, pexelizumab, pidilizumab, placulumab, plozalizumab, ponezumab, porgaviximab, prezalumab, priliximab, pritoxaximab, pritumumab, quilizumab, racotumomab, radretumab, rafivirumab, ralpancizumab, ramucirumab, ranevetmab, ranibizumab, raxibacumab, refanezumab, regavirumab, remtolumab, reslizumab, rilotumumab, rinucumab, risankizumab, rivabazumab, robatumumab, roledumab, romosozumab, rontalizumab, rosmantuzumab, rovelizumab, rozanolixizumab, ruplizumab, sacituzumab, samalizumab, sarilumab, satralizumab, satumomab, secukinumab, selicrelumab, seribantumab, setoxaximab, sevirumab, sibrotuzumab, sifalimumab, siltuximab, simtuzumab, siplizumab, sirukumab, solanezumab, solitomab, sontuzumab, stamulumab, sulesomab, suptavumab, suvizumab, suvratoxumab, tabalumab, tadocizumab, talizumab, tamtuvetmab, tanezumab, taplitumomab, tarextumab, tavolixizumab, fanolesomab, nofetumomab, pintumomab, tefibazumab, telimomab, telisotuzumab, tenatumomab, teneliximab, teplizumab, teprotumumab, tesidolumab, tezepelumab, tigatuzumab, tildrakizumab, timigutuzumab, timolumab, tocilizumab, tomuzotuximab, toralizumab, tosatoxumab, tositumomab, tovetumab, tralokinumab, tregalizumab, tremelimumab, trevogrumab, tucotuzumab, tuvirumab, ublituximab, ulocuplumab, urelumab, urtoxazumab, ustekinumab, utomilumab, vantictumab, vanucizumab, vapaliximab, varisakumab, varlilumab, vatelizumab, vedolizumab, veltuzumab, vepalimomab, vesencumab, visilizumab, vobarilizumab, volociximab, vonlerolizumab, votumumab, vunakizumab, tacatuzumab, zalutumumab, zanolimumab, ziralimumab, zolimomab, camidanlumab, cofetuzumab, ladiratuzumab, loncastuximab, telisotuzumab, enapotamab, an antibody of AMG 595 or anti-embigin antibody, or a pharmaceutically acceptable salt thereof.

[Item 17]

The antibody-drug conjugate according to any one of items 14 to 16, wherein mAb is brentuximab, trastuzumab, inotuzumab, gemtuzumab, labetuzumab, polatuzumab, coltuximab, indatuximab, anetumab, rituximab, denintuzumab, laprituximab, vadastuximab, glembatumumab, cetuximab, alemtuzumab, depatuxizumab or anti-embigin antibody, or a pharmaceutically acceptable salt thereof.

[Item 18]

The antibody-drug conjugate according to any one of items 14 to 17, wherein mAb is brentuximab, trastuzumab, rituximab or anti-embigin antibody, or a pharmaceutically acceptable salt thereof.

[Item 19]

The antibody-drug conjugate according to any one of items 14 to 18, wherein h is 5, or a pharmaceutically acceptable salt thereof.

[Item 20]

The antibody-drug conjugate according to any one of items 14 to 19, wherein $(G)_g$ is *²-Gly-, *²-Gly-Gly-, *²-Lys-, *²-Lys-Phe-, *²-Lys-Val-, *²-Lys-Ala-, *²-Cit-Val-, *²-Cit-Phe-, *²-Cit-Leu-, *²-Arg-Phe-, *²-Cit-Ile-, *²-Cit-Trp-, *²-Lys-Phe-Phe-, *²-Lys-Phe-Ala-, *²-Lys-Phe-Gly-, *²-Asn-, *²-Asn-Ala-, *²-Asn-Ala-Ala-, *²-Asn-Ala-Thr-, *²-Asn-Ala-Pro-, *²-Asn-Ala-Val-, *²-Asn-Ala-Phe-, *²-Asn-Ala-Tyr-, *²-Asn-Ala-Leu-, *²-Asn-Ala-Gly-, *²-Asn-Thr-Ala-, *2-Asn-Thr-Pro-, *²-Asn-Thr-Thr-, *²-Gly-Phe-Gly-Gly-, *²-Gly-Leu-Phe-Gly- or *²-Leu-Ala-Leu-Ala-; and terminus *² of $(G)_g$ is bonded to Y, or a pharmaceutically acceptable salt thereof.

[Item 21]

The antibody-drug conjugate according to any one of items 14 to 19, wherein $(G)_g$ is a group represented by formula (G-1), formula (G-2), formula (G-3) or formula (G-4):

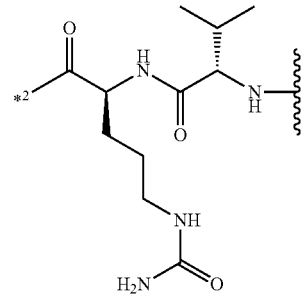

(G-1)

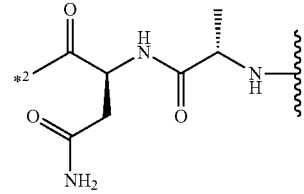

(G-2)

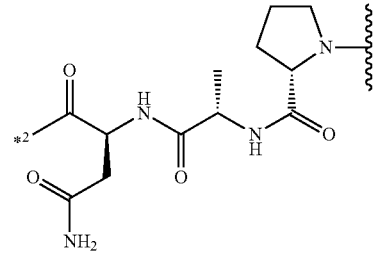

(G-3)

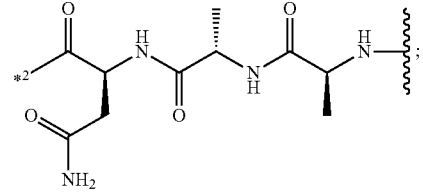

(G-4)

and terminus *² of $(G)_g$ is bonded to Y, or a pharmaceutically acceptable salt thereof.

[Item 22]

The antibody-drug conjugate according to any one of items 14 to 21, wherein $R^3$ is a fluorine atom, a $C_{1-3}$ alkyl group or a $C_{1-3}$ alkoxy group, and when there is a plurality of $R^3$s, each $R^3$ may be the same as or different from each other, or a pharmaceutically acceptable salt thereof.

[Item 23]

The antibody-drug conjugate according to any one of items 14 to 21, wherein f is 0, or a pharmaceutically acceptable salt thereof.

[Item 24]

The antibody-drug conjugate according to any one of items 14 to 23, wherein Z is a group represented by formula (Z-2), formula (Z-3) or formula (Z-4);

Q is an unsubstituted phenyl group or a group represented by formula (Q-2):

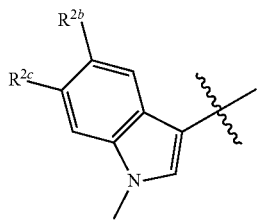
(Q-2)

where $R^{2b}$ and $R^{2c}$ each independently represent a hydrogen atom, a fluorine atom or a methoxy group;
$R^5$ and $R^7$ are —OH; and
n is 1 or 2,
or a pharmaceutically acceptable salt thereof.

[Item 25]
The antibody-drug conjugate according to any one of items 14 to 23, wherein Z is a group represented by formula (Z-2), formula (Z-3) or formula (Z-4);
Q is an unsubstituted phenyl group or a group represented by formula (Q-2):

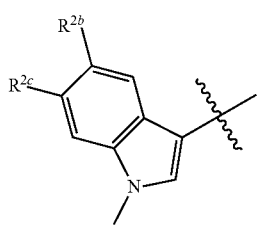
(Q-2)

where $R^{2b}$ and $R^{2e}$ each independently represent a hydrogen atom, a fluorine atom or a methoxy group;
$R^5$ and $R^7$ are -(AB)$_p$; and
n is 0 and p is 2, or n and p are each 1,
or a pharmaceutically acceptable salt thereof.

[Item 26]
The antibody-drug conjugate according to any one of items 14 to 21, wherein Z-Y is a group represented by formula (ZY-1):

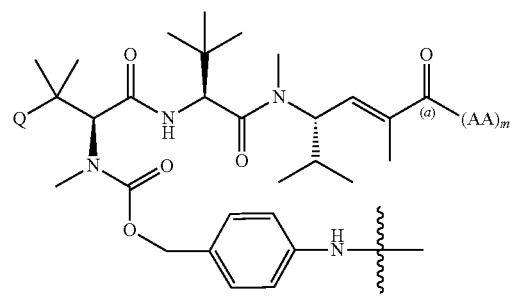
(ZY-1)

where AA and m are as defined above; and
Q is an unsubstituted phenyl group or a group represented by formula (Q-2):

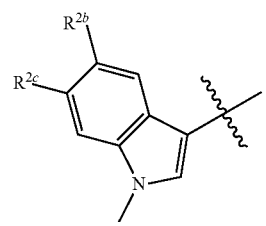
(Q-2)

where $R^{2b}$ and $R^{2c}$ each independently represent a hydrogen atom, a fluorine atom or a methoxy group,
or a pharmaceutically acceptable salt thereof.

[Item 27]
The antibody-drug conjugate according to any one of items 14 to 21, wherein Z-Y is a group represented by formula (ZY-2):

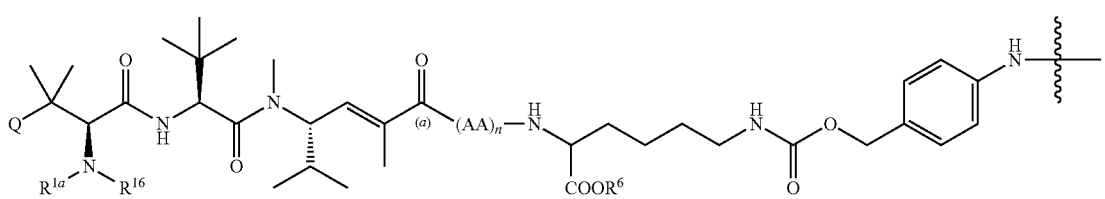
(ZY-2)

where AA, $R^{1a}$, $R^{1b}$, $R^6$ and n are as defined above; and Q is an unsubstituted phenyl group or a group represented by formula (Q-2):

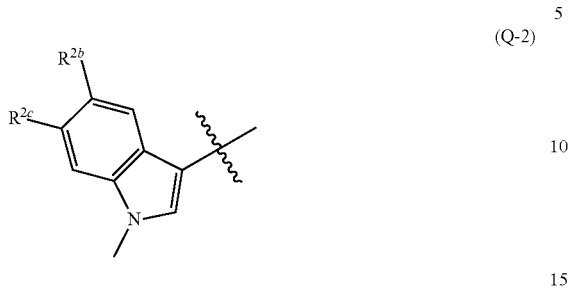
(Q-2)

where $R^{2b}$ and $R^{2c}$ each independently represent a hydrogen atom, a fluorine atom or a methoxy group, or a pharmaceutically acceptable salt thereof.

[Item 28]

The antibody-drug conjugate according to any one of items 14 to 19, wherein formula (2) is formula (YG-1), formula (YG-2), formula (YG-3) or formula (YG-4):

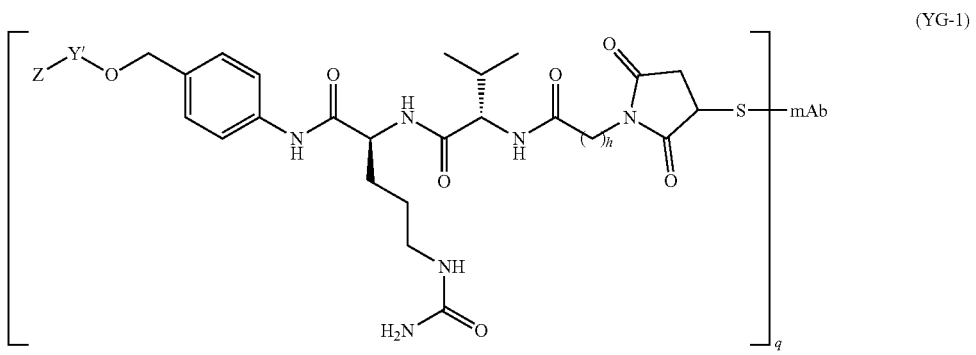
(YG-1)

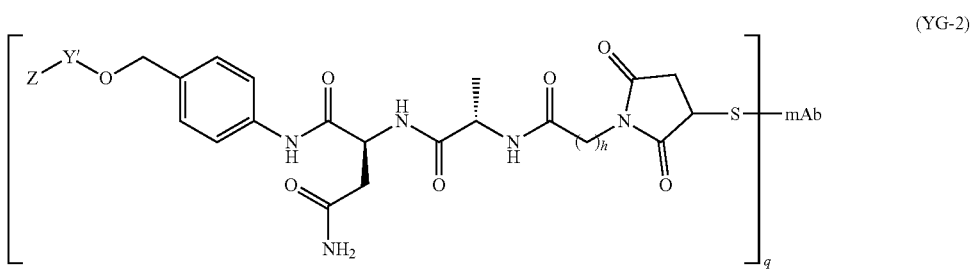
(YG-2)

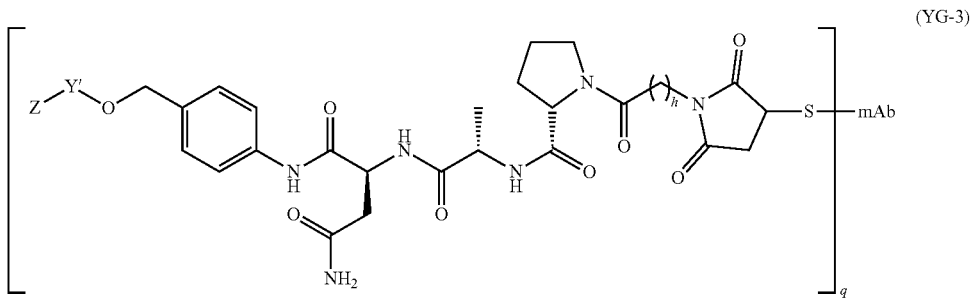
(YG-3)

-continued

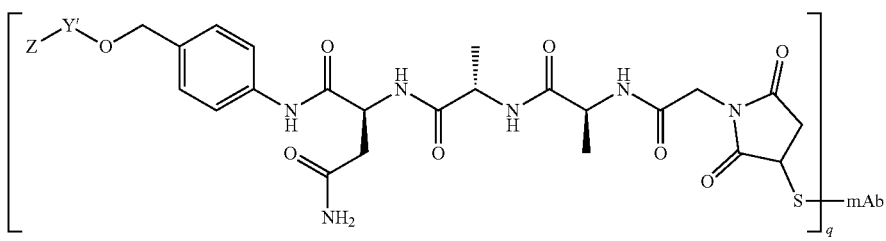

where mAb, Z, Y', h and q are as defined above, or a pharmaceutically acceptable salt thereof.

[Item 29]

A compound represented by formula (3-1) or formula (3-2):

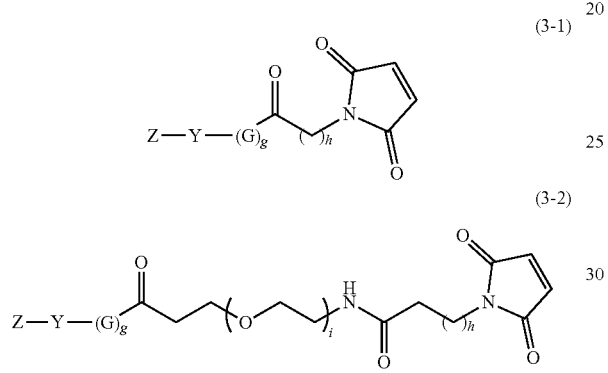

wherein h represents an integer of 1 to 5;

G represents an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr), a valine residue (Val) or a citrulline residue (Cit), and when there is a plurality of Gs, each G may be the same as or different from each other and Gs are bonded to each other via an amide bond;

g represents an integer of 1 to 4;

Y is a single bond or a group represented by formula (Y-1):

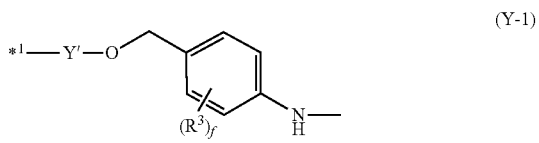

where

Y' represents a single bond or a carbonyl group;

$R^3$ represents a halogen atom, a cyano group, a $C_{1-6}$ alkyl group optionally substituted with 1 to 5 fluorine atoms or a $C_{1-6}$ alkoxy group optionally substituted with 1 to 5 fluorine atoms, and when there is a plurality of $R^3$s, each $R^3$ may be the same as or different from each other; and f represents an integer of 0 to 2;

terminus *1 of formula (Y-1) is bonded to Z;

Z is a group represented by formula (Z-1), formula (Z-2), formula (Z-3), formula (Z-4), formula (Z-5), formula (Z-6), formula (Za-1), formula (Za-2), formula (Za-3), formula (Za-4), formula (Za-5), formula (Za-6), formula (Za-7), formula (Za-8), formula (Za-9) or formula (Za-10):

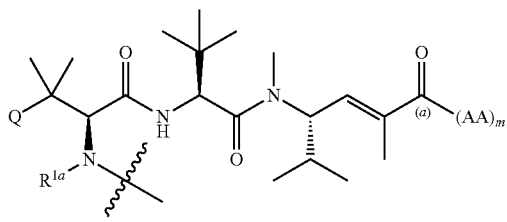

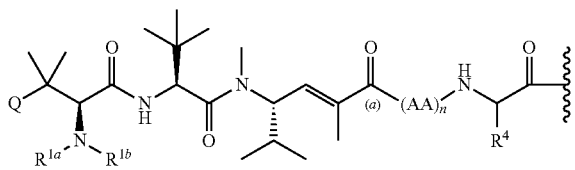

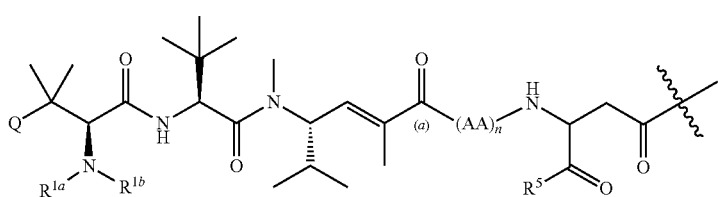

(Z-4)
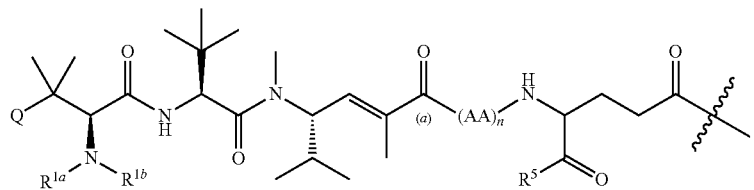
(Z-5)
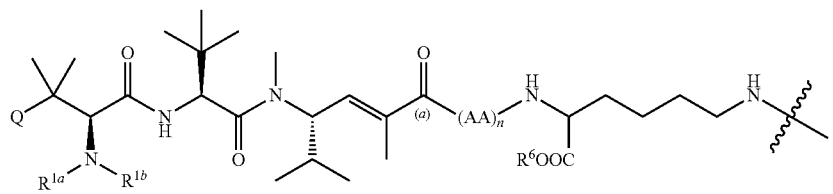
(Z-6)
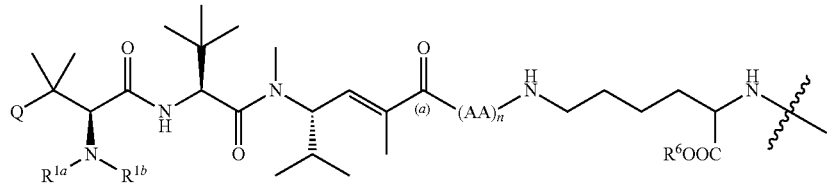
(Za-1)
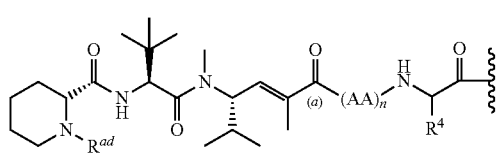
(Za-2)
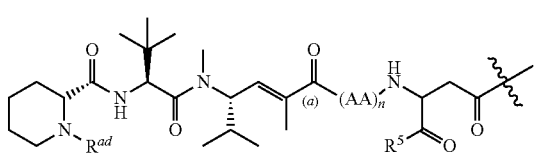
(Za-3)
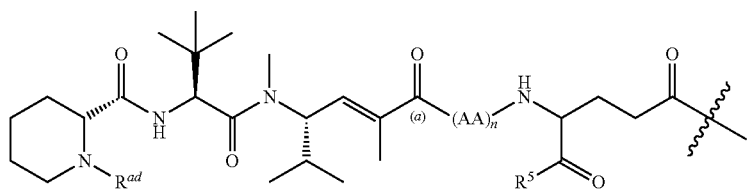
(Za-4)
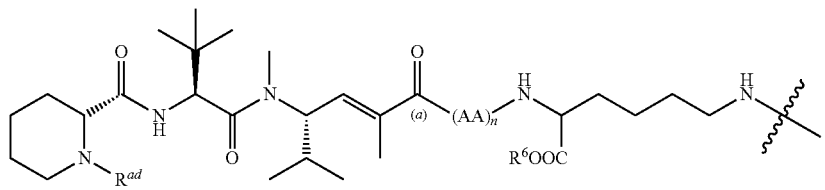
(Za-5)
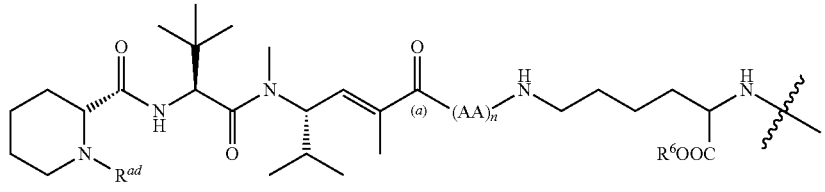
(Za-6)
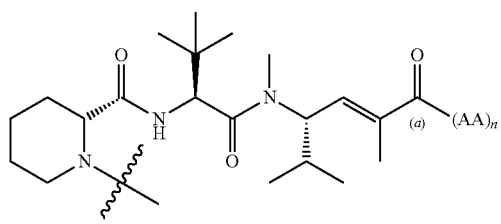
(Za-7)
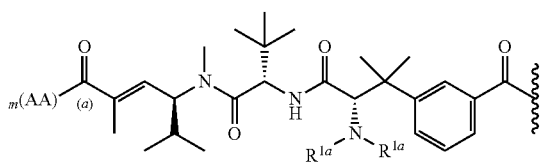

-continued (Za-8)
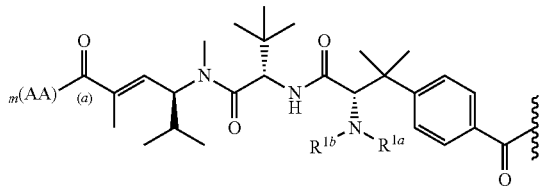

(Za-9)
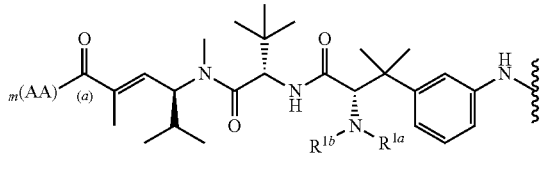

(Za-10)
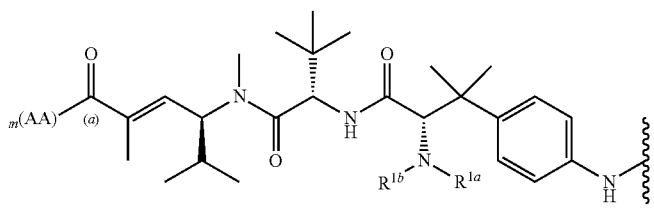

where
- AA represents Glu, Asp, Lys, Cys, a phosphotyrosine residue, a phosphoserine residue or a cysteic acid residue, or a $C_{1-6}$ alkyl ester thereof, and when there is a plurality of AAs, each AA may be the same as or different from each other and AAs are bonded to each other via an amide bond;
- an N-terminal nitrogen atom of $(AA)_m$ forms an amide bond together with carbonyl group (a);
- an N-terminal nitrogen atom of $(AA)_n$ forms an amide bond together with carbonyl group (a);
- Q represents a group represented by formula (Q-1), formula (Qa-2), formula (Qa-3), formula (Qa-4), formula (Qa-5), formula (Qa-6) or formula (Qa-7):

(Q-1)
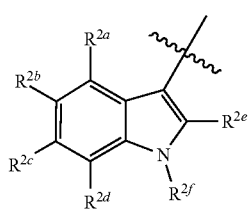

(Qa-2)
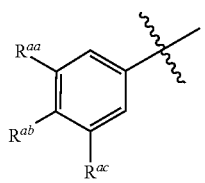

(Qa-3)
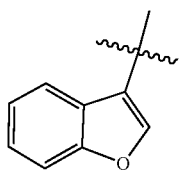

(Qa-4)
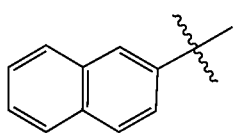

(Qa-5)
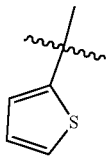

(Qa-6)
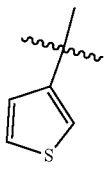

(Qa-7)
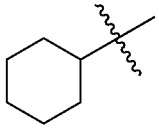

where
- $R^{2a}$, $R^{2b}$, $R^{2c}$, $R^{2d}$ and $R^{2e}$ each independently represent a hydrogen atom, a halogen atom, a $C_{1-6}$ alkyl group optionally substituted with 1 to 5 fluorine atoms or a $C_{1-6}$ alkoxy group optionally substituted with 1 to 5 fluorine atoms;
- $R^{2f}$ represents a hydrogen atom or a $C_{1-6}$ alkyl group; and
- $R^{aa}$, $R^{ab}$ and $R^{ac}$ each independently represent a hydrogen atom, a halogen atom, a hydroxy group, a cyano group, an amino group, a carboxyl group, a phenyl group, or a $C_{1-6}$ alkyl group, $C_{1-6}$ alkoxy group or $C_{1-6}$ alkyl ester group optionally substituted with 1 to 3 fluorine atoms;
- $R^{1a}$ and $R^{1b}$ each independently represent a hydrogen atom or a $C_{1-6}$ alkyl group;
- $R^{ad}$ represents a hydrogen atom or a $C_{1-6}$ alkyl group;
- m represents an integer of 1 to 10;
- n represents an integer of 0 to 4;
- $R^4$ represents —$(CH_2)_u$—$COR^7$;
- u represents 1 or 2;
- $R^5$ and $R^7$ each independently represent —$OR^8$ or -$(AB)_p$;
- $R^6$ and $R^8$ each independently represent a hydrogen atom or a $C_{1-6}$ alkyl group;

AB represents Glu, Asp or Lys, and when there is a plurality of ABs, each AB may be the same as or different from each other and ABs are bonded to each other via an amide bond; and p represents an integer of 1 to 4;

with a proviso that when $R^5$ or $R^7$ is -(AB)$_p$, a sum of n and p is an integer of 1 to 5; and i represents an integer of 1 to 12;

with a proviso that when Y' is a single bond, Z is a group represented by formula (Z-2), formula (Z-3), formula (Z-4), formula (Za-1), formula (Za-2), formula (Za-3), formula (Za-7) or formula (Za-8), or a salt thereof.

[Item 30]

The compound according to item 29, represented by formula (3-1) or formula (3-2):

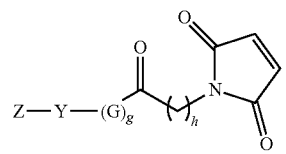
(3-1)

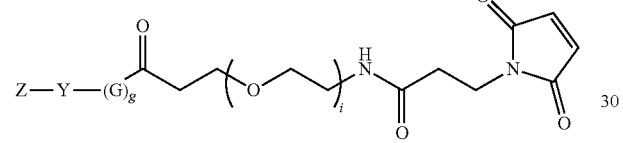
(3-2)

wherein h represents an integer of 1 to 5;

G represents an alanine residue (Ala), an arginine residue (Arg), an asparagine residue (Asn), an aspartic acid residue (Asp), a cysteine residue (Cys), a glutamine residue (Gln), a glutamic acid residue (Glu), a glycine residue (Gly), a histidine residue (His), an isoleucine residue (Ile), a leucine residue (Leu), a lysine residue (Lys), a methionine residue (Met), a phenylalanine residue (Phe), a proline residue (Pro), a serine residue (Ser), a threonine residue (Thr), a tryptophan residue (Trp), a tyrosine residue (Tyr), a valine residue (Val) or a citrulline residue (Cit), and when there is a plurality of Gs, each G may be the same as or different from each other and Gs are bonded to each other via an amide bond;

g represents an integer of 1 to 4;

Y is a single bond or a group represented by formula (Y-1):

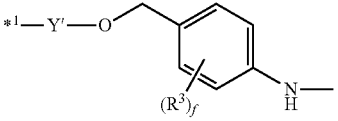
(Y-1)

where

Y' represents a single bond or a carbonyl group;

$R^3$ represents a halogen atom, a cyano group, a $C_{1-6}$ alkyl group optionally substituted with 1 to 5 fluorine atoms or a $C_{1-6}$ alkoxy group optionally substituted with 1 to 5 fluorine atoms, and when there is a plurality of $R^3$s, each $R^3$ may be the same as or different from each other; and f represents an integer of 0 to 2;

terminus *$^1$ of formula (Y-1) is bonded to Z;

Z is a group represented by formula (Z-1), formula (Z-2), formula (Z-3), formula (Z-4), formula (Z-5) or formula (Z-6):

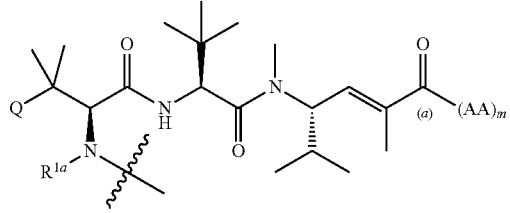
(Z-1)

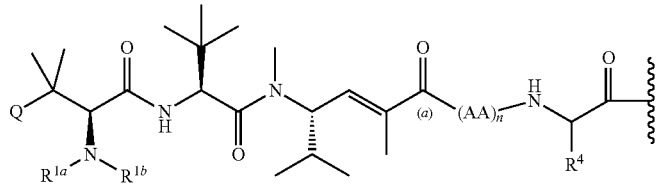
(Z-2)

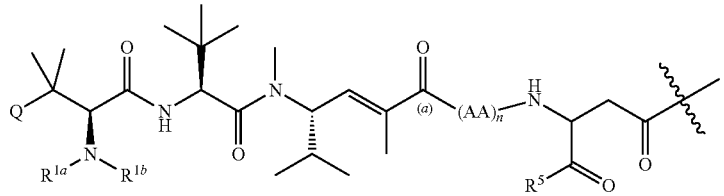
(Z-3)

(Z-4)
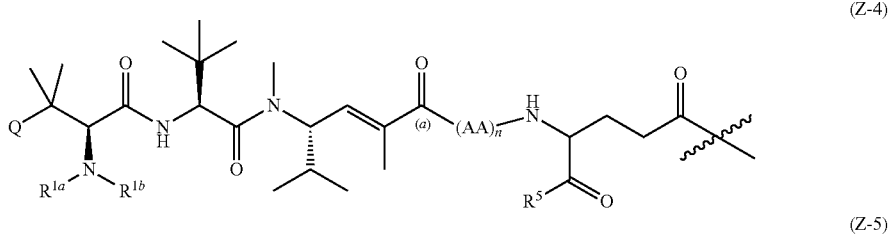

(Z-5)
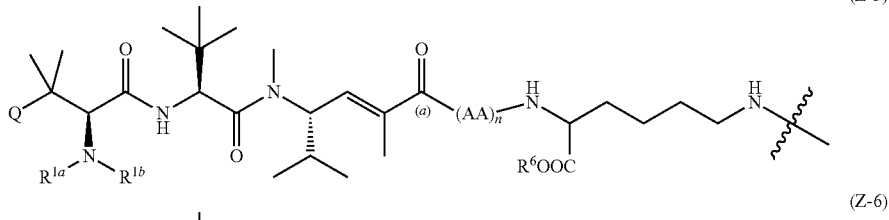

(Z-6)
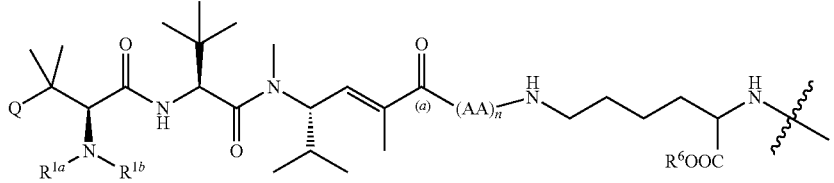

where
AA represents Glu, Asp, Lys or Cys, or a $C_{1-6}$ alkyl ester thereof, and when there is a plurality of AAs, each AA may be the same as or different from each other and AAs are bonded to each other via an amide bond;
an N-terminal nitrogen atom of $(AA)_m$ forms an amide bond together with carbonyl group (a);
an N-terminal nitrogen atom of $(AA)_n$ forms an amide bond together with carbonyl group (a);
Q represents an unsubstituted phenyl group or a group represented by formula (Q-1):

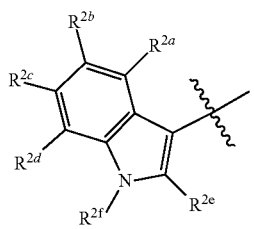

(Q-1)

where
$R^{2a}$, $R^{2b}$, $R^{2c}$, $R^{2d}$ and $R^{2e}$ each independently represent a hydrogen atom, a halogen atom, a $C_{1-6}$ alkyl group optionally substituted with 1 to 5 fluorine atoms or a $C_{1-6}$ alkoxy group optionally substituted with 1 to 5 fluorine atoms; and
$R^{2f}$ represents a hydrogen atom or a $C_{1-6}$ alkyl group;
$R^{1a}$ and $R^{1b}$ each independently represent a hydrogen atom or a $C_{1-6}$ alkyl group;
m represents an integer of 1 to 10;
n represents an integer of 0 to 4;
$R^4$ represents —$(CH_2)_u$—$COR^7$;
u represents 1 or 2;
$R^5$ and $R^7$ each independently represent —$OR^8$ or -$(AB)_p$;
$R^6$ and $R^8$ each independently represent a hydrogen atom or a $C_{1-6}$ alkyl group;
AB represents Glu, Asp or Lys, and when there is a plurality of ABs, each AB may be the same as or different from each other and ABs are bonded to each other via an amide bond; and
p represents an integer of 1 to 4;
with a proviso that when $R^5$ or $R^7$ is -$(AB)_p$, a sum of n and p is an integer of 1 to 5; and
i represents an integer of 1 to 12;
with a proviso that when Y' is a single bond, Z is a group represented by formula (Z-2), formula (Z-3) or formula (Z-4),
or a salt thereof.

[Item 31]
The compound according to item 29 or 30, represented by formula (3-1), or a salt thereof.

[Item 32]
The compound according to any one of items 29 to 31, wherein h is 5, or a salt thereof.

[Item 33]
The compound according to item 29 or 30, wherein i is 2, or a salt thereof.

[Item 34]
The compound according to any one of items 29 to 33, wherein $(G)_g$ is *²-Gly-, *2-Gly-Gly-, *²-Lys-, *²-Lys-Phe-, *²-Lys-Val-, *²-Lys-Ala-, *²-Cit-Val-, *²-Cit-Phe-, *²-Cit-Leu-, *²-Arg-Phe-, *²-Cit-Ile-, *²-Cit-Trp-, *²-Lys-Phe-Phe-, *²-Lys-Phe-Ala-, *²-Lys-Phe-Gly-, *²-Asn-, *²-Asn-Ala-, *²-Asn-Ala-Ala-, *2-Asn-Ala-Thr-, *²-Asn-Ala-Pro-, *²-Asn-Ala-Val-, *²-Asn-Ala-Phe-, *²-Asn-Ala-Tyr-, *²-Asn-Ala-Leu-, *²-Asn-Ala-Gly-, *²-Asn-Thr-Ala-, *²-Asn-Thr-Pro-, *²-Asn-Thr-Thr-, *²-Gly-Phe-Gly-Gly-, *2-Gly-Leu-Phe-Gly- or *²-Leu-Ala-Leu-Ala-; and
terminus *² of $(G)_g$ is bonded to Y,
or a salt thereof.

[Item 35]
The compound according to any one of items 29 to 33, wherein $(G)_g$ is a group represented by formula (G-1), formula (G-2), formula (G-3) or formula (G-4):

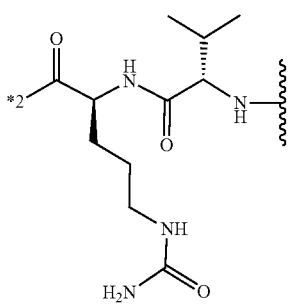
(G-1)

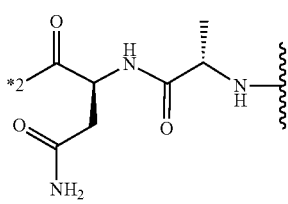
(G-2)

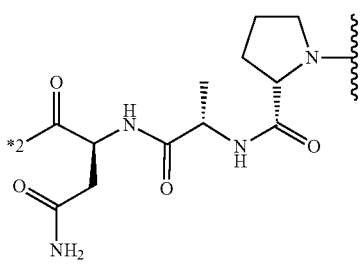
(G-3)

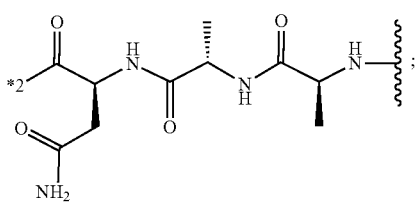
(G-4)

terminus *² of (G)_g is bonded to Y,
or a salt thereof.

[Item 36]

The compound according to any one of items 29 to 35, wherein $R^3$ is a fluorine atom, a $C_{1-3}$ alkyl group or a $C_{1-3}$ alkoxy group, and when there is a plurality of $R^3$s, each $R^3$ may be the same as or different from each other, or a salt thereof.

[Item 37]

The compound according to any one of items 29 to 35, wherein f is 0, or a salt thereof.

[Item 38]

The compound according to any one of items 29 to 37, wherein Z is a group represented by formula (Z-2), formula (Z-3) or formula (Z-4); Q is an unsubstituted phenyl group or a group represented by formula (Q-2):

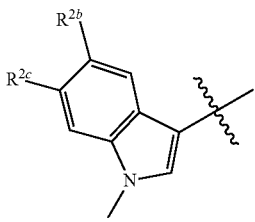
(Q-2)

where $R^{2b}$ and $R^{2c}$ each independently represent a hydrogen atom, a fluorine atom or a methoxy group;

$R^5$ and $R^7$ are —OH; and n is 1 or 2, or a salt thereof.

[Item 39]

The compound according to any one of items 29 to 37, wherein Z is a group represented by formula (Z-2), formula (Z-3) or formula (Z-4);

Q is an unsubstituted phenyl group or a group represented by formula (Q-2):

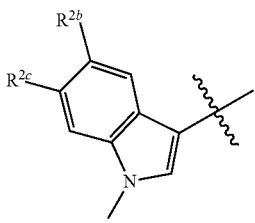
(Q-2)

where $R^{2b}$ and $R^{2c}$ each independently represent a hydrogen atom, a fluorine atom or a methoxy group;

$R^5$ and $R^7$ are -(AB)$_p$; and n is 0 and p is 2, or n and p are each 1, or a salt thereof.

[Item 40]

The compound according to any one of items 29 to 35, wherein Z-Y is a group represented by formula (ZY-1):

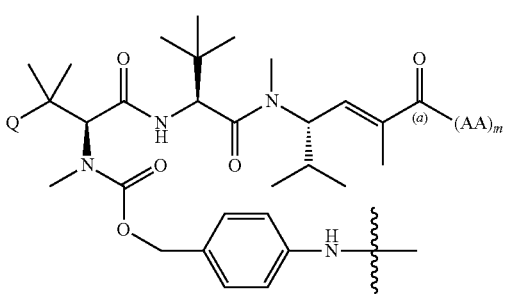
(ZY-1)

where

AA and m are as defined above; and

Q is an unsubstituted phenyl group or a group represented by formula (Q-2):

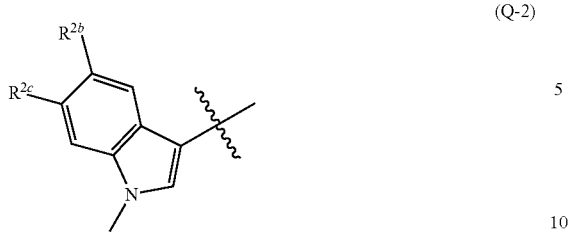

where $R^{2b}$ and $R^{2e}$ each independently represent a hydrogen atom, a fluorine atom or a methoxy group, or a salt thereof.

[Item 41]

The compound according to any one of items 29 to 35, wherein Z-Y is a group represented by formula (ZY-2):

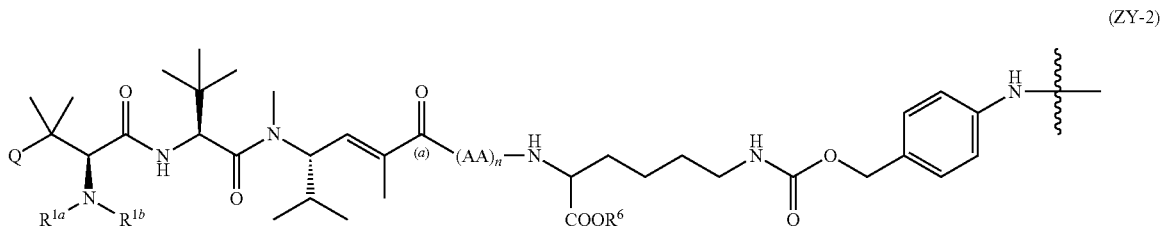

where
AA, $R^{1a}$, $R^{1b}$, $R^6$ and n are as defined above; and
Q is an unsubstituted phenyl group or a group represented by formula (Q-2):

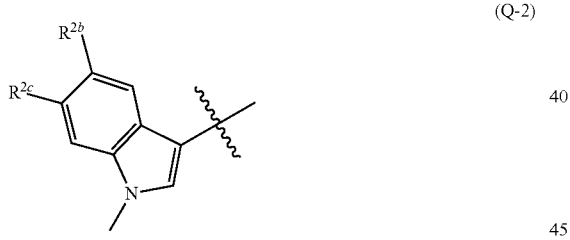

where $R^{2b}$ and $R^{2c}$ each independently represent a hydrogen atom, a fluorine atom or a methoxy group, or a salt thereof.

[Item 42]

The compound according to any one of items 29 to 32, wherein formula (3-1) is formula (MDF-1), formula (MDF-2), formula (MDF-3) or formula (MDF-4):

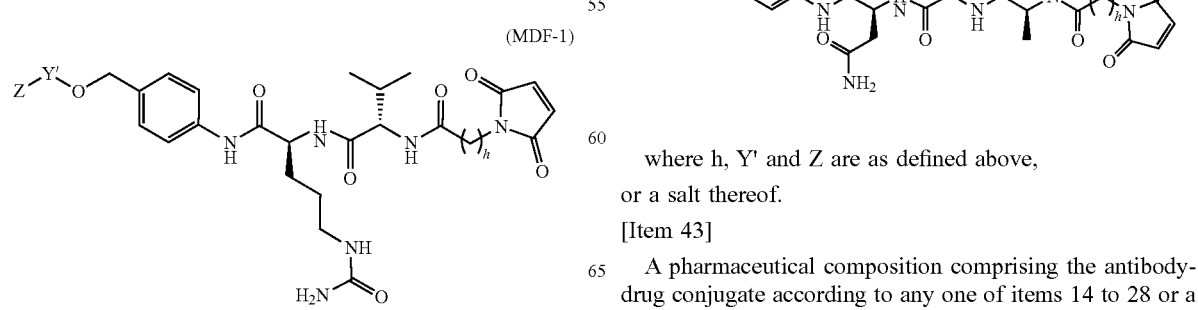

where h, Y' and Z are as defined above, or a salt thereof.

[Item 43]

A pharmaceutical composition comprising the antibody-drug conjugate according to any one of items 14 to 28 or a pharmaceutically acceptable salt thereof.

[Item 44]
A pharmaceutical composition comprising:
the antibody-drug conjugate according to any one of items 14 to 28 or a pharmaceutically acceptable salt thereof; and
one or more anticancer compounds selected from the group consisting of an anticancer alkylating agent, an anticancer antimetabolite, an anticancer antibiotic, an anticancer platinum coordination compound, an anticancer camptothecin derivative, an anticancer tyrosine kinase inhibitor, an anticancer serine-threonine kinase inhibitor, an anticancer phospholipid kinase inhibitor, an anticancer monoclonal antibody, an interferon, a biological response modifier, a hormonal agent, an immune checkpoint inhibitor, an epigenetics-related molecule inhibitor and a post-translational protein modification inhibitor, or pharmaceutically acceptable salts thereof.

[Item 45]
An anticancer agent comprising the antibody-drug conjugate according to any one of items 14 to 28, or a pharmaceutically acceptable salt thereof.

[Item 46]
The anticancer agent according to item 45, wherein cancer is breast cancer, gastric cancer, lung cancer, liver cancer, cervical cancer, large bowel cancer, rectal cancer, colon cancer, glioma, lymphoma, ovarian cancer, pancreatic cancer, prostate cancer, renal cancer, urothelial cancer, skin cancer, thyroid cancer, bladder cancer, head and neck cancer, endometrial cancer, mesothelioma, melanoma, multiple myeloma or leukemia.

[Item 47]
A method of treating cancer, comprising administering the antibody-drug conjugate according to any one of items 14 to 28 or a pharmaceutically acceptable salt thereof to a patient in need thereof.

[Item 48]
Use of the compound according to any one of items 1 to 13 or a salt thereof for producing an anticancer agent.

[Item 49]
Use of the antibody-drug conjugate according to any one of items 14 to 28 or a pharmaceutically acceptable salt thereof for producing an anticancer agent.

[Item 50]
Use of the compound according to any one of items 29 to 42 or a salt thereof for producing an anticancer agent.

[Item 51]
The antibody-drug conjugate according to any one of items 14 to 28 or a pharmaceutically acceptable salt thereof for use in treatment of cancer.

[Item 52]
The antibody-drug conjugate according to any one of items 14 to 28 or a pharmaceutically acceptable salt thereof for use in combination with one or more anticancer compounds selected from the group consisting of an anticancer alkylating agent, an anticancer antimetabolite, an anticancer antibiotic, an anticancer platinum coordination compound, an anticancer camptothecin derivative, an anticancer tyrosine kinase inhibitor, an anticancer serine-threonine kinase inhibitor, an anticancer phospholipid kinase inhibitor, an anticancer monoclonal antibody, an interferon, a biological response modifier, a hormonal agent, an immune checkpoint inhibitor, an epigenetics-related molecule inhibitor and a post-translational protein modification inhibitor, to treat cancer.

Advantageous Effects of Invention

Antibody-drug conjugates formed of the hemiasterlin derivatives according to the present invention and antibodies exhibit cytotoxic activity specifically to antigen-expressing cells and have low cytotoxicity in cells other than the antigen-expressing cells, and therefore, can be anticancer agents excellent in safety.

DESCRIPTION OF EMBODIMENTS

<Hemiasterlin Derivative>

Figure 1:
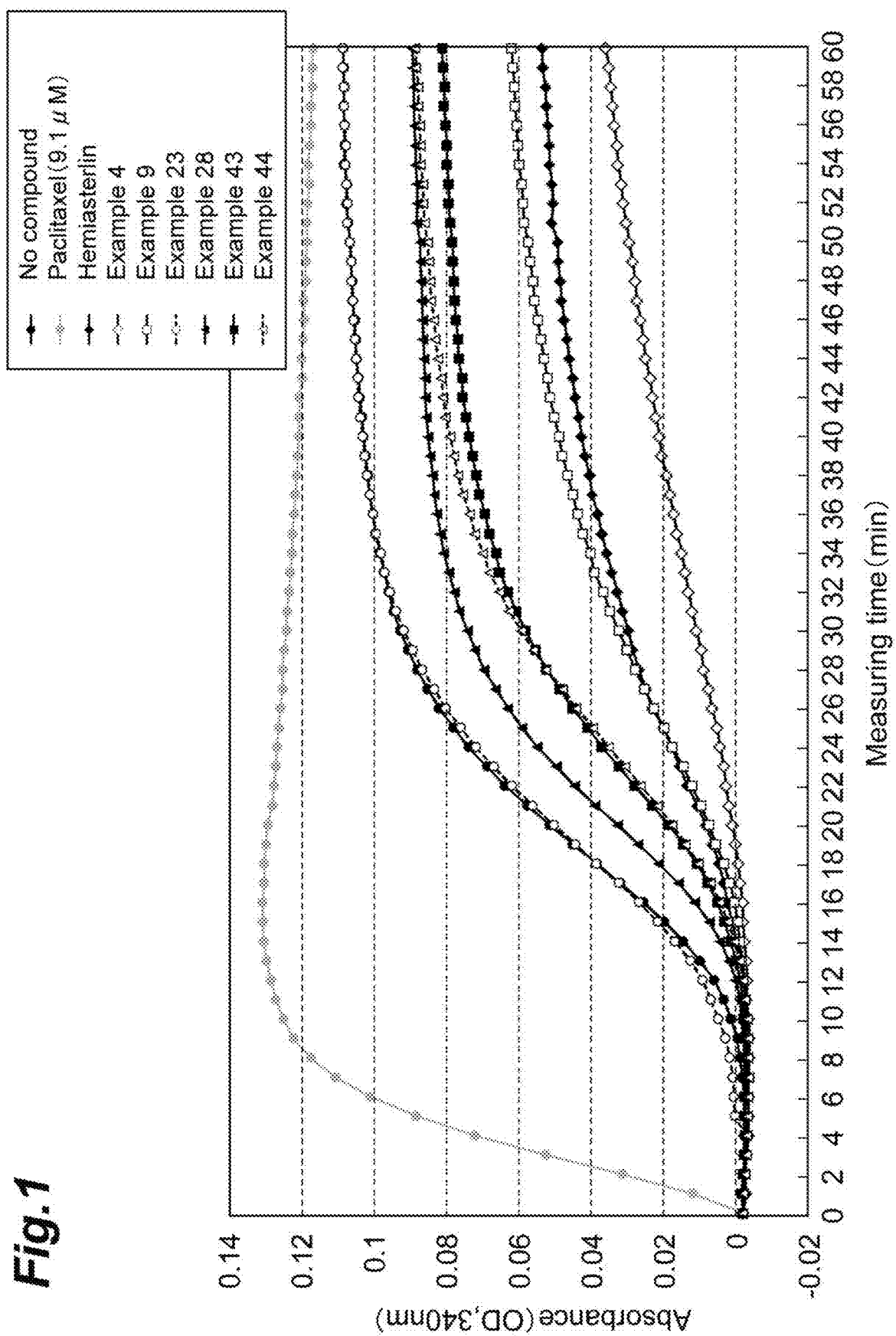
FIG. 1 shows activities of Examples 4, 9, 23, 28, 43 and 44 to inhibit polymerization of porcine tubulins.

A compound represented by formula (1) or formula (1a), or a salt thereof (hereinafter, may be referred to as the "hemiasterlin derivative according to the present invention") is as follows:

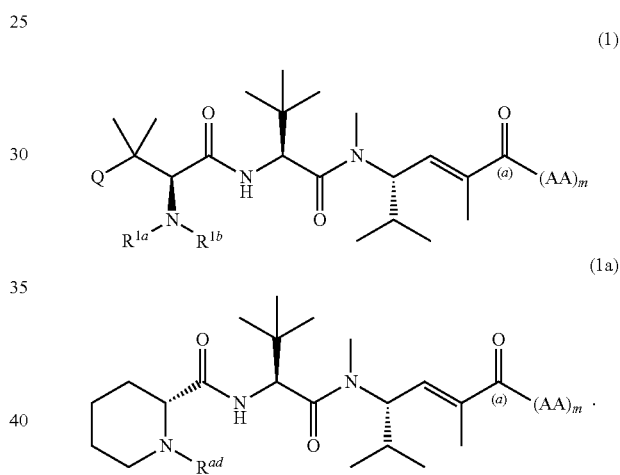

(1)

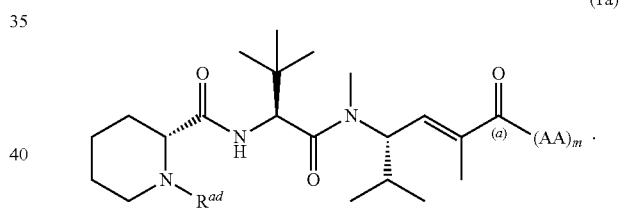

(1a)

AA represents a glutamic acid residue, an aspartic acid residue, a lysine residue, a cysteine residue, a phosphotyrosine residue, a phosphoserine residue or a cysteic acid residue, or a $C_{1-6}$ alkyl ester thereof.

In the present specification, except when it is particularly necessary to make distinction, the three letter abbreviated notations shown below may be used for representing both α-amino acids and corresponding amino acid residues. In addition, the optical activity of the α-amino acids may include any of DL form, D form and L form unless otherwise specified. For example, "glutamic acid" or "Glu" represents DL-glutamic acid or a residue thereof, D-glutamic acid or a residue thereof, or L-glutamic acid or a residue thereof.

Ala: alanine, Arg: arginine, Asn: asparagine, Asp: aspartic acid, Cit: citrulline, Cys: cysteine, Gln: glutamine, Glu: glutamic acid, Gly: glycine, His: histidine, Ile: isoleucine, Leu: leucine, Lys: lysine, Met: methionine, Phe: phenylalanine, Pro: proline, Ser: serine, Trp: tryptophan, Thr: threonine, Tyr: tyrosine, Val: valine.

When AA is an amino acid residue, the hemiasterlin derivative has a $(AA)_m$ structure containing a certain amino acid residue, and therefore, its cell membrane permeability becomes low, and even if a free hemiasterlin derivative is present in the blood, it is unlikely to be taken into cells, and therefore, cell damage to normal cells is suppressed.

Examples of AA that is an amino acid residue preferably include Glu or Asp, and more specifically include D-Glu, L-Glu, D-Asp or L-Asp. When there is a plurality of AAs, each AA may be the same as or different from each other.

On the other hand, when AA is a $C_{1-6}$ alkyl ester of an amino acid residue, the cell membrane permeability of the hemiasterlin derivative is higher than when AA is an amino acid residue, but when it is administered as a drug, the ester bond is quickly hydrolyzed by an enzyme that is present in the blood, such as esterase. Accordingly, the hemiasterlin derivative having a $(AA)_m$ structure containing a $C_{1-6}$ alkyl ester of a certain amino acid residue is turned into a hemiasterlin derivative having a $(AA)_m$ structure containing a certain amino acid residue in the blood, and therefore, the cell membrane permeability becomes low and cell damage to normal cells is suppressed.

The "$C_{1-6}$ alkyl ester" means an ester, in which R' of the ester (—COOR') is the "$C_{1-6}$ alkyl group" described below.

The "$C_{1-6}$ alkyl group" means a linear or branched saturated hydrocarbon group having 1 to 6 carbon atoms.

Examples of the "$C_{1-6}$ alkyl group" preferably include a "$C_{1-4}$ alkyl group", more preferably include a "$C_{1-3}$ alkyl group", further preferably include a methyl group, an ethyl group, a propyl group or an isopropyl group, and particularly preferably include a methyl group or an ethyl group.

Specific examples of the "$C_{1-3}$ alkyl group" include a methyl group, an ethyl group, a propyl group and an isopropyl group. Specific examples of the "$C_{1-4}$ alkyl group" include a butyl group, a 1,1-dimethylethyl group, a 1-methylpropyl group and a 2-methylpropyl group in addition to those mentioned as the specific examples of the "$C_{1-3}$ alkyl group". Specific examples of the "$C_{1-6}$ alkyl group" include a pentyl group, a 3-methylbutyl group, a 2-methylbutyl group, a 2,2-dimethylpropyl group, a 1-ethylpropyl group, a 1,1-dimethylpropyl group, a hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group and a 1,2-dimethylbutyl group in addition to those mentioned as the specific examples of the "$C_{1-4}$ alkyl group".

Examples of the "$C_{1-6}$ alkyl ester" preferably include a "$C_{1-4}$ alkyl ester", more preferably include a "$C_{1-3}$ alkyl ester", further preferably include a methyl ester, an ethyl ester, an isopropyl ester or a tert-butyl ester, and particularly preferably include a methyl ester or an ethyl ester.

Specific examples of the "$C_{1-3}$ alkyl ester" include a methyl ester, an ethyl ester, a propyl ester and an isopropyl ester. Specific examples of the "$C_{1-4}$ alkyl ester" include a butyl ester and a tert-butyl ester in addition to those mentioned as the specific examples of the "$C_{1-3}$ alkyl ester". Specific examples of the "$C_{1-6}$ alkyl ester" include a pentyl ester, a 3-methylbutyl ester, a 2-methylbutyl ester, a 2,2-dimethylpropyl ester, a 1-ethylpropyl ester, a 1,1-dimethyl-propyl ester, a hexyl ester, a 4-methylpentyl ester, a 3-methylpentyl ester, a 2-methylpentyl ester, a 1-methylpentyl ester, a 3,3-dimethylbutyl ester, a 2,2-dimethylbutyl ester, a 1,1-dimethylbutyl ester and a 1,2-dimethylbutyl ester in addition to those mentioned as the specific examples of the "$C_{1-4}$ alkyl ester".

m is 1, 2, 3, 4, 5, 6, 7, 8, 9 or 10. Examples of one aspect of m include an integer of 1 to 5 or an integer of 1 to 3, and examples of another aspect thereof include an integer of 2 to 10 or an integer of 3 to 10.

When there is a plurality of AAs, each AA may be the same as or different from each other and AAs are bonded to each other via an amide bond. "AAs are bonded to each other via an amide bond" means that the carboxyl group of one amino acid or a $C_{1-6}$ alkyl ester thereof and the amino group of another amino acid or a $C_{1-6}$ alkyl ester thereof are condensed to form an amide bond. For example, when m is 2 and two AAs are both Glu in formula (1), nitrogen atom (d) of one Glu and carbonyl group (c) of the other Glu may be linked by forming an amide bond, as represented by the following formula:

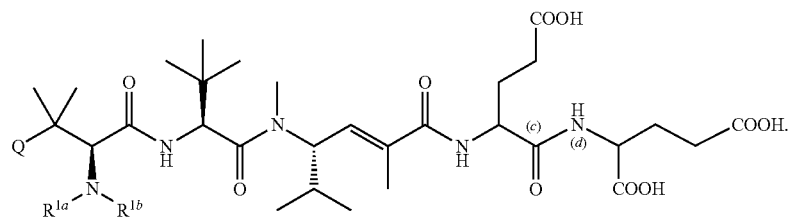

In one aspect, m is an integer of 2 to 10 and $(AA)_m$ is a linear peptide residue. In another aspect, m is an integer of 3 to 10 and $(AA)_m$ is a branched peptide residue having 1 or 2 branching points.

The "linear peptide residue" means that 2 to 10 amino acids or $C_{1-6}$ alkyl esters thereof independently selected from the group consisting of Glu, Asp, Lys, Cys, phosphotyrosine, phosphoserine and cysteic acid are forming a single chain amino acid linked structure by condensing the carboxyl group of one amino acid or a $C_{1-6}$ alkyl ester thereof and the amino group of another amino acid or a $C_{1-6}$ alkyl ester thereof to form an amide bond (—CONH—). Examples of the "linear peptide residue" preferably include a linear peptide residue composed of 3 to 7 amino acid residues, more preferably include a linear peptide residue composed of 3 to 5 amino acid residues, and further preferably include a linear peptide residue composed of 3 amino acid residues.

The "branched peptide residue having 1 or 2 branching points" means that 3 to 10 amino acids independently selected from the group consisting of Glu, Asp, Lys, Cys, phosphotyrosine, phosphoserine and cysteic acid are forming an amino acid linked structure having 1 or 2 branched parts therein by condensing the carboxyl group of one amino acid or a $C_{1-6}$ alkyl ester thereof and the amino group of another amino acid or a $C_{1-6}$ alkyl ester thereof to form an amide bond. Examples of the "branched peptide residue having 1 or 2 branching points" preferably include a branched peptide group having 1 or 2 branching points composed of 3 to 7 amino acid residues, more preferably include a branched peptide residue having 1 or 2 branching points composed of 3 to 5 amino acid residues, and further preferably include a branched peptide residue having 1 branching point composed of 3 amino acid residues.

It is preferable that $(AA)_m$ is a group represented by formula (A-1):

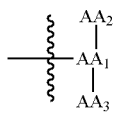

(A-1)

wherein $AA_1$, $AA_2$ and $AA_3$ each independently represent Glu, Asp or Lys. It is preferable that $AA_2$-$AA_1$-$AA_3$ is Glu-Glu-Glu.

The N-terminal nitrogen atom of $(AA)_m$ forms an amide bond together with carbonyl group (a). "The N-terminal nitrogen atom of AA forms an amide bond together with carbonyl group (a)" means that, for example, when AA is Asp, nitrogen atom (b) of Asp and carbonyl group (a) are linked to form an amide bond, as represented by the following formula:

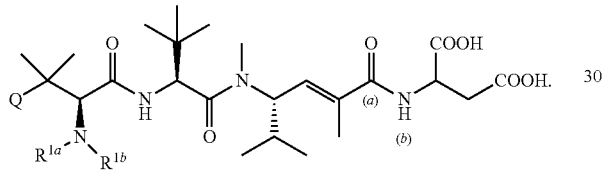

$R^{1a}$ and $R^{1b}$ each independently represent a hydrogen atom or a $C_{1-6}$ alkyl group. Examples of $R^{1a}$ and $R^{1b}$, each independently, preferably include a hydrogen atom or a $C_{1-3}$ alkyl group, more preferably include a hydrogen atom, a methyl group or an ethyl group, and particularly preferably include a hydrogen atom or a methyl group. Most preferably, $R^{1a}$ is a methyl group and $R^{1b}$ is a hydrogen atom.

In the present specification, a hydrogen atom may be $^1H$ or $^2H(D)$. That is, for example, a deuterated product in which one or two or more $^1H$ of the compound represented by formula (1) are converted into $^2H(D)$ is also encompassed in the compound represented by formula (1).

$R^{ad}$ represents a hydrogen atom or a $C_{1-6}$ alkyl group. $R^{ad}$ is preferably a hydrogen atom, a methyl group, an ethyl group, a propyl group or an isopropyl group.

Q represents a group represented by formula (Q-1), formula (Qa-2), formula (Qa-3), formula (Qa-4), formula (Qa-5), formula (Qa-6) or formula (Qa-7):

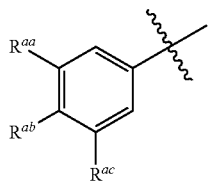

(Q-1)

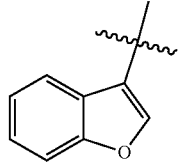

(Qa-2)

(Qa-3)

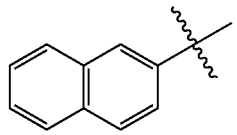

(Qa-4)

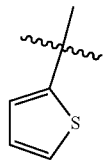

(Qa-5)

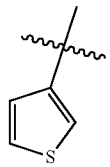

(Qa-6)

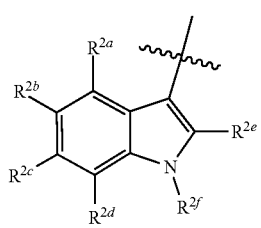

(Qa-7)

In formula (Q-1), $R^{2a}$, $R^{2b}$, $R^{2c}$, $R^{2d}$ and $R^{2e}$ each independently represent a hydrogen atom, a halogen atom, a $C_{1-6}$ alkyl group optionally substituted with 1 to 5 fluorine atoms or a $C_{1-6}$ alkoxy group optionally substituted with 1 to 5 fluorine atoms, and $R^{2f}$ represents a hydrogen atom or a $C_{1-6}$ alkyl group. In formula (Qa-2), $R^{aa}$, $R^{ab}$ and $R^{ac}$ each independently represent a hydrogen atom, a halogen atom, a hydroxy group, a cyano group, an amino group, a carboxyl group, a phenyl group, or a $C_{1-6}$ alkyl group, $C_{1-6}$ alkoxy group or $C_{1-6}$ alkyl ester group optionally substituted with 1 to 3 fluorine atoms.

The "$C_{1-6}$ alkyl group" is as defined above. There is no particular limitation on the number of substituents in a group defined to be "optionally substituted" as long as that group can be substituted, except when there is particular specification. In addition, except when there is particular specification, description for each group is applicable to cases where that group is a part of another group or a substituent thereof.

The "$C_{1-6}$ alkoxy group" means an oxy group substituted with a "$C_{1-6}$ alkyl group". Examples of the "$C_{1-6}$ alkoxy group" preferably include a "$C_{1-4}$ alkoxy group", more preferably include a "$C_{1-3}$ alkoxy group", further preferably include a methoxy group, an ethoxy group, a propoxy group or a 1-methylethoxy group, and particularly preferably include a methoxy group or an ethoxy group.

Specific examples of the "$C_{1-3}$ alkoxy group" include a methoxy group, an ethoxy group, a propoxy group or a 1-methylethoxy group. Specific examples of the "$C_{1-4}$ alkoxy group" include a butoxy group, a 1,1-dimethylethoxy group, a 1-methylpropoxy group and a 2-methylpropoxy group in addition to those mentioned as the specific examples of the "$C_{1-3}$ alkoxy group". Specific examples of the "$C_{1-6}$ alkoxy group" include a pentyloxy group, a 3-methylbutoxy group, a 2-methylbutoxy group, a 2,2-dimethylpropoxy group, a 1-ethylpropoxy group, a 1,1-dimethylpropoxy group, a hexyloxy group, a 4-methylpentyloxy group, a 3-methylpentyloxy group, a 2-methylpentyloxy group, a 1-methylpentyloxy group, a 3,3-dimethylbutoxy group, a 2,2-dimethylbutoxy group, a 1,1-dimethylbutoxy group and a 1,2-dimethylbutoxy group in addition to those mentioned as the specific examples of the "$C_{1-4}$ alkoxy group".

Examples of the "halogen atom" include a fluorine atom, a chlorine atom, a bromine atom or an iodine atom. Preferably, examples thereof include a fluorine atom or a chlorine atom, and more preferably, examples thereof include a fluorine atom.

Examples of $R^{2a}$, $R^{2b}$, $R^{2c}$, $R^{2d}$ and $R^{2e}$, each independently, preferably include a hydrogen atom, a halogen atom, a $C_{1-3}$ alkyl group optionally substituted with 1 to 5 fluorine atoms or a $C_{1-3}$ alkoxy group optionally substituted with 1 to 5 fluorine atoms, more preferably include a hydrogen atom, a fluorine atom, a chlorine atom, a $C_{1-3}$ alkyl group or a $C_{1-3}$ alkoxy group, further preferably include a hydrogen atom, a fluorine atom or a $C_{1-3}$ alkoxy group, particularly preferably include a hydrogen atom, a fluorine atom or a methoxy group, and most preferably include a hydrogen atom. $R^{2a}$, $R^{2b}$, $R^{2c}$, $R^{2d}$ and $R^{2e}$ may be the same or different.

Examples of $R^{2f}$ preferably include a hydrogen atom or a $C_{1-3}$ alkyl group, more preferably include a hydrogen atom, a methyl group or an ethyl group, particularly preferably include a hydrogen atom or a methyl group, and most preferably include a methyl group.

$R^{aa}$, $R^{ab}$ and $R^{ac}$ are, preferably, each independently a hydrogen atom, a fluorine atom, a chlorine atom, a bromine atom, a hydroxy group, a cyano group, a carboxyl group, a phenyl group, a trifluoromethyl group, a methyl group, a methoxy group, a methyl ester group, an ethyl ester group or a tert-butyl ester group, and more preferably, are all a hydrogen atom.

Q may be a group represented by formula (Qa-2) or formula (Q-1), may be an unsubstituted phenyl group or a group represented by formula (Q-1), or may be a group represented by formula (Q-2):

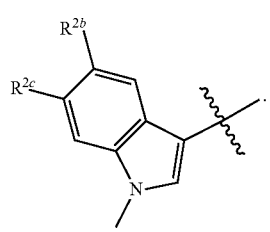

(Q-2)

In formula (Q-2), $R^{2b}$ and $R^{2c}$ are, preferably, each independently a hydrogen atom, a halogen atom, a $C_{1-6}$ alkyl group or a $C_{1-6}$ alkoxy group, more preferably, each independently a hydrogen atom, a fluorine atom or a methoxy group, and further preferably are each a hydrogen atom.

Examples of one aspect of the hemiasterlin derivative according to the present invention include the following (1-A).

(1-A)

A compound, wherein, in formula (1),

AA is Glu or Asp;

Q is a group represented by formula (Q-2);

$R^{1a}$ is a methyl group;

$R^{1b}$ is a hydrogen atom;

$R^{2b}$ and $R^{2c}$ are hydrogen atoms; and m is 1 or 2, or a salt thereof.

Examples of one aspect of the hemiasterlin derivative according to the present invention include the following (1-B).

(1-B)

A compound, wherein, in formula (1),

AA is Glu or Asp;

Q is an unsubstituted phenyl group;

$R^{1a}$ is a methyl group;

$R^{1b}$ is a hydrogen atom; and m is 1 or 2, or a salt thereof.

Examples of one aspect of the hemiasterlin derivative according to the present invention include the following (1-C).

(1-C)

A compound, wherein, in formula (1),

AA is Glu, Asp, Lys or Cys;

Q is a group represented by formula (Q-2);

$R^{1a}$ is a methyl group;

$R^{1b}$ is a hydrogen atom;

$R^{2b}$ and $R^{2c}$ are hydrogen atoms; and m is 1, or a salt thereof.

Examples of one aspect of the hemiasterlin derivative according to the present invention include the following (1-D).

(1-D)

A compound, wherein, in formula (1),

AA is Glu, Asp, Lys or Cys;

Q is an unsubstituted phenyl group;

$R^{1a}$ is a methyl group;

$R^{1b}$ is a hydrogen atom; and m is 1, or a salt thereof.

Examples of one aspect of the hemiasterlin derivative according to the present invention include the following compounds:

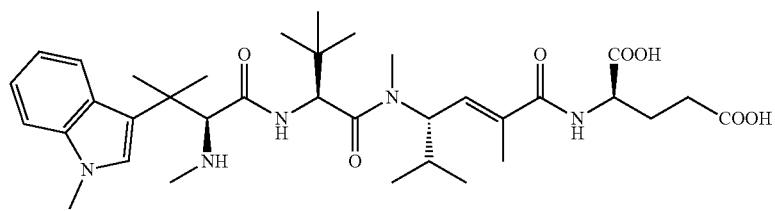
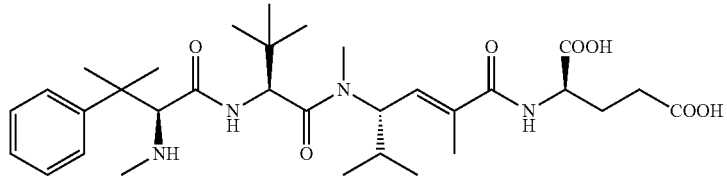
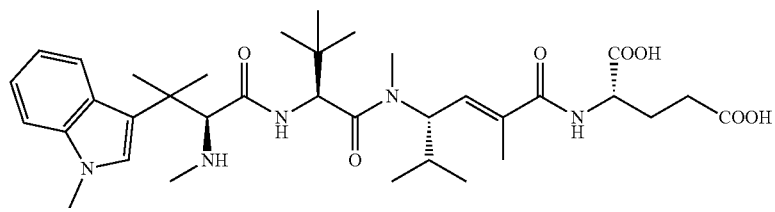
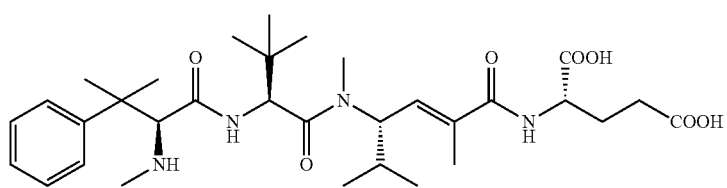
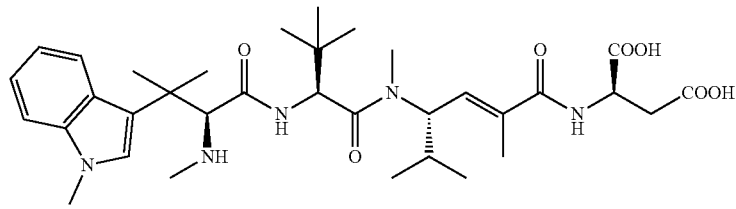
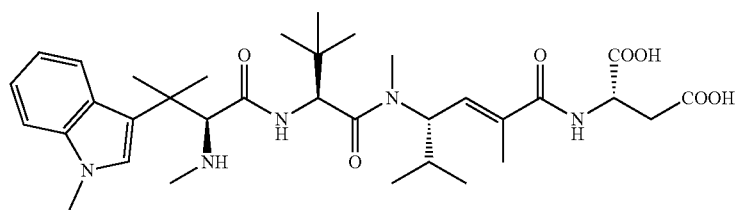
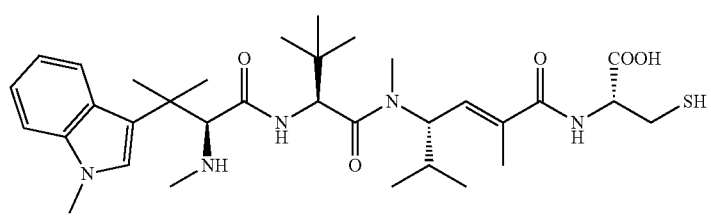
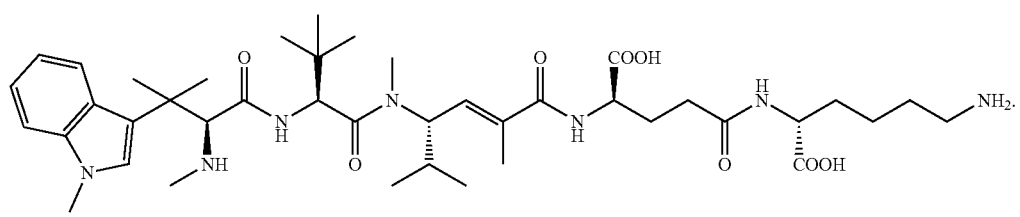

<Antibody-Drug Conjugate>

An antibody-drug conjugate represented by formula (2), or a pharmaceutically acceptable salt thereof (hereinafter, may be referred to as the "antibody-drug conjugate according to the present invention") is, as shown below, a conjugate in which the antibody moiety derived from an antibody molecule and a drug moiety derived from a drug molecule are covalently bonded via a linker. In the present specification, the "antibody-drug conjugate" may be referred to as "ADC".

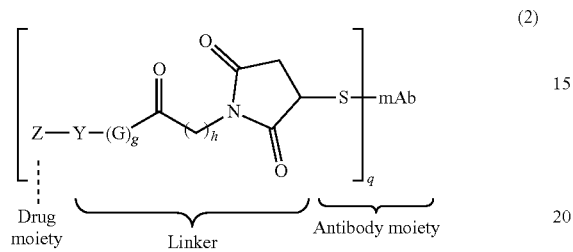

Z of the drug moiety is a group represented by the following formula (Z-1), formula (Z-2), formula (Z-3), formula (Z-4), formula (Z-5), formula (Z-6), formula (Za-1), formula (Za-2), formula (Za-3), formula (Za-4), formula (Za-5), formula (Za-6), formula (Za-7), formula (Za-8), formula (Za-9) or formula (Za-10):

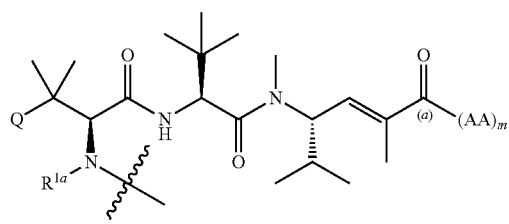

(Z-1)

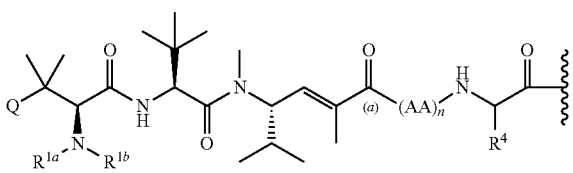

(Z-2)

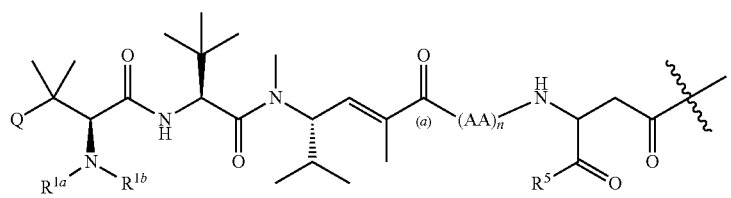

(Z-3)

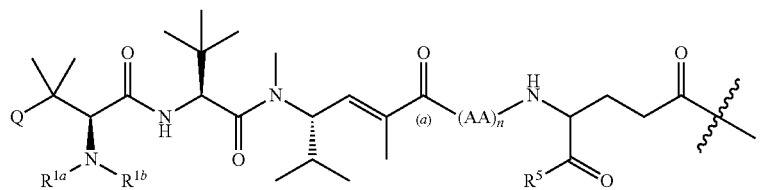

(Z-4)

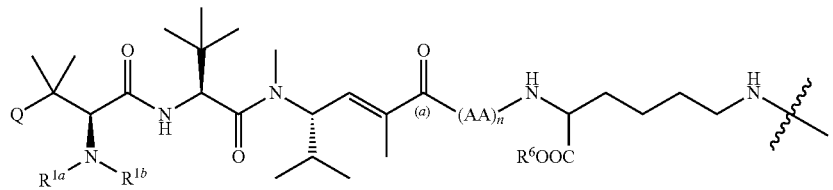

(Z-5)

(Z-6)
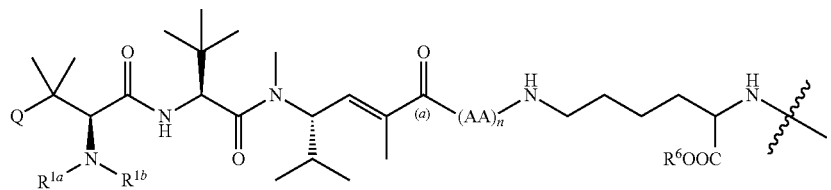
(Za-1)
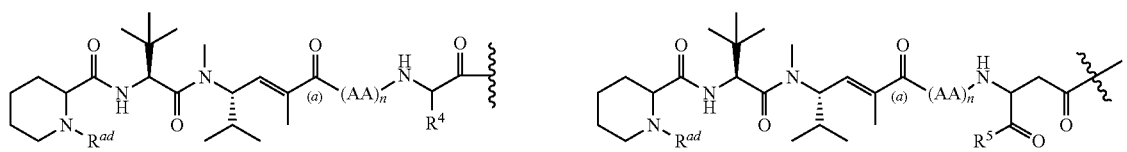
(Za-2)
(Za-3)
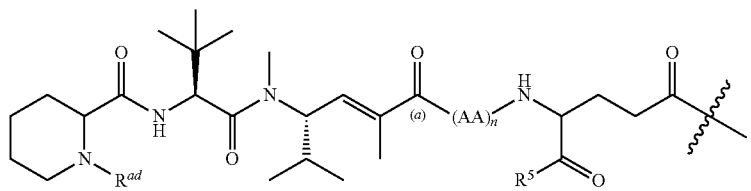
(Za-4)
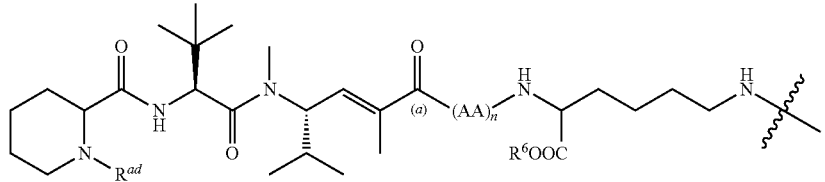
(Za-5)
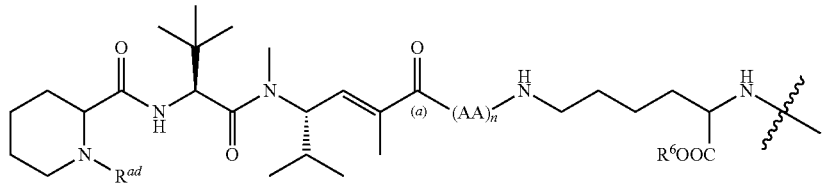
(Za-6)
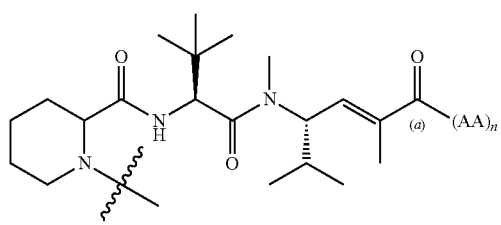
(Za-7)
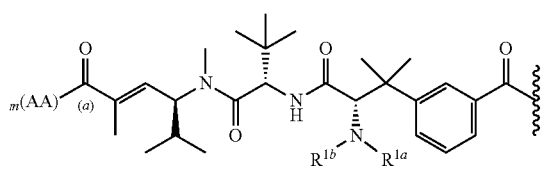
(Za-8)
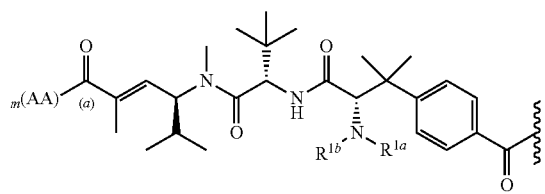
(Za-9)
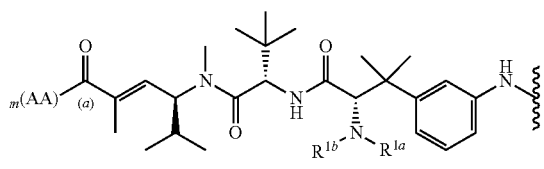

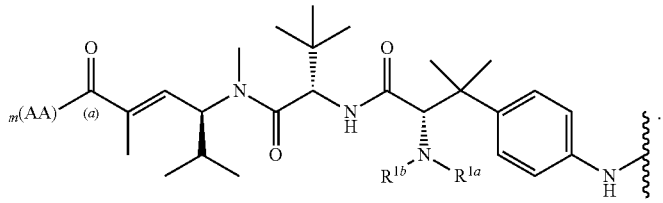

(Za-10)

When Y', which will be mentioned later, is a single bond, Z is a group represented by formula (Z-2), formula (Z-3), formula (Z-4), formula (Za-1), formula (Za-2), formula (Za-3), formula (Za-7) or formula (Za-8).

Details for AA, $(AA)_m$, Q, $R^{1a}$, $R^{1b}$ and $R^{ad}$ in these formulas are described in the description of the compound of formula (1) or formula (1a) described above, except when there is particular specification. The description that the N-terminal nitrogen atom of $(AA)_n$ forms an amide bond together with carbonyl group (a) means that the N-terminal nitrogen atom of $(AA)_m$ forms an amide bond together with carbonyl group (a), as described above.

Examples of one aspect of Z include a group represented by formula (Z-1), formula (Z-5) or formula (Z-6), and examples of another aspect thereof include a group represented by formula (Z-2), formula (Z-3) or formula (Z-4).

n is 0, 1, 2, 3 or 4. Examples of one aspect of n include an integer of 0 to 2; examples of another aspect thereof include 0 or 1; examples of another aspect thereof include 1 or 2; examples of another aspect thereof include an integer of 1 to 3; and examples of another aspect thereof include 0.

$R^4$ represents $—(CH_2)_u—COR^7$, and u represents 1 or 2. $R^5$ and $R^7$ each independently represent $—OR^8$ or $-(AB)_p$. AB represents Glu, Asp or Lys, and when there is a plurality of ABs, each AB may be the same as or different from each other and ABs are bonded to each other via an amide bond.

p is 1, 2, 3 or 4. Examples of one aspect of p include 1 or 2; examples of another aspect thereof include 1; examples of another aspect thereof include 2; examples of another aspect thereof include an integer of 1 to 3; and examples of another aspect thereof include 3.

When $R^5$ or $R^7$ is $-(AB)_p$, the sum of n and p is 1, 2, 3, 4 or 5. Examples of one aspect of the sum of n and p include an integer of 1 to 4; examples of another aspect thereof include an integer of 1 to 3; and examples of another aspect thereof include 1 or 2.

$R^6$ and $R^8$ each independently represent a hydrogen atom or a $C_{1-6}$ alkyl group. Examples of $R^6$ and $R^8$, each independently, preferably include a hydrogen atom or a $C_{1-3}$ alkyl group, more preferably include a hydrogen atom, a methyl group or an ethyl group, particularly preferably include a hydrogen atom or a methyl group, and most preferably include a hydrogen atom.

Y, which is a part of the linker moiety and is bonded to drug moiety Z, is a single bond or a group represented by formula (Y-1), and terminus *[1] of the group represented by formula (Y-1) is bonded to Z.

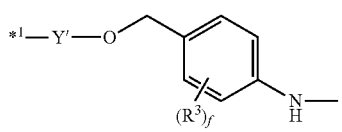

(Y-1)

In formula (Y-1), Y' represents a single bond or a carbonyl group; and $R^3$ represents a halogen atom, a cyano group, a $C_{1-6}$ alkyl group optionally substituted with 1 to 5 fluorine atoms or a $C_{1-6}$ alkoxy group optionally substituted with 1 to 5 fluorine atoms, and when there is a plurality of $R^3$s, each $R^3$ may be the same as or different from each other. Examples of one aspect of $R^3$ include a fluorine atom, a $C_{1-3}$ alkyl group or a $C_{1-3}$ alkoxy group, and when there is a plurality of $R^3$s, each $R^3$ may be the same as or different from each other. f is an integer of 0 to 2, and examples of one aspect of f include 0; examples of another aspect thereof include 1; and examples of another aspect thereof include 2.

G in $(G)_g$, which is a part of the linker moiety and is bonded to Y, represents Ala, Arg, Asn, Asp, Cys, Gln, Glu, Gly, His, Ile, Leu, Lys, Met, Phe, Pro, Ser, Thr, Trp, Tyr, Val or Cit. When there is a plurality of Gs, each G may be the same as or different from each other, Gs are also bonded to each other via an amide bond, and terminus *[2] of $(G)_g$ is bonded to Y.

Examples of one aspect of $(G)_g$ include an aspect of *[2]-Gly-, *[2]-Gly-Gly-, *[2]-Lys-, *[2]-Lys-Phe-, *[2]-Lys-Val-, *[2]-Lys-Ala-, *[2]-Cit-Val-, *[2]-Cit-Phe-, *[2]-Cit-Leu-, *[2]-Arg-Phe-, *[2]-Cit-Ile-, *[2]-Cit-Trp-, *[2]-Lys-Phe-Phe-, *[2]-Lys-Phe-Ala-, *[2]-Lys-Phe-Gly-, *[2]-Asn-, *[2]-Asn-Ala-, *[2]-Asn-Ala-Ala-, *[2]-Asn-Ala-Thr-, *[2]-Asn-Ala-Pro-, *[2]-Asn-Ala-Val-, *[2]-Asn-Ala-Phe-, *[2]-Asn-Ala-Tyr-, *[2]-Asn-Ala-Leu-, *[2]-Asn-Ala-Gly-, *[2]-Asn-Thr-Ala-, *[2]-Asn-Thr-Pro-, *[2]-Asn-Thr-Thr-, *2-Gly-Phe-Gly-Gly-, *2-Gly-Leu-Phe-Gly- or *[2]-Leu-Ala-Leu-Ala-, wherein terminus *[2] of $(G)_g$ is bonded to Y.

In an organism, the antibody-drug conjugate according to the present invention is assumed to be cleaved at the bond of Y-$(G)_g$ in formula (2) at first, and then cleaved at the bond between Z and Y, thereby releasing drug moiety Z.

The bond of Y-$(G)_g$ is cleaved by intracellular peptidase, protease (for example, lysosomal protease or endosomal protease) or the like, which is present in an intracellular environment (for example, in lysosome, endosome or caveola).

As a protease present in an intracellular environment, for example, cathepsin B is known. Cleavage of the Y-$(G)_g$ bond by cathepsin B is described in Dubowchik G. M., et al, 1998, Bioorg. Med. Chem. Lett., 8: 3341-3346 and the like. Specific examples of Y-$(G)_g$ cleaved by cathepsin B include Y-Lys-Phe, Y-Lys-Val, Y-Lys-Ala, Y-Lys-Phe-Phe, Y-Lys-Phe-Ala, Y-Lys-Phe-Gly, Y-Lys, Y-Cit-Val, Y-Cit-Phe, Y-Cit-Leu, Y-Cit-Ile, Y-Cit-Trp and Y-Arg-Phe.

As another protease present in an intracellular environment, for example, asparagine endopeptidase is known. Cleavage of the Y-$(G)_g$ bond by asparagine endopeptidase is described in Dando M. P., et al, 1999, Biochem. J. 339: 743-749 and the like. Specific examples of Y-$(G)_g$ cleaved by asparagine endopeptidase include Y-Asn-Ala-Ala, Y-Asn-Ala-Thr, Y-Asn-Ala-Val, Y-Asn-Ala-Pro, Y-Asn-Ala-Phe, Y-Asn-Ala-Tyr, Y-Asn-Ala-Leu and Y-Asn-Ala-Gly.

Putative mechanisms in which a drug is released from the antibody-drug conjugate according to the present invention, wherein Y is a group represented by formula (Y-1), in an intracellular environment, are shown below. These drug release mechanisms are based on the report by Toki, et al (Non Patent Literature 7).

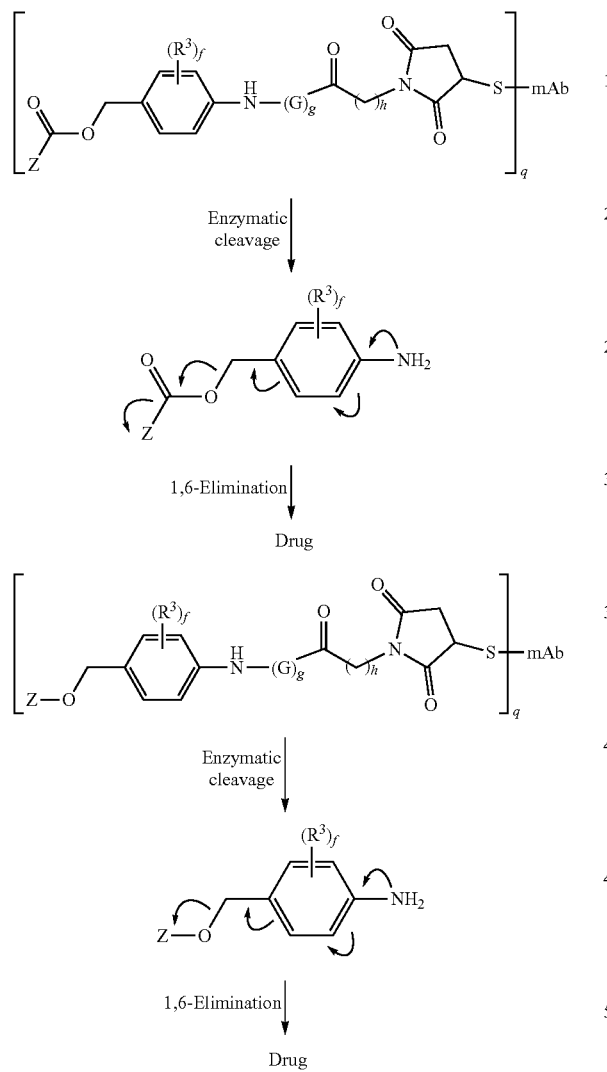

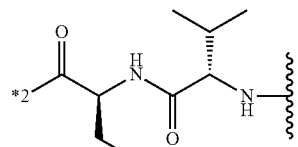

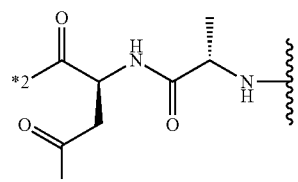

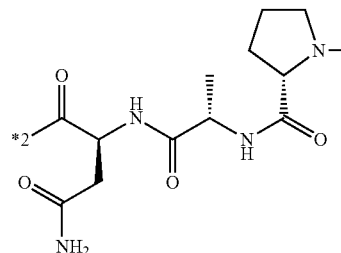

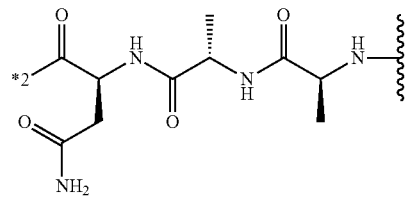

Examples of one aspect of $(G)_g$ include *²-Lys-Phe-, *²-Lys-Val-, *²-Lys-Ala-, *²-Lys-Phe-Phe-, *²-Lys-Phe-Ala-, *²-Lys-Phe-Gly-, *²-Lys-, *²-Cit-Val-, *²-Cit-Phe-, *²-Cit-Leu-, *²-Cit-Ile-, *²-Cit-Trp- and *²-Arg-Phe-. Examples of another aspect of $(G)_g$ include *²-Asn-Ala-Ala-, *²-Asn-Ala-Tyr-, *²-Asn-Ala-Val-, *²-Asn-Ala-Pro-, *²-Asn-Ala-Phe-, *²-Asn-Ala-Leu- and *²-Asn-Ala-Gly-.

Examples of another aspect of $(G)_g$ include a group represented by formula (G-1), formula (G-2), formula (G-3) or formula (G-4). Here, "*2" indicates a terminus that is bonded to Y among the two termini of $(G)_g$. Namely, $(G)_g$ is bonded to Y on the side of *2 g is 1, 2, 3 or 4. Examples of one aspect of g include an integer of 1 to 3, and examples of another aspect thereof include 2 or 3.

h is 1, 2, 3, 4 or 5. Examples of one aspect of h include an integer of 2 to 5; examples of another aspect thereof include an integer of 3 to 5; and examples of another aspect thereof include 4 or 5.

One aspect of the antibody-drug conjugate according to the present invention is an antibody-drug conjugate, wherein, in formula (2),
  Z is a group represented by formula (Z-2), formula (Z-3) or formula (Z-4);
  Q is an unsubstituted phenyl group or a group represented by formula (Q-2);
  $R^5$ and $R^7$ are —OH; and
  n is 0 or 1,
or a pharmaceutically acceptable salt thereof.

One aspect of the antibody-drug conjugate according to the present invention is an antibody-drug conjugate, wherein, in formula (2),
  Z is a group represented by formula (Z-2), formula (Z-3) or formula (Z-4);
  Q is an unsubstituted phenyl group or a group represented by formula (Q-2);
  $R^5$ and $R^7$ are -(AB)$_p$; and
  n is 0 and p is 2, or n and p are each 1,
or a pharmaceutically acceptable salt thereof.

One aspect of Z-Y in the antibody-drug conjugate according to the present invention is a group represented by the following formula (ZY-1):

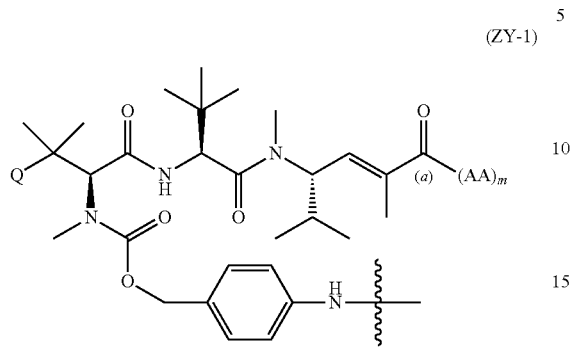

(ZY-1)

wherein AA and m are as defined above and Q is an unsubstituted phenyl group or a group represented by formula (Q-2).

One aspect of Z-Y in the antibody-drug conjugate according to the present invention is a group represented by the following formula (ZY-2):

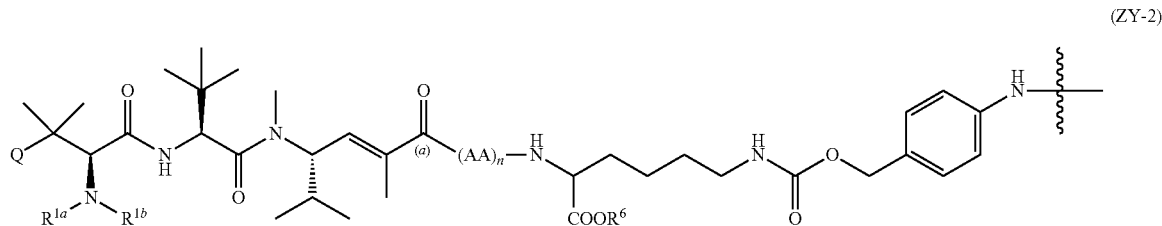

(ZY-2)

wherein AA, $R^{1a}$, $R^{1b}$, $R^6$ and n are as defined above and Q is an unsubstituted phenyl group or a group represented by formula (Q-2).

q indicates the drug antibody ratio (alternatively, referred to as DAR) in the antibody-drug conjugate represented by formula (2). Drug antibody ratio q means the number of drug molecules per antibody molecule in one molecule of the antibody-drug conjugate, that is, per antibody-drug conjugate molecule. Note that antibody-drug conjugates obtained through chemical synthesis are often a mixture of a plurality of antibody-drug conjugate molecules that may have different drug antibody ratio q. In the present specification, the overall drug antibody ratio in such a mixture of antibody-drug conjugates (that is, the average value of drug antibody ratio q of each antibody-drug conjugate) is referred to as the "average drug antibody ratio" or "average DAR".

q is 1, 2, 3, 4, 5, 6, 7 or 8. Examples of one aspect of q include an integer of 2 to 8; examples of another aspect thereof include an integer of 2 to 6; examples of another aspect thereof include an integer of 4 to 8; examples of another aspect thereof include 2 or 4; examples of another aspect thereof include 6 or 8; and examples of another aspect thereof include 8.

Examples of one aspect of the average DAR include 2 to 8; examples of another aspect thereof include 3.5 to 4.5; and examples of another aspect thereof include 1 to 2, 2 to 3, 3 to 4, 4 to 5, 5 to 6, 6 to 7 or 7 to 8. It is possible to determine the average DAR by methods conventionally used to determine the average DAR, such as SDS-PAGE, mass spectrometry, ELISA (enzyme-linked immunosorbent assay) and HPLC (high performance liquid chromatography). It is possible to separate, purify and characterize an antibody-drug conjugate of a particular DAR from a mixture of a plurality of antibody-drug conjugates having different DARs by methods such as hydrophobic interaction column (HIC) HPLC, reversed phase HPLC and electrophoresis.

The antibody mAb is not particularly limited as long as it is an antibody that can recognize antigens present on the surface of target cells. It is sufficient that the target cell be a cell in need of treatment with a hemiasterlin derivative, and it is preferable that the target cell be a cancer cell. It is preferable that the antigen present on the surface of target cells be an antigen specific for the target cells, not expressed or expressed in a small amount in normal cells. Examples of one aspect of mAb include the known antibodies recited above; examples of another aspect thereof include brentuximab, trastuzumab, inotuzumab, gemtuzumab, glembatumumab, labetuzumab, sacituzumab, lifastuzumab, indusatumab, polatuzumab, pinatuzumab, coltuximab, indatuximab, milatuzumab, rovalpituzumab, anetumab, tisotumab, mirvetuximab, lorvotuzumab, rituximab, depatuxizumab, denintuzumab, telisotuzumab, vandortuzumab, sofituzumab, vorsetuzumab, mirvetuximab, naratuximab, cantuzumab, laprituximab, bivatuzumab, vadastuximab, lupartumab, aprutumab, abagovomab, abciximab, abituzumab, abrilumab, actoxumab, adalimumab, adecatumumab, aducanumab, afasevikumab, afelimomab, alacizumab, alemtuzumab, alirocumab, altumomab, amatuximab, anatumomab, anifrolumab, anrukinzumab, apolizumab, arcitumomab, ascrinvacumab, aselizumab, atezolizumab, atinumab, atorolimumab, avelumab, azintuxizumab, bapineuzumab, basiliximab, bavituximab, bectumomab, begelomab, belimumab, benralizumab, bertilimumab, besilesomab, bevacizumab, bezlotoxumab, biciromab, bimagrumab, bimekizumab, bleselumab, blinatumomab, blontuvetmab, blosozumab, bococizumab, brazikumab, briakinumab, brodalumab, brolucizumab, brontictuzumab, burosumab, cabiralizumab, camrelizumab, caplacizumab, capromab, carlumab, carotuximab, catumaxomab, cedelizumab, certolizumab, cetuximab, citatuzumab, cixutumumab, clenoliximab, clivatuzumab, codrituzumab, conatumumab, concizumab, cosfroviximab, crenezumab, crizanlizumab, crotedumab, dacetuzumab, daclizumab, dalotuzumab, dapirolizumab, daratumumab, dectrekumab, demcizumab, denosumab, detumomab, dezamizumab, dinutuximab, diridavumab, domagrozumab, dorlimomab, drozitumab, duligotuzumab, dupilumab, durvalumab, dusigitumab, duvortuxizumab, ecromeximab, eculizumab, edobacomab, edrecolomab, efalizumab, efungumab, eldelumab, elezanumab, elotuzumab, elsilimomab, emactuzumab, emapalumab, emibetuzumab, emicizumab, enavatuzumab, enlimomab, enoblituzumab, enokizumab, enoticumab, ensituximab, epitumomab, epratuzumab, eptinezumab, erenumab, erlizumab, ertumaxomab, etaracizumab, etrolizumab, evinacumab, evolocumab, exbivirumab, faralimomab, farletuzumab, fasinumab, felvizumab, fezakinumab, ficlatuzumab, figitumumab, firivumab, flanvotumab, fletikumab, fontolizumab, foralumab, foravirumab, fremanezumab, fresolimumab, frunevetmab, fulranumab, futuximab, galcanezumab, galiximab, ganitumab, gantenerumab, gatipotuzumab, gavilimomab, gedivumab, gevokizumab, gilvetmab, girentuximab, golimumab, guselkumab, ibalizumab, ibritumomab, icrucumab, idarucizumab, ifabotuzumab, igovomab, imalumab, imciromab, imgatuzumab, inclacumab, inebilizumab, infliximab, inolimomab, intetumumab, ipilimumab, iratumumab, isatuximab, itolizumab, ixekizumab, keliximab, lacnotuzumab, lampalizumab, lanadelumab, landogrozumab, larcaviximab, lebrikizumab, lemalesomab, lenzilumab, lerdelimumab, lesofavumab, letolizumab, lexatumumab, libivirumab, lifatuzumab, ligelizumab, lilotomab, lintuzumab, lirilumab, lodelcizumab, lokivetmab, lorvotuzumab, losatuximab, lucatumumab, lulizumab, lumretuzumab, lutikizumab, mapatumumab, margetuximab, maslimomab, matuzumab, mavrilimumab, mepolizumab, metelimumab, minretumomab, mitumomab, modotuximab, mogamulizumab, monalizumab, morolimumab, motavizumab, moxetumomab, muromonab, nacolomab, namilumab, naptumomab, narnatumab, natalizumab, navicixizumab, navivumab, nebacumab, necitumumab, nemolizumab, nerelimomab, nesvacumab, nimotuzumab, nivolumab, obiltoxaximab, obinutuzumab, ocaratuzumab, ocrelizumab, odulimomab, ofatumumab, olaratumab, oleclumab, olendalizumab, olokizumab, omalizumab, onartuzumab, ontuxizumab, opicinumab, oportuzumab, oregovomab, oreticumab, orticumab, otelixizumab, otlertuzumab, oxelumab, ozanezumab, ozoralizumab, pagibaximab, palivizumab, pamrevlumab, panitumumab, panobacumab, parsatuzumab, pascolizumab, pasotuximab, pateclizumab, patritumab, pembrolizumab, perakizumab, pertuzumab, pexelizumab, pidilizumab, placulumab, plozalizumab, ponezumab, porgaviximab, prezalumab, priliximab, pritoxaximab, pritumumab, quilizumab, racotumomab, radretumab, rafivirumab, ralpancizumab, ramucirumab, ranevetmab, ranibizumab, raxibacumab, refanezumab, regavirumab, remtolumab, reslizumab, rilotumumab, rinucumab, risankizumab, rivabazumab, robatumumab, roledumab, romosozumab, rontalizumab, rosmantuzumab, rovelizumab, rozanolixizumab, ruplizumab, samalizumab, sarilumab, satralizumab, satumomab, secukinumab, selicrelumab, seribantumab, setoxaximab, sevirumab, sibrotuzumab, sifalimumab, siltuximab, simtuzumab, siplizumab, sirukumab, solanezumab, solitomab, sontuzumab, stamulumab, sulesomab, suptavumab, suvizumab, suvratoxumab, tabalumab, tadocizumab, talizumab, tamtuvetmab, tanezumab, taplitumomab, tarextumab, tavolixizumab, fanolesomab, nofetumomab, pintumomab, tefibazumab, telimomab, telisotuzumab, tenatumomab, teneliximab, teplizumab, teprotumumab, tesidolumab, tezepelumab, tigatuzumab, tildrakizumab, timigutuzumab, timolumab, tocilizumab, tomuzotuximab, toralizumab, tosatoxumab, tositumomab, tovetumab, tralokinumab, tregalizumab, tremelimumab, trevogrumab, tucotuzumab, tuvirumab, ublituximab, ulocuplumab, urelumab, urtoxazumab, ustekinumab, utomilumab, vantictumab, vanucizumab, vapaliximab, varisakumab, varlilumab, vatelizumab, vedolizumab, veltuzumab, vepalimomab, vesencumab, visilizumab, vobarilizumab, volociximab, vonlerolizumab, votumumab, vunakizumab, tacatuzumab, zalutumumab, zanolimumab, ziralimumab, zolimomab or anti-embigin antibody; examples of another aspect thereof include brentuximab, trastuzumab, inotuzumab, gemtuzumab, labetuzumab, polatuzumab, coltuximab, indatuximab, anetumab, rituximab, denintuzumab, laprituximab, vadastuximab, glembatumumab, cetuximab, alemtuzumab, depatuxizumab or anti-embigin antibody; examples of another aspect thereof include brentuximab, trastuzumab, rituximab or anti-embigin antibody; and examples of another aspect thereof include brentuximab or trastuzumab.

Examples of another aspect of mAb include anti-19A antibody, anti-AXL antibody, anti-BCMA antibody, anti-C4.4a antibody, anti-CA6 antibody, anti-CA9 antibody, anti-CA-125 antibody, anti-cadherin-6 antibody, anti-CD166 antibody, anti-CD19 antibody, anti-CD20 antibody, anti-CD22 antibody, anti-CD25 antibody, anti-CD27 antibody, anti-CD30 antibody, anti-CD33 antibody, anti-CD37 antibody, anti-CD40 antibody, anti-CD41 antibody, anti-CD44v6 antibody, anti-CD51 antibody, anti-CD52 antibody, anti-CD56 antibody, anti-CD70 antibody, anti-CD74 antibody, anti-CD79 antibody, anti-CD79b antibody, anti-CEACAM5 antibody, anti-c-Met antibody, anti-DLL3 antibody, anti-DPEP3 antibody, anti-EGFR antibody, anti-EGFRvIII antibody, anti-ENPP3 antibody, anti-EpCAM antibody, anti-EphA4 antibody, anti-FGFR2 antibody, anti-FGFR3 antibody, anti-FTL3 antibody, anti-folate receptor a antibody, anti-gripican 3 antibody, anti-gpNMB antibody, anti-HER2 antibody, anti-HER3 antibody, anti-IL-3RA antibody, anti-LAMPI antibody, anti-LIV-1 antibody, anti-LRRC15 antibody, anti-Ly6E antibody, anti-mesothelin antibody, anti-MUC-16 antibody, anti-NaPi2b antibody, anti-nectin-4 antibody, anti-CD352 antibody, anti-P-cadherin antibody, anti-PMSA antibody, anti-protein tyrosine kinase 7 antibody, anti-SLITRK antibody, anti-STEAP1 antibody, anti-CD138 antibody, anti-tissue factor antibody, anti-CD71 antibody, anti-TIM-1 antibody, anti-Trop2 antibody, anti-5T4 antibody, anti-B7-H3 antibody, anti-CD163 macrophage receptor antibody, anti-CD38 antibody, anti-CD48 antibody, anti-cKit antibody, anti-guanylate cyclase C antibody, anti-gastrin releasing peptide antibody, anti-solute carrier antibody, anti-tumor-associated MUC-1 antibody, anti-GD2 antibody, anti-α4β7 integrin antibody or anti-embigin antibody. Examples of another aspect of mAb include anti-CD19 antibody, anti-CD20 antibody, anti-CD22 antibody, anti-CD30 antibody, anti-CD33 antibody, anti- CD52 antibody, anti-CD70 antibody, anti-CD79b antibody, anti-CEACAM5 antibody, anti-EGFR antibody, anti-EGFRvIII antibody, anti-gpNMB antibody, anti-HER2 antibody, anti-mesothelin antibody, anti-CD138 antibody, anti-CD38 antibody or anti-GD2 antibody. Examples of another aspect of mAb include anti-CD19 antibody, anti-CD20 antibody, anti-CD22 antibody, anti-CD30 antibody, anti-CD33 antibody, anti-CD52 antibody, anti-CD79b antibody, anti-CEACAM5 antibody, anti-EGFR antibody, anti-EGFRvIII antibody, anti-gpNMB antibody, anti-HER2 antibody, anti-mesothelin antibody or anti-CD138 antibody.

Here, it is sufficient that the "antibody" be an antibody including at least a heavy chain variable domain and a light chain variable domain, and it may be a complete antibody or a fragment of a complete antibody that is an antigen-binding fragment having an antigen-recognition site. The complete antibody has two full length light chains and two full length heavy chains, and respective light chains and heavy chains are linked by disulfide bonds. The complete antibody includes IgA, IgD, IgE, IgM and IgG, and IgG includes $IgG_1$, $IgG_2$, $IgG_3$ and $IgG_4$ as subtypes. In addition, it is preferable that the antibody be a monoclonal antibody. The antibody moiety and the linker moiety are linked via a sulfhydryl group obtained by reducing a disulfide bond in the antibody.

In addition, the antibody is not limited to human antibodies, and includes antibodies of monkey, mouse, rat, goat, rabbit or the like.

The "antibody of AMG 595" means anti-EGFRvIII antibody that can be obtained by the method described in Mol. Cancer Ther., 2015, 14, 1614-1624.

Examples of one aspect of the antibody-drug conjugate according to the present invention include the following (2-A).

(2-A)
An antibody-drug conjugate, wherein, in formula (2),
mAb is brentuximab or trastuzumab;
q is an integer of 1 to 8;
h is 2, 3, 4 or 5;
$(G)_g$ is a group represented by formula (G-1);
Y is a group represented by formula (Y-1);
Y' is a carbonyl group;
f is 0;
Z is a group represented by formula (Z-1);
Q is an unsubstituted phenyl group or a group represented by formula (Q-2);
$R^{1a}$ is a methyl group;
$R^{2b}$ and $R^{2c}$ are hydrogen atoms;
AA is Glu or Asp; and
m is 1 or 2,
or a pharmaceutically acceptable salt thereof.

Examples of one aspect of the antibody-drug conjugate according to the present invention include the following (2-B).

(2-B)
An antibody-drug conjugate, wherein, in formula (2),
mAb is brentuximab or trastuzumab;
q is an integer of 1 to 8;
h is 2, 3, 4 or 5;
$(G)_g$ is a group represented by formula (G-2), formula (G-3) or formula (G-4);
Y is a group represented by formula (Y-1);
Y' is a carbonyl group;
f is 0;
Z is a group represented by formula (Z-1);
Q is an unsubstituted phenyl group or a group represented by formula (Q-2);
$R^{1a}$ is a methyl group;
$R^{2b}$ and $R^{2c}$ are hydrogen atoms;
AA is Glu or Asp; and
m is 1 or 2,
or a pharmaceutically acceptable salt thereof.

Examples of one aspect of the antibody-drug conjugate according to the present invention include the following (2-C).

(2-C)
An antibody-drug conjugate, wherein, in formula (2),
mAb is brentuximab or trastuzumab;
q is an integer of 1 to 8;
$(G)_g$ is a group represented by formula (G-1);
h is 2, 3, 4 or 5;
Y is a group represented by formula (Y-1);
Y' is a carbonyl group;
f is 0;
Z is a group represented by formula (Z-5) or formula (Z-6);
Q is an unsubstituted phenyl group or a group represented by formula (Q-2);
$R^{1a}$ is a methyl group;
$R^{1b}$ is a hydrogen atom;
$R^{2b}$ and $R^{2c}$ are hydrogen atoms;
AA is Glu or Asp;
n is 1; and
$R^6$ is a hydrogen atom,
or a pharmaceutically acceptable salt thereof.

Examples of one aspect of the antibody-drug conjugate according to the present invention include the following (2-D).

(2-D)
An antibody-drug conjugate, wherein, in formula (2),
mAb is brentuximab or trastuzumab;
q is an integer of 1 to 8;
h is 2, 3, 4 or 5;
$(G)_g$ is a group represented by formula (G-2), formula (G-3) or formula (G-4);
Y is a group represented by formula (Y-1);
Y' is a carbonyl group;
f is 0;
Z is a group represented by formula (Z-5) or formula (Z-6);
Q is an unsubstituted phenyl group or a group represented by formula (Q-2);
$R^{1a}$ is a methyl group;
$R^{1b}$ is a hydrogen atom;
$R^{2b}$ and $R^{2c}$ are hydrogen atoms;
AA is Glu or Asp;
n is 1; and
$R^6$ is a hydrogen atom,
or a pharmaceutically acceptable salt thereof.

Examples of one aspect of the antibody-drug conjugate according to the present invention include the following (2-E).

(2-E)
An antibody-drug conjugate, wherein, in formula (2),
mAb is brentuximab or trastuzumab;
q is an integer of 1 to 8;
h is 2, 3, 4 or 5;
$(G)_g$ is a group represented by formula (G-2), formula (G-3) or formula (G-4);
Y is a single bond;
Z is a group represented by formula (Z-1);

Q is an unsubstituted phenyl group or a group represented by formula (Q-2);
R$^{1a}$ is a methyl group;
R$^{2b}$ and R$^{2c}$ are hydrogen atoms;
AA is Glu or Asp; and
m is 1 or 2,
or a pharmaceutically acceptable salt thereof.

Examples of one aspect of the antibody-drug conjugate according to the present invention include the following (2-F).

(2-F)
An antibody-drug conjugate, wherein, in formula (2),
mAb is brentuximab or trastuzumab;
q is an integer of 1 to 8;
h is 2, 3, 4 or 5;
(G)$_g$ is a group represented by formula (G-2), formula (G-3) or formula (G-4);
Y is a single bond;
Z is a group represented by formula (Z-5) or formula (Z-6);
Q is an unsubstituted phenyl group or a group represented by formula (Q-2);
R$^{1a}$ is a methyl group;
R$^{1b}$ is a hydrogen atom;
R$^{2b}$ and R$^{2e}$ are hydrogen atoms;
AA is Glu or Asp;
n is 1; and
R$^6$ is a hydrogen atom,
or a pharmaceutically acceptable salt thereof.

Examples of one aspect of the antibody-drug conjugate according to the present invention include the following (2-G).

(2-G)
An antibody-drug conjugate, wherein, in formula (2),
mAb is inotuzumab, gemtuzumab, labetuzumab, polatuzumab, coltuximab, indatuximab, anetumab, rituximab, denintuzumab, laprituximab, vadastuximab, glembatumumab, cetuximab, alemtuzumab, depatuxizumab or anti-embigin antibody;
q is an integer of 1 to 8;
h is 2, 3, 4 or 5;
(G)$_g$ is a group represented by formula (G-1);
Y is a group represented by formula (Y-1);
Y' is a carbonyl group;
f is 0;
Z is a group represented by formula (Z-1);
Q is an unsubstituted phenyl group or a group represented by formula (Q-2);
R$^{1a}$ is a methyl group;
R$^{2b}$ and R$^{2c}$ are hydrogen atoms;
AA is Glu or Asp; and
m is 1 or 2,
or a pharmaceutically acceptable salt thereof.

Examples of one aspect of the antibody-drug conjugate according to the present invention include an antibody-drug conjugate represented by the following formula (YG-1), formula (YG-2), formula (YG-3) or formula (YG-4):

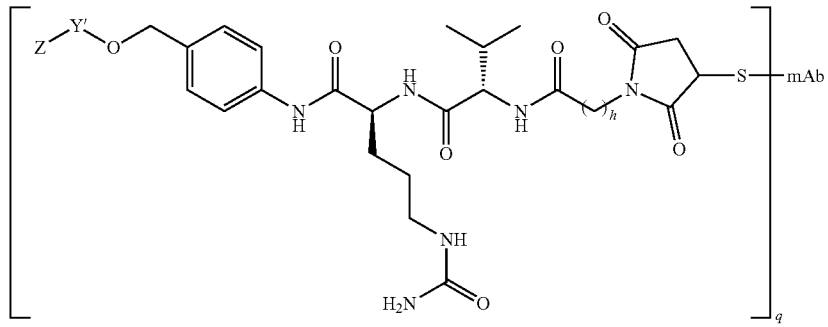

(YG-1)

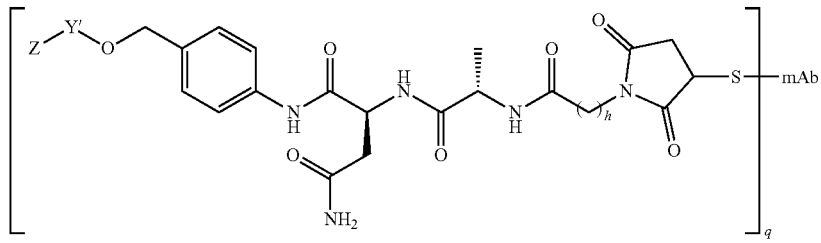

(YG-2)

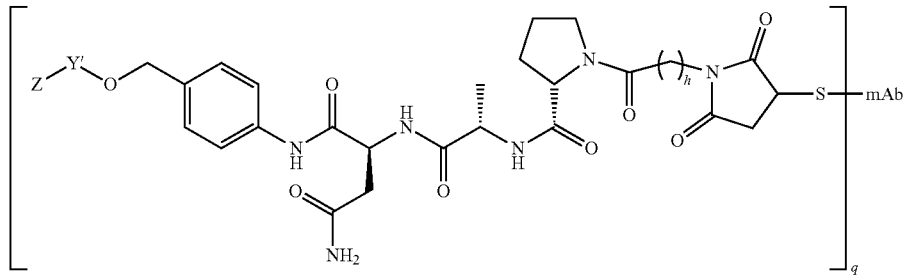

(YG-3)

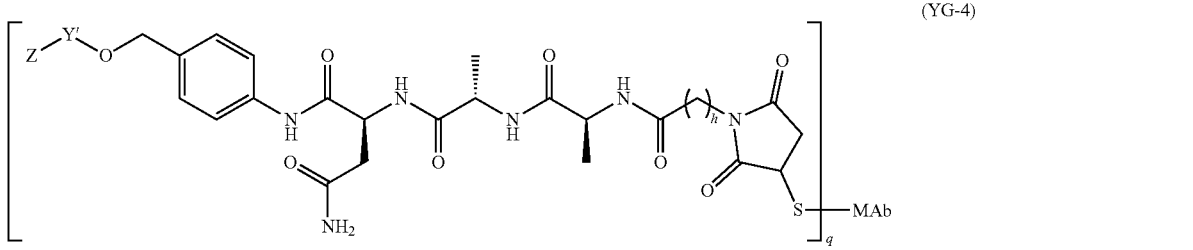

(YG-4)

wherein mAb, Z, Y', h and q are as defined above, or a pharmaceutically acceptable salt thereof.

In general, it is possible to carry out production and analysis of the antibody-drug conjugate by an arbitrary method known to a person having ordinary skill in the art. Examples of such a method include the method described in Antibody-Drug Conjugates (edited by Laurent Ducry, published by Humana Press, 2013).

The antibody-drug conjugate according to the present invention may be formed by, for example, reducing a disulfide bond in the antibody into a sulfhydryl group and allowing this sulfhydryl group to react with an ADC intermediate. Here, the ADC intermediate can be obtained by having a linker compound containing a maleimide group bonded to a hemiasterlin derivative.

It is speculated that the antibody-drug conjugate is delivered specifically into particular antigen-expressing cells through uptake into cells utilizing antibody-antigen reaction, and then releases the drug moiety through the mechanisms mentioned above, thereby exerting drug efficacy only in the particular cells. The antibody-drug conjugate can be taken up specifically into cancer cells, and therefore, can be expected to exert strong drug efficacy against cancer cells.

On the other hand, it is believed that some antibody-drug conjugates may be broken down by protease or the like contained in the blood before being delivered to target cells, releasing the drug moiety into the blood. At that time, in case of conventional antibody-drug conjugates, cell membrane permeability of the drug moiety is high, and therefore, the drug released into the blood is also passively diffused into and taken up by normal cells. As a result, unintentional systemic exposure is caused, which is unfavorable because side effects tend to occur.

In contrast, the drug moiety of the antibody-drug conjugate according to the present invention has low cell membrane permeability, and thus, even if the drug moiety is released in the blood before reaching target cells, the drug is unlikely to be passively diffused into normal cells and is quickly metabolized and excreted; therefore, it can be expected that side effects due to systemic exposure is small.

Furthermore, when a compound with low membrane permeability is used as the drug moiety, the drug moiety released in target cells is hindered from flowing outside the cells via the cell membrane, and therefore, the drug can remain in the target cells for a long period of time and it is expected that satisfactory drug efficacy is exerted.

That is, because the antibody-drug conjugate according to the present invention has a hemiasterlin derivative with low cell membrane permeability as the drug moiety, it is expected to exert drug efficacy specifically to cancer cells, and also to have small influence on normal cells and high safety.

<ADC Intermediate>

A synthetic intermediate for synthesizing the antibody-drug conjugate according to the present invention (hereinafter, may be referred to as the "ADC intermediate according to the present invention") is a compound represented by the following formula (3-1) or formula (3-2), or a salt thereof.

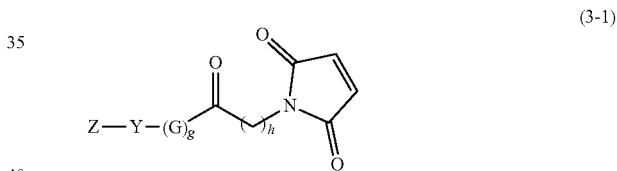

(3-1)

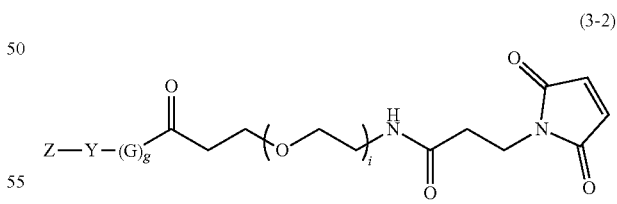

(3-2)

Details for each symbol in the formulas above are as described in the description of the compounds of formula (1) or formula (1a) and formula (2) described above, except when there is particular specification. i is an integer of 1 to 12.

Examples of the ADC intermediate according to the present invention preferably include a compound represented by formula (MDF-1), formula (MDF-2), formula (MDF-3) or formula (MDF-4):

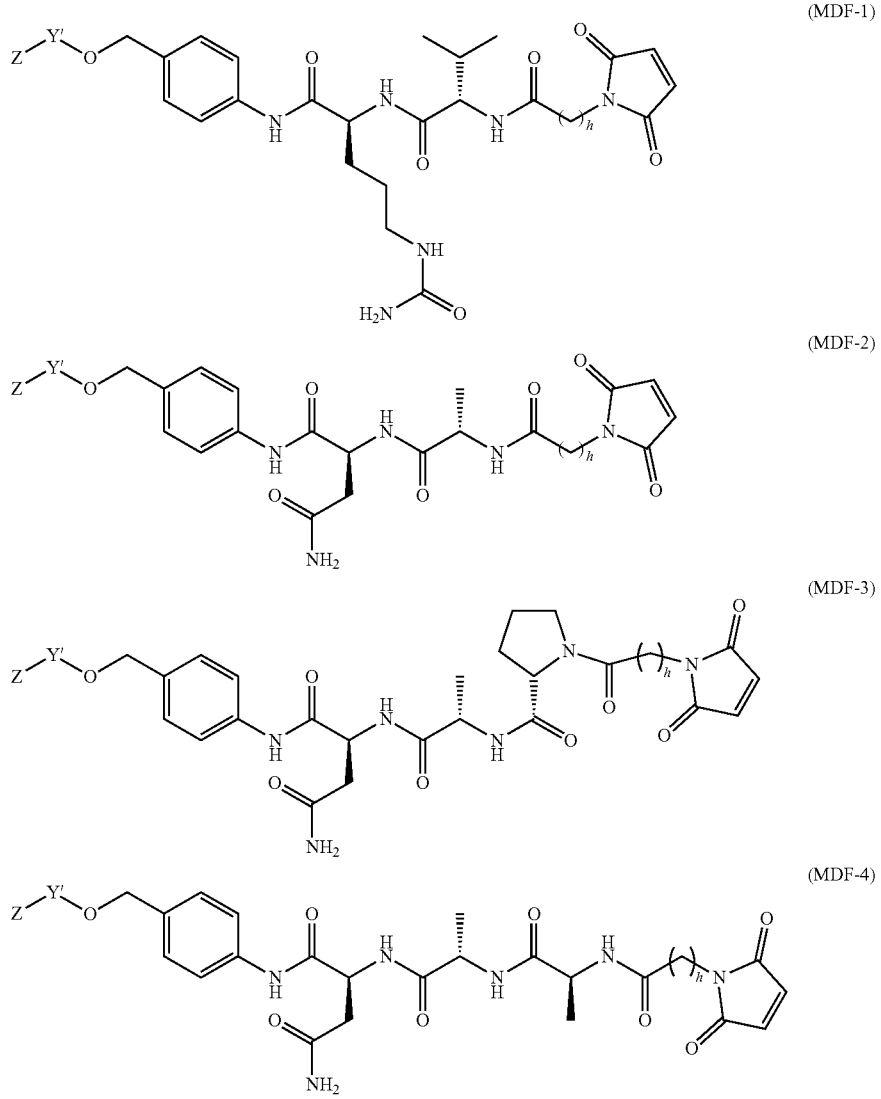

wherein h, Y' and Z are as defined above,
or a salt thereof.

Examples of one aspect of the ADC intermediate according to the present invention include the following (3-1-A).

(3-1-A)
A compound, wherein, in formula (3-1),
(G)$_g$ is a group represented by formula (G-1);
h is 2, 3, 4 or 5;
Y is a group represented by formula (Y-1);
Y' is a carbonyl group;
f is 0;
Z is a group represented by formula (Z-1);
Q is an unsubstituted phenyl group or a group represented by formula
R$^{1a}$ is a methyl group;
R$^{2b}$ and R$^{2c}$ are hydrogen atoms;
AA is Glu or Asp; and
m is 1 or 2,
or a salt thereof.

Examples of one aspect of the ADC intermediate according to the present invention include the following (3-1-B).

(3-1-B)
A compound, wherein, in formula (3-1),
(G)$_g$ is a group represented by formula (G-2), formula (G-3) or formula (G-4);
h is 2, 3, 4 or 5;
Y is a group represented by formula (Y-1);
Y' is a carbonyl group;
f is 0;
Z is a group represented by formula (Z-1);
Q is an unsubstituted phenyl group or a group represented by formula (Q-2);
R$^{1a}$ is a methyl group;
R$^{2b}$ and R$^{2c}$ are hydrogen atoms;
AA is Glu or Asp; and
m is 1 or 2,
or a salt thereof.

Examples of one aspect of the ADC intermediate according to the present invention include the following (3-1-C).

(3-1-C)
A compound, wherein, in formula (3-1),
(G)$_g$ is a group represented by formula (G-1);
h is 2, 3, 4 or 5;
Y is a group represented by formula (Y-1);

Y' is a carbonyl group;
f is 0;
Z is a group represented by formula (Z-5) or formula (Z-6);
Q is an unsubstituted phenyl group or a group represented by formula (Q-2);
$R^{1a}$ is a methyl group;
$R^{1b}$ is a hydrogen atom;
$R^{2b}$ and $R^{2c}$ are hydrogen atoms;
AA is Glu or Asp;
n is 1; and
$R^6$ is a hydrogen atom,
or a salt thereof.

Examples of one aspect of the ADC intermediate according to the present invention include the following (3-1-D).

(3-1-D)
A compound, wherein, in formula (3-1),
$(G)_g$ is a group represented by formula (G-2), formula (G-3) or formula (G-4);
h is 2, 3, 4 or 5;
Y is a group represented by formula (Y-1);
Y' is a carbonyl group;
f is 0;
Z is a group represented by formula (Z-5) or formula (Z-6);
Q is an unsubstituted phenyl group or a group represented by formula (Q-2);
$R^{1a}$ is a methyl group;
$R^{1b}$ is a hydrogen atom;
$R^{2b}$ and $R^{2c}$ are hydrogen atoms;
AA is Glu or Asp;
n is 1; and
$R^6$ is a hydrogen atom,
or a salt thereof.

Examples of one aspect of the ADC intermediate according to the present invention include the following (3-1-E).

(3-1-E)
A compound, wherein, in formula (3-1),
$(G)_g$ is a group represented by formula (G-2), formula (G-3) or formula (G-4);
h is 2, 3, 4 or 5;
Y is a single bond;
Z is a group represented by formula (Z-1);
Q is an unsubstituted phenyl group or a group represented by formula (Q-2);
$R^{1a}$ is a methyl group;
$R^{2b}$ and $R^{2c}$ are hydrogen atoms;
AA is Glu or Asp; and
m is 1 or 2,
or a salt thereof.

Examples of one aspect of the ADC intermediate according to the present invention include the following (3-1-F).

(3-1-F)
A compound, wherein, in formula (3-1),
$(G)_g$ is a group represented by formula (G-2), formula (G-3) or formula (G-4);
h is 2, 3, 4 or 5;
Y is a single bond;
Z is a group represented by formula (Z-5) or formula (Z-6);
Q is an unsubstituted phenyl group or a group represented by formula (Q-2);
$R^{1a}$ is a methyl group;
$R^{1b}$ is a hydrogen atom;
$R^{2b}$ and $R^{2c}$ are hydrogen atoms;
AA is Glu or Asp;
n is 1; and
$R^6$ is a hydrogen atom,
or a salt thereof.

The "salt" is a suitable salt of the hemiasterlin derivative and ADC intermediate according to the present invention and is acceptable as a pharmaceutical raw material, and is preferably a common non-toxic salt. For the "salt", for example, in addition to acid addition salts such as organic acid salts (for example, acetate, trifluoroacetate, maleate, fumarate, citrate, tartrate, methanesulfonate, benzenesulfonate, formate, p-toluenesulfonate or the like) and inorganic acid salts (for example, hydrochloride, hydrobromide, hydroiodide, sulfate, nitrate, phosphateor the like); salts with amino acids (for example, arginine, aspartic acid, glutamic acid or the like); metal salts such as alkali metal salts (for example, sodium salt, potassium salt or the like) and alkaline earth metal salts (for example, calcium salt, magnesium salt or the like); ammonium salts; or organic base salts (for example, trimethylamine salt, triethylamine salt, pyridine salt, picoline salt, dicyclohexylamine salt, N,N'-dibenzylethylenediamine salt or the like), a person having ordinary skill in the art may select appropriate salts as appropriate.

Examples of the "pharmaceutically acceptable salt" include acid addition salts and base addition salts. Examples of the acid addition salt include inorganic acid salts such as hydrochloride, hydrobromide, sulfate, hydroiodide, nitrate and phosphate, or organic acid salts such as citrate, oxalate, phthalate, fumarate, maleate, succinate, malate, acetate, formate, propionate, benzoate, trifluoroacetate, methanesulfonate, benzenesulfonate, p-toluenesulfonate and camphorsulfonate. In addition, examples of the base addition salt include inorganic base salts such as sodium salt, potassium salt, calcium salt, magnesium salt, barium salt and aluminum salt, or organic base salts such as trimethylamine, triethylamine, pyridine, picoline, 2,6-lutidine, ethanolamine, diethanolamine, triethanolamine, tromethamine[tris(hydroxymethyl)methylamine], tert-butylamine, cyclohexylamine, dicyclohexylamine and N,N-dibenzylethylamine. Furthermore, examples of the "pharmaceutically acceptable salt" include salts (amino acid salts) with basic amino acids or acidic amino acids such as arginine, lysine, orithine, aspartic acid and glutamic acid.

When it is desired to acquire a salt of the hemiasterlin derivative, antibody-drug conjugate or ADC intermediate according to the present invention, if the target compound is obtained in the form of salt, that compound may be purified as is, and if the target compound is obtained in the free form, that compound may be dissolved or suspended in an appropriate organic solvent, to which an acid or base is added to form a salt by a conventional method.

The hemiasterlin derivative, antibody-drug conjugate and ADC intermediate according to the present invention may be present in the form of hydrates and/or solvates (ethanolate and the like) with various solvents, and these hydrates and/or solvates are also included in the hemiasterlin derivative, antibody-drug conjugate and ADC intermediate according to the present invention. Furthermore, all modes of crystal forms of the hemiasterlin derivative, antibody-drug conjugate and ADC intermediate according to the present invention are also included in the present invention.

Among the hemiasterlin derivative, antibody-drug conjugate and ADC intermediate according to the present invention, some may have optical isomers based on the optically active center, atropisomers based on axial or planar chirality caused by restraint of intramolecular rotation, and all of the other stereoisomers, tautomers and geometrical isomers, and all possible isomers including the above are encompassed within the scope of the present invention.

In particular, optical isomers and atropisomers may be obtained as racemate, and when optically active starting materials or intermediates are used, optically active substances may be obtained. If necessary, at an appropriate stage in the following production methods, corresponding raw material, intermediate or racemate, the final product, may be optically resolved into optical enantiomers physically or chemically through known separation methods such as a method using an optically active column and fractional crystallization method. Specifically, for example, in diastereomer method, two diastereomers are formed from racemate through a reaction using an optically active resolving agent. In general, these different diastereomers have different physical properties, and thus, can be optically resolved by known methods such as fractional crystallization.

Production methods for the hemiasterlin derivative according to the present invention will be mentioned below. The hemiasterlin derivative according to the present invention represented by formula (1) or formula (1a) may be produced by, for example, the following production method A to F, L to P, T or W.

Production Method A

When Q is a group represented by formula (Q-1), the compound represented by formula (1) may be produced by, for example, the following production method:

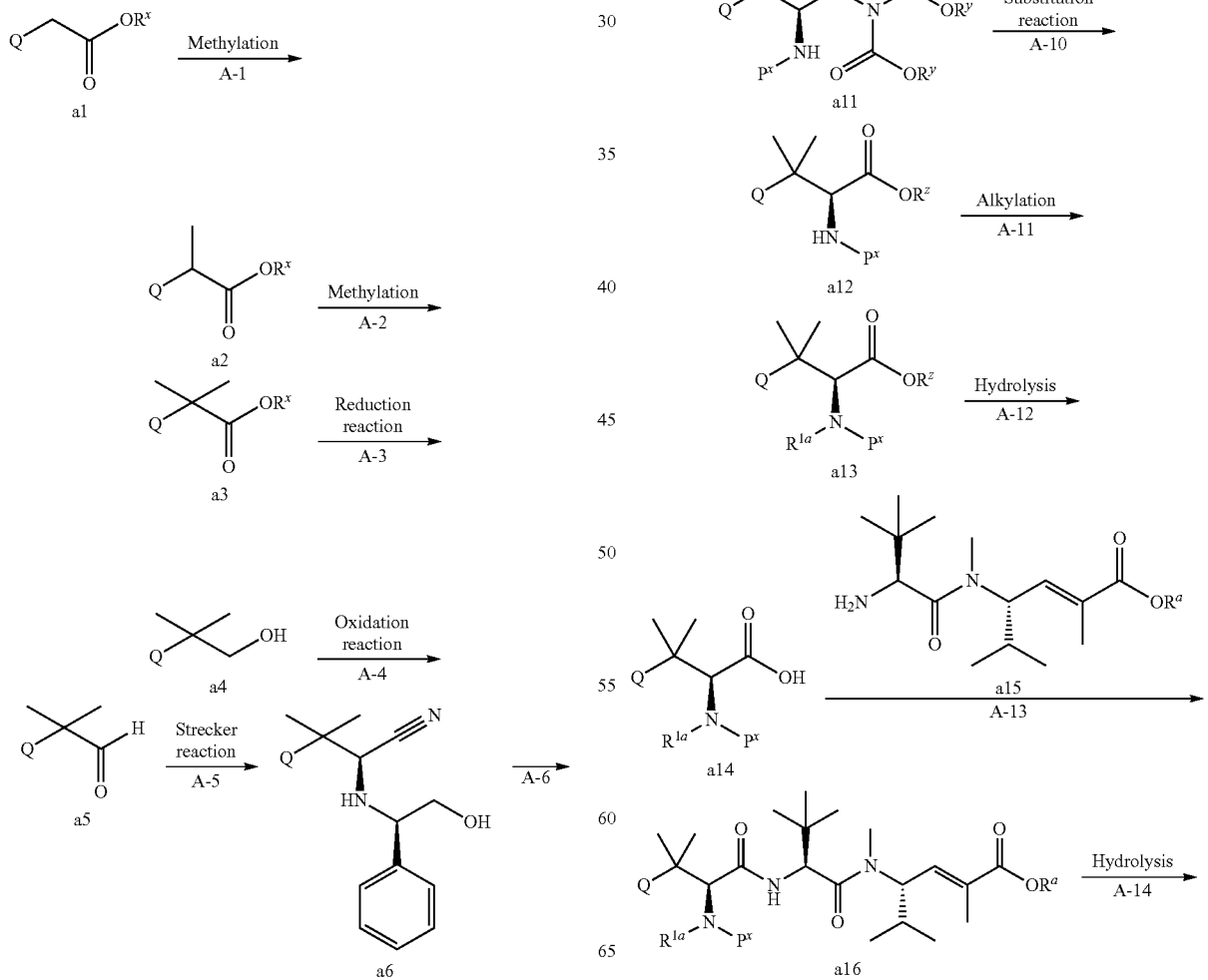

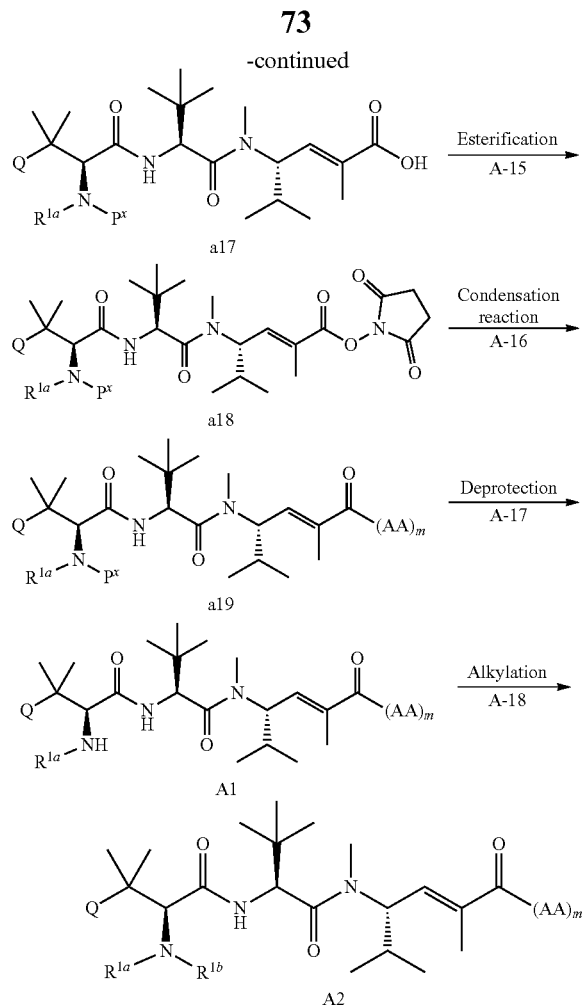

wherein, $R^{1a}$, $R^{1b}$, Q, AA and m are as defined in item 2; $R^a$, $R^x$, $R^y$ and $R^z$ each independently represent a $C_{1-6}$ alkyl group or a benzyl group; and $P^x$ represents a protecting group for the amino group.

As the above protecting group for the amino group, represented by $P^x$, the protecting groups described in Protective Groups in Organic Synthesis (authored by Theodora W. Greene, Peter G. M. Wuts, issued by John Wiley & Sons, Inc., 1999) and the like may be used.

Compound a1 may be produced by the method described in, for example, J. Med. Chem., 2007, 50, 4329-4339 and the like, or may be purchased as a commercial product. Compound a15 may be produced by the method described in, for example, Tetrahedron Lett., 1997, 38, 317-320 and the like, or may be purchased as a commercial product.

[A-1 Step]

Compound a2 may be produced by allowing compound a1 to react with various methylating reagents in an appropriate solvent in the presence of an appropriate base. Examples of the methylating reagent include methyl halide, and preferably include methyl iodide, methyl bromide and methyl chloride. Examples of the base preferably include potassium hexamethyldisilazide. Examples of the solvent preferably include tetrahydrofuran. The reaction time is normally 5 minutes to 48 hours, and is preferably 10 minutes to 2 hours. The reaction temperature is normally −78° C. to 100° C., and is preferably −78° C. to 10° C. This step may be carried out in accordance with the method described in J. Nat. Prod. 2003, 66, 183-199 and the like.

[A-2 Step]

Compound a3 may be produced from compound a2 in accordance with the method described in the above A-1 step.

[A-3 Step]

Compound a4 may be produced by allowing compound a3 to react with an appropriate reducing agent in an appropriate solvent. The reducing agent is selected from reducing agents used in usual organic synthesis reactions as appropriate, and examples thereof preferably include diisobutylaluminum hydride.

Examples of the solvent preferably include diethyl ether. The reaction time is normally 5 minutes to 48 hours, and is preferably 10 minutes to 24 hours. The reaction temperature is normally −78° C. to 100° C., and is preferably −78° C. to 50° C. This step may be carried out in accordance with the method described in J. Nat. Prod. 2003, 66, 183-199 and the like.

[A-4 Step]

Compound a5 may be produced by oxidizing compound a4 using an appropriate oxidizing agent in an appropriate solvent. The oxidizing agent may be selected from oxidizing agents used in usual organic synthesis reactions as appropriate, and examples thereof preferably include tetrapropylammonium perruthenate. Examples of the solvent preferably include dichloromethane. The reaction time is normally 5 minutes to 72 hours, and is preferably 30 minutes to 24 hours. The reaction temperature is normally −78° C. to 100° C., and is preferably −78° C. to 50° C. This step may be carried out in accordance with the method described in J. Nat. Prod. 2003, 66, 183-199 and the like.

[A-5 Step]

Compound a6 may be produced by α-aminocyanating the aldehyde of the compound a5 in an appropriate solvent. Examples of the solvent preferably include toluene and dichloromethane. The reaction time is normally 5 minutes to 96 hours, and is preferably 24 hours to 72 hours. The reaction temperature is normally 0° C. to 200° C., and is preferably 0° C. to 100° C. This step may be carried out in accordance with the method described in Org. Lett. 2002, 4, 695-697 and the like.

[A-6 Step]

Compound a7 may be produced from compound a6 by using an appropriate oxidizing agent in an appropriate solvent in the presence of or in the absence of an appropriate base. The oxidizing agent may be selected from oxidizing agents used in usual organic synthesis reactions as appropriate, and examples thereof preferably include hydrogen peroxide. Examples of the base preferably include potassium carbonate. Examples of the solvent preferably include methanol. The reaction time is normally 5 minutes to 72 hours, and is preferably 30 minutes to 24 hours. The reaction temperature is normally 0° C. to 200° C., and is preferably 0° C. to 60° C. This step may be carried out in accordance with the method described in J. Org. Chem. 2001, 66, 7355-7364 and the like.

[A-7 Step]

Compound a8 may be produced by reducing compound a7 using an appropriate reducing agent in an appropriate solvent in the presence of an appropriate catalyst. The reducing agent may be selected from reducing agents used in usual organic synthesis reactions as appropriate, and examples thereof preferably include hydrogen, formate such as ammonium formate, or hydrazine. Examples of the catalyst include transition metals such as palladium, nickel, rhodium, cobalt and platinum, salts thereof or complexes thereof, or supports such as polymer having the above transition metals supported thereon. Examples of the solvent preferably include ethanol or methanol. The reaction time is normally 5 minutes to 72 hours, and is preferably 30 minutes to 24 hours. The reaction temperature is normally 0° C. to 200° C., and is preferably 0° C. to 100° C. This step may be carried out in accordance with the method described in J. Org. Chem. 2001, 66, 7355-7364 and the like.

[A-8 Step]

Compound a9 may be produced by protecting the amino group of compound a8 with protecting group $P^X$. This step may be carried out in accordance with the method described in Protective Groups in Organic Synthesis (authored by Theodora W. Greene, Peter G. M. Wuts, issued by John Wiley & Sons, Inc., 1999) and the like.

[A-9 Step]

Compound a11 may be produced by allowing compound a9 to react with various acylating reagents (for example, compound a10) in an appropriate solvent in the presence of or in the absence of an appropriate base. Examples of the acylating reagent include carboxylic halide and carboxylic anhydride, and preferably include di-tert-butyl dicarbonate. Examples of the base preferably include diisopropylethylamine. Examples of the solvent preferably include chloroform. The reaction time is normally 5 minutes to 72 hours, and is preferably 30 minutes to 24 hours. The reaction temperature is normally 0° C. to 200° C., and is preferably 0° C. to 50° C.

[A-10 Step]

Compound a12 may be produced by allowing compound a11 to react with an appropriate alkali metal alkoxide in an appropriate solvent. The alkali metal alkoxide may be selected from alkali metal alkoxides used in usual organic synthesis reactions as appropriate, and examples thereof preferably include lithium methoxide or lithium ethoxide. Examples of the solvent preferably include methanol or ethanol. The reaction time is normally 5 minutes to 72 hours, and is preferably 30 minutes to 6 hours. The reaction temperature is normally −78° C. to 200° C., and is preferably −78° C. to 50° C.

[A-11 Step]

Compound a13 may be produced by allowing compound a12 to react with various alkylating reagents in an appropriate solvent in the presence of an appropriate base. Examples of the alkylating reagent include alkyl halide, and preferably include alkyl iodide, alkyl bromide and alkyl chloride. Examples of the base preferably include sodium hydride. Examples of the solvent preferably include tetrahydrofuran. The reaction time is normally 5 minutes to 48 hours, and is preferably 10 minutes to 2 hours. The reaction temperature is normally −78° C. to 100° C., and is preferably −78° C. to 10° C.

[A-12 Step]

Compound a14 may be produced by hydrolyzing the ester of compound a13, in an appropriate solvent in the presence of an appropriate base. Examples of the base preferably include lithium hydroxide. Examples of the solvent preferably include water or methanol. The reaction time is normally 5 minutes to 72 hours, and is preferably 30 minutes to 24 hours. The reaction temperature is normally 0° C. to 200° C., and is preferably 0° C. to 100° C.

[A-13 Step]

Compound a16 may be produced by condensing compound a14 and compound a15 using various condensing agents in an appropriate solvent in the presence of an appropriate base. As the condensing agent, various condensing agents used in usual organic synthesis reactions may be used, and examples thereof preferably include (1-ethyl-3-(3-dimethylaminopropyl)carbodiimide or bromotripyrrolidinophosphonium hexafluorophosphate. In addition a carbonyl activating reagent such as 1-hydroxybenzotriazole may be used together as necessary, in order to improve efficiency of the condensation reaction. Examples of the base preferably include diisopropylethylamine. Examples of the solvent preferably include N,N-dimethylformamide. The reaction time is normally 5 minutes to 72 hours, and is preferably 30 minutes to 24 hours. The reaction temperature is normally −78° C. to 200° C., and is preferably 0° C. to 100° C. This step may be carried out in accordance with the method described in Tetrahedron Lett., 1997, 38, 317-320 and the like.

[A-14 Step]

Compound a17 may be produced by hydrolyzing the ester of compound a16, in accordance with the method described in the above A-12 step. This step may be carried out in accordance with the method described in Tetrahedron Lett., 1997, 38, 317-320 and the like.

[A-15 Step]

Compound a18 may be produced by allowing compound a17 to react with N-hydroxysuccinimide using various condensing agents in an appropriate solvent in the presence of an appropriate base. As the condensing agent, various condensing agents used in usual organic synthesis reactions may be used, and examples thereof preferably include (1-ethyl-3-(3-dimethylaminopropyl)carbodiimide, bromotripyrrolidinophosphonium hexafluorophosphate or O-(7-azabenzotriazol-1-yl)-N,N,N',N'-tetramethyluronium hexafluorophosphate. In addition, a carbonyl activating reagent such as 1-hydroxybenzotriazole may be used together as necessary, in order to improve efficiency of the reaction. Examples of the base preferably include diisopropylethylamine. Examples of the solvent preferably include N,N-dimethylformamide. The reaction time is normally 5 minutes to 72 hours, and is preferably 30 minutes to 24 hours. The reaction temperature is normally −78° C. to 200° C., and is preferably 0° C. to 100° C.

[A-16 Step]

Compound a19 may be produced by allowing compound a18 to react with an amino acid or a peptide which is a raw material for group $-(AA)_m$, in an appropriate solvent in the presence of an appropriate base. Examples of the base preferably include diisopropylethylamine. Examples of the solvent preferably include N,N-dimethylformamide. The reaction time is normally 5 minutes to 72 hours, and is preferably 30 minutes to 24 hours. The reaction temperature is normally 0° C. to 200° C., and is preferably 0° C. to 100° C.

[A-17 Step]

Compound A1 may be produced by deprotecting the protecting group $P^X$ for the amino group of compound a19. This step may be carried out in accordance with the method described in Protective Groups in Organic Synthesis (authored by Theodora W. Greene, Peter G. M. Wuts, issued by John Wiley & Sons, Inc., 1999) and the like. In addition, when $(AA)_m$ has an ester, hydrolysis of the ester may also be carried out in the present deprotecting step, as necessary.

[A-18 Step]

Compound A2 may be produced by allowing compound A1 and an alkyl aldehyde to react together with an appropriate reducing agent in an appropriate solvent. Examples of the solvent preferably include acetonitrile. As the reducing agent, various reducing agents used in usual organic synthesis reactions may be used, and examples thereof preferably include sodium triacetoxyborohydride. The reaction time is normally 5 minutes to 72 hours, and is preferably 30 minutes to 24 hours. The reaction temperature is normally 0° C. to about 200° C., and is preferably 0° C. to 100° C.

Production Method B

When $R^{1a}$ and $R^{1b}$ are hydrogen atoms, the compound represented by formula (1) may be produced by, for example, the following production method:

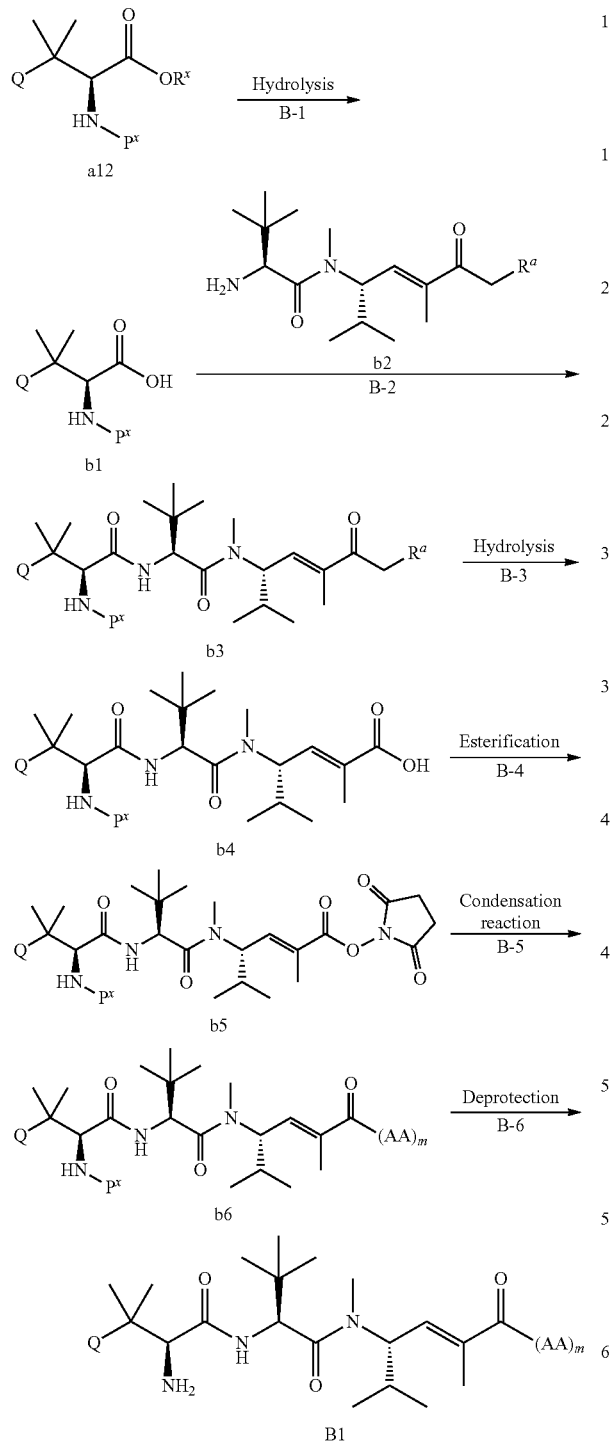

wherein, Q, AA and m are as defined in item 2; and $R^a$, $R^x$ and $P^x$ are as defined above.

Compound b2 may be produced by the method described in, for example, Tetrahedron Lett., 1997, 38, 317-320 and the like, or may be purchased as a commercial product.

[B-1 Step]

Compound b1 may be produced from compound a12 in accordance with the method described in the above A-12 step.

[B-2 Step]

Compound b3 may be produced from compound b1 and compound b2 in accordance with the method described in the above A-13 step.

[B-3 Step]

Compound b4 may be produced from compound b3 in accordance with the method described in the above A-14 step.

[B-4 Step]

Compound b5 may be produced from compound b4 in accordance with the method described in the above A-15 step.

[B-5 Step]

Compound b6 may be produced from compound b5 in accordance with the method described in the above A-16 step.

[B-6 Step]

Compound B1 may be produced from compound b6 in accordance with the method described in the above A-17 step.

Production Method C

The compound represented by formula (1) may be produced by, for example, the following production method:

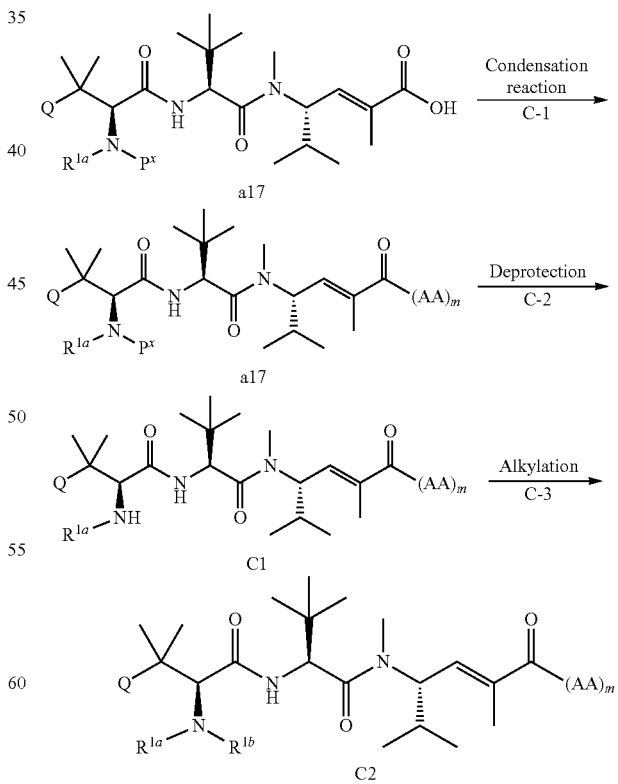

wherein, $R^{1a}$, $R^{1b}$, Q, AA and m are as defined in item 2; and $P^x$ is as defined above.

[C-1 Step]

Compound c1 may be produced by allowing compound a17 to react with an amino acid or a peptide which is a raw material for group -(AA)$_m$, in accordance with the method described in the above A-13 step.

[C-2 Step]

Compound C1 may be produced from compound c1 in accordance with the method described in the above A-17 step.

[C-3 Step]

Compound C2 may be produced from compound C1 in accordance with the method described in the above A-18 step.

Production Method D

The compound represented by formula (1) may be produced by, for example, the following production method:

having k amino acid residues in accordance with the method described in the above A-13 step.

[D-3 Step]

Compound D2 may be produced from compound d2 in accordance with the method described in the above A-17 step.

[D-4 Step]

Compound D2 may be produced from compound D in accordance with the method described in the above A-18 step.

Production Method E

The compound represented by formula (1) may be produced by, for example, the following production method:

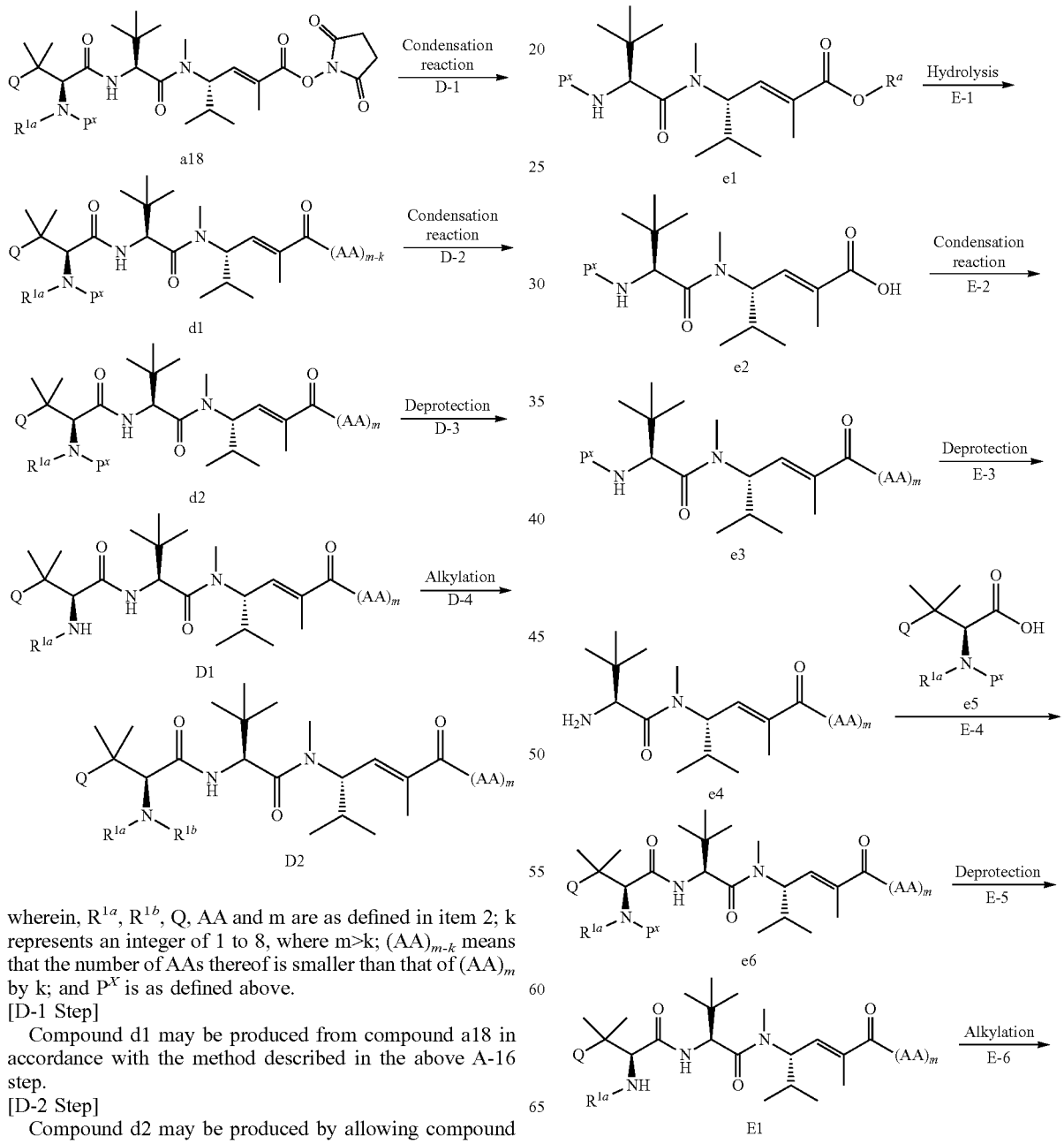

wherein, $R^{1a}$, $R^{1b}$, Q, AA and m are as defined in item 2; k represents an integer of 1 to 8, where m>k; (AA)$_{m-k}$ means that the number of AAs thereof is smaller than that of (AA)$_m$ by k; and $P^x$ is as defined above.

[D-1 Step]

Compound d1 may be produced from compound a18 in accordance with the method described in the above A-16 step.

[D-2 Step]

Compound d2 may be produced by allowing compound d1 to react with a peptide (or with an amino acid when k=1)

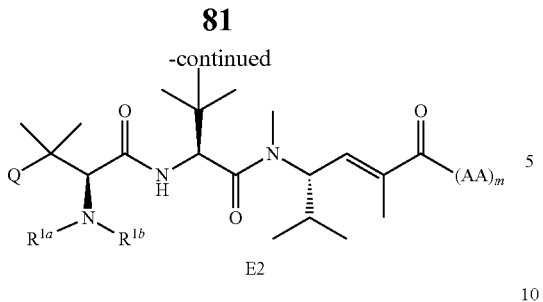

E2 wherein, $R^{1a}$, $R^{1b}$, Q, AA and m are as defined in item 2; and $R^a$ and $P^X$ are as defined above.

Compound e1 may be produced by the method described in, for example, Tetrahedron Lett., 1997, 38, 317-320 and the like, or may be purchased as a commercial product. Compound e5 may be produced by the methods described in, for example, J. Nat. Prod. 2003, 66, 183-199; J. Med. Chem., 2004, 47, 4774-4786: and the like, or may be purchased as a commercial product.

[E-1 Step]

Compound e2 may be produced from compound e1 in accordance with the method described in the above A-12 step.

[E-2 Step]

Compound e3 may be produced by allowing compound e2 to react with an amino acid or a peptide which is a material for group $-(AA)_m$, in accordance with the method described in the above A-13 step.

[E-3 Step]

Compound e4 may be produced from compound e3 in accordance with the method described in the above A-17 step.

[E-4 Step]

Compound e6 may be produced from compound e4 and compound e5 in accordance with the method described in the above A-13 step.

[E-5 Step]

Compound E1 may be produced from compound e6 in accordance with the method described in the above A-17 step.

[E-6 Step]

Compound E2 may be produced from compound E1 in accordance with the method described in the above A-18 step.

Production Method F

When Q is an unsubstituted phenyl group, the compound represented by formula (1) may be produced by, for example, the following production method:

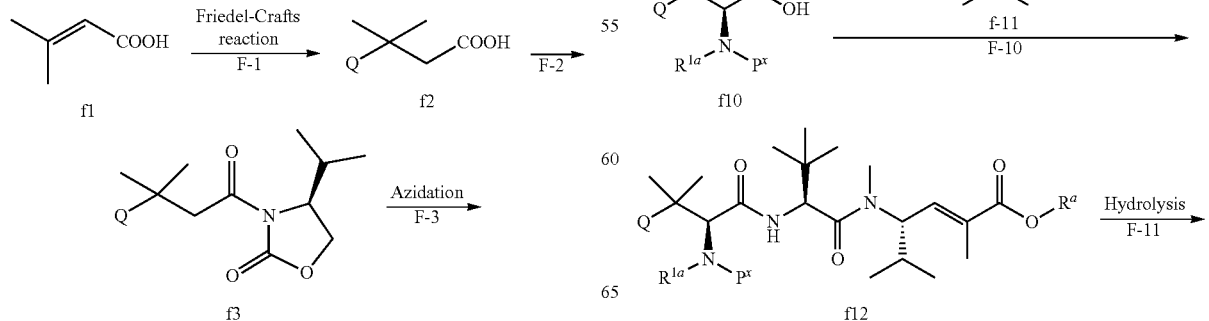

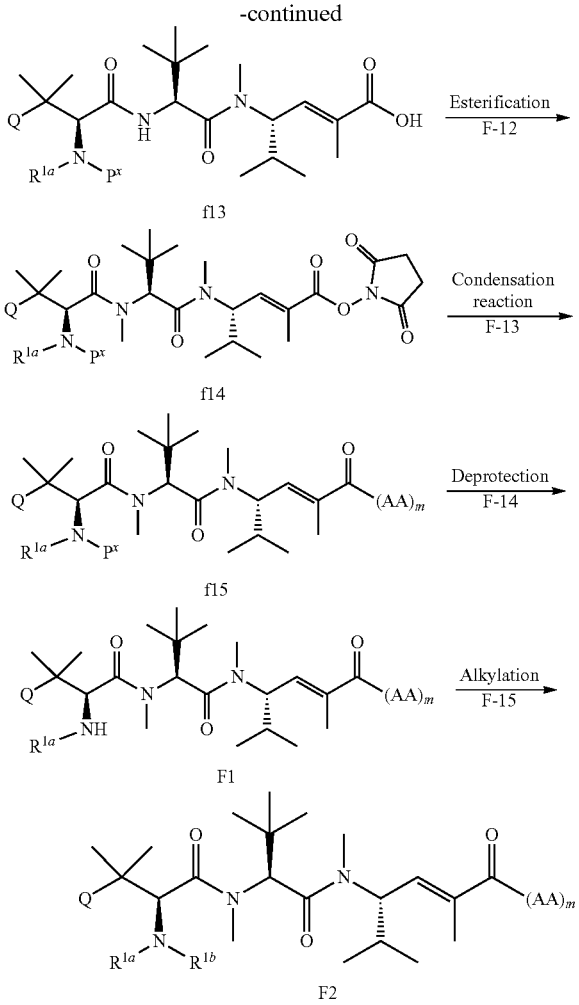

wherein, $R^{1a}$, $R^{1b}$, AA and m are as defined in item 2; and $R^a$, $R^x$ and $P^x$ are as defined above.

Compound f1 may be, for example, purchased as a commercial product. Compound f11 may be produced by the method described in, for example, Tetrahedron Lett., 1997, 38, 317-320 and the like, or may be purchased as a commercial product.

[F-1 Step]

Compound f2 may be produced by allowing compound f1 to react with benzene in the presence of various Lewis acids. Examples of the Lewis acid include boron halide, aluminum halide, gallium halide, iron halide and titanium halide, and preferably include aluminum chloride and iron chloride. The reaction time is normally 5 minutes to 48 hours, and is preferably 30 minutes to 4 hours. The reaction temperature is normally −78° C. to 200° C., and is preferably 50° C. to 150° C. This step may be carried out in accordance with the method described in J. Nat. Prod. 2003, 66, 183-199 and the like.

[F-2 Step]

Compound f3 may be produced by allowing compound f2 to react with various carboxylic halides and then to react with an alkali metallized 4-alkyl-2-oxazolidinone in an appropriate solvent in the presence of an appropriate base. Examples of the base preferably include triethylamine or diisopropylethylamine. Examples of the solvent preferably include tetrahydrofuran. Examples of the carboxylic halide include carboxylic chloride, and preferably include pivaloyl chloride. Examples of the alkali metallized 4-alkyl-2-oxazolidinone include 4-alkyl-2-oxazolidinone lithium and 4-alkyl-2-oxazolidinone sodium, and preferably include 4-isopropyl-2-oxazolidinone lithium. The reaction time is normally 5 minutes to 48 hours, and is preferably 10 minutes to 24 hours. The reaction temperature is normally −78° C. to 100° C., and is preferably −78° C. to 50° C. This step may be carried out in accordance with the method described in J. Nat. Prod. 2003, 66, 183-199 and the like.

[F-3 Step]

Compound f4 may be produced by allowing compound f3 to react with various azidating reagents in an appropriate solvent in the presence of an appropriate base. Examples of the azidating reagent include sodium azide, trimethylsilyl azide and diphenylphosphoryl azide, and preferably include trimethylsilyl azide. Examples of the base preferably include potassium hexamethyldisilazide. Examples of the solvent preferably include tetrahydrofuran. The reaction time is normally 5 minutes to 72 hours, and is preferably 30 minutes to 24 hours. The reaction temperature is normally −78° C. to 200° C., and is preferably −78° C. to 75° C. This step may be carried out in accordance with the method described in J. Nat. Prod. 2003, 66, 183-199 and the like.

[F-4 Step]

Compound f5 may be produced from compound f4 in accordance with the method described in the above A-7 step.

[F-5 Step]

Compound f6 may be produced from compound f5 in accordance with the method described in the above A-8 step.

[F-6 Step]

Compound f7 may be produced from compound f6 by using an appropriate oxidizing agent in an appropriate solvent in the presence of an appropriate base. Examples of the base preferably include lithium hydroxide. Examples of the solvent preferably include methanol, tetrahydrofuran or water. The oxidizing agent may be selected from oxidizing agents used in usual organic synthesis reactions as approproate, and examples thereof preferably include hydrogen peroxide. The reaction time is normally 5 minutes to 72 hours, and is preferably 30 minutes to 24 hours. The reaction temperature is normally 0° C. to 200° C., and is preferably 0° C. to 60° C. This step may be carried out in accordance with the method described in J. Nat. Prod. 2003, 66, 183-199 and the like.

[F-7 Step]

Compound f8 may be produced by allowing compound f7 to react with various alkylating reagents in an appropriate solvent in the presence of an appropriate base. Examples of the alkylating reagent include alkyl halide, and preferably include alkyl iodide, alkyl bromide and alkyl chloride. Examples of the base preferably include sodium carbonate and potassium carbonate. Examples of the solvent preferably include N,N-dimethylformamide. The reaction time is normally 5 minutes to 48 hours, and is preferably 10 minutes to 2 hours. The reaction temperature is normally −78° C. to 100° C., and is preferably −10° C. to 25° C. This step may be carried out in accordance with the method described in Protective Groups in Organic Synthesis (authored by Theodora W. Greene, Peter G. M. Wuts, issued by John Wiley & Sons, Inc., 1999) and the like.

[F-8 Step]

Compound f9 may be produced from compound f8 in accordance with the method described in the above A-11 step.

85

[F-9 Step]

Compound f10 may be produced from compound f9 in accordance with the method described in the above A-12 step.

[F-10 Step]

Compound f12 may be produced from compound f10 and compound f11 in accordance with the method described in the above A-13 step.

[F-11 Step]

Compound f13 may be produced by hydrolyzing the ester of compound f12 in accordance with the method described in the above A-12 step.

[F-12 Step]

Compound f14 may be produced from compound f13 in accordance with the method described in the above A-15 step.

[F-13 Step]

Compound f15 may be produced from compound f14 in accordance with the method described in the above A-16 step.

[F-14 Step]

Compound F1 may be produced from compound f15 in accordance with the method described in the above A-17 step.

[F-15 Step]

Compound F2 may be produced from compound F1 in accordance with the method described in the above A-18 step.

Production Method L

Compound l6 is a production intermediate of the compound represented by formula (1), wherein Q is a group represented by formula (Q-1), formula (Qa-2), formula (Qa-3), formula (Qa-4), formula (Qa-5) or formula (Qa-6). Compound l6 may be produced by, for example, the following production method. In addition, compound Li may be produced from compound l6 in accordance with the production method described in A-16 step to A-18 step of Production Method A:

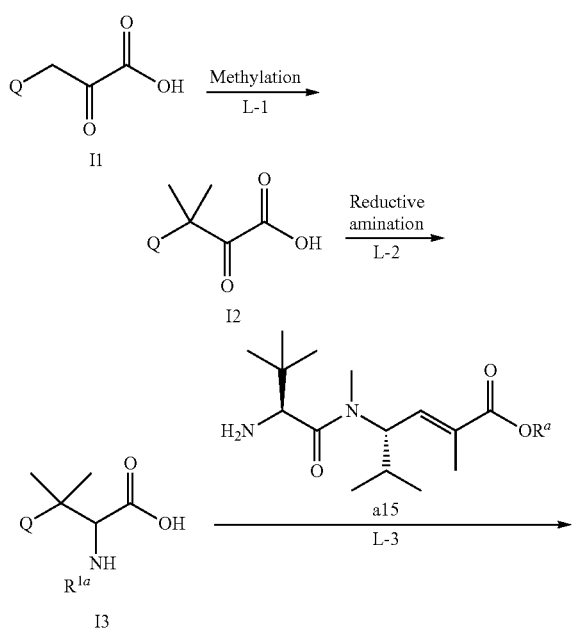

86

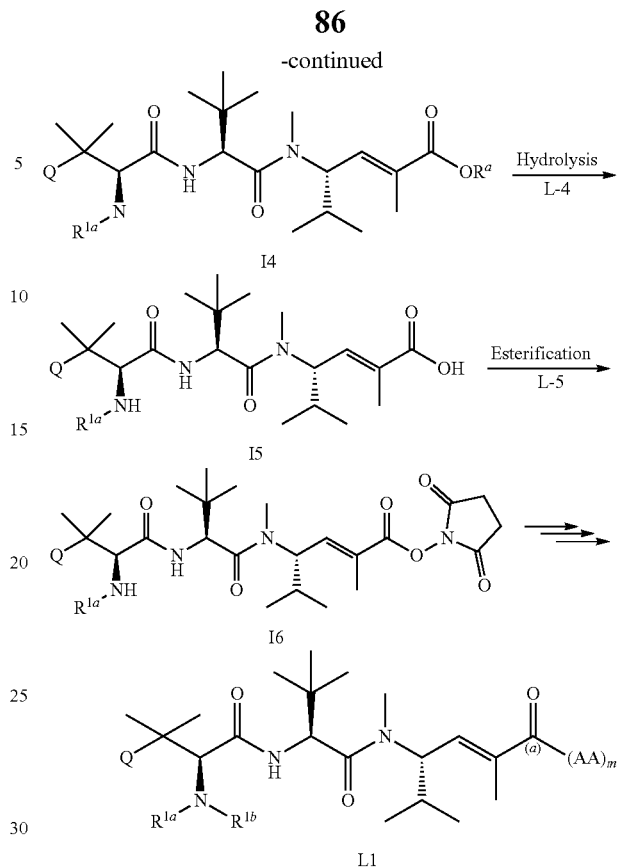

wherein, $R^{1a}$, $R^{1b}$, AA, m and (a) are as defined in item 1; and $R^a$ represents a $C_{1-6}$ alkyl group.

Compound l1 may be, for example, purchased as a commercial product. Compound a15 may be produced by, for example, the method described in Production Method A.

[L-1 Step]

Compound l2 may be produced in accordance with the method described in, for example, Bioorg. Med. Chem. Lett. 14 (2004) 5317-5322 and the like.

[L-2 Step]

Compound l3 may be produced in accordance with the method described in, for example, Bioorg. Med. Chem. Lett. 14 (2004) 5317-5322 and the like.

[L-3 Step]

Compound l4 may be produced in accordance with the method described in, for example, Bioorg. Med. Chem. Lett. 14 (2004) 5317-5322 and the like.

[L-4 Step]

Compound l5 may be produced from compound l4 in accordance with A-14 step of Production Method A.

[L-5 Step]

Compound l6 may be produced from compound l5 in accordance with A-15 step of Production Method A.

Production Method M

Compound m7 is a production intermediate of the compound represented by formula (1), wherein Q is a group represented by formula (Qa-7). Compound m7 may be produced by, for example, the following production method. In addition, compound Mal may be produced from compound m7 in accordance with the production method described in A-16 step to A-18 step of Production Method A:

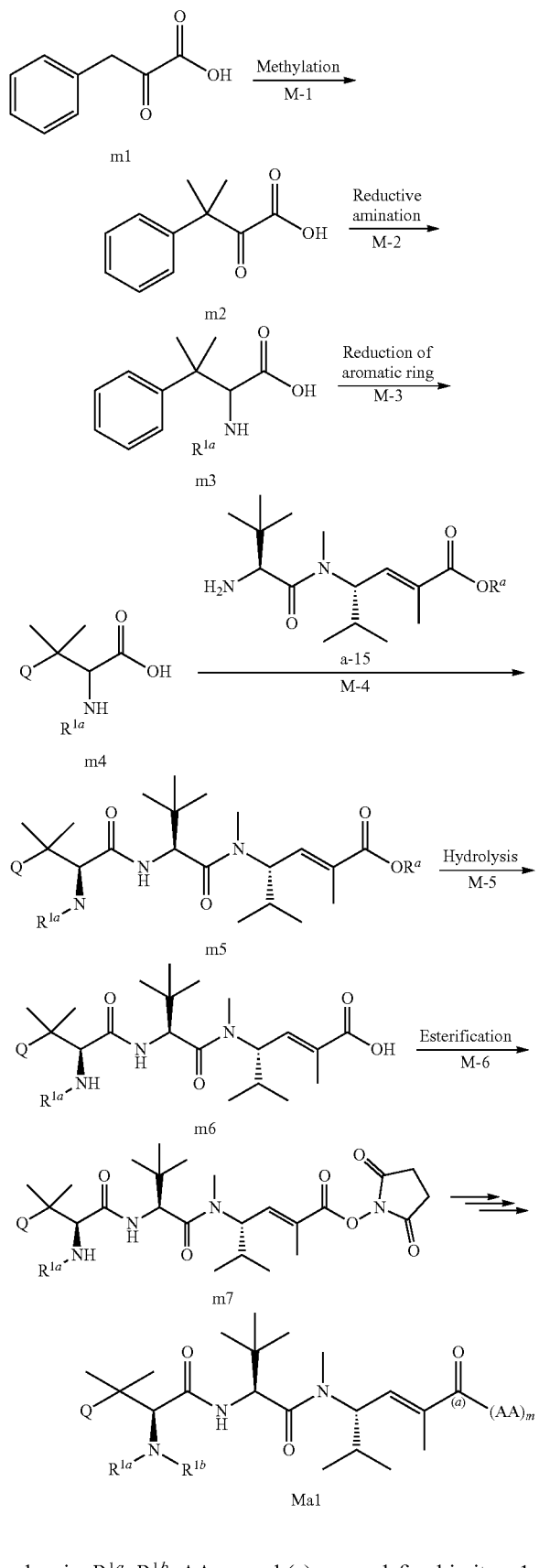

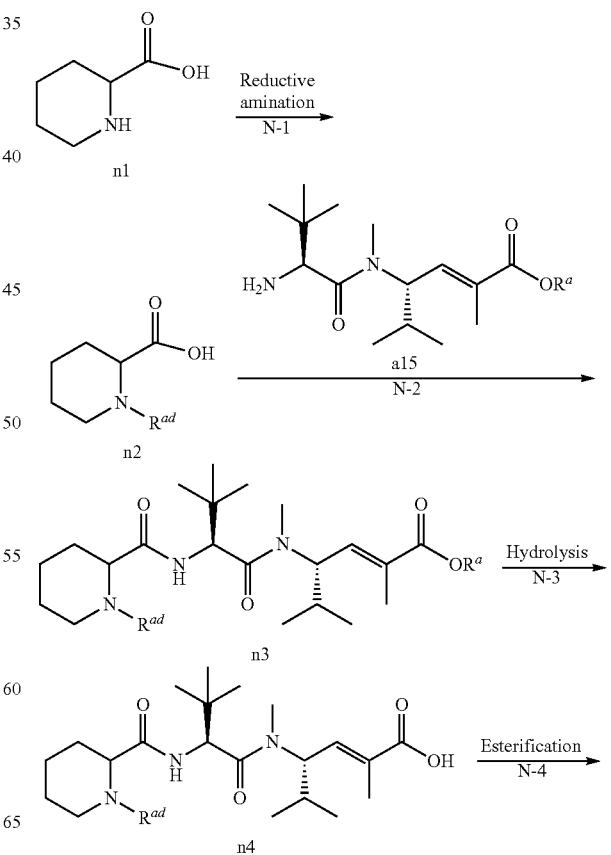

wherein, $R^{1a}$, $R^{1b}$, AA, m and (a) are as defined in item 1; and $R^a$ represents a $C_{1-6}$ alkyl group.

Compound m1 may be, for example, purchased as a commercial product. Compound a15 may be produced by, for example, the method described in Production Method A.

[M-1 Step]
Compound m2 may be produced in accordance with the method described in, for example, Bioorg. Med. Chem. Lett. 14 (2004) 5317-5322 and the like.

[M-2 Step]
Compound m3 may be produced in accordance with the method described in, for example, Bioorg. Med. Chem. Lett. 14 (2004) 5317-5322 and the like.

[M-3 Step]
Compound m4 may be produced in accordance with the method described in, for example, J. Med. Chem. 2004, 47, 4774-4786 and the like.

[M-4 Step]
Compound m5 may be produced in accordance with the method described in, for example, Bioorg. Med. Chem. Lett. 14 (2004) 5317-5322 and the like.

[M-5 Step]
Compound m6 may be produced from compound m5 in accordance with A-14 step of Production Method A.

[M-6 Step]
Compound m7 may be produced from compound m6 in accordance with A-15 step of Production Method A.

Production Method N

Compound n5 is a production intermediate of the compound represented by formula (1a). Compound n5 may be produced by, for example, the following production method. In addition, compound N1 may be produced from compound n5 in accordance with the production method described in A-16 step to A-17 step of Production Method A:

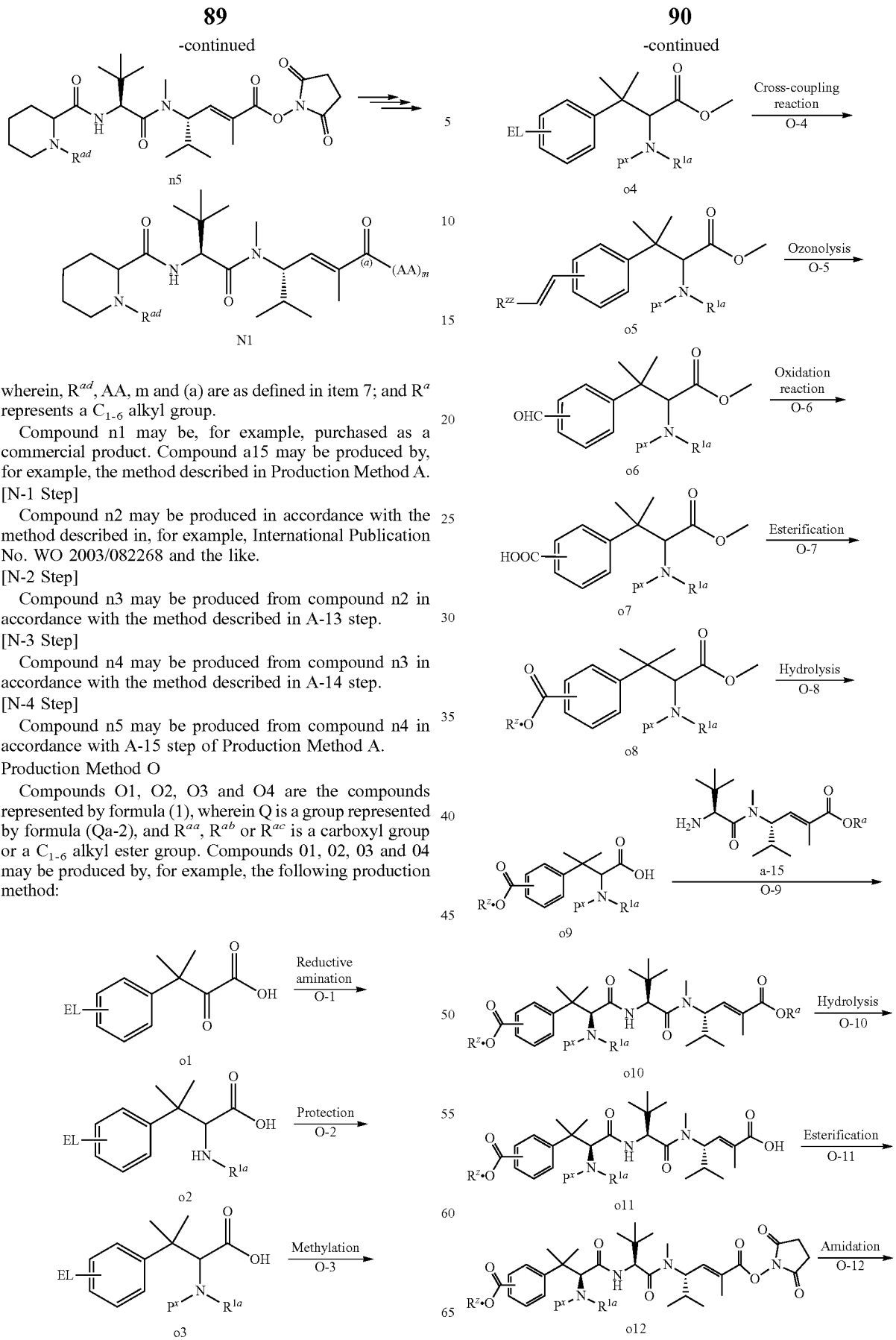

wherein, $R^{ad}$, AA, m and (a) are as defined in item 7; and $R^a$ represents a $C_{1-6}$ alkyl group.

Compound n1 may be, for example, purchased as a commercial product. Compound a15 may be produced by, for example, the method described in Production Method A.

[N-1 Step]

Compound n2 may be produced in accordance with the method described in, for example, International Publication No. WO 2003/082268 and the like.

[N-2 Step]

Compound n3 may be produced from compound n2 in accordance with the method described in A-13 step.

[N-3 Step]

Compound n4 may be produced from compound n3 in accordance with the method described in A-14 step.

[N-4 Step]

Compound n5 may be produced from compound n4 in accordance with A-15 step of Production Method A.

Production Method O

Compounds O1, O2, O3 and O4 are the compounds represented by formula (1), wherein Q is a group represented by formula (Qa-2), and $R^{aa}$, $R^{ab}$ or $R^{ac}$ is a carboxyl group or a $C_{1-6}$ alkyl ester group. Compounds 01, 02, 03 and 04 may be produced by, for example, the following production method:

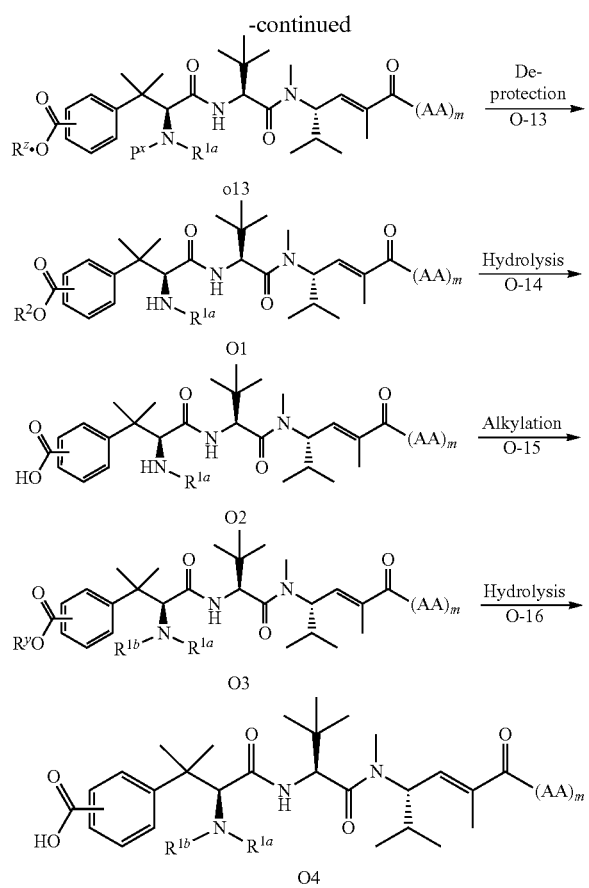

wherein, AA, $R^{1a}$, $R^{1b}$ and m are as defined in item 1; EL represents a chlorine atom, a bromine atom, an iodine atom, a trifluoromethylsulfonyl group or a tosyl group; $R^{zz}$ represents a hydrogen atom or —COO$R^a$; $P^x$ represents a protecting group for the amino group; and $R^a$, $R^y$ and $R^z$ represent a $C_{1-6}$ alkyl group.

Compound o1 may be produced by the methods described in, for example, International Publication No. WO 2004/026293, International Publication No. WO 2016/123582 and the like, or may be purchased as a commercial product. Compound a15 may be produced by, for example, the method described in Production Method A.

[O-1 Step]

Compound o2 may be produced from compound o1 in accordance with the methods described in, for example, International Publication No. WO 2004/026293; Bioorg. Med. Chem. Lett. 14 (2004) 5317-5322; and the like.

[O-2 Step]

Compound o3 may be produced from compound o2 in accordance with the method described in the above A-8 step.

[O-3 Step]

Compound o4 may be produced from compound o3 in accordance with the method described in the above A-11 step.

[O-4 Step]

Compound o5 may be produced from compound o4 by the method described in, for example, International Publication No. WO 2004/026293 and the like.

[O-5 Step]

Compound o6 may be produced from compound o5 by the method described in, for example, International Publication No. WO 2004/026293 and the like.

[O-6 Step]

Compound o7 may be produced from compound o6 by the method described in, for example, WO 2004/026293 A2.

[O-7 Step]

Compound o8 may be produced by esterifying the carboxyl group of compound o7. This step may be carried out in accordance with the method described in Protective Groups in Organic Synthesis (authored by Theodora W. Greene, Peter G. M. Wuts, issued by John Wiley & Sons, Inc., 1999) and the like.

[O-8 Step]

Compound o9 may be produced from compound o8 in accordance with the method described in the above A-12 step.

[O-9 Step]

Compound o10 may be produced from compound o9 in accordance with the method described in the above A-13 step.

[O-10 Step]

Compound o11 may be produced from compound o10 in accordance with the method described in the above A-14 step.

[O-11 Step]

Compound o12 may be produced from compound o11 in accordance with the method described in the above A-15 step.

[O-12 Step]

Compound o13 may be produced from compound o12 in accordance with the method described in the above A-16 step.

[O-13 Step]

Compound O1 may be produced from compound o13 by deprotecting the protecting group $P^x$. This step may be carried out in accordance with the method described in Protective Groups in Organic Synthesis (authored by Theodora W. Greene, Peter G. M. Wuts, issued by John Wiley & Sons, Inc., 1999) and the like. In addition, when $(AA)_m$ has an ester or a protected amino group, hydrolysis of the ester and deprotection of the protecting group for the amino group may also be carried out as necessary after the condensation reaction, in accordance with the method described in Protective Groups in Organic Synthesis (authored by Theodora W. Greene, Peter G. M. Wuts, issued by John Wiley & Sons, Inc., 1999) and the like.

[O-14 Step]

Compound O2 may be produced from compound O1 in accordance with the method described in Protective Groups in Organic Synthesis (authored by Theodora W. Greene, Peter G. M. Wuts, issued by John Wiley & Sons, Inc., 1999) and the like.

[O-15 Step]

Compound O3 may be produced from compound O2 in accordance with the methods described in the above A-11 step and the above A-18 step.

[O-16 Step]

Compound O4 may be produced from compound O3 in accordance with the method described in the above O-13 step.

Production Method P

Compound P1 and compound P2 are the compounds represented by formula (1), wherein Q is a group represented by formula (Qa-2), and $R^{aa}$, $R^{ab}$ or $R^{ac}$ is a hydroxy group. Compound P1 and compound P2 may be produced by, for example, the following production method:

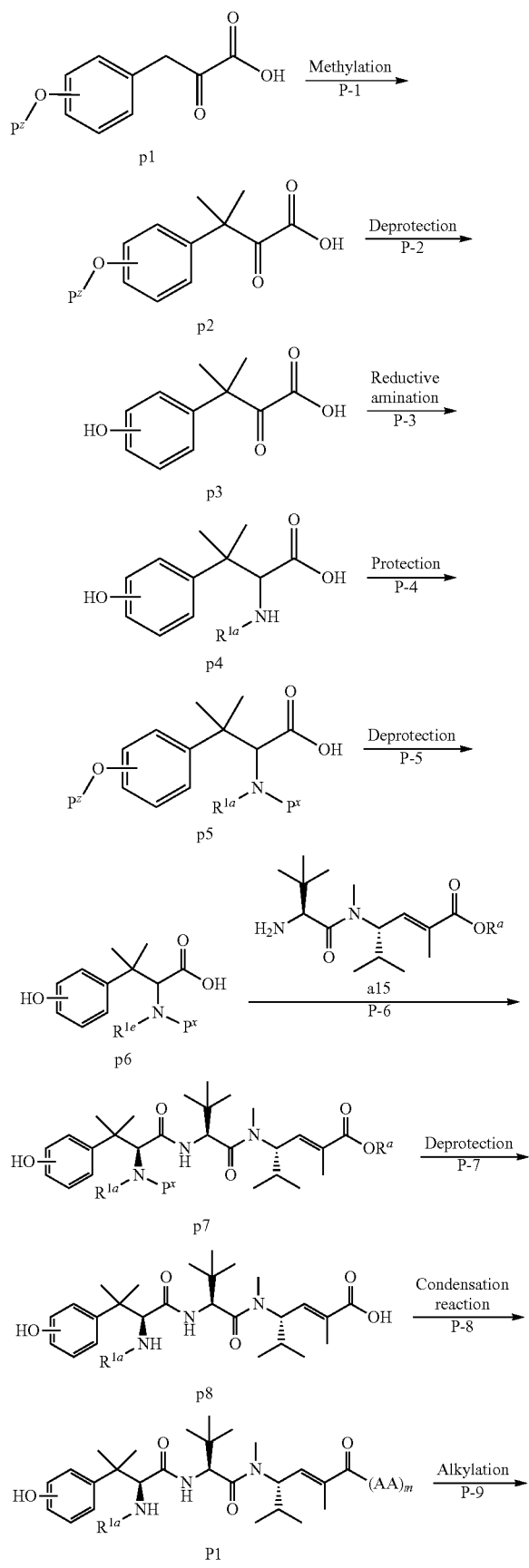

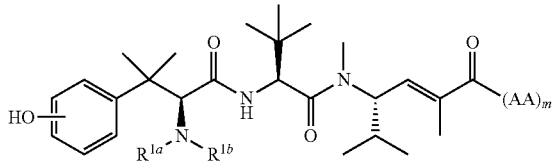

P2 wherein, AA, m, $R^{1a}$ and $R^{1b}$ are as defined in item 1; $P^x$ represents a protecting group for the amino group; $P^z$ represents a protecting group for the hydroxy group; and $R^a$ represents a $C_{1-6}$ alkyl group.

Compound p1 may be, for example, purchased as a commercial product. Compound a15 may be produced by, for example, the method described in Production Method A.

[P-1 Step]

Compound p2 may be produced from compound p1 in accordance with the method described in, for example, International Publication No. WO 2004/026293 and the like.

[P-2 Step]

Compound p3 may be produced from compound p2 by deprotecting the protecting group $P^z$. This step may be carried out in accordance with the method described in Protective Groups in Organic Synthesis (authored by Theodora W. Greene, Peter G. M. Wuts, issued by John Wiley & Sons, Inc., 1999) and the like.

[P-3 Step]

Compound p4 may be produced from compound p3 in accordance with the method described in, for example, International Publication No. WO 2004/026293 and the like.

[P-4 Step]

Compound p5 may be produced by protecting the amino group and the hydroxy group of compound p4 with protecting group $P^x$ and protecting group $P^z$, respectively. This step may be carried out in accordance with the method described in Protective Groups in Organic Synthesis (authored by Theodora W. Greene, Peter G. M. Wuts, issued by John Wiley & Sons, Inc., 1999) and the like.

[P-5 Step]

Compound p6 may be produced from compound p5 by deprotecting the protecting group $P^z$. This step may be carried out in accordance with the method described in Protective Groups in Organic Synthesis (authored by Theodora W. Greene, Peter G. M. Wuts, issued by John Wiley & Sons, Inc., 1999), or Tetrahedron Lett. 45 (2004) 495-499 and the like.

[P-6 Step]

Compound p7 may be produced from compound p6 in accordance with the method described in A-13 step.

[P-7 Step]

Compound p8 may be produced from compound p7 in accordance with the method described in the above A-18 step.

[P-8 Step]

Compound P1 may be produced from compound p8 by carrying out condensation in accordance with the method described in the above A-13 step. In addition, when $(AA)_m$ has an ester or a protected amino group, hydrolysis of the ester and deprotection of the protecting group for the amino group may also be carried out as necessary after the condensation reaction, in accordance with the method described in Protective Groups in Organic Synthesis (authored by Theodora W. Greene, Peter G. M. Wuts, issued by John Wiley & Sons, Inc., 1999) and the like.

[P-9 Step]

Compound P2 may be produced from compound P1 in accordance with the method described in the above A-18 step.

Production Method T

Compound T1 and compound T2 are the compounds represented by formula (1), wherein Q is a group represented by formula (Qa-2) and $R^{aa}$, $R^{ab}$ or $R^{ac}$ is an amino group. Compound T1 and compound T2 may be produced by, for example, the following production method:

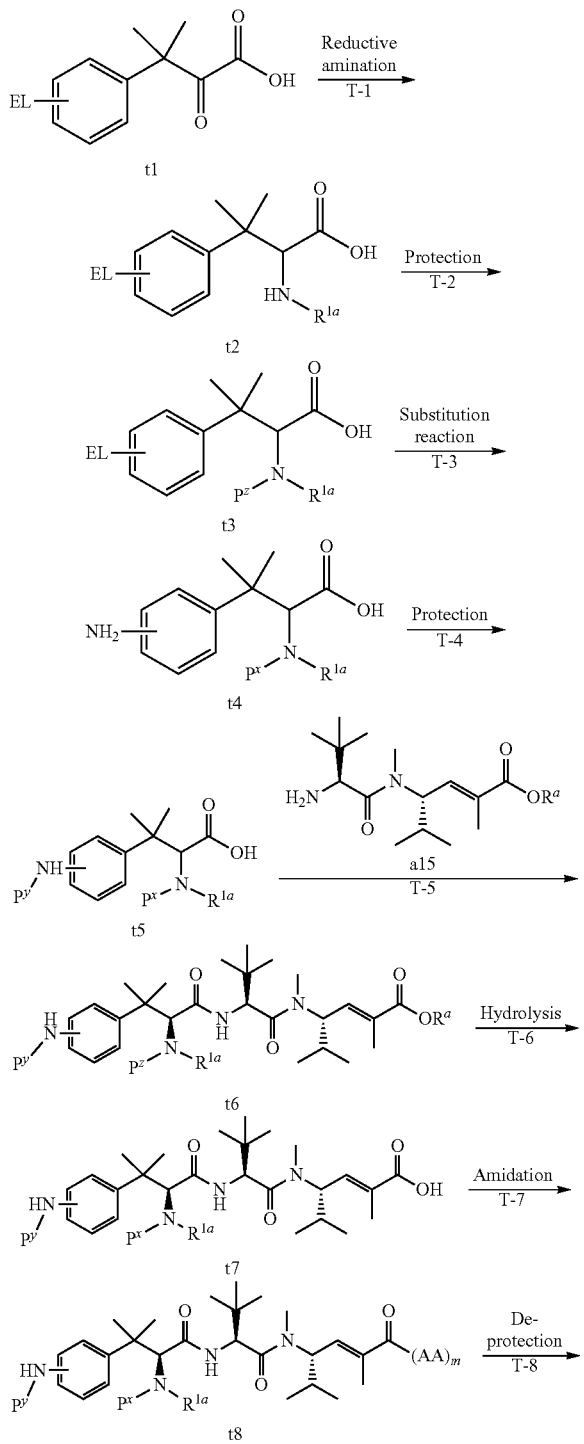

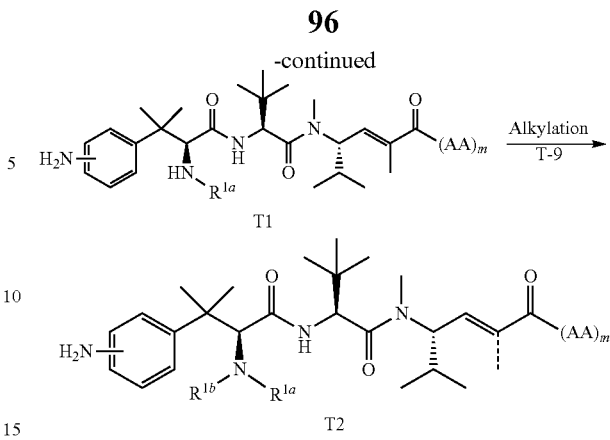

wherein, AA, m, $R^{1a}$ and $R^{1b}$ are as defined in item 1; EL represents a chlorine atom, a bromine atom, an iodine atom, a trifluoromethylsulfonyl group or a tosyl group; $P^x$ and $P^y$ represent a protecting group for the amino group; and $R^a$ represents a $C_{1-6}$ alkyl group.

Compound t1 may be produced by the methods described in, for example, WO 2004026293 A2, WO 2016123582 A1 and the like, or may be purchased as a commercial product. Compound a15 may be produced by, for example, the method described in Production Method A.

[T-1 Step]

Compound t2 may be produced from compound t1 in accordance with the methods described in, for example, International Publication No. WO 2004/026293; Bioorg. Med. Chem. Lett. 14 (2004) 5317-5322; and the like.

[T-2 Step]

Compound t3 may be produced from compound t2 in accordance with the method described in the above A-8 step.

[T-3 Step]

Compound t4 may be produced from compound t3 by the method described in, for example, International Publication No. WO 2016/123582 and the like.

[T-4 Step]

Compound t5 may be produced by protecting the amino group of compound t4 with protecting group $P^y$. This step may be carried out in accordance with the method described in Protective Groups in Organic Synthesis (authored by Theodora W. Greene, Peter G. M. Wuts, issued by John Wiley & Sons, Inc., 1999) and the like.

[T-5 Step]

Compound t6 may be produced from compound t5 in accordance with the method described in the above A-13 step.

[T-6 Step]

Compound t7 may be produced from compound t6 in accordance with the method described in the above A-14 step.

[T-7 Step]

Compound t8 may be produced from compound t7 in accordance with the method described in the above A-13 step.

[T-8 Step]

Compound T1 may be produced by deprotecting the protecting groups $P^x$ and $P^y$ of compound t8. This step may be carried out in accordance with the methods described in Protective Groups in Organic Synthesis (authored by Theodora W. Greene, Peter G. M. Wuts, issued by John Wiley & Sons, Inc., 1999), Tetrahedron Lett. 45 (2004) 495-499 and the like. In addition, when $(AA)_m$ has an ester or a protected amino group, hydrolysis of the ester and deprotection of the protecting group for the amino group may also be carried out in the present deprotecting step, as necessary.

[T-9 Step]

Compound T2 may be produced from compound T1 in accordance with the method described in the above A-18 step.

Production Method W

W1, which is a compound represented by formula (1a), wherein $R^{ad}$ is a hydrogen atom, may be produced by, for example, the following production method:

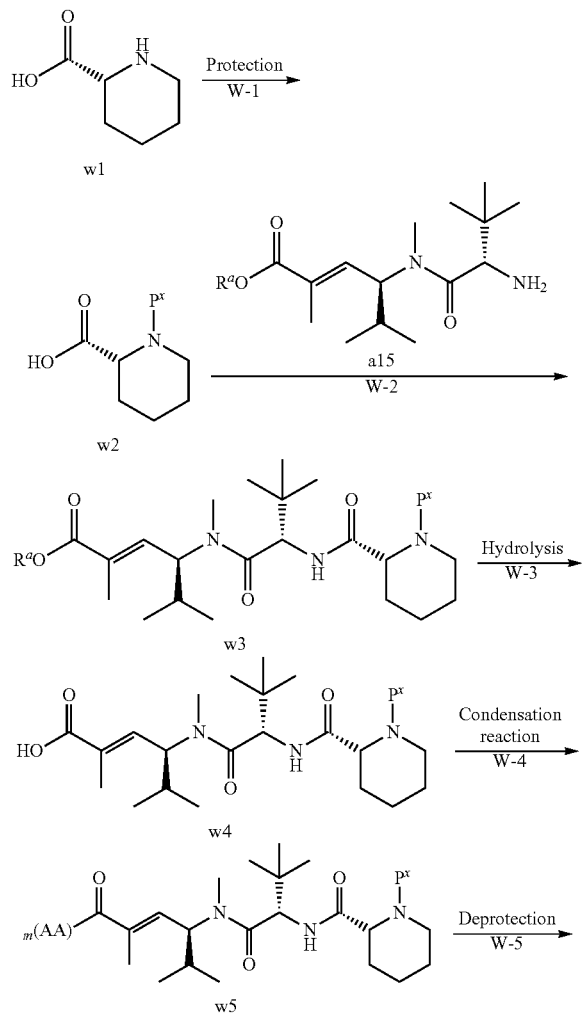

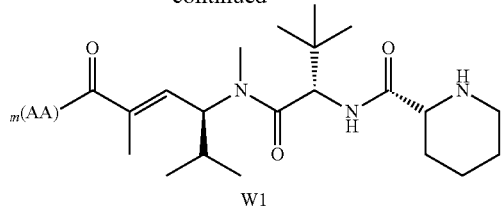

wherein, AA and m are as defined in item 7; $P^x$ represents a protecting group for the amino group; and $R^a$ represents a $C_{1-6}$ alkyl group.

Compound w1 may be, for example, purchased as a commercial product. Compound a15 may be produced by, for example, the method described in Production Method A.

[W-1 Step]

Compound w2 may be produced by protecting the amino group of compound w1 with protecting group $P^x$. This step may be carried out in accordance with the method described in Protective Groups in Organic Synthesis (authored by Theodora W. Greene, Peter G. M. Wuts, issued by John Wiley & Sons, Inc., 1999) and the like.

[W-2 Step]

Compound w3 may be produced from compound w2 in accordance with the method described in the above A-13 step.

[W-3 Step]

Compound w4 may be produced from compound w3 in accordance with the method described in the above A-14 step.

[W-4 Step]

Compound w5 may be produced from compound w4 in accordance with the method described in the above A-13 step.

[W-5 Step]

Compound W1 may be produced by deprotecting the protecting groups $P^x$ of compound w5. This step may be carried out in accordance with the methods described in Protective Groups in Organic Synthesis (authored by Theodora W. Greene, Peter G. M. Wuts, issued by John Wiley & Sons, Inc., 1999), Tetrahedron Lett. 45 (2004) 495-499 and the like. In addition, when $(AA)_m$ has an ester or a protected amino group, hydrolysis of the ester and deprotection of the protecting group for the amino group may also be carried out in the present deprotecting step, as necessary.

The compound represented by formula (3-1) may be produced by, for example, the following production method MA, MB, MC, MD, ME, MF, MG, MH or MI:

Production Method MA

When Y is a group represented by formula (Y-1); Y' is a carbonyl group; and Z is a group represented by formula (Z-1), the compound represented by formula (3-1) may be produced by, for example, the following production method:

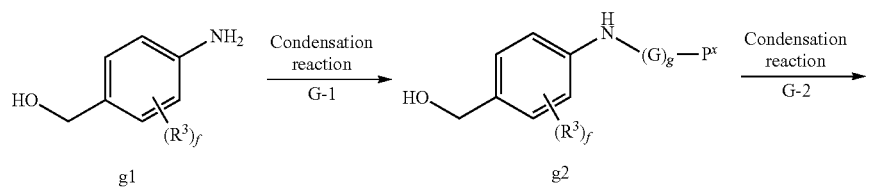

-continued
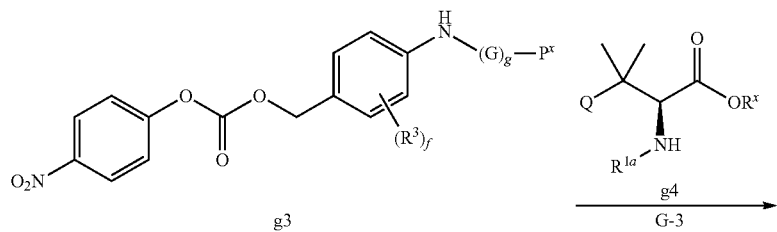
g3
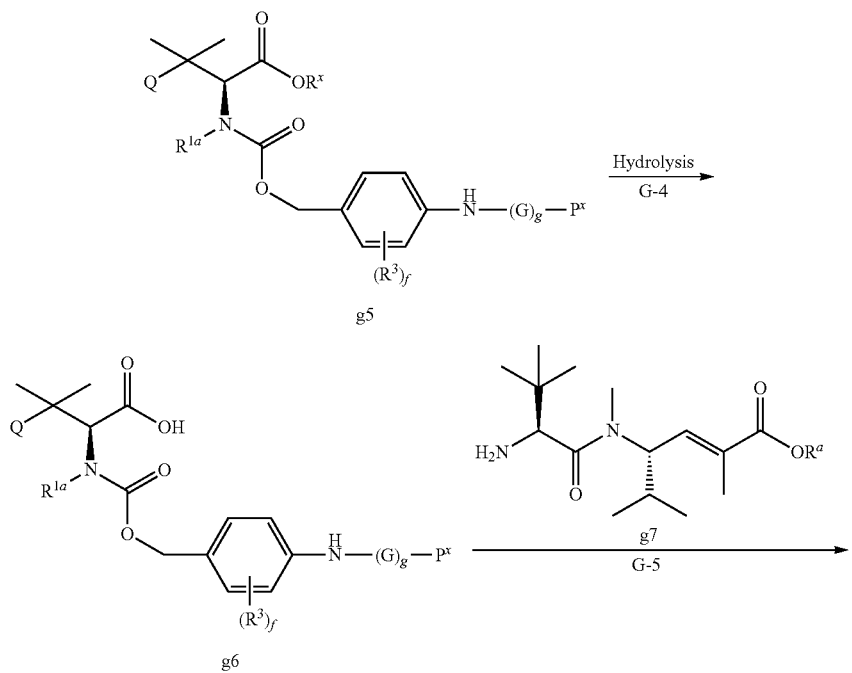
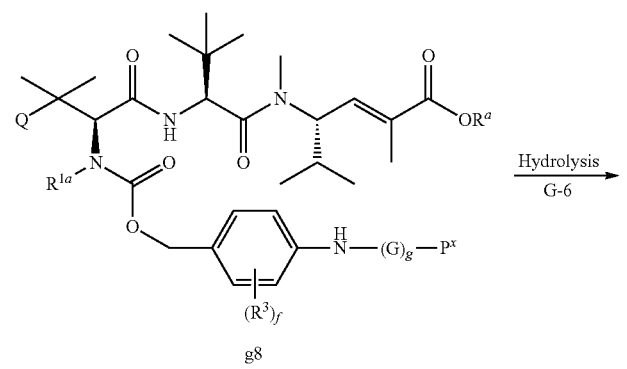
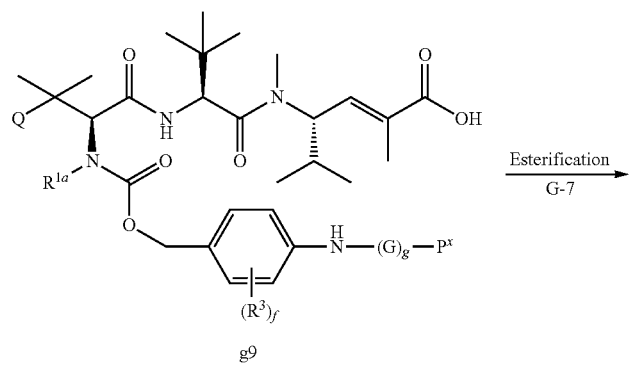

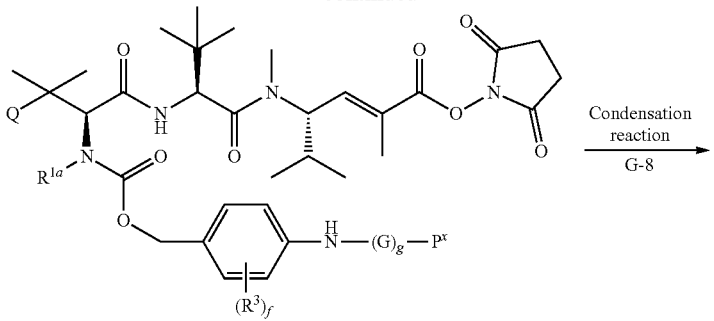

g10

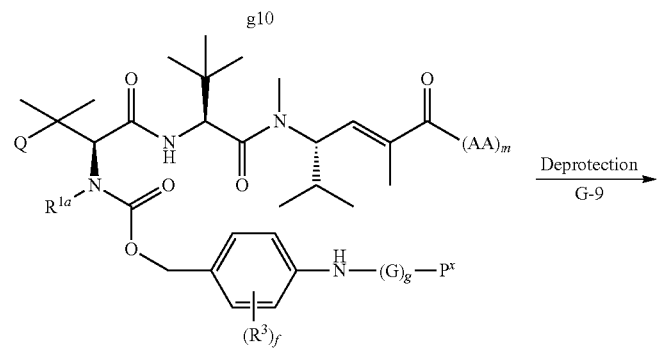

g11

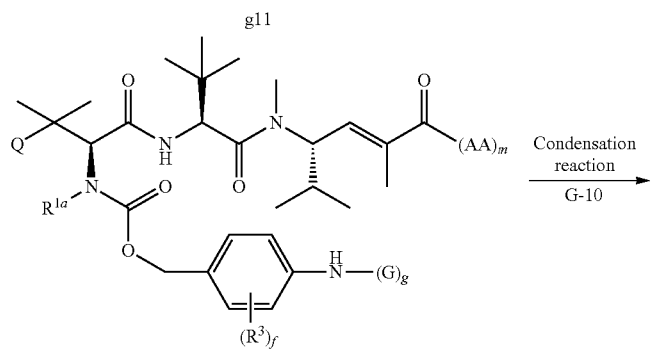

g12

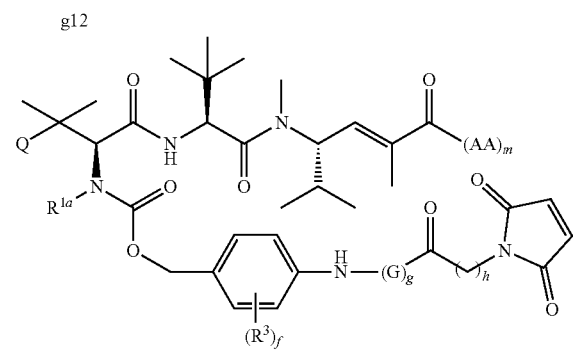

G1 wherein, Q, $R^{1a}$, AA, m, $R^3$, f, G, g and h are as defined in item 30; and $R^a$, $R^x$ and $P^x$ are as defined above.

Compound g1 may be, for example, purchased as a commercial product. Compound g4 may be produced by the methods described in, for example, J. Nat. Prod. 2003, 66, 183-199; J. Med. Chem., 2004, 47, 4774-4786: and the like, or may be purchased as a commercial product. Compound g7 may be produced by the method described in, for example, Tetrahedron Lett., 1997, 38, 317-320 and the like, or may be purchased as a commercial product.

[G-1 Step]

Compound g2 may be produced by condensing compound g1 and an amino acid or a peptide which is a raw material for group -(G)$_g$, using various condensing agents in an appropriate solvent in the presence of an appropriate base. As the condensing agent, various condensing agents used in usual organic synthesis reactions may be used, and examples thereof preferably include 1-ethoxycarbonyl-2-ethoxy-1,2-dihydroquinoline (EEDQ). In addition, a carbonyl activating reagent such as 1-hydroxybenzotriazole may be used together as necessary, in order to improve efficiency of the condensation reaction. Examples of the base preferably include diisopropylethylamine. Examples of the solvent preferably include dichloromethane. The reaction time is normally 5 minutes to 72 hours, and is preferably 30 minutes to 24 hours. The reaction temperature is normally −78° C. to 200° C., and is preferably 0° C. to 50° C. This step may be carried out in accordance with the method described in Bioconjugate Chem. 2002, 13, 855-869 and the like.

[G-2 Step]

Compound g3 may be produced by allowing compound g2 to react with various p-nitrophenyl carbonate esterifying reagents in an appropriate solvent in the presence of an appropriate base. Examples of the p-nitrophenyl carbonate esterifying reagent include 4-nitrophenyl chloroformate and bis(4-nitrophenyl)carbonate, and preferably include bis(4-nitrophenyl)carbonate. Examples of the base preferably include N,N-diisopropylethylamine. Examples of the solvent preferably include tetrahydrofuran, dichloromethane and N,N-dimethylformamide. The reaction time is normally 5 minutes to 72 hours, and is preferably 1 hour to 24 hours. The reaction temperature is normally −78° C. to 200° C., and is preferably 10° C. to 50° C. This step may be carried out in accordance with the methods described in Bioconjugate Chem. 2002, 13, 855-869, Bioconjugate Chem. 2015, 26, 650-659 and the like.

[G-3 Step]

Compound g5 may be produced by allowing compound g3 and compound g4 to react in an appropriate solvent in the presence of an appropriate base. In addition, a carbonyl activating reagent such as 1-hydroxy-7-benzotriazole may be used together as necessary, in order to improve efficiency of the condensation reaction. Examples of the base preferably include triethylamine, diisopropylethylamine and 2,6-lutidine. Examples of the solvent preferably include N,N-dimethylformamide. The reaction time is normally 5 minutes to 72 hours, and is preferably 1 hour to 24 hours. The reaction temperature is normally −78° C. to 200° C., and is preferably 10° C. to 50° C. This step may be carried out in accordance with the methods described in Bioconjugate Chem. 2002, 13, 855-869, Bioconjugate Chem. 2015, 26, 650-659 and the like.

[G-4 Step]

Compound g6 may be produced by hydrolyzing the ester of compound g5, in accordance with the method described in the above A-12 step.

[G-5 Step]

Compound g8 may be produced from compound g6 and compound g7 in accordance with the method described in the above A-13 step.

[G-6 Step]

Compound g9 may be produced by hydrolyzing the ester of compound g8, in accordance with the method described in the above A-12 step.

[G-7 Step]

Compound g10 may be produced from compound g9 in accordance with the method described in the above A-15 step.

[G-8 Step]

Compound g11 may be produced from compound g10 in accordance with the method described in the above A-16 step.

[G-9 Step]

Compound g12 may be produced from compound g11 in accordance with the method described in the above A-17 step.

[G-10 Step]

Compound G1 may be produced from compound g12 in accordance with the method described in the above A-13 step or A-16 step.

Production Method MB

When Y is a group represented by formula (Y-1); Y' is a carbonyl group; and Z is a group represented by formula (Z-1), the compound represented by formula (3-2) may be produced by, for example, the following production method:

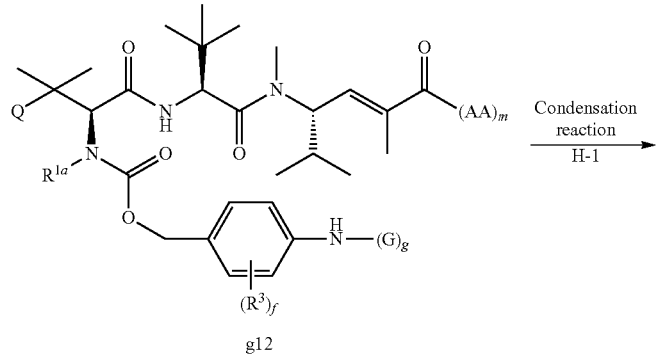

g12

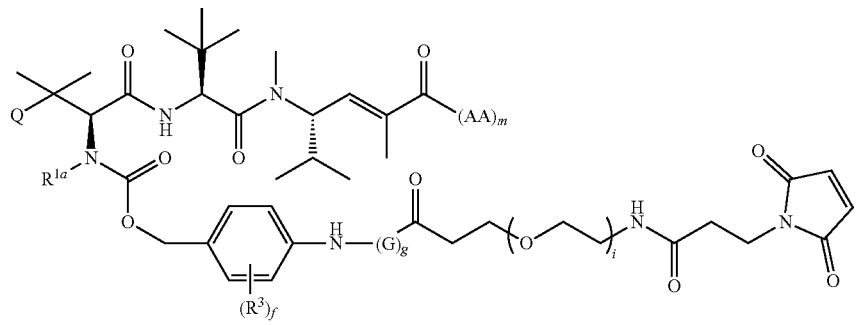

H1 wherein, Q, $R^{1a}$, AA, m, $R^3$, f, G, g and i are as defined in item 30.

[H-1 Step]

Compound H1 may be produced from compound g12 in accordance with the method described in the above A-13 step or A-16 step.

Production Method MC

When Y is a group represented by formula (Y-1); Y' is a single bond; and Z is a group represented by formula (Z-2), formula (Z-3) or formula (Z-4), the compound represented by formula (3-1) may be produced by, for example, the following production method:

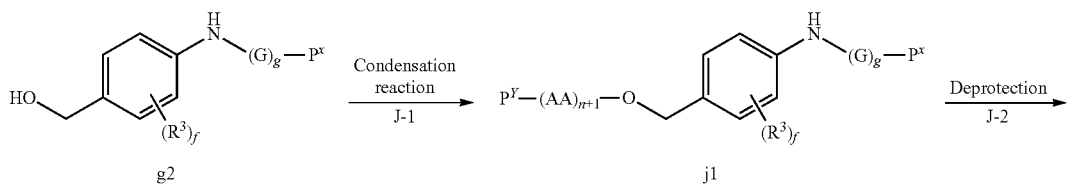

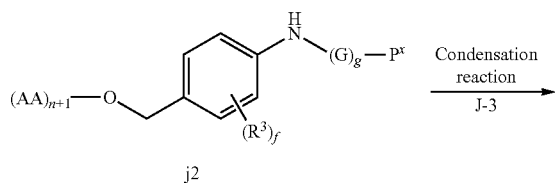

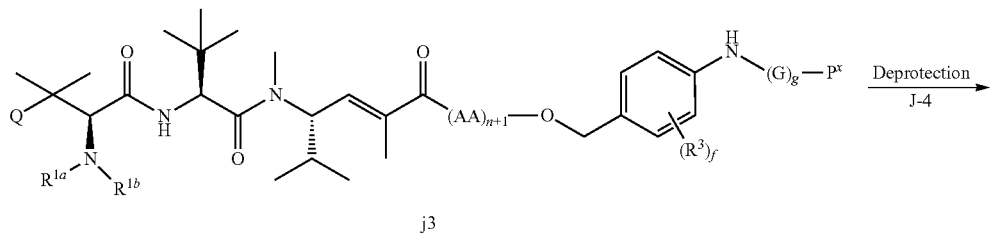

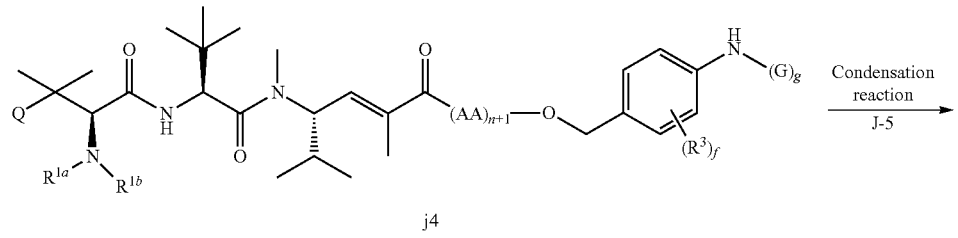

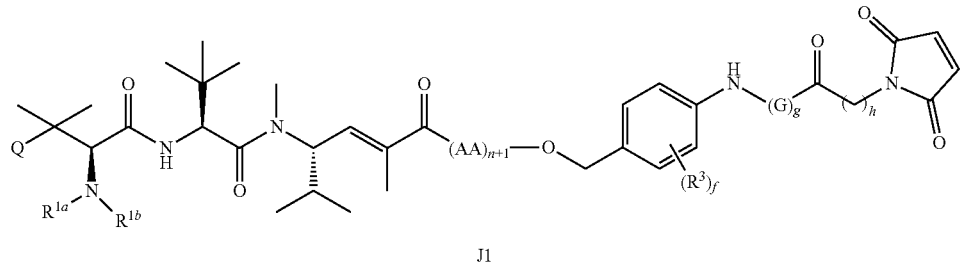

wherein, Q, $R^{1a}$, $R^{1b}$, AA, n, h, G, g, $R^3$ and f are as defined in item 30; $P^X$ is as defined above; and $P^Y$ represents a protecting group for the amino group.

[J-1 Step]

Compound j1 may be produced by subjecting compound g2 and an amino acid derivative to condensation reaction in an appropriate solvent in the presence of an appropriate sulfonylating reagent and imidazole. Examples of the sulfonylating reagent include methylsulfonyl chloride and p-toluenesulfonyl chloride, and preferably include p-toluenesulfonyl chloride. Examples of the imidazole include imidazole and 1-methylimidazole, and preferably include 1-methylimidazole. Examples of the solvent preferably include acetonitrile. The reaction time is normally 5 minutes to 72 hours, and is preferably 30 minutes to 24 hours. The reaction temperature is normally −78° C. to 200° C., and is preferably 0° C. to 50° C.

[J-2 Step]

Compound j2 may be produced from compound j1 in accordance with the method described in the above A-17 step.

[J-3 Step]

Compound j3 may be produced from compound j2 in accordance with the method described in the above A-13 step or A-16 step.

[J-4 Step]

Compound j4 may be produced from compound j3 in accordance with the method described in the above A-17 step.

[J-5 Step]

Compound J1 may be produced from compound j4 in accordance with the method described in the above A-13 step or A-16 step.

Production Method MD

When Y is a group represented by formula (Y-1); Y' is a carbonyl group; and Z is a group represented by formula (Z-5) or formula (Z-6), the compound represented by formula (3-1) may be produced by, for example, the following production method:

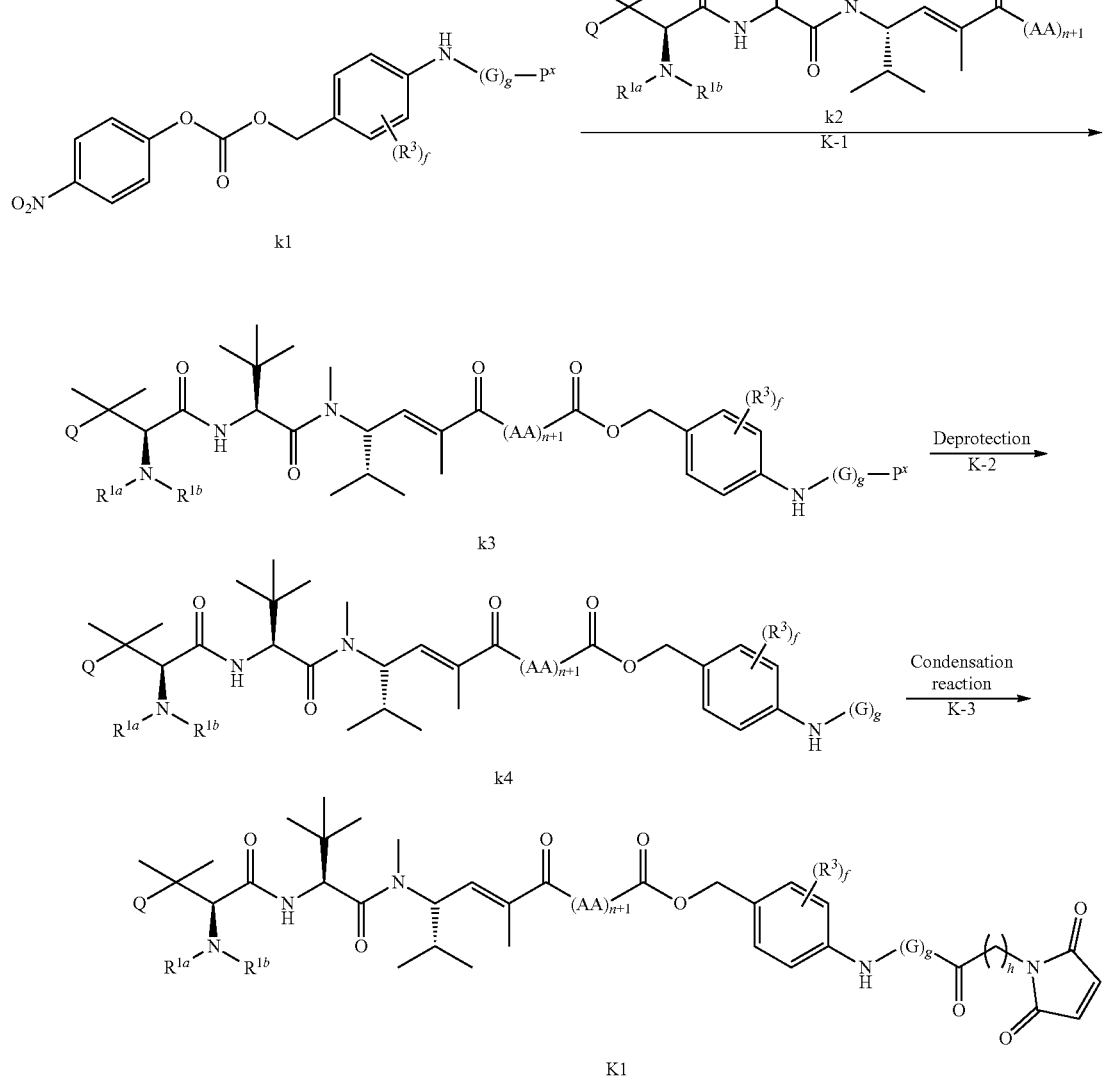

wherein, Q, $R^{1a}$, $R^{1b}$ and AA, n, h, G, g, $R^3$ and f are as defined in item 30; and $P^x$ is as defined above.

[K-1 Step]

Compound k3 may be produced from compound k1 and compound k2 in accordance with the method described in the above G-3 step.

[K-2 Step]

Compound k4 may be produced from compound k3 in accordance with the method described in the above A-17 step.

[K-3 Step]

Compound K1 may be produced from compound k4 in accordance with the method described in the above A-13 step or A-16 step.

Production Method ME

When Y is a group represented by formula (Y-1); Y' is a single bond; and Z is a group represented by formula (Za-1), formula (Za-2) or formula (Za-3), the compound represented by formula (3-1) may be produced by, for example, the following production method:

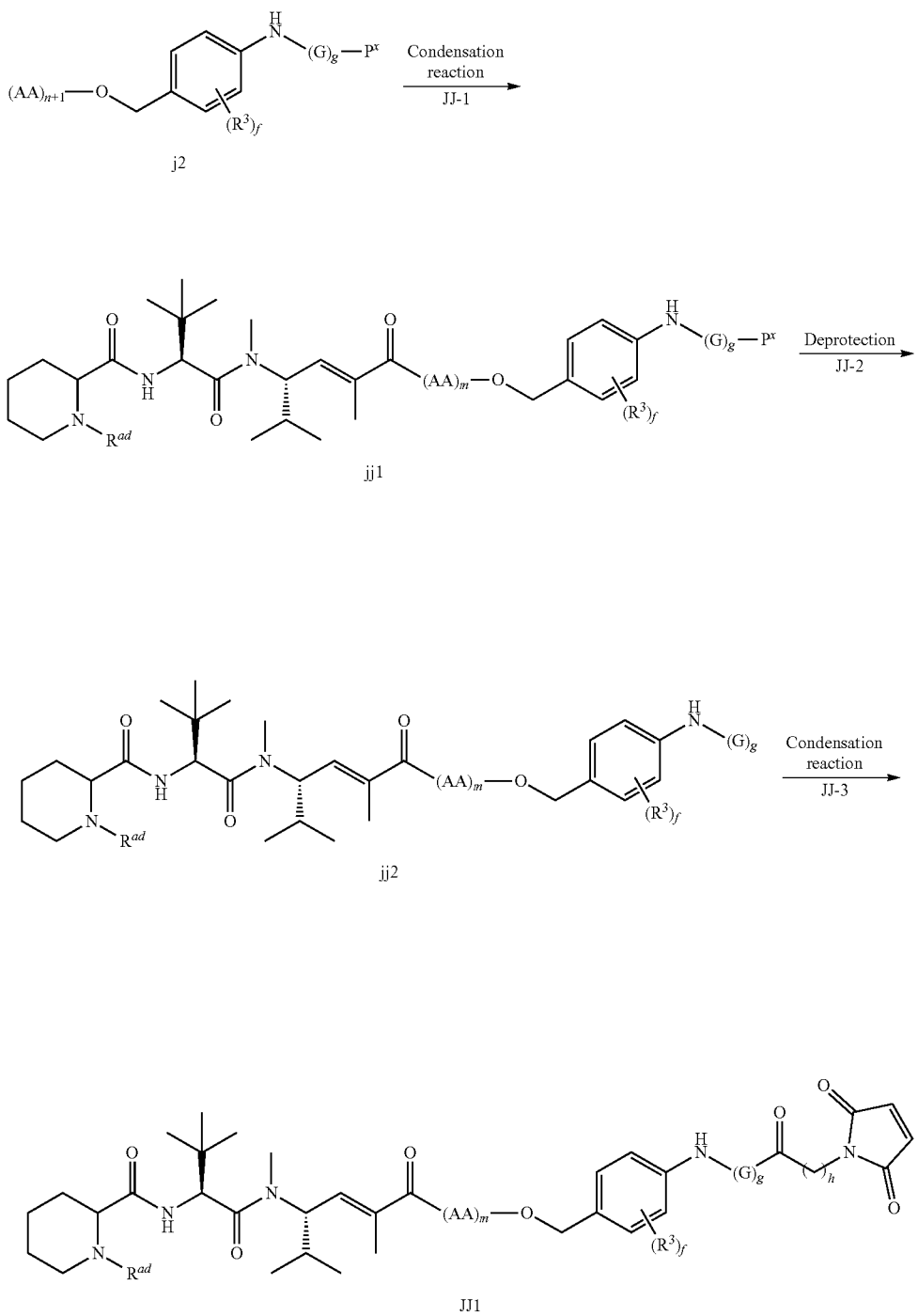

wherein, $R^{ad}$, AA, m, h, G, g, $R^3$ and f are as defined in item 29; and $P^x$ is as defined above.

[JJ-1 Step]

Compound jj1 may be produced from compound j2 in accordance with the method described in the above A-13 step or A-16 step.

[JJ-2 Step]

Compound jj2 may be produced from compound jj1 in accordance with the method described in the above A-17 step.

[JJ-3 Step]

Compound JJ1 may be produced from compound jj2 in accordance with the method described in the above A-13 step or A-16 step.

Production Method MF

When Y is a group represented by formula (Y-1); Y' is a carbonyl group; and Z is a group represented by formula (Za-4) or formula (Za-5), the compound represented by formula (3-1) may be produced by, for example, the following production method:

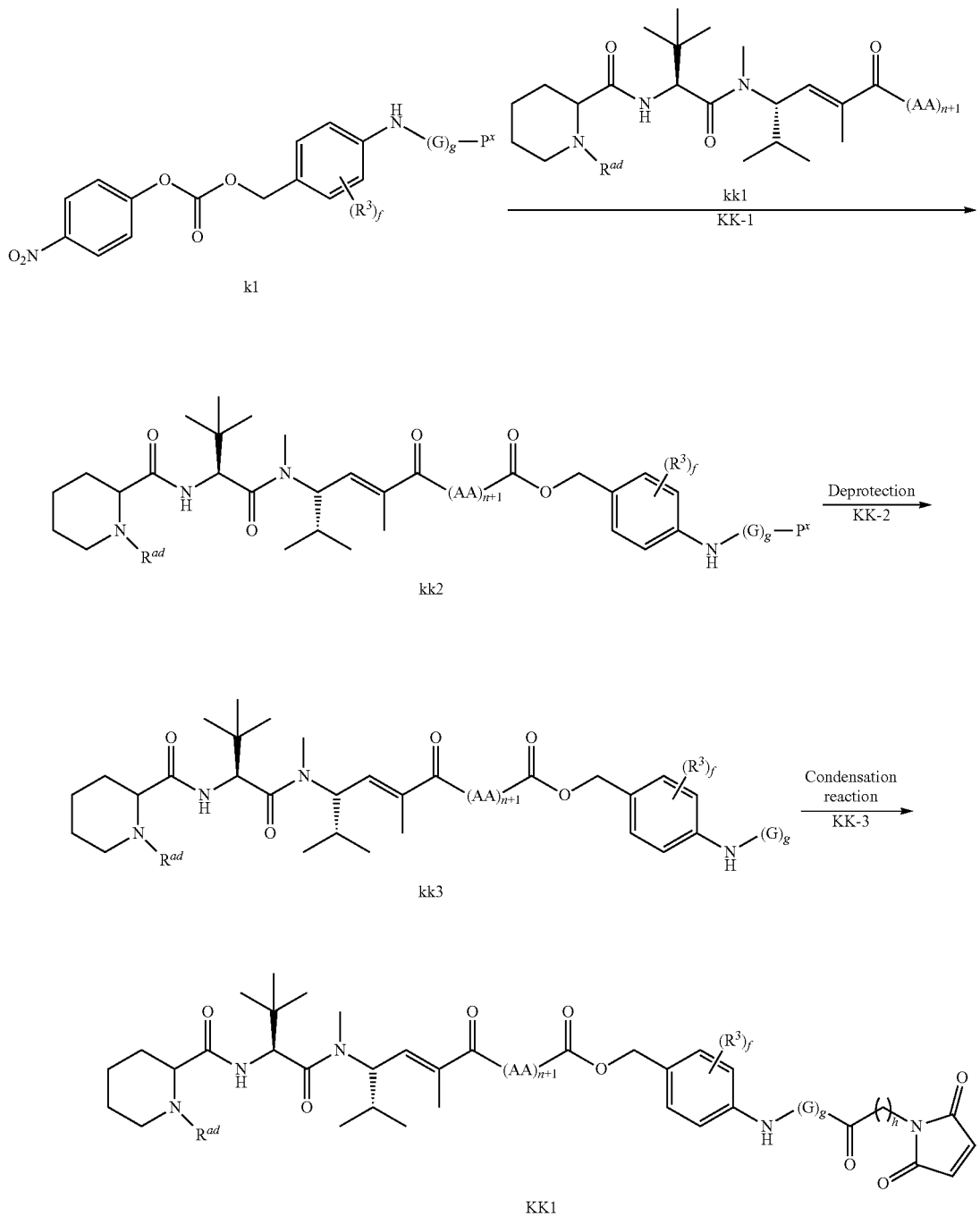

wherein, $R^{ad}$, AA, n, h, G, g, $R^3$ and f are as defined in item 29; and $P^x$ is as defined above.

[KK-1 Step]

Compound kk2 may be produced from compound k1 and compound kk1 in accordance with the method described in the above G-3 step.

[KK-2 Step]

Compound kk3 may be produced from compound kk2 in accordance with the method described in the above A-17 step.

[KK-3 Step]

Compound KK1 may be produced from compound kk3 in accordance with the method described in the above A-13 step or A-16 step.

Production Method MG

When Y is a group represented by formula (Y-1); Y' is a carbonyl group; and Z is a group represented by formula (Za-6), the compound represented by formula (3-1) may be produced by, for example, the following production method:

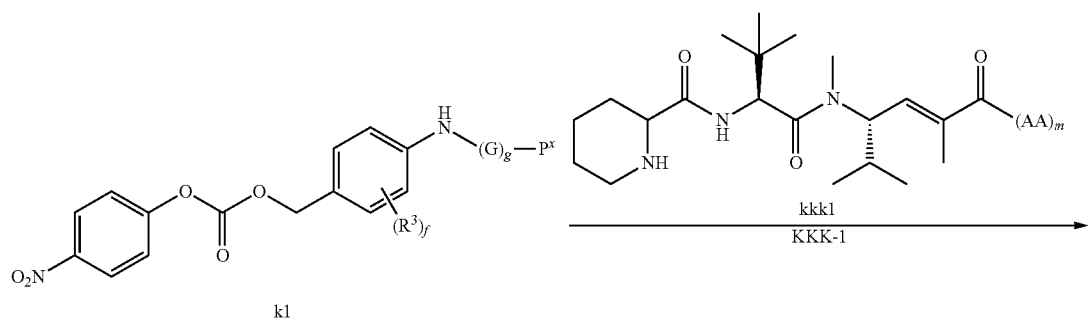

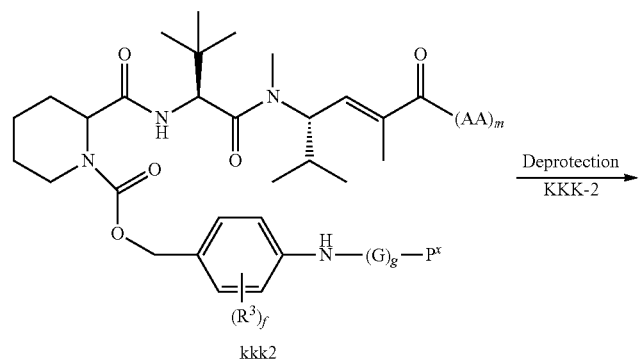

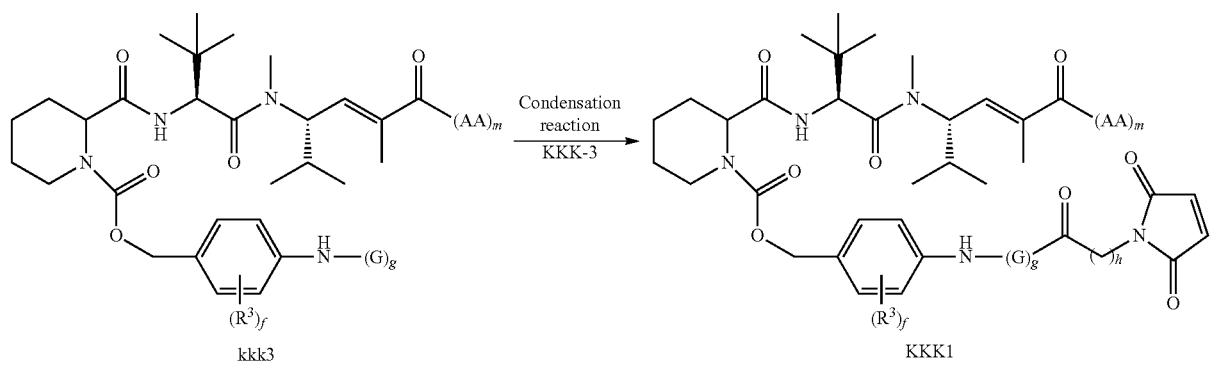

wherein, AA, m, h, G, g, R³ and f are as defined in item 29; and P^x is as defined above.

[KKK-1 Step]
Compound kkk2 may be produced from compound k1 and compound kkk1 in accordance with the method described in the above G-3 step.

[KKK-2 Step]
Compound kkk3 may be produced from compound kkk2 in accordance with the method described in the above A-17 step.

[KKK-3 Step]
Compound KKK1 may be produced from compound kkk3 in accordance with the method described in the above A-13 step or A-16 step.

Production Method MH
When Y is a group represented by formula (Y-1); Y' is a single bond; and Z is a group represented by formula (Za-7) or formula (Za-8), the compound represented by formula (3-1) may be produced by, for example, the following production method:

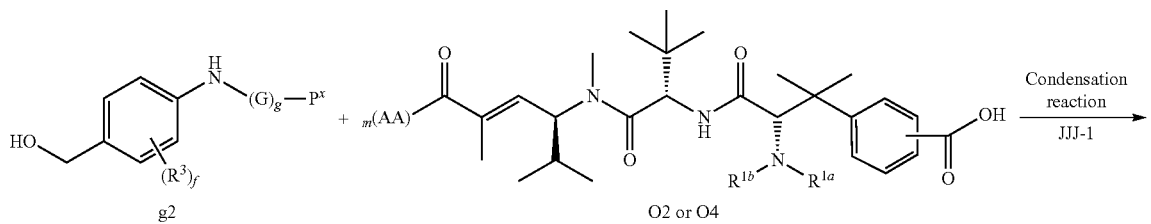

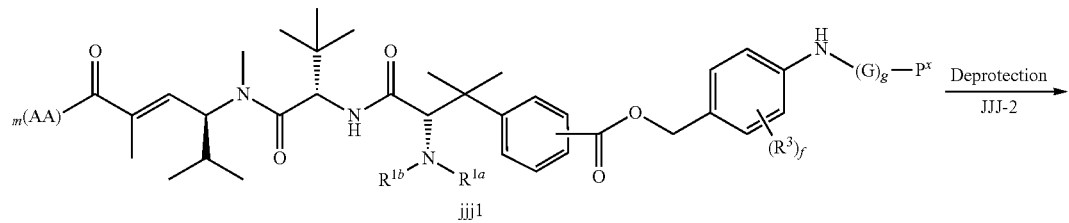

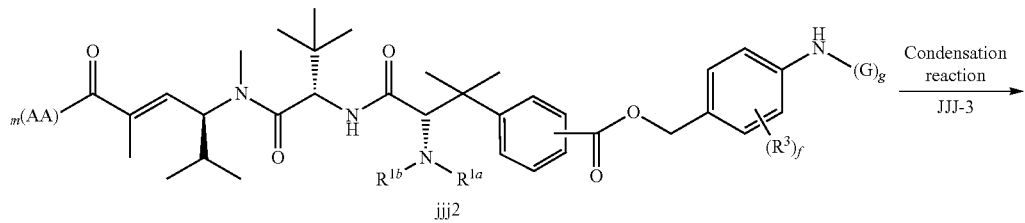

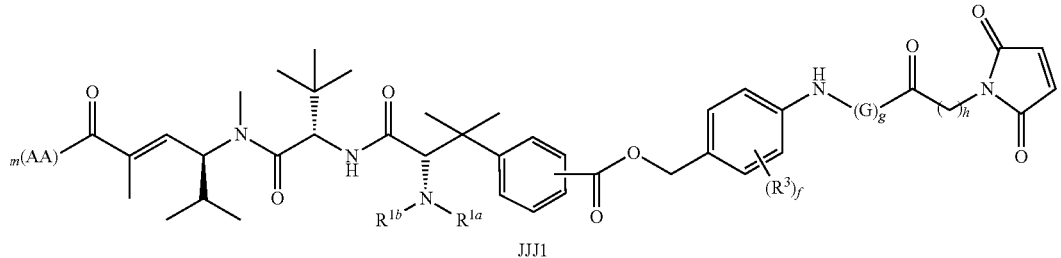

wherein, $R^{1a}$, $R^{1b}$, AA, m, h, G, g, $R^3$ and f are as defined in item 29; and $P^x$ is as defined above.

[JJJ-1 Step]

Compound jjj1 may be produced from compound g2 and compound O2 or compound O4 in accordance with the method described in the above J-1 step.

[JJJ-2 Step]

Compound jjj2 may be produced from compound jjj1 in accordance with the method described in the above A-17 step.

[JJJ-3 Step]

Compound JJJ1 may be produced from compound jjj2 in accordance with the method described in the above A-13 step or A-16 step.

Production Method MI

When Y is a group represented by formula (Y-1); Y' is a carbonyl group; and Z is a group represented by formula (Za-9) or formula (Za-10), the compound represented by formula (3-1) may be produced by, for example, the following production method:

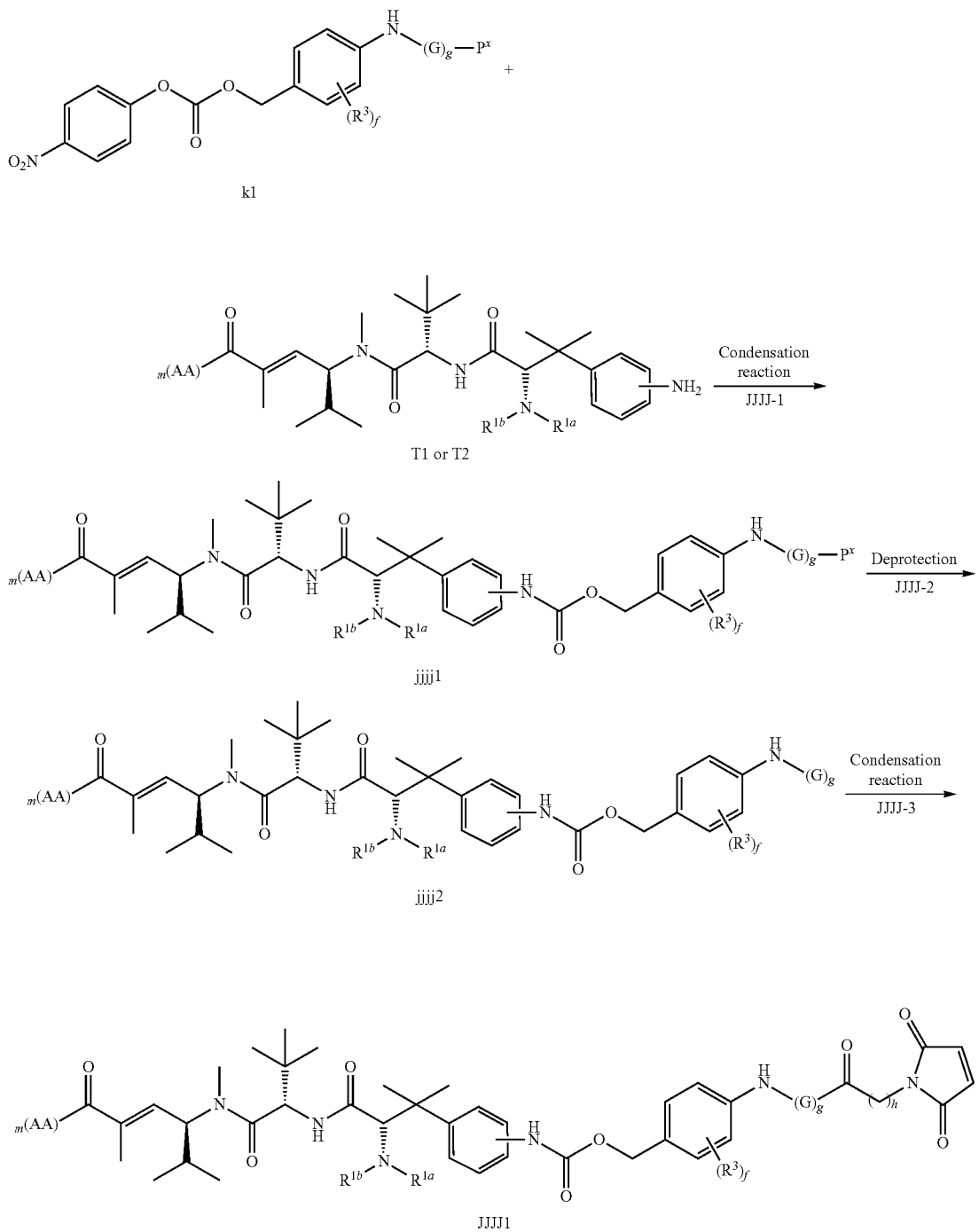

wherein, $R^{1a}$, $R^{1b}$ and AA, m, h, G, g, $R^3$ and f are as defined in item 29; and $P^X$ is as defined above.
[JJJJ-1 Step]
Compound jjjj1 may be produced from compound k1 and compound T1 or compound T2 in accordance with the method described in the above G-3 step.
[JJJJ-2 Step]
Compound jjjj2 may be produced from compound jjjj1 in accordance with the method described in the above A-17 step.
[JJJJ-3 Step]
Compound JJJJ1 may be produced from compound jjjj2 in accordance with the method described in the above A-13 step or A-16 step.

The antibody-drug conjugate of the present invention represented by formula (2) may be produced by, for example, the following production method AA:
Production Method AA

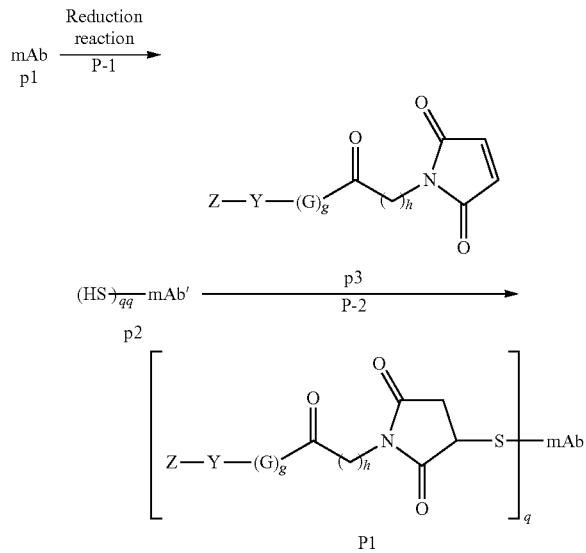

wherein, mAb, q, h, G, g, Y and Z are as defined in item 14; mAb' represents mAb in which a disulfide bond is reduced; and qq represents an integer of 1 to 8.
[P-1 Step]
Compound p2 may be produced by allowing compound p1 to react with an appropriate disulfide reducing agent in an appropriate buffer solution. Examples of the disulfide reducing agent include dithiothreitol, mercaptoethanol and tris(2-carboxyethyl)phosphine; and preferably include tris(2-carboxyethyl)phosphine. Examples of the buffer solution include Tris-HCl, PBS, HEPES, acetate, borate, phosphate and carbonate buffers, and preferably include Tris-HCl and PBS. The pH upon reaction is normally 2 to 12, and is preferably 4 to 9. The reaction time is normally 5 minutes to 24 hours, and is preferably 5 minutes to 5 hours. The reaction temperature is normally −10° C. to 50° C., and is preferably 0° C. to 40° C.
[P-2 Step]
Compound P1 may be produced by allowing compound p2 and compound p3 to react in an appropriate buffer solution. Examples of the buffer solution include Tris-HCl, PBS, HEPES, acetate, borate, phosphate and carbonate buffers, and preferably include Tris-HCl and PBS. The pH upon reaction is normally 2 to 12, and is preferably 4 to 9. The reaction time is normally 5 minutes to 72 hours, and is preferably 30 minutes to 24 hours. The reaction temperature is normally −78° C. to 200° C., and is preferably 0° C. to 25° C.

Appropriate bases used in each step of the above production methods should be selected as appropriate depending on reactions, types of raw material compounds and the like, and examples thereof include alkali bicarbonates such as sodium bicarbonate and potassium bicarbonate; alkali carbonates such as sodium carbonate and potassium carbonate; metal hydrides such as sodium hydride and potassium hydride; alkali metal hydroxides such as sodium hydroxide and potassium hydroxide; alkali metal alkoxides such as sodium methoxide and sodium t-butoxide; organometallic bases such as butyllithium and lithium diisopropylamide; and organic bases such as triethylamine, diisopropylethylamine, pyridine, 4-dimethylaminopyridine (DMAP) and 1,8-diazabicyclo[5.4.0]-7-undecene (DBU).

Appropriate solvents used in each step of the above production methods should be selected as appropriate depending on reactions, types of raw material compounds and the like, and examples thereof include alcohols such as methanol, ethanol and isopropanol; ketones such as acetone and methyl ketone; halogenated hydrocarbons such as methylene chloride and chloroform; ethers such as tetrahydrofuran (THF) and dioxane; aromatic hydrocarbons such as toluene and benzene; aliphatic hydrocarbons such as hexane and heptane; esters such as ethyl acetate and propyl acetate; amides such as N,N-dimethylformamide (DMF) and N-methyl-2-pyrrolidone; sulfoxides such as dimethylsulfoxide (DMSO); nitriles such as acetonitrile; distilled water; and the like, and one of these solvents may be used singly, or two or more of them may be mixed for use. In addition, depending on the type of reactions, organic bases such as triethylamine, diisopropylethylamine and pyridine may be used as the solvent.

The hemiasterlin derivative, antibody-drug conjugate and ADC intermediate according to the present invention may be separated and purified by methods known to a person having ordinary skill in the art. Examples thereof include extraction, partitioning, reprecipitation, column chromatography (for example, silica gel column chromatography, ion exchange column chromatography or preparative liquid chromatography) or recrystallization.

As the recrystallization solvent, for example, alcohol solvents such as methanol, ethanol and 2-propanol; ether solvents such as diethyl ether; ester solvents such as ethyl acetate; aromatic hydrocarbon solvents such as benzene and toluene; ketone solvents such as acetone; halogenated solvents such as dichloromethane and chloroform; hydrocarbon solvents such as hexane; aprotic solvents such as dimethylformamide acetonitrile; water; or mixed solvents thereof may be used.

As other purification method, the method described in The Experimental Chemistry (edited by The Chemical Society of Japan, Maruzen), vol. 1 and the like may be used. In addition, determination of the molecular structure of the hemiasterlin derivative, antibody-drug conjugate and ADC intermediate according to the present invention may be readily carried out by spectroscopic approaches such as nuclear magnetic resonance, infrared absorption technique and circular dichroism spectroscopy, or mass spectrometry, with reference to the structure derived from their respective raw material compounds.

In addition, intermediates or final products in the above production methods may also be derivatized into other compounds included in the present invention by converting their functional groups as appropriate, in particular, by extending various side chains using an amino group, hydroxy group, carbonyl group, halogen atom or the like as the basis, and upon this, by carrying out protection and deprotection of the above functional groups as necessary. The conversion of functional groups and extension of side chains may be carried out by general methods that are conventionally performed (for example, see Comprehensive Organic Transformations, R. C. Larock, John Wiley & Sons Inc. (1999) and the like).

The hemiasterlin derivative, antibody-drug conjugate and ADC intermediate according to the present invention may have asymmetry or may have a substituent having an asymmetric carbon, and optical isomers are present in such compounds. Optical isomers may be produced in accordance with conventional methods. Examples of the production method include a method of using a raw material having an asymmetric point or a method of introducing asymmetry in the midway stage. For example, in the case of optical isomers, optical isomers may be obtained by using optically active raw materials or by carrying out optical resolution or the like at an appropriate stage during the production process. When the hemiasterlin derivative according to the present invention or an intermediate thereof has a basic functional group, examples of the optical resolution method include a diastereomer method, in which a salt is formed using an optically active acid (for example, monocarboxylic acids such as mandelic acid, N-benzyloxyalanine and lactic acid; dicarboxylic acids such as tartaric acid, o-diisopropylidene tartaric acid and malic acid; sulfonic acids such as camphorsulfonic acid and bromocamphorsulfonic acid) in an inert solvent (for example, an alcohol solvent such as methanol, ethanol and 2-propanol; an ether solvent such as diethyl ether; an ester solvent such as ethyl acetate; a hydrocarbon solvent such as toluene; an aprotic solvent such as acetonitrile; or a mixed solvent of two or more selected from the above solvents). When the hemiasterlin derivative, antibody-drug conjugate or ADC intermediate according to the present invention has an acidic functional group such as a carboxyl group, optical resolution can also be carried out by using an optically active amine (for example, an organic amine such as 1-phenylethylamine, quinine, quinidine, cinchonidine, cinchonine and strychnine) to form a salt.

Examples of the temperature at which the salt is formed include the range from −50° C. to the boiling point of the solvent, preferably include the range from 0° C. to the boiling point, and more preferably include the range from room temperature to the boiling point of the solvent. In order to improve optical purity, it is desirable that the temperature be once raised to the vicinity of the boiling point of the solvent. Upon separating the precipitated salt by filtration, the yield may be improved by cooling as necessary. Examples of the amount of the optically active acid or amine to be used include the range of about 0.5 to about 2.0 equivalent to the substrate, and preferably include the range around 1 equivalent. As necessary, an optically active salt with high purity can be obtained by recrystallizing a crystal in an inert solvent (for example, an alcohol solvent such as methanol, ethanol and 2-propanol; an ether solvent such as diethyl ether; an ester solvent such as ethyl acetate; a hydrocarbon solvent such as toluene; an aprotic solvent such as acetonitrile; or a mixed solvent of two or more selected from the above solvents). In addition, a free form may be obtained by treating a salt that has been optically resolved with an acid or base through a conventional method, as necessary.

Among the raw materials or intermediates in the production methods described above, those, for which the production method was not described, are either commercially available compounds or may be synthesized from commercially available compounds by methods known to a person having ordinary skill in the art or methods equivalent thereto.

The antibody-drug conjugate according to the present invention, and a pharmaceutical composition containing the antibody-drug conjugate or a pharmaceutically acceptable salt thereof is useful as an anticancer agent (for example, a therapeutic drug for breast cancer, gastric cancer, lung cancer, liver cancer, cervical cancer, large bowel cancer, rectal cancer, colon cancer, glioma, lymphoma, ovarian cancer, pancreatic cancer, prostate cancer, renal cancer, urothelial cancer, skin cancer, thyroid cancer, bladder cancer, head and neck cancer, endometrial cancer, mesothelioma, melanoma, multiple myeloma, leukemia and the like).

The antibody-drug conjugate according to the present invention may be administered through oral administration or parenteral administration, directly or as a formulation using an appropriate dosage form. Examples of the dosage form include, but are not limited to, liquid, suspension and injection. These formulations are produced by known methods, using a pharmaceutically acceptable additive.

For the additive, excipients, disintegrating agents, binders, glidants, lubricants, coating agents, solubilizing agents, solubilization aids, thickening agents, dispersing agents, stabilizers, sweetening agents, perfumes and the like may be used depending on purposes. Specifically, examples thereof include lactose, mannitol, crystalline cellulose, low substituted hydroxypropyl cellulose, corn starch, partially pregelatinized starch, carmellose calcium, croscarmellose sodium, hydroxypropyl cellulose, hydroxypropyl methylcellulose, polyvinyl alcohol, magnesium stearate, sodium stearyl fumarate, polyethylene glycol, propylene glycol, titanium oxide and talc.

Examples of an "anticancer compound" that may be used in combination with or combined with the antibody-drug conjugate according to the present invention include one or more anticancer compounds selected from the group consisting of anticancer alkylating agents, anticancer antimetabolites, anticancer antibiotics, anticancer platinum coordination compounds, anticancer camptothecin derivatives, anticancer tyrosine kinase inhibitors, anticancer serine-threonine kinase inhibitors, anticancer phospholipid kinase inhibitors, anticancer monoclonal antibodies, interferons, biological response modifiers, hormonal agents, immune checkpoint inhibitors, epigenetics-related molecule inhibitors, post-translational protein modification inhibitors and other antitumor agents. Specific examples of the "anticancer compound" that may be used in combination with or combined with the antibody-drug conjugate according to the present invention include azacitidine, vorinostat, decitabine, romidepsin, idarubicin, daunorubicin, doxorubicin, enocitabine, cytarabine, mitoxantrone, thioguanine, etoposide, ifosfamide, cyclophosphamide, dacarbazine, temozolomide, nimustine, busulfan, procarbazine, melphalan, ranimustine, all-trans-retinoic acid, tamibarotene, cisplatin, carboplatin, oxaliplatin, irinotecan, bleomycin, mitomycin C, methotrexate, paclitaxel, docetaxel, gemcitabine, tamoxifen, thiotepa, tegafur, fluorouracil, everolimus, temsirolimus, gefitinib, erlotinib, imatinib, crizotinib, osimertinib, afatinib, dasatinib, bosutinib, vandetanib, sunitinib, axitinib, pazopanib, lenvatinib, lapatinib, nilotinib, ibrutinib, ceritinib, alectinib, tofacitinib, baricitinib, ruxolitinib, olaparib, sorafenib, vemurafenib, dabrafenib, trametinib, palbociclib, bortezomib, carfilzomib, rituximab, cetuximab, trastuzumab, bevacizumab, panitumumab, nivolumab, atezolizumab, mogamulizumab, alemtuzumab, ofatumumab, ipilimumab, ramucirumab, brentuximab vedotin, trastuzumab emtansine, gemtuzumab ozogamicin and inotuzumab ozogamicin.

From the above, the antibody-drug conjugate according to the present invention and a pharmaceutical composition containing the same may be used for treatment of cancer. That is, it can also be said that one aspect of the present invention is a method of treating cancer, comprising administering the antibody-drug conjugate or a pharmaceutical composition comprising the same to a subject suffering from cancer. The subject suffering from cancer may be a human patient or animals other than human.

Hereinafter, the present invention will be explained further specifically with reference to Reference Examples, Examples and Test Examples, but the present invention is not limited to them, of course. Note that the names of compounds shown in the following Reference Examples and Examples do not necessarily follow the IUPAC nomenclature of chemistry.

Compounds of Reference Examples and Examples may be obtained as an acid addition salt such as a TFA salt, depending on a method of treatment after the reaction and the like.

In order to simplify description of the specification, abbreviations as shown below may be used in Examples and the tables in Examples. As abbreviations used for substituents, Me represents a methyl group, Et represents an ethyl group, Boc represents a tert-butoxycarbonyl group, Fmoc represents a 9-fluorenylmethyloxycarbonyl group, trt represents a trityl group, Ph represents a phenyl group, and tBu represents a tert-butyl group. Alko represents p-alkoxybenzyl alcohol and PEG represents polyethylene glycol. TFA represents trifluoroacetic acid, DMF represents N,N-dimethylformamide, TCEP represents tris(2-carboxyethyl)phosphine, Tris-HCl represents trishydroxymethylaminomethane hydrochloride, PBS represents phosphate buffered saline, HEPES represents 2-[4-(2-hydroxyethyl)piperazin-1-yl]ethanesulfonic acid, and PIPES represents piperazine-1,4-bis(2-ethanesulfonic acid). NMR means nuclear magnetic resonance. For symbols used for NMR, s means a singlet, d means a doublet, dd means a doublet of doublets, t means a triplet, q means a quartet, m means a multiplet, br means broad, brs means a broad singlet, brd means a broad doublet, brm means a broad multiplet, and J means the binding constant.

High Performance Liquid Chromatography-Mass Spectrometer; measurement conditions for LCMS are as follows, and the observed value of mass spectrometry [MS (m/z)] is shown as $[M+nH]^{n+}/n$, $[M+Na]+$ or $[M-nH]^{n-}/n$, and the retention time is shown as Rt (min). Note that, for each found value, the measurement conditions used for the measurement are denoted by A to G or J.

Measurement Condition A
 Detection Equipment: Shimadzu LCMS-IT-TOF
 Column: Phenomenex Kinetex (1.7 μm C18, 50 mm×2.10 mm)
 Solvents: solution A: 0.1% HCOOH/CH$_3$CN, solution B: 0.1% HCOOH/H$_2$O
 Gradient Condition:
  0.0 min; A/B=1:99
  0.0 to 1.4 min; Linear gradient from 1% to 95% A
  1.4 to 1.6 min; A/B=95:5
  1.6 to 2.0 min; A/B=1:99
 Flow Rate: 1.2 mL/min
 UV: 220/254 nm
 Column Temperature: 40° C.
Measurement Condition B
 Detection Equipment: Shimadzu LCMS-IT-TOF
 Column: Phenomenex Kinetex (1.7 μm C18, 50 mm×2.10 mm)
 Solvents: solution A: 0.1% HCOOH/CH$_3$CN, solution B: 0.1% HCOOH/H$_2$O
 Gradient Condition:
  0.0 min; A/B=10:90
  0.0 to 1.4 min; Linear gradient from 10% to 90% A
  1.4 to 1.6 min; A/B=90:10
  1.6 to 2.0 min; A/B=10:90
 Flow Rate: 1.2 mL/min
 UV: 220/254 nm
 Column Temperature: 40° C.
Measurement Condition C
 Detection Equipment: Shimadzu LCMS-IT-TOF
 Column: Phenomenex Kinetex (1.7 m C8, 50 mm×2.10 mm)
 Solvents: solution A: 0.1% HCOOH/CH$_3$CN, solution B: 0.1% HCOOH/H$_2$O
 Gradient Condition:
  0.0 min; A/B=1:99
  0.0 to 1.4 min; Linear gradient from 1% to 95% A
  1.4 to 1.6 min; A/B=95:5
  1.6 to 2.0 min; A/B=1:99
 Flow Rate: 1.2 mL/min
 UV: 220/254 nm
 Column Temperature: 40° C.
Measurement Condition D
 Detection Equipment: Shimadzu LCMS-IT-TOF
 Column: Phenomenex Kinetex (1.7 m C8, 50 mm×2.10 mm)
 Solvents: solution A: 0.1% HCOOH/CH$_3$CN, solution B: 0.1% HCOOH/H$_2$O
 Gradient Condition:
  0.0 min; A/B=10:90
  0.0 to 1.4 min; Linear gradient from 10% to 90% A
  1.4 to 1.6 min; A/B=90:10
  1.6 to 2.0 min; A/B=10:90
 Flow Rate: 1.2 mL/min
 UV: 220/254 nm
 Column Temperature: 40° C.
Measurement Condition E
 Detection Equipment: ACQUITY (registered Trademark) SQdetecter (Waters Corporation)
 HPLC: ACQUITY (registered Trademark) system
 Column: Waters ACQUITY UPLC (registered Trademark) BEH C18 (1.7 m, 2.1 mm×30 mm)
 Solvents: solution A: 0.06% formic acid/CH$_3$CN, solution B: 0.06% formic acid/H$_2$O
 Gradient Condition: 0.0 to 1.3 min Linear gradient from 2% to 96% A
 Flow Rate: 0.8 mL/min
 UV: 220/254 nm
 Column Temperature: 25° C.
Measurement Condition F
 Detection Equipment: Perkin-Elmer Sciex API 150EX Mass spectrometer
 HPLC: Shimadzu LC 10 ATVP
 Column: Shiseido CAPCELL PAK C18 ACR (S-5 μm, 4.6 mm×50 mm)
 Solvents: solution A: 0.035% TFA/CH$_3$CN, solution B: 0.05% TFA/H$_2$O Gradient Condition: 0.0 to 0.5 min solution A 10%, 0.5 to 4.8 min solution A Linear gradient from 10% to 99% A, 4.8 to 5.0 min
Flow Rate: 3.5 mL/min solution A 99%
UV: 220/254 nm
Column Temperature: 25° C.
Measurement Condition G
  Detection Equipment: Perkin-Elmer Sciex API 150EX Mass spectrometer (40 eV)
  HPLC: Shimadzu LC 10ATVP
  Column: Shiseido CAPCELL PAK C18 ACR (S-5 m, 4.6 mm×50 mm)
  Solvents: solution A: 0.035% TFA/CH$_3$CN, solution B: 0.05% TFA/H$_2$O
  Gradient Condition: 0.0 to 0.5 min solution A 40%, 0.5 to 4.8 min solution A Linear gradient from 40% to 99% A, 4.8 to 5.0 min
  Flow Rate: 3.5 mL/min solution A 99%
  UV: 220/254 nm
  Column Temperature: 25° C.
Measurement Condition J
  Detection Equipment: Shimadzu LCMS-IT-TOF
  Column: Phenomenex Kinetex (1.7 μm C8, 50 mm×2.10 mm)
  Solvents: solution A: 0.1% HCOOH/CH$_3$CN, solution B: 0.1% HCOOH/H$_2$O
  Gradient Condition:
    0.0 min; A/B=10:90
    0.0 to 1.4 min; Linear gradient from 10% to 95% A
    1.4 to 1.6 min; A/B=95:5
    1.6 to 2.0 min; A/B=10:90
  Flow Rate: 1.2 mL/min
  UV: 220/254 nm
  Column Temperature: 40° C.

High Performance Liquid Chromatography; measurement conditions for determining the average DAR are as follows, and the retention time is shown as Rt (min). Note that, for each found value, the measurement conditions used for the measurement are denoted by H or I.

Measurement Condition H
  HPLC: Shimadzu LC-10A series
  Column: nonporous TSKgel Butyl-NPR column (Tosoh Bioscience, 2.5 μm, 35 mm×4.6 mm)
  Solvents: solution A: 1.5 mol/L ammonium sulfate, 25 mmol/L aqueous sodium phosphate solution (pH 6.95), solution B: 25% isopropanol/25 mmol/L aqueous sodium phosphate solution (pH 6.95)
  Gradient Condition:
    0.0 min; A/B=100:0
    0.0 to 12.0 min; Linear gradient from 0% to 100% B
    12.1 to 18.0 min; A/B=100:0
  Flow Rate: 0.8 mL/min
  UV: 230 nm
  Column Temperature: 25° C.
Measurement Condition I
  HPLC: Shimadzu LC-10A series
  Column: nonporous TSKgel Butyl-NPR column (Tosoh Bioscience, 2.5 m, 35 mm×4.6 mm)
  Solvents: solution A: 1.5 mol/L ammonium sulfate, 25 mmol/L aqueous sodium phosphate solution (pH 6.95), solution B: 25% isopropanol/25 mmol/L aqueous sodium phosphate solution (pH 6.95)
  Gradient Condition:
    0.0 min; A/B=100:0
    0.0 to 24.0 min; Linear gradient from 0% to 100% B
    24.1 to 60.0 min; A/B=100:0
  Flow Rate: 0.8 mL/min
  UV: 230 nm
  Column Temperature: 25° C.

EXAMPLES

Reference Example 1

Methyl N-(tert-butoxycarbonyl)-N,β,β,1-tetramethyl-L-tryptophanate

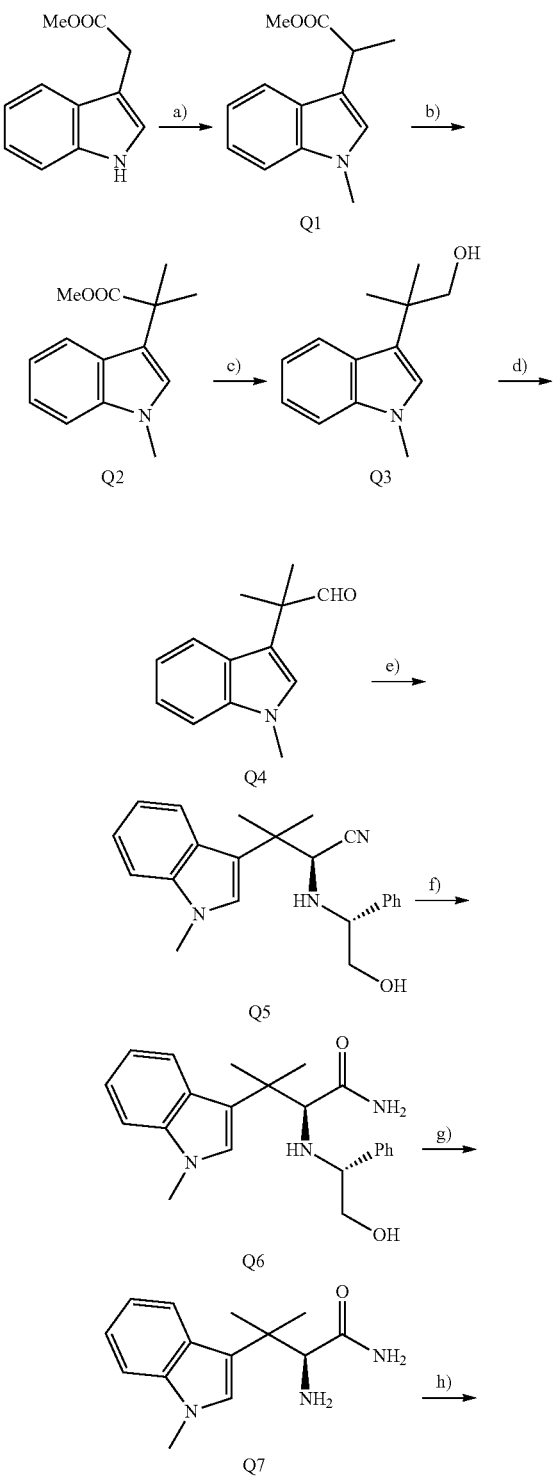

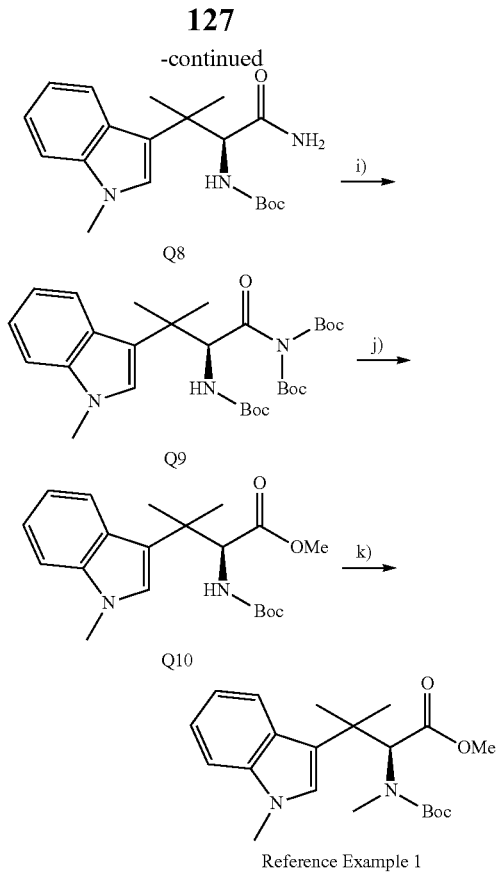

Reference Example 1 a) Production of methyl 2-(1-methyl-1H-indol-3-yl) propanoate (Compound Q1)

Under nitrogen atmosphere, to a solution of indole-3-acetic acid methyl ester (3.8 g) in tetrahydrofuran (87 mL) at −78° C., potassium hexamethyldisilazide (1 mol/L tetrahydrofuran solution, 65.5 mL) was added dropwise, and the resultant mixture was then stirred at 0° C. for 2 hours. After cooling the reaction solution to −78° C., methyl iodide (23 g) was added dropwise thereto, and the reaction solution was then stirred at 0° C. for 3 hours. After the reaction ended, water was added and the resultant mixture was extracted with diethyl ether. The organic layer was washed with saturated brine, followed by drying over anhydrous magnesium sulfate, and the solvent was distilled off under reduced pressure. The residue was purified by silica gel column chromatography (eluting solvent; hexane:ethyl acetate) to give compound Q1 (3.95 g).
$^1$H-NMR (400 MHz, CDCl$_3$):1.60 (3H, d, J=7.1 Hz), 3.67 (3H, s), 3.76 (3H, s), 4.02 (1H, q, J=7.1 Hz), 7.00 (1H, s), 7.12 (1H, t, J=7.8 Hz), 7.23 (1H, t, J=7.8 Hz), 7.29 (1H, d, J=7.8 Hz), 7.66 (1H, d, J=7.8 Hz).

b) Production of methyl 2-methyl-2-(1-methyl-1H-indol-3-yl) propanoate (Compound Q2)

Under nitrogen atmosphere, to a solution of compound Q1 (3.94 g) in tetrahydrofuran (200 mL) at −78° C., potassium hexamethyldisilazide (1 mol/L tetrahydrofuran solution, 27.7 mL) was added dropwise, and the resultant mixture was then stirred at 0° C. for 2 hours. After cooling the reaction solution to −78° C., methyl iodide (15.4 g) was added dropwise thereto, and the reaction solution was then stirred at 0° C. for 3 hours. After the reaction ended, water was added and the resultant mixture was extracted with diethyl ether. The organic layer was washed with saturated brine, followed by drying over anhydrous magnesium sulfate, and the solvent was distilled off under reduced pressure. The residue was purified by silica gel column chromatography (eluting solvent; hexane:ethyl acetate) to give compound Q2 (3.59 g).
$^1$H-NMR (400 MHz, CDCl$_3$):1.66 (6H, s), 3.61 (3H, s), 3.73 (3H, s), 6.91 (1H, s), 7.06 (1H, t, J=8.0 Hz), 7.19 (1H, t, J=8.0 Hz), 7.27 (1H, d, J=8.0 Hz), 7.61 (1H, d, J=7.9 Hz).

c) Production of 2-methyl-2-(1-methyl-1H-indol-3-yl) propan-1-ol (Compound Q3)

Under nitrogen atmosphere, to a solution of compound Q2 (3.59 g) in diethyl ether (169 mL) and dichloromethane (47 mL) at −78° C., diisobutylaluminum hydride (1 mol/L n-hexane solution, 38.8 mL) was added dropwise, and the resultant mixture was then stirred at 0° C. for 1 hour. After the reaction ended, water was added, and then, to the reaction mixture at 25° C., a saturated aqueous solution of potassium sodium tartrate was added, and the resultant mixture was then extracted with diethyl ether. The organic layer was washed with saturated brine, followed by drying over anhydrous magnesium sulfate, and the solvent was distilled off under reduced pressure. The residue was purified by silica gel column chromatography (eluting solvent; hexane:ethyl acetate) to give compound Q3 (3.14 g).
$^1$H-NMR (400 MHz, CDCl$_3$):1.42 (6H, s), 3.74 (3H, s), 3.77 (2H, s), 6.87 (1H, s), 7.07 (1H, t, J=7.9 Hz), 7.20 (1H, t, J=7.9 Hz), 7.29 (1H, d, J=8.0 Hz), 7.75 (1H, d, J=8.0 Hz).

d) Production of 2-methyl-2-(1-methyl-1H-indol-3-yl)propanal (Compound Q4)

Under nitrogen atmosphere, a mixed solution of compound Q3 (3.14 g), tetrapropylammonium perruthenate (271 mg), N-methylmorpholine-N-oxide (3.26 g) and molecular sieve 4A (7.7 g) in dichloromethane (110 mL) was stirred at 25° C. for 1 hour. After the reaction ended, the reaction solution was filtered through celite and the solvent was then distilled off, and the residue was purified by silica gel column chromatography (eluting solvent; hexane:ethyl acetate) to give compound Q4 (2.4 g).
$^1$H-NMR (400 MHz, CDCl$_3$):1.53 (6H, s), 3.77 (3H, s), 6.94 (1H, s), 7.07 (1H, t, J=8.0 Hz), 7.22 (1H, t, J=8.0 Hz), 7.30 (1H, d, J=8.0 Hz), 7.53 (1H, d, J=8.0 Hz), 9.47 (1H, s).

e) Production of (2S)-2-{[(1R)-2-hydroxy-1-phenylethyl]amino}-3-methyl-3-(1-methyl-1H-indol-3-yl) butanenitrile (Compound Q5)

Under nitrogen atmosphere, a solution of compound Q4 (2.4 g) and (R)-(−)-2-phenylglycinol (1.63 g) in toluene (47 mL) was subjected to heating reflux for 1.5 hours, and after distilling off water with a Dean-Stark apparatus, the solvent was distilled off. Under nitrogen atmosphere, dichloromethane (69 mL) at 0° C. was added to the residue and trimethylsilyl cyanide (2.36 g) was then added, and the resultant mixture was stirred at 25° C. for 96 hours. To the reaction solution, tetra-n-butylammonium fluoride (1 mol/L tetrahydrofuran solution, 1 mL) was added, and after stirring the solution for further 30 minutes, water was added and the resultant mixture was extracted with chloroform. The organic layer was dried over anhydrous sodium sulfate, and the solvent was distilled off under reduced pressure. The residue was purified by silica gel column chromatography (eluting solvent; hexane:ethyl acetate) to give compound Q5 (2.74 g).

$^1$H-NMR (400 MHz, CDCl$_3$):1.64 (3H, s), 1.65 (3H, s), 3.49-3.55 (1H, m), 3.73 (1H, dd, J=10.9, 4.2 Hz), 3.79 (1H, s), 3.80 (3H, s), 4.05 (1H, dd, J=7.9, 3.6 Hz), 6.96-7.00 (2H, m), 7.11 (2H, d, J=8.0 Hz), 7.21-7.40 (6H, m).

f) Production of Nα-[(1R)-2-hydroxy-1-phenyl-ethyl]-β,β,1-trimethyl-L-tryptophanamide (Compound Q6)

To a suspension of compound Q5 (2.74 g), dimethyl sulfoxide (6.16 g) and potassium carbonate (10.9 g) in methanol (50 mL) and water (2.1 mL), a 30% aqueous hydrogen peroxide solution (8.94 mL) was added at 0° C., and the resultant mixture was stirred at 45° C. for 1.5 hours. After the reaction ended, a saturated aqueous sodium thiosulfate solution was added, and the resultant mixture was extracted with ethyl acetate. The organic layer was washed with water and then dried over anhydrous sodium sulfate, and the solvent was distilled off under reduced pressure. The residue was purified by silica gel column chromatography (eluting solvent; chloroform:methanol) to give compound Q6 (2.32 g).

$^1$H-NMR (400 MHz, CDCl$_3$):1.49 (3H, s), 1.51 (3H, s), 2.06-2.14 (1H, br), 2.37 (1H, dd, J=6.0, 6.0 Hz), 3.44-3.50 (1H, m), 3.50-3.54 (1H, m), 3.56-3.63 (m, 2H), 3.75 (3H, s), 5.52 (1H, brs), 6.14 (1H, brs), 6.71-6.73 (2H, m), 6.81-6.85 (2H, m), 6.97-7.00 (2H, m), 7.10-7.18 (2H, m), 7.24-7.28 (2H, m).

g) Production of β,β,1-trimethyl-L-tryptophanamide (Compound Q7)

To a solution of compound Q6 (2.32 g) in methanol (65 mL), palladium hydroxide/carbon (2.8 g) was added, and the resultant mixture was stirred at room temperature for 3 hours under hydrogen atmosphere. The reaction solution was filtered through celite and the solvent was then distilled off, and the residue was purified by silica gel column chromatography (eluting solvent; chloroform:methanol) to give compound Q7 (1.27 g).

$^1$H-NMR (400 MHz, DMSO-d6):1.24 (2H, brs), 1.28 (3H, s), 1.42 (3H, s), 3.68 (1H, s), 3.71 (3H, s), 6.93-7.00 (2H, m), 7.06 (1H, s), 7.11 (1H, t, J=7.7 Hz), 7.29 (1H, brs), 7.36 (1H, d, J=8.3 Hz), 7.88 (1H, d, J=8.2 Hz).

h) Production of Nα-(tert-butoxycarbonyl)-β,β,1-trimethyl-L-tryptophanamide (Compound Q8)

A mixed solution of compound Q7 (1.27 g), sodium bicarbonate (522 mg), di-tert-butyl dicarbonate (1.35 g), tetrahydrofuran (13 mL), chloroform (13 mL) and water (6.5 mL) was stirred at 25° C. for 16 hours. After the reaction ended, water was added and the resultant mixture was extracted with chloroform. The organic layer was dried over anhydrous sodium sulfate, and the solvent was distilled off under reduced pressure. The residue was purified by silica gel column chromatography (eluting solvent; chloroform:methanol) to give compound Q8 (1.80 g).

$^1$H-NMR (400 MHz, CDCl$_3$):1.33 (3H, s), 1.47 (9H, s), 1.50 (3H, s), 3.73 (3H, d, J=1.3 Hz), 4.51 (1H, brs), 4.86 (1H, brs), 5.02 (1H, brd, J=8.2 Hz), 5.59 (1H, brd, J=6.4 Hz), 6.83 (1H, d, J=1.8 Hz), 7.15 (1H, t, J=7.3 Hz), 7.21-7.25 (1H, m), 7.30 (1H, d, J=8.2 Hz), 8.05 (1H, brd, J=7.3 Hz).

LC-MS: 346 (M+H)$^+$ (1.211 min, Measurement Condition A)

i) Production of N,N,Nα-tris(tert-butoxycarbonyl)-β,β,1-trimethyl-L-tryptophanamide (Compound Q9)

A mixed solution of compound Q8 (1.79 g), di-tert-butyl dicarbonate (2.8 g), N,N-diisopropylethylamine (2.68 g), 4-dimethylaminopyridine (0.19 g) and chloroform (20 mL) was stirred at 25° C. for 2.5 hours. After the reaction ended, water was added and the resultant mixture was extracted with chloroform. The organic layer was washed with saturated brine and then dried over anhydrous sodium sulfate, and the solvent was distilled off under reduced pressure. The residue was purified by silica gel column chromatography (eluting solvent; hexane:ethyl acetate) to give compound Q9 (1.99 g).

$^1$H-NMR (400 MHz, CDCl$_3$):1.08-1.58 (33H, m), 3.70 (3H, s), 4.67-4.90 (0.2H, m), 5.25-5.45 (0.8H, m), 6.00-6.03 (1H, m), 6.81-6.87 (1H, m), 7.04-7.09 (1H, m), 7.13-7.18 (1H. m), 7.21-7.27 (1H, m), 7.91-7.94 (1H, m).

LC-MS: 546 (M+H)$^+$ (1.630 min, Measurement Condition A)

j) Production of methyl N-(tert-butoxycarbonyl)-β,β,1-trimethyl-L-tryptophanate (Compound Q10)

Under nitrogen atmosphere, to a solution of compound Q9 (2.29 g) in methanol (21 mL), lithium methoxide (176 mg) was added at 0° C., and the resultant mixture was then stirred at 25° C. for 2 hours. After the reaction ended, a saturated aqueous ammonium chloride solution was added, and the reaction mixture was extracted with ethyl acetate. The organic layer was washed with saturated brine and then dried over anhydrous sodium sulfate, and the solvent was distilled off under reduced pressure. The residue was purified by silica gel column chromatography (eluting solvent; hexane:ethyl acetate) to give compound Q10 (927 mg).

$^1$H-NMR (400 MHz, CDCl$_3$):1.17-1.59 (15H, m), 3.45 and 3.58 (3H, 2brs), 3.71 (3H, s), 4.56-4.73 (1.2H, m), 5.06 (0.8H, brd, J=7.3 Hz), 6.81-6.82 (1H, m), 7.05-7.10 (1H, m), 7.16-7.21 (1H, m), 7.24-7.29 (1H, m), 7.73-7.80 (1H, m).

LC-MS: 361 (M+H)$^+$ (1.379 min, Measurement Condition A).

k) Production of methyl N-(tert-butoxycarbonyl)-N,β,β,1-tetramethyl-L-tryptophanate (Reference Example 1)

Under nitrogen atmosphere, to a solution of compound Q10 (927 mg) in N,N-dimethylformamide (13 mL), sodium hydride 60% dispersion (168 mg) was added at 0° C., and the resultant mixture was then stirred at 25° C. for 15 minutes. After cooling the reaction suspension to 0° C., methyl iodide (1.1 g) was added thereto, and the reaction solution was then stirred at 25° C. for 1 hour. After the reaction ended, water was added and the resultant mixture was extracted with ethyl acetate. The organic layer was dried over anhydrous sodium sulfate, and the solvent was distilled off under reduced pressure. The residue was purified by silica gel column chromatography (eluting solvent; hexane:ethyl acetate) to give Reference Example 1 (915 mg).

$^1$H-NMR (400 MHz, CDCl$_3$):1.42 (9H, s), 1.52 and 1.64 (6H, 2s), 2.80 and 2.86 (3H, 2s), 3.46 (3H, s), 3.71 (3H, s), 5.27 and 5.52 (1H, 2s), 6.85 (1H, s), 7.07-7.27 (3H, m), 7.78 and 7.92 (1H, 2d, J=7.88 Hz).

LC-MS: 397 (M+Na)$^+$ (1.406 min, Measurement Condition B)

Reference Example 2

N-(tert-Butoxycarbonyl)-N,β,β,1-tetramethyl-L-tryptophyl-N-{(3S,4E)-6-[(2,5-dioxopyrrolidin-1-yl)oxy]-2,5-dimethyl-6-oxohex-4-en-3-yl}-N,3-dimethyl-L-valinamide

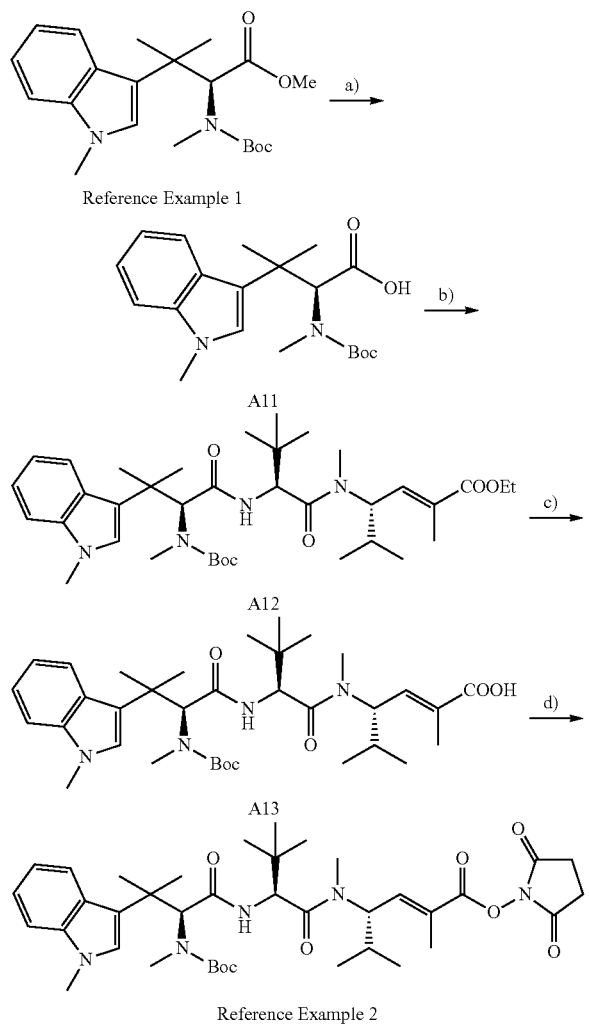

Reference Example 2 a) Production of N-(tert-butoxycarbonyl)-N,β,β,1-tetramethyl-L-tryptophan (Compound A11)

To a solution of Reference Example 1 (639 mg) in water (11 mL)-methanol (44 mL), 1 mol/L lithium hydroxide (13.5 mL) was added, and the resultant mixture was stirred at 60° C. for 24 hours. After the reaction ended, a 1 mol/L aqueous oxalic acid solution was added to change the pH of the reaction solution to 4, and water was then added and the resultant mixture was extracted with chloroform. The organic layer was washed with saturated brine and then dried over anhydrous sodium sulfate, and the solvent was distilled off under reduced pressure. The residue was purified by silica gel column chromatography (eluting solvent; chloroform:methanol) to give compound A11 (610 mg).

$^1$H-NMR (400 MHz, CDCl$_3$):1.43 (9H, s), 1.53 (3H, s), 1.63 (3H, s), 2.76 and 2.89 (3H, 2s), 3.71 (3H, s), 5.36 and 5.44 (1H, 2s), 6.85 and 6.87 (1H, 2s), 7.02-7.11 (1H, m), 7.18 (1H, t, J=7.3 Hz), 7.24-7.27 (1H, m), 7.81 and 7.96 (1H, 2d, J=7.9 Hz).

LC-MS: 361 (M+H)$^+$, 359 (M−H)$^-$ (1.300 min, Measurement Condition A).

b) Production of N-(tert-butoxycarbonyl)-N,β,β,1-tetramethyl-L-tryptophyl-N-[(3S,4E)-6-ethoxy-2,5-dimethyl-6-oxohex-4-en-3-yl]-N,3-dimethyl-L-valinamide (Compound A12)

A mixed solution of compound A11 (500 mg), ethyl (2E,4S)-2,5-dimethyl-4-[methyl(3-methyl-L-valyl)amino]hex-2-enoate (520 mg), 1-ethyl-3-(3-dimethylaminopropyl)carbodiimide hydrochloride (399 mg), 1-hydroxy-1H-benzotriazole monohydrate (425 mg) and N,N-dimethylformamide (5 mL) was stirred at 25° C. for 16 hours. After the reaction ended, water was added and the resultant mixture was extracted with chloroform. The organic layer was washed with saturated brine and then dried over anhydrous sodium sulfate, and the solvent was distilled off under reduced pressure. The residue was purified by silica gel column chromatography (eluting solvent; hexane:ethyl acetate) to give compound A12 (759 mg).

LC-MS: 655 (M+H)$^+$ (1.714 min, Measurement Condition A)

c) Production of N-(tert-butoxycarbonyl)-N,β,β,1-tetramethyl-L-tryptophyl-N-[(3S,4E)-5-carboxy-2-methylhex-4-en-3-yl]-N,3-dimethyl-L-valinamide (Compound A13)

To a solution of compound A12 (127 mg) in water (1.55 mL)-methanol (4.65 mL), 1 mol/L lithium hydroxide (1.65 mL) was added, and the resultant mixture was stirred at 25° C. for 24 hours. After the reaction ended, a 1 mol/L aqueous oxalic acid solution was added to change the pH of the reaction solution to 4, and water was then added and the resultant mixture was extracted with chloroform. The organic layer was washed with saturated brine and then dried over anhydrous sodium sulfate, and the solvent was distilled off under reduced pressure. The residue was purified by silica gel column chromatography (eluting solvent; chloroform:methanol) to give compound A13 (93 mg).

LC-MS: 627 (M+H)$^+$ (1.508 min, Measurement Condition A)

d) Production of N-(tert-butoxycarbonyl)-N,β,β,1-tetramethyl-L-tryptophyl-N-{(3S,4E)-6-[(2,5-dioxopyrrolidin-1-yl)oxy]-2,5-dimethyl-6-oxohex-4-en-3-yl}-N,3-dimethyl-L-valinamide (Reference Example 2)

A mixed solution of compound A13 (185 mg), N-hydroxysuccinimide (97 mg), bromotripyrrolidinophosphonium hexafluorophosphate (391 mg), 4-dimethylaminopyridine (102 mg), N,N-diisopropylethylamine (108 mg) and N,N-dimethylformamide (2.8 mL) was stirred at 25° C. for 4 hours. After the reaction ended, water was added and the resultant mixture was extracted with ethyl acetate. The organic layer was washed with water and then dried over anhydrous sodium sulfate, and the solvent was distilled off under reduced pressure. The residue was purified by silica gel column chromatography (eluting solvent; chloroform:methanol) to give Reference Example 2 (166 mg).

$^1$H-NMR (400 MHz, CDCl$_3$):8.27 and 7.96 (1H, 2d, J=7.9 Hz), 7.16-7.04 (4H, m), 6.88 (1H, d, J=9.1 Hz), 6.17 and 6.09 (1H, 2d, J=8.5 Hz), 5.96 and 5.66 (1H, 2s), 5.07 (1H, t, J=9.3 Hz), 4.45 and 3.87 (1H, 2d, J=8.6 Hz), 3.74 and 3.73 (3H, 2s), 2.99 (3H, s), 2.95 (3H, s), 2.83 (4H, brs), 1.97 (3H, s), 1.92-1.86 (1H, m), 1.57-1.42 (14H, m), 0.89 (3H, d, J=6.1 Hz), 0.83-0.80 (3H, m), 0.48 and 0.41 (9H, 2s).

LC-MS: 724 (M+H)$^+$ (1.573 min, Measurement Condition A)

Reference Example 3

(6S,9S,12S,13E,17R)-9-tert-Butyl-17-(ethoxycarbonyl)-2,2,5,11,14-pentamethyl-6-[2-(1-methyl-1H-indol-3-yl)propan-2-yl]-4,7,10,15-tetraoxo-12-(propan-2-yl)-3-oxa-5,8,11,16-tetraazaicos-13-en-20-oic acid Reference Example 3

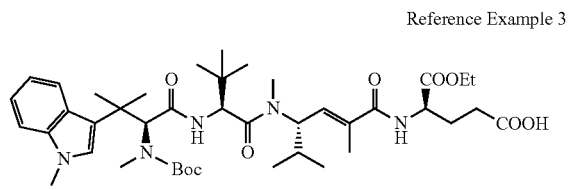 [SMILES: CCOC(=O)[C@@H](CCC(=O)O)NC(=O)/C(C)=C/[C@H](C(C)C)N(C)C(=O)[C@@H](NC(=O)[C@@H](N(C)C(=O)OC(C)(C)C)C(C)(C)c1cn(C)c2ccccc12)C(C)(C)C]

A mixed solution of Reference Example 2 (160 mg), D-glutamic acid α-ethyl ester-trifluoroacetate (122 mg), N,N-diisopropylethylamine (100 mg) and N,N-dimethylformamide (2.2 mL) was stirred at 25° C. for 6 hours. After the reaction ended, a 1 mol/L aqueous oxalic acid solution was added to change the pH to 4, and the resultant mixture was extracted with chloroform. The organic layer was washed with water and saturated brine and then dried over anhydrous sodium sulfate, and the solvent was distilled off under reduced pressure. The residue was purified by silica gel column chromatography (eluting solvent; chloroform:methanol) to give Reference Example 3 (155 mg).

$^1$H-NMR (400 MHz, CDCl$_3$):8.26 and 7.97 (1H, 2d, J=7.9 Hz), 7.32-7.05 (4H, m), 6.71 (1H, t, J=6.7 Hz), 6.45 (1H, d, J=8.6 Hz), 6.31-6.26 (1H, m), 5.95 and 5.63 (1H, 2s), 4.94-4.82 (1H, m), 4.64-4.59 (1H, m), 4.51 and 4.41 (1H, 2d, J=9.1 Hz), 4.21 (2H, q, J=7.3 Hz), 3.75 and 3.74 (3H, 2s), 3.00 (3H, s), 2.97 and 2.95 (3H, 2s), 2.52-2.38 (2H, m), 2.29-2.20 (1H, m), 2.10-2.00 (1H, m), 1.98-1.90 (1H, m), 1.90 (3H, s), 1.57-1.45 (14H, m), 1.28 (3H, t, J=7.3 Hz), 0.88 (3H, d, J=6.1 Hz), 0.82 (3H, d, J=6.7 Hz), 0.53 and 0.46 (9H, 2s).

LC-MS: 784 (M+H)$^+$, 782 (M-H)$^-$ (1.472 min, Measurement Condition A)

Reference Example 4

N-(tert-Butoxycarbonyl)-N,β,β,1-tetramethyl-L-tryptophyl-N-[(3S,4E)-6-{[(1R)-1,3-dicarboxypropyl]amino}-2,5-dimethyl-6-oxohex-4-en-3-yl]-N,3-dimethyl-L-valinamide Reference Example 4

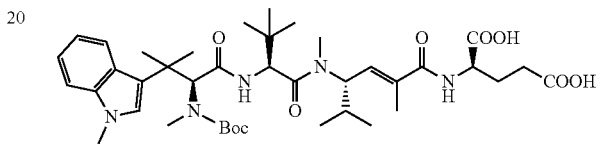

To a solution of Reference Example 3 (103 mg) in water (0.8 mL)-methanol (3.3 mL), 1 mol/L lithium hydroxide (1 mL) was added, and the resultant mixture was stirred at 25° C. for 16 hours. After the reaction ended, a 1 mol/L aqueous oxalic acid solution was added to change the pH of the reaction solution to 4, and then the reaction solution was purified by silica gel column chromatography (eluting solvent; chloroform:methanol) to give Reference Example 4 (100 mg).

LC-MS: 756 (M+H)$^+$, 754 (M-H)$^-$ (1.388 min, Measurement Condition A)

Reference Example 5

N-[(2E,4S)-4-{[N-(tert-Butoxycarbonyl)-N,β,β,1-tetramethyl-L-tryptophyl-3-methy 1-L-valyl](methyl)amino}-2,5-dimethylhex-2-enoyl]-L-α-aspartyl-L-α-aspartyl-L-α-aspartyl-L-α-aspartyl-L-α-aspartic acid Reference Example 5

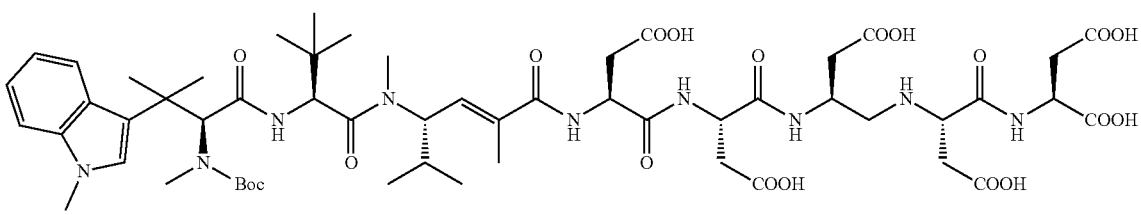

A mixed solution of Reference Example 2 (20 mg), L-α-aspartyl-L-α-aspartyl-L-α-aspartyl-L-α-aspartyl-L-α-aspartic acid (16 mg), N,N-diisopropylethylamine (10 mg) and N,N-dimethylformamide (1 mL) was stirred at 25° C. for 68 hours. After the reaction ended, the reaction solution was purified by reversed phase column chromatography (eluting solvent; acetonitrile with 0.1% TFA:water) to give Reference Example 5 (16 mg).

LC-MS: 1200 (M−H)⁻ (1.304 min, Measurement Condition D)

Reference Example 6

N-(tert-Butoxycarbonyl)-N,β,β,1-tetramethyl-L-tryptophyl-N-[(3S,4E)-6-({(2R)-1-tert-butoxy-6-[(tert-butoxycarbonyl)amino]-1-oxohexan-2-yl}amino)-2,5-dimethyl-6-oxohex-4-en-3-yl]-N,3-dimethyl-L-valinamide

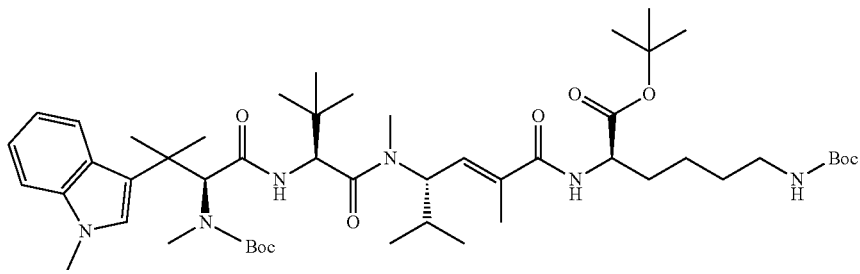

Reference Example 6

By the same approach as Reference Example 2-b), from compound A13 (50 mg), Reference Example 6 (57 mg) was obtained.

LC-MS: 911 (M+H)⁺ (1.756 min, Measurement Condition D)

Reference Example 7 tert-Butyl

N-[(2E,4S)-4-{[N-(tert-butoxycarbonyl)-N,β,β,1-tetramethyl-L-tryptophyl-3-methyl-L-valyl](methyl)amino}-2,5-dimethylhex-2-enoyl]-D-γ-glutamyl-N⁶-(tert-butoxycarbonyl)-D-lysinate

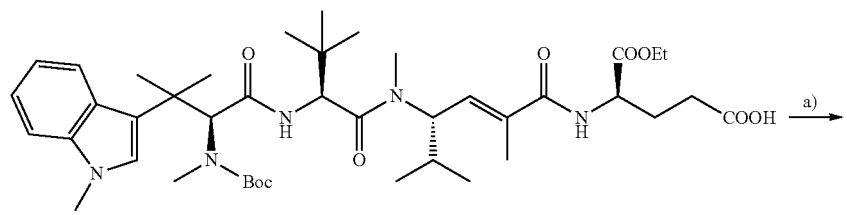

Reference Example 3

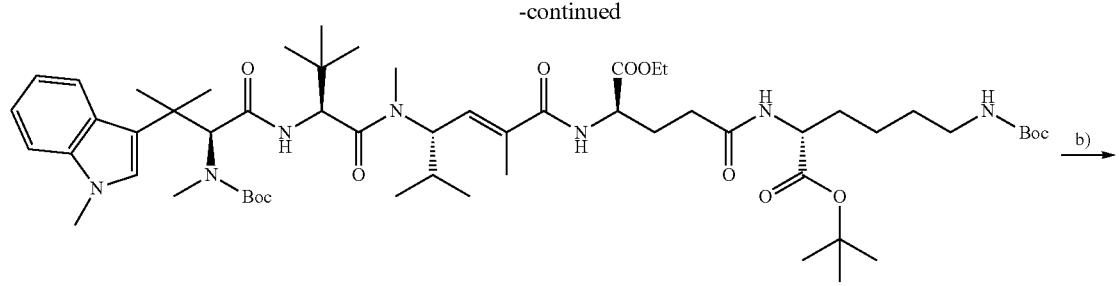

G1

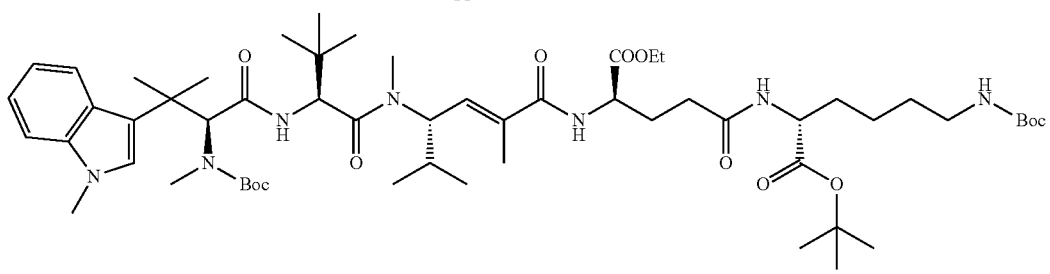

Reference Example 7 a) Production of 22-tert-butyl 17-ethyl(6S,9S,12S, 13E,17R, 22R)-9-tert-butyl-2,2,5,11,14,30,30-heptamethyl-6-[2-(1-methyl-1H-indol-3-yl)propan-2-yl]-4,7,10,15,20,28-hexaoxo-12-(propan-2-yl)-3,29-dioxa-5,8,11,16,21,27-hexaazahentriacont-13-ene-17,22-dicarboxylate (Compound G1)

By the same approach as Reference Example 2-b), from Reference Example 3 (40 mg), compound G1 (54 mg) was obtained.
LC-MS: 1068 (M+H)$^+$ (1.751 min, Measurement Condition D).

b) Production of tert-butyl N-[(2E,4S)-4-{[N-(tert-butoxycarbonyl)-N,β, β,1-tetramethyl-L-tryptophyl-3-methyl-L-valyl](methyl)amino}-2,5-dimethylhex-2-enoyl]-D-γ-glutamyl-N$^6$-(tert-butoxycarbonyl)-D-lysinate (Reference Example 7)

By the same approach as Reference Example 4, from compound G1 (54 mg), Reference Example 7 (37 mg) was obtained.
LC-MS: 1038 (M–H)$^-$ (1.672 min, Measurement Condition D).

Reference Example 8

(2R)-2-{[(6S,9S,12S,13E)-9-tert-Butyl-2,2,11,14-tetramethyl-6-[2-(1-methyl-1H-indol-3-yl)propan-2-yl]-4,7,10,15-tetraoxo-12-(propan-2-yl)-3-oxa-5,8,11-triazapentadec-13-en-15-yl]amino}pentane diethyl diester

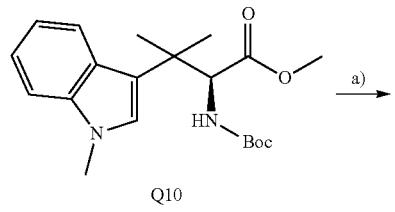

Q10

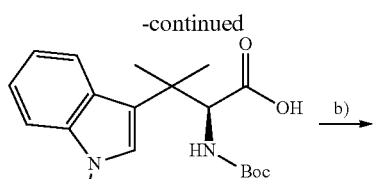

B1

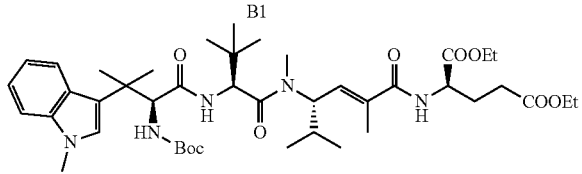

Reference Example 8 a) Production of N-(tert-butoxycarbonyl)-β,β,1-trimethyl-L-tryptophan (Compound B1)

By the same approach as Reference Example 2-a), from compound Q10 (40 mg), compound B1 (38 mg) was obtained.
$^1$H-NMR (400 MHz, CDCl$_3$):1.34 (9H, s), 1.48 (3H, s), 1.53 (3H, s), 3.72 (3H, s), 4.88 (1H, brd, J=4.3 Hz), 5.11 (1H, brd, J=6.7 Hz), 6.85 (1H, s), 7.09 (1H, t, J=7.3 Hz), 7.20 (1H, t, J=8.5 Hz), 7.28 (1H, d, J=8.0 Hz), 7.88 (1H, brd, J=7.3 Hz).

b) Production of (2R)-2-{[(6S,9S,12S,13E)-9-tert-butyl-2,2,11,14-tetramethyl-6-[2-(1-methyl-1H-indol-3-yl)propan-2-yl]-4,7,10,15-tetraoxo-12-(propan-2-yl)-3-oxa-5,8,11-triazapentadec-13-en-15-yl]amino}pentane diethyl diester (Reference Example 8)

By the same approach as Reference Example 2-b), from compound B1 (38 mg), Reference Example 8 (80 mg) was obtained.
LC-MS: 798 (M+H)$^+$ (1.606 min, Measurement Condition D)

Reference Example 9

(2S)-2-{[(6S,9S,12S,13E)-9-tert-Butyl-2,2,5,11,14-pentamethyl-4,7,10,15-tetraoxo-6-(2-phenylpropan-2-yl)-12-(propan-2-yl)-3-oxa-5,8,11-triazapentadec-13-en-15-yl]amino}pentane diethyl diester

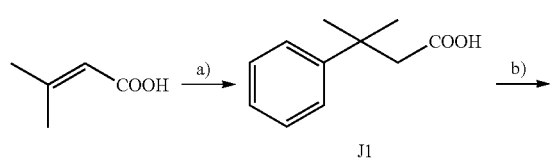

Reference Example 9 a) Production of 3-methyl-3-phenylbutanoic acid (Compound J1)

To a solution of 3-methyl-2-butenoic acid (15 g) in benzene (100 mL), aluminum chloride (24.1 g) was added at 10° C., and the resultant mixture was stirred for 30 minutes and then stirred at 40° C. for 1 hour. After cooling the reaction solution to 0° C., ice water was added, and the resultant mixture was extracted with tert-butyl methyl ether, concentrated to some extent, and the organic layer was extracted with a saturated aqueous sodium bicarbonate solution. The pH of the aqueous layer was changed to 2 with concentrated hydrochloric acid, and the resultant mixture was extracted with tert-butyl methyl ether. The organic layer was dried over anhydrous magnesium sulfate, and the solvent was distilled off under reduced pressure to give compound J1 (26.3 g).

$^1$H-NMR (400 MHz, CDCl$_3$):1.46 (6H, s), 2.65 (2H, s), 7.20 (1H, t, J=7.2 Hz), 7.31 (1H, t, J=7.2 Hz), 7.37 (2H, d, J=7.2 Hz).

b) Production of (4S)-3-(3-methyl-3-phenylbutanoyl)-4-(propan-2-yl)-1,3-oxazolidin-2-one (Compound J2)

To a solution of compound J1 (17.2 g) in THF (900 mL), triethylamine (23.7 mL) and pivaloyl chloride (15.3 mL)

was added at −78° C. After raising the temperature to 0° C., the resultant mixture was stirred for 1 hour. Separately, to a solution of (S)-isopropyloxazolidinone (19.5 g) in THF (760 mL), n-butyllithium (1.64 mol/L hexane solution, 89.8 mL) was added at −78° C., the resultant mixture was stirred for 30 minutes to prepare a lithium salt. The previous reaction solution was cooled to −78° C., the lithium salt was added dropwise, the resultant mixture was stirred for 1 hour, and the temperature was then raised to 0° C. After stirring the mixture for further 30 minutes, water was added, and the resultant mixture was extracted with tert-butyl methyl ether. The organic layer was washed with saturated brine and dried over anhydrous magnesium sulfate. The solvent was distilled off under reduced pressure, and the residue was purified by silica gel column chromatography (eluting solvent; hexane:tert-butyl methyl ether) to give compound J2 (27.0 g).

$^1$H-NMR (400 MHz, CDCl$_3$):0.723 (3H, d, J=6.8 Hz), 0.80 (3H, d, J=6.8 Hz), 1.49 (s, 6H), 2.13-2.18 (m, 1H), 3.36 (s, 3H), 3.99-4.09 (m, 2H), 4.20-4.23 (m, 1H), 7.16-7.20 (m, 1H), 7.28-7.32 (m, 2H), 7.38-7.40 (m, 2H).

c) Production of (4S)-3-[(2S)-2-azido-3-methyl-3-phenylbutanoyl]-4-(propan-2-yl)-1,3-oxazolidin-2-one (Compound J3)

A suspension of compound J2 (27.0 g) in THF (560 mL) was cooled to −78° C., potassium hexamethyldisilazide (1.06 mol/L tetrahydrofuran solution, 99.5 mL) was added, and the resultant mixture was stirred for 1.5 hours. A solution of 2,4,6-triisopropylbenzenesulfonyl azide (40 g) in THF (330 mL) at −78° C. was added, and after 10 minutes, acetic acid (24.5 mL) was added, the temperature was raised to 40° C., and the resultant mixture was stirred for 1 hour. Saturated brine was added, and the resultant mixture was extracted with tert-butyl methyl ether. The organic layer was washed with a saturated aqueous sodium bicarbonate solution and saturated brine, and the organic layer was then dried over anhydrous magnesium sulfate. The solvent was distilled off under reduced pressure, and the residue was purified by silica gel column chromatography (eluting solvent; hexane:chloroform) to give compound J3 (16.4 g).

$^1$H-NMR (400 MHz, CDCl$_3$):0.80 (3H, d, J=6.8 Hz), 0.84 (3H, d, J=7.2 Hz), 1.54 (3H, s), 1.56 (3H, s), 2.28-2.33 (1H, m), 3.54-3.59 (1H, m), 3.87-3.90 (1H, m), 3.95-3.98 (1H, m), 5.66 (1H, s), 7.23-7.420 (5H, m).

d) Production of tert-butyl {(2S)-3-methyl-1-oxo-1-[(4S)-2-oxo-4-(propan-2-yl)-1,3-oxazolidin-3-yl]-3-phenylbutan-2-yl}carbamate (Compound J4)

To a solution of compound J3 (16.4 g) in ethyl acetate (1200 mL), di-tert-butyl dicarbonate (24.0 g) and 10% Pd-C (11.6 g, 50% wet) were added, and the resultant mixture was stirred for 2 hours under hydrogen atmosphere. The reaction solution was filtered through celite, and was washed with ethyl acetate. The solvent was distilled off under reduced pressure, and the residue was purified by silica gel column chromatography (eluting solvent; hexane:tert-butyl methyl ether) to give compound J4 (16.1 g).

$^1$H-NMR (400 MHz, CDCl$_3$):0.77 (3H, d, J=6.8 Hz), 0.82 (3H, d, J=6.8 Hz), 1.42 (3H, s), 1.43 (9H, s), 1.48 (3H, s), 2.20-2.29 (1H, m), 3.45 (1H, t, J=8.8 Hz), 3.80-3.83 (1H, m), 3.89-3.92 (1H, dd, J=2.0 Hz, J=8.4 Hz), 5.16 (1H, brs), 6.13 (1H, d, J=9.6 Hz), 7.21-7.26 (1H, m), 7.29-7.33 (2H, m). 7.42 (2H, d, J=7.2 Hz).

e) Production of N-(tert-butoxycarbonyl)-β,β-dimethyl-L-phenylalanine (Compound J5)

To a solution of compound J4 (16.1 g) in THF (468 mL) and water (117 mL), a 30% aqueous hydrogen peroxide solution (32.5 mL) and an aqueous lithium hydroxide solution (1 mol/L, 119 mL) were added at 0° C., the temperature was raised to 25° C., and the resultant mixture was stirred for 3 hours. An aqueous sodium bisulfate solution (1.5 mol/L, 470 mL) was added at 0° C., the temperature was raised to 25° C., and the resultant mixture was stirred for 1 hour. The pH was changed to 3 with an aqueous citric acid solution (1 mol/L), and the resultant mixture was extracted with tert-butyl methyl ether. The organic layer was washed with saturated brine, and the organic layer was dried over anhydrous magnesium sulfate. The solvent was distilled off under reduced pressure to give compound J5 (14.2 g).

$^1$H-NMR (400 MHz, CDCl$_3$):1.38 (9H, s), 1.44 (3H, s), 1.46 (3H, s), 4.56 (1H, brd, J=11.6 Hz), 4.94 (1H, brd, J=14.4 Hz), 7.21-7.38 (5H, m).

f) Production of N-(tert-butoxycarbonyl)-β,β-dimethyl-L-phenylalanine methyl ester (Compound J6)

To a solution of compound J5 (14.2 g) in N,N-dimethylformamide (84 ml), sodium carbonate (8.44 g) and methyl iodide (9.91 mL) were added, and the resultant mixture was stirred at 25° C. for 15 hours. After cooling the mixture to 0° C., chilled water was added and the resultant mixture was extracted with tert-butyl methyl ether, and the organic layer thus obtained was washed with saturated brine and then dried over anhydrous magnesium sulfate. The solvent was distilled off under reduced pressure, and the residue was purified by silica gel column chromatography (eluting solvent; hexane:tert-butyl methyl ether) to give compound J6 (11.1 g).

$^1$H-NMR (400 MHz, CDCl$_3$):1.36 (9H, s), 1.37 (3H, s), 1.41 (3H, s), 3.48 (3H, brs), 4.49 (1H, brd, J=9.8 Hz), 4.98 (1H, brd, J=9.1 Hz), 7.18-7.22 (1H, m), 7.27-7.33 (4H, m).

g) Production of N-(tert-butoxycarbonyl)-N,β,β-trimethyl-L-phenylalanine methyl ester (Compound J7)

By the same approach as Reference Example 1-k), from compound J6 (307 mg), compound J7 (245 mg) was obtained.

LC-MS: 344 (M+Na)$^+$ (1.589 min, Measurement Condition C)

h) Production of N-(tert-butoxycarbonyl)-N,β,β-trimethyl-L-phenylalanine (Compound J8)

By the same approach as Reference Example 2-a), from compound J7 (235 mg), compound J8 (195 mg) was obtained.

LC-MS: 330 (M+Na)$^+$ (1.420 min, Measurement Condition C)

i) Production of N-(tert-butoxycarbonyl)-N,β,β-trimethyl-L-phenylalanyl-N-[(3S,4E)-6-ethoxy-2,5-dimethyl-6-oxohex-4-en-3-yl]-N,3-dimethyl-L-valinamide (Compound J9)

By the same approach as Reference Example 2-b), from compound J8 (195 mg), J9 (307 mg) was obtained.

LC-MS: 624 (M+Na)$^+$ (1.797 min, Measurement Condition C)

j) Production of N-(tert-butoxycarbonyl)-N,β,β-trimethyl-L-phenylalanyl-N-[(3S,4E)-5-carboxy-2-methylhex-4-en-3-yl]-N,3-dimethyl-L-valinamide (Compound J10)

By the same approach as Reference Example 2-c), from compound J9 (307 mg), J10 (286 mg) was obtained.

LC-MS: 596 (M+Na)$^+$, 572 (M−H)$^−$ (1.596 min, Measurement Condition C)

k) Production of N-(tert-butoxycarbonyl)-N,β,β-trimethyl-L-phenylalanyl-N-{(3S,4E)-6-[(2,5-dioxopyrrolidin-1-yl)oxy]-2,5-dimethyl-6-oxohex-4-en-3-yl}-N,3-dimethyl-L-valinamide (Compound J11)

By the same approach as Reference Example 2-d), from compound J10 (286 mg), J11 (227 mg) was obtained.

LC-MS: 693 (M+Na)$^+$ (1.658 min, Measurement Condition C)

l) Production of (2S)-2-{[(6S,9S,12S,13E)-9-tert-butyl-2,2,5,11,14-pentamethyl-4,7,10,15-tetraoxo-6-(2-phenylpropan-2-yl)-12-(propan-2-yl)-3-oxa-5,8,11-triazapentadec-13-en-15-yl]amino}pentane diethyl diester (Reference Example 9)

By the same approach as Reference Example 3, from compound J11 (227 mg), Reference Example 9 (232 mg) was obtained.

LC-MS: 781 (M+Na)$^+$ (1.707 min, Measurement Condition C)

Reference Example 10

The compound shown in the following table was synthesized through the reaction and treatment in accordance with the method described in Molecules 2015, 20(6), 10004-10031.

TABLE 1

| Reference Example | Structural Formula | LC-MS/Rt (min) | LC-MS Measurement Condition |
|---|---|---|---|
| 10 | | 347 (M + H)$^+$/0.969 | C |

Reference Example 11

Tetraethyl 2,2'-(((S)-2-aminopentanedioyl)bis(azanediyl))(2S,2'S)-diglutarate

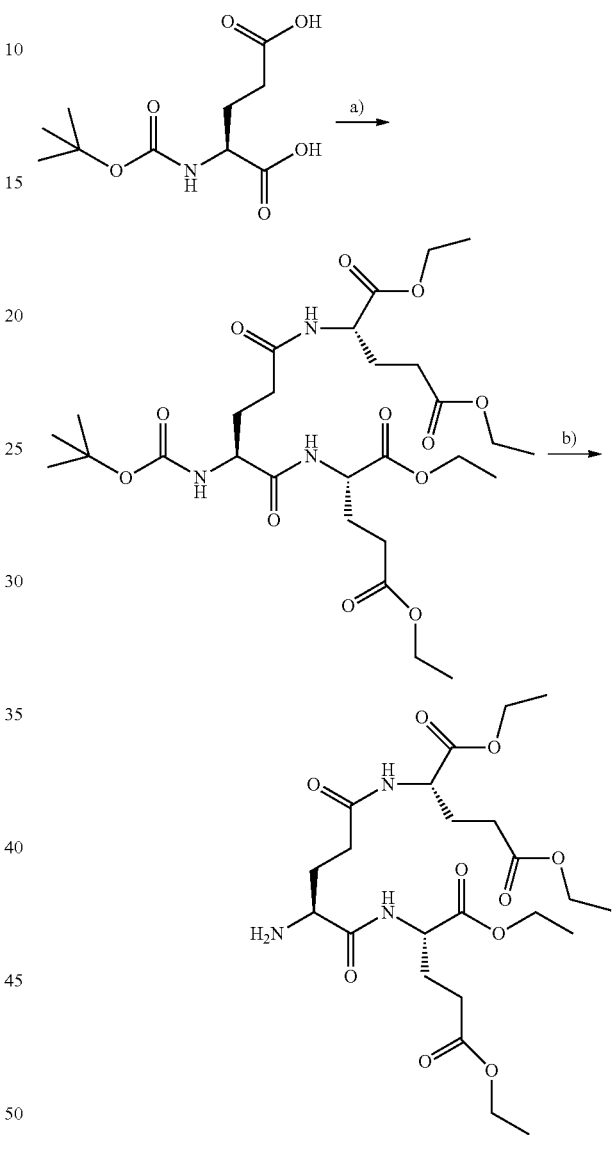

Reference Example 11 a) Production of (2S,2'S)-tetraethyl 2,2'-(((S)-2-((tert-butoxycarbonyl)amino)pentanedioyl)bis(azanediyl))dipentanedioate By the same approach as Reference Example 2-b), from (S)-2-((tert-butoxycarbonyl)amino)pentanedioic acid (500 mg), (2S,2'S)-tetraethyl 2,2'-(((S)-2-((tert-butoxycarbonyl)amino)pentanedioyl)bis(azanediyl))dipentanedioate (741 mg) was obtained.

LC-MS: 618 (M+H)$^+$/1.267 min, Measurement Condition C b) Production of tetraethyl 2,2'-(((S)-2-aminopentanedioyl)bis (azanediyl))(2S,2'S)-diglutarate (Reference Example 11)

By the same approach as Reference Example 101-a) step, Reference Example 11 (450 mg) was obtained.
LC-MS: 518 (M+H)$^+$/1.263 min, Measurement Condition C

Reference Examples 12 to 15

Using Fmoc-Glu(OtBu)-Alko-PEG resin (1.00 g, manufactured by WATANABE CHEMICAL INDUSTRIES, LTD.; 0.23 mmol/g, 0.23 mmol) as a starting raw material, synthesis of the peptides shown in the following table was carried out through solid phase synthesis via Fmoc method. Note that the Fmoc method may be carried out by the method described in Fundamentals and Experiments of Peptide Synthesis (authored by Nobuo Izumiya, Tetsuo Kato, Haruhiko Aoyagi and Michinori Waki, issued by Maruzen Co., Ltd., 1985) and the like. For the solid phase synthesis, a peptide synthesizer (model CS336X, manufactured by CSBio) was used. Deprotection of the Fmoc group was carried out through treatment in a 20% solution of piperidine in DMF for 25 minutes. Coupling reaction for the peptide synthesis was carried out by allowing a solution of a Fmoc-protected amino acid (1.05 mmol), O-(benzotriazol-1-yl)-N,N,N'N'-tetramethyluronium hexafluorophosphate (1 mmol) and N,N-diisopropylethylamine (2 mmol) in DMF to react with the amino acids or peptide on the resin (0.23 mmol) for 1 hour. By washing the resin thus obtained with DMF and ether, followed by drying under reduced pressure, a peptide resin was obtained. To this peptide resin, a mixed solution (10 mL) of TFA/water/triisopropylsilane (volume ratio: 95/2.5/2.5) was added, and the resultant mixture was shaken at room temperature for 2 hours. After filtering off the resin, the reaction solution was concentrated under reduced pressure. The reaction solution was ice-cooled, and diethyl ether (50 mL) was added. The produced precipitate was separated by filtration, washed with diethyl ether and then dried under reduced pressure, thereby obtaining a crude peptide. The crude peptide thus obtained was dissolved in a mixed solution of a 20% aqueous acetic acid solution and acetonitrile (volume ratio 1/1), and purified by reversed phase HPLC (the mobile phase was water with 0.1% v/v TFA and acetonitrile with 0.035% v/v TFA) to obtain the peptides shown in the following table.

TABLE 2

| Reference Example | Structural Formula | LC-MS/Rt (min) | LC-MS Measurement Condition |
|---|---|---|---|
| 12 | (structure) | 664 (M + H)$^+$/0.299 | J |
| 13 | (structure) | 1309/(M + H)$^+$/0.640 | J |
| 14 | (structure) | 1169 (M + H)$^+$/0.317 | J |

TABLE 2-continued

| Reference Example | Structural Formula | LC-MS/Rt (min) | LC-MS Measurement Condition |
|---|---|---|---|
| 15 | | 664 (M + H)⁺/ 0.277 | C |

Reference Example 16

Diethyl ((S,E)-4-((S)-2-amino-N,3,3-trimethylbutanamido)-2,5-dimethylhex-2-enoyl)-D-glutamate

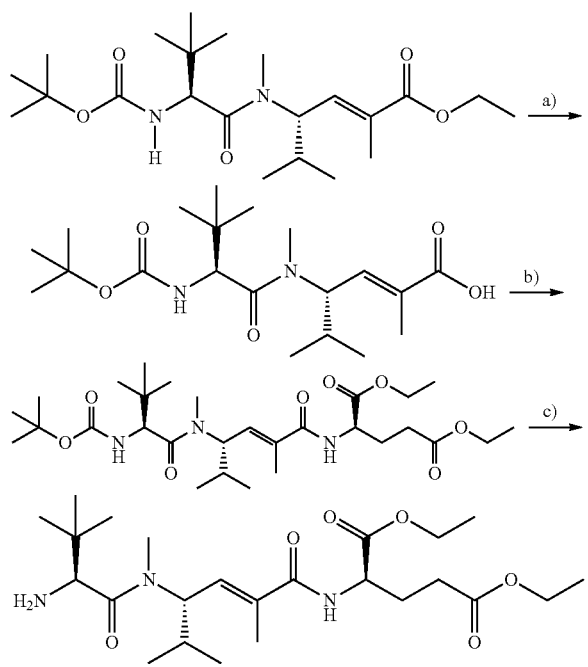

Reference Example 16 a) Production of (S,E)-4-((S)-2-((tert-butoxycarbonyl)amino)-N,3,3-trimethylbutanamido)-2,5-dimethylhex-2-enoic acid By the same approach as Reference Example 2-c), from ethyl (S,E)-4-((S)-2-((tert-butoxycarbonyl)amino)-N,3,3-trimethylbutanamido)-2,5-dimethylhex-2-enoate (1.64 g), (S,E)-4-((S)-2-((tert-butoxycarbonyl)amino)-N,3,3-trimethylbutanamido)-2,5-dimethylhex-2-enoic acid (1.55 g) was obtained.

LC-MS: 385 (M+H)⁺/0.986 min, Measurement Condition E b) Production of diethyl ((S,E)-4-((S)-2-((tert-butoxycarbonyl) amino)-N,3,3-trimethylbutanamido)-2,5-dimethylhex-2-enoyl)-D-glutamate By the same approach as Reference Example 2-b), from (S,E)-4-((S)-2-((tert-butoxycarbonyl)amino)-N,3,3-trimethylbutanamido)-2,5-dimethylhex-2-enoic acid (376 mg), diethyl ((S,E)-4-((S)-2-((tert-butoxycarbonyl)amino)-N,3,3-trimethylbutanamido)-2,5-dimethylhex-2-enoyl)-D-glutamate (500 mg) was obtained.

c) Production of diethyl ((S,E)-4-((S)-2-amino-N,3,3-trimethylbutanamido)-2,5-dimethylhex-2-enoyl)-D-glutamate (Reference Example 16)

By the same approach as Reference Example 101-a), from diethyl ((S,E)-4-((S)-2-((tert-butoxycarbonyl)amino)-N,3,3-trimethyl butanamido)-2,5-dimethylhex-2-enoyl)-D-glutamate (528 mg), Reference Example 16 (515 mg) was obtained.

LC-MS: 470 (M+H)⁺/1.223 min, Measurement Condition C

Reference Example 17

Diethyl ((R)-2-((S,E)-4-((S)-2-amino-N,3,3-trimethylbutanamido)-2,5-dimethylhex-2-enamido)-5-methoxy-5-oxopentanoyl)-D-glutamate

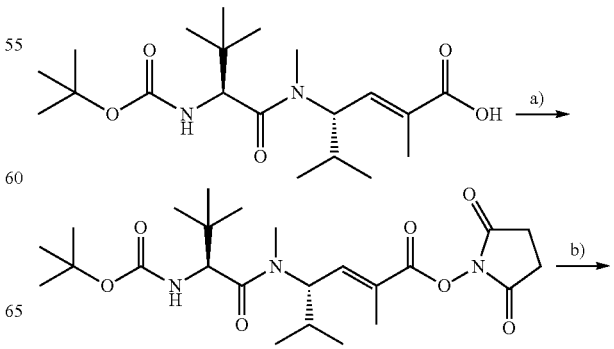

-continued

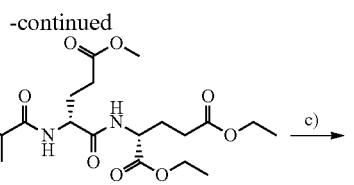

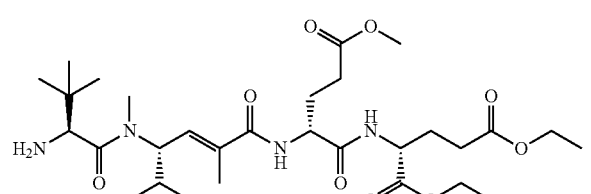

Reference Example 17 a) Production of 2,5-dioxopyrrolidin-1-yl (S,E)-4-((S)-2-((tert-butoxycarbonyl)amino)-N,3,3-trimethylbutanamido)-2,5-dimethylhex-2-enolate By the same approach as Reference Example 2-d) step, from (S,E)-4-((S)-2-((tert-butoxycarbonyl)amino)-N,3,3-trimethylbutanamido)-2,5-dimethylhex-2-enoic acid (192 mg), 2,5-dioxopyrrolidin-1-yl (S,E)-4-((S)-2-((tert-butoxycarbonyl)amino)-N,3,3-trimethylbutanamido)-2,5-dimethylhex-2-enolate (220 mg) was obtained.

LC-MS: 482 (M+H)$^+$/1.404 min, Measurement Condition C b) Production of diethyl ((R)-2-((S,E)-4-((S)-2-((tert-butoxycarbonyl)amino)-N,3,3-trimethylbutanamido)-2,5-dimethylhex-2-enamido)-5-methoxy-5-oxopentanoyl)-D-glutamate By the same approach as Reference Example 3, from 2,5-dioxopyrrolidin-1-yl (S,E)-4-((S)-2-((tert-butoxycarbonyl)amino)-N,3,3-trimethylbutanamido)-2,5-dimethylhex-2-enolate (48 mg), diethyl ((R)-2-((S,E)-4-((S)-2-((tert-butoxycarbonyl)amino)-N,3,3-trimethylbutanamido)-2,5-dimethylhex-2-enamido)-5-methoxy-5-oxopentanoyl)-D-glutamate (51.2 mg) was obtained.

LC-MS: 735 (M+Na)$^+$/1.469 min, Measurement Condition J c) Production of diethyl ((R)-2-((S,E)-4-((S)-2-amino-N,3,3-trimethylbutanamido)-2,5-dimethylhex-2-enamido)-5-methoxy-5-oxopentanoyl)-D-glutamate (Reference Example 17)

By the same approach as Reference Example 101-a) step, from diethyl((R)-2-((S,E)-4-((S)-2-((tert-butoxycarbonyl)amino)-N,3,3-trimethylbutanamido)-2,5-dimethylhex-2-enamido)-5-methoxy-5-oxopentanoyl)-D-glutamate (51.2 mg), Reference Example 17 (41.2 mg) was obtained.

LC-MS: 613 (M+H)$^+$/1.066 min, Measurement Condition J

Reference Example 18

The compound shown in the following table was obtained through the same reaction and treatment as Reference Example 1 and Reference Example 2, using a corresponding raw material compound.

TABLE 3

| Reference Example | Structural Formula | LC-MS/ Rt (min) | LC-MS Measurement Condition |
|---|---|---|---|
| 18 | | 627(M + H)$^+$/ 1.117 min | J |

Reference Examples 19 to 21

The compounds shown in the following table were obtained through the same reaction and treatment as Reference Example 1 and Reference Example 2, using corresponding raw material compounds.

TABLE 4

| Reference Example | Structural Formula | LC-MS/ Rt (min) | LC-MS Measurement Condition |
|---|---|---|---|
| 19 | | 742(M + H)+/ 1.488 | J |
| 20 | | 754(M + H)+/ 1.557 | J |
| 21 | | 742(M + H)+/ 1.582 | C |

Reference Example 22 tert-Butyl ((S)-3-methyl-1-(((S)-1-((4-((((4-nitrophenoxy)carbonyl)oxy) methyl)phenyl)amino)-11-oxo-5-ureidopentan-2-yl)amino)-1-oxobutan-2-yl)carbamate

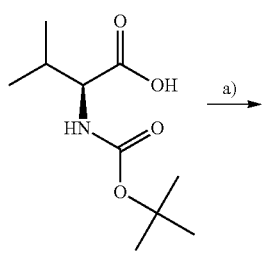
a) →

-continued

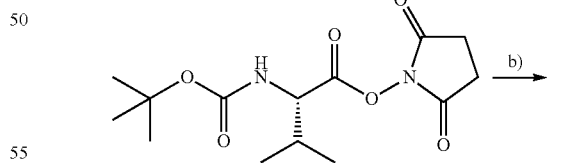
b) →

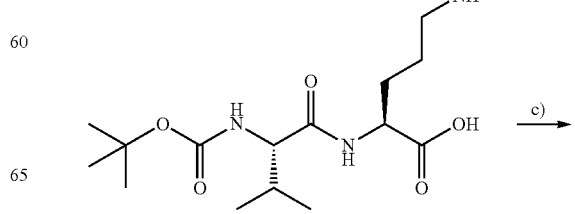
c) →

153

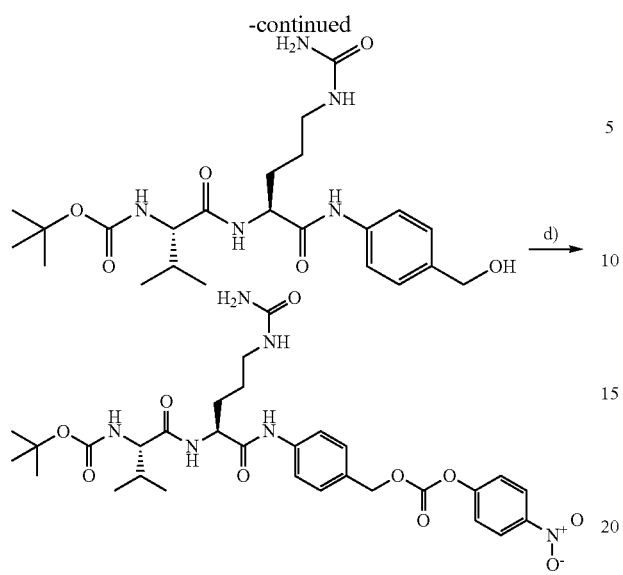

Reference Example 22 a) Production of 2,5-dioxopyrrolidin-1-yl (tert-butoxycarbonyl)-L-valinate

By the same approach as Reference Example 2-d), from (tert-butoxycarbonyl)-L-valine (3.72 g), 2,5-dioxopyrrolidin-1-yl (tert-butoxycarbonyl)-L-valinate (4.9 g) was obtained. 1H-NMR (400 MHz, CDCl$_3$): 1.01 (3H, d, J=7.2 Hz), 1.05 (3H, d, J=6.8 Hz), 1.44 (9H, s), 2.28 (1H, m), 2.82 (4H, s), 4.58 (1H, m), 4.97 (1H, m)

b) Production of (S)-2-((S)-2-((tert-butoxycarbonyl)amino)-3-methylbutanamido)-5-ureidopentanoic acid By the same approach as Reference Example 3, from 2,5-dioxopyrrolidin-1-yl (tert-butoxycarbonyl)-L-valinate (4.9 g), (S)-2-((S)-2-((tert-butoxycarbonyl)amino)-3-methylbutanamido)-5-ureidopentanoic acid (5.31 g) was obtained.

LC-MS:375 (M+H)$^+$/0.972 min, Measurement Condition C c) Production of tert-butyl ((S)-1-(((S)-1-((4-(hydroxymethyl) phenyl)amino)-1-oxo-5-ureidopentan-2-yl)amino)-3-methyl-1-oxobutan-2-yl)carbamate A mixed solution of (S)-2-((S)-2-((tert-butoxycarbonyl) amino)-3-methylbutanamido)-5-ureidopentanoic acid (701 mg), 4-aminobenzyl alcohol (461 mg), ethyl 2-ethoxyquinoline-1(2H)-carboxylate (926 mg), methanol (10 mL) and dichloromethane (20 mL) was stirred at room temperature for 24 hours under shading. After distilling off the solvent under reduced pressure, through purification by silica gel column chromatography (eluting solvent; chloroform: methanol), tert-butyl ((S)-1-(((S)-1-((4-(hydroxymethyl) phenyl)amino)-1-oxo-5-ureidopentan-2-yl)amino )-3-methyl-1-oxobutan-2-yl)carbamate (243 mg) was obtained.

LC-MS:480 (M+H)$^+$/1.583 min, Measurement Condition J

154 d) Production of tert-butyl ((S)-3-methyl-1-(((S)-1-((4-((((4-nitrophenoxy)carbonyl)oxy)methyl)phenyl) amino)-1-oxo-5-ureidopentan-2-yl) amino)-1-oxobutan-2-yl)carbamate (Reference Example 22)

A mixed solution of tert-butyl ((S)-1-(((S)-1-((4-(hydroxymethyl)phenyl)amino)-1-oxo-5-ureidopentan-2-yl) amino )-3-methyl-1-oxobutan-2-yl)carbamate (2.0 g), bis(4-nitrophenyl)carbonate (3.81 g), N,N-diisopropylethylenediamine (2.179 mL) and N,N-dimethylformamide was stirred at room temperature for 2 hours. After distilling off the solvent under reduced pressure, the residue was purified by silica gel chromatography (eluting solvent; chloroform:methanol) to give Reference Example 22 (2.1 g).

LC-MS:645 (M+H)$^+$/1.225 min, Measurement Condition J

Reference Example 23 tert-Butyl ((S)-3-methyl-1-(((S)-1-((4-((((4-nitrophenoxy)carbonyl)oxy)methyl)phenyl)amino)-1-oxopropan-2-yl) amino)-1-oxobutan-2-yl)carbamate

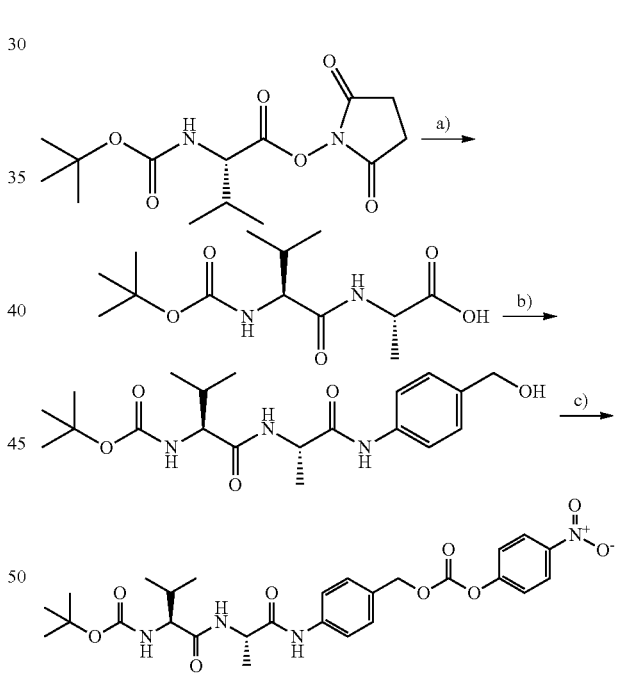

Reference Example 23 a) Production of (tert-butoxycarbonyl)-L-valyl-L-alanine

By the same approach as Reference Example 3, from 2,5-dioxopyrrolidin-1-yl (tert-butoxycarbonyl)-L-valinate (1.0 g), (tert-butoxycarbonyl)-L-valyl-L-alanine (676 mg) was obtained.

LC-MS:278 (M−H)$^−$/0.925 min, Measurement Condition J b) Production of tert-butyl ((S)-1-(((S)-1-((4-(hydroxymethyl)phenyl)amino)-1-oxopropan-2-yl)amino)-3-methyl-1-oxobutan-2-yl)carbamate By the same approach as c) step of Reference Example 22, from (tert-butoxycarbonyl)-L-valyl-L-alanine (676 mg), tert-butyl ((S)-1-(((S)-1-((4-(hydroxymethyl)phenyl)amino)-1-oxopropan-2-yl)amino)-3-meth yl-1-oxobutan-2-yl)carbamate (400 mg) was obtained.

LC-MS:394 (M+H)$^+$/0.974 min, Measurement Condition J c) Production of tert-butyl ((S)-3-methyl-1-(((S)-1-((4-(((((4-nitrophenoxy)carbonyl)oxy)methyl)phenyl)amino)-1-oxopropan-2-yl)amino)-1-oxobutan-2-yl)carbamate (Reference Example 23)

By the same approach as d) step of Reference Example 22, from tert-butyl ((S)-1-(((S)-1-((4-(hydroxymethyl)phenyl)amino)-1-oxopropan-2-yl)amino)-3-meth yl-1-oxobutan-2-yl)carbamate (400 mg), Reference Example 23 (567 mg) was obtained.

LC-MS:559 (M+H)$^+$/1.217 min, Measurement Condition J

Reference Examples 24 to 26

The compounds shown in the following table were obtained through the same reaction and treatment as Reference Example 103, using the F3 intermediate of Reference Example 103 and using corresponding raw material compounds.

TABLE 5

| Reference Example | Structural Formula | LC-MS/ Rt (min) | LC-MS Measurement Condition |
|---|---|---|---|
| 24 | | 785(M + H)$^+$/ 1.043 | B |
| 25 | | 759(M + H)$^+$/ 0.948 | B |
| 26 | | 688(M + H)$^+$/ 0.781 | E |

Reference Examples 27 to 45

The compounds shown in the following tables were obtained through the same reaction and treatment as Reference Example 3, using corresponding raw material compounds.

TABLE 6-1

| Reference Example | Structural Formula | LC-MS/ Rt (min) | LC-MS Measurement Condition |
|---|---|---|---|
| 27 | | 770(M + H)+/ 1.22 | E |
| 28 | | 770(M + H)+/ 1.21 | E |
| 29 | | 770(M + H)+/ 1.21 | E |
| 30 | | 770(M + H)+/ 1.22 | E |
| 31 | | 1485(M + H)+/ 1.944 | J |

TABLE 6-1-continued
| Reference Example | Structural Formula | LC-MS/ Rt (min) | LC-MS Measurement Condition |
|---|---|---|---|
| 32 | 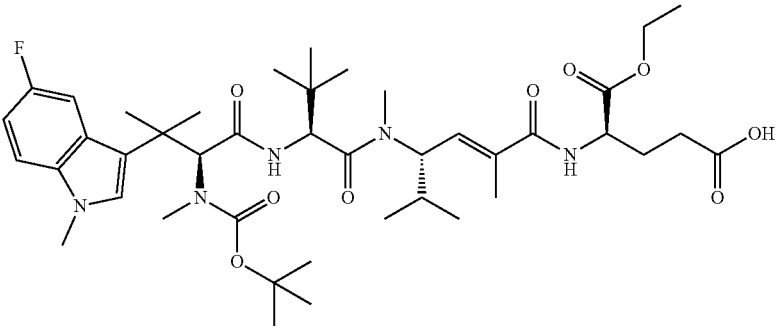 [SMILES: CCOC(=O)[C@@H](CCC(=O)O)NC(=O)/C(C)=C/[C@H](C(C)C)N(C)C(=O)[C@@H](NC(=O)[C@@H](N(C)C(=O)OC(C)(C)C)C(C)(C)c1cn(C)c2ccc(F)cc12)C(C)(C)C] | 802(M + H)+/ 1.395 | J |
| 33 | 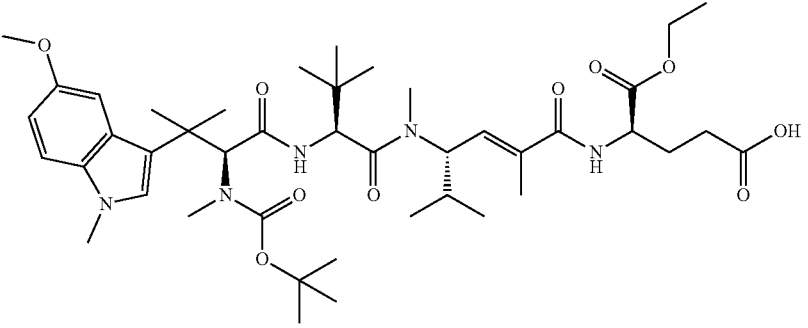 [SMILES: CCOC(=O)[C@@H](CCC(=O)O)NC(=O)/C(C)=C/[C@H](C(C)C)N(C)C(=O)[C@@H](NC(=O)[C@@H](N(C)C(=O)OC(C)(C)C)C(C)(C)c1cn(C)c2ccc(OC)cc12)C(C)(C)C] | 814(M + H)+/ 1.403 | J |
TABLE 6-2
| 34 | 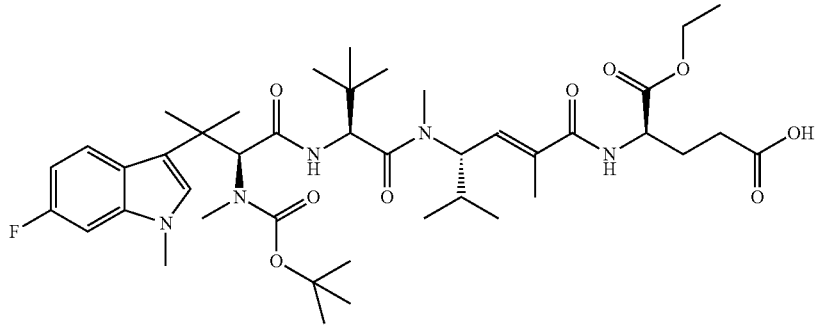 [SMILES: CCOC(=O)[C@@H](CCC(=O)O)NC(=O)/C(C)=C/[C@H](C(C)C)N(C)C(=O)[C@@H](NC(=O)[C@@H](N(C)C(=O)OC(C)(C)C)C(C)(C)c1cn(C)c2cc(F)ccc12)C(C)(C)C] | 802 (M + H)+/ 1.434 | J |
| 35 | 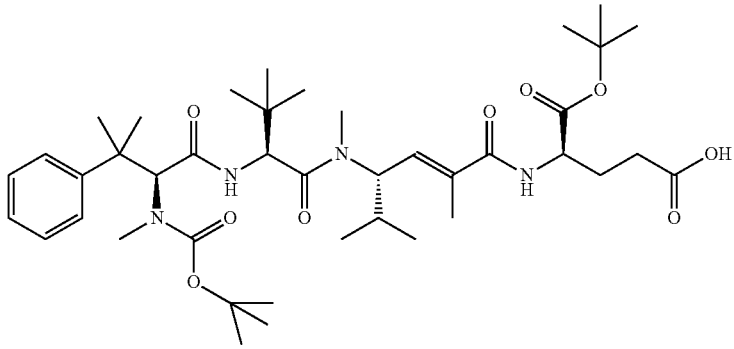 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)N[C@H](CCC(=O)O)C(=O)OC(C)(C)C] | 759 (M + H)+/ 1.427 | C |

TABLE 6-2-continued
| 36 | 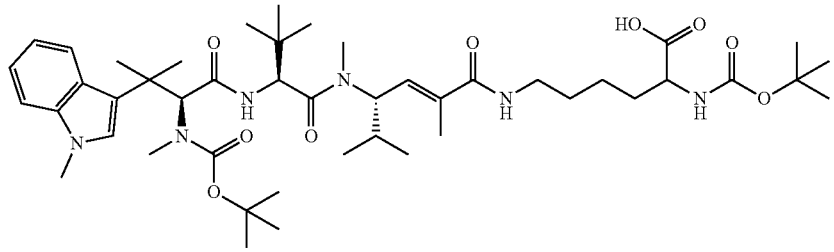 [SMILES: C/C(=C\[C@H](C(C)C)N(C)C(=O)[C@@H](NC(=O)[C@@H](N(C)C(=O)OC(C)(C)C)C(C)(C)c1cn(C)c2ccccc12)C(C)(C)C)C(=O)NCCCCC(NC(=O)OC(C)(C)C)C(=O)O] | 855 (M + H)⁺/ 1.588 | J |
| 37 | 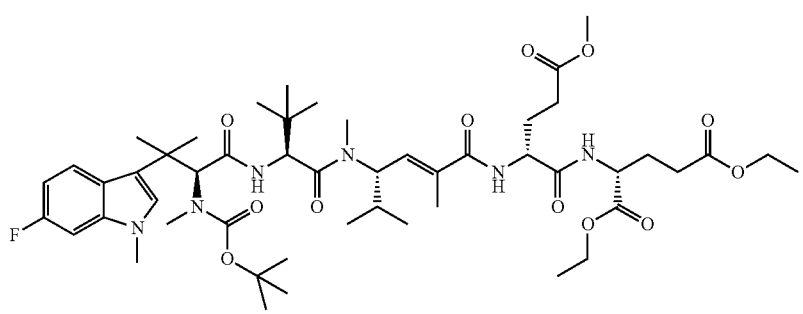 | 977 (M + H)⁺/ 1.618 | J |
| 38 | 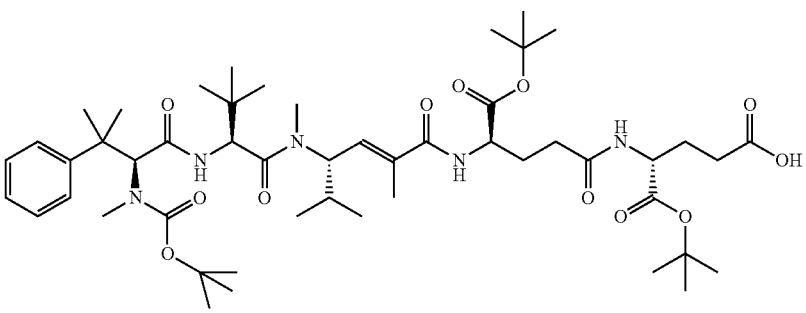 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)N[C@H](CCC(=O)N[C@H](CCC(=O)O)C(=O)OC(C)(C)C)C(=O)OC(C)(C)C] | 944 (M + H)⁺/ 1.407 | J |
| 39 | 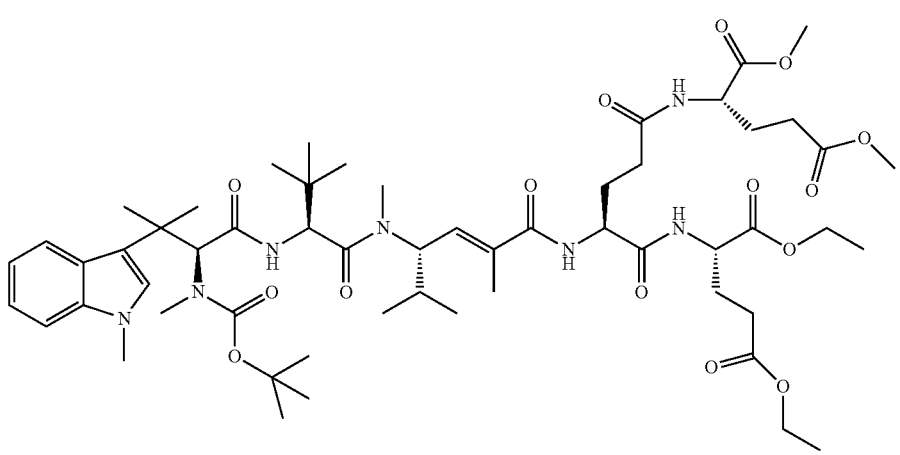 | 1126 (M + H)⁺/ 1.620 | J |

TABLE 6-3

| | | | |
|---|---|---|---|
| 40 | [structure] | 1270 (M − H)⁻/ 1.27 | J |
| 41 | [structure] | 957 (M − 2H)²⁻/ 0.955 | J |
| 42 | [structure] | 887 (M − 2H)²⁻/ 1.229 | J |
| 43 | [structure] | 1270 (M − H)⁻/ 1.248 | J |
| 44 | [structure] | 806 (M + Na)⁺/ 1.652 | J |

TABLE 6-3-continued
| | | | |
|---|---|---|---|
| 45 | 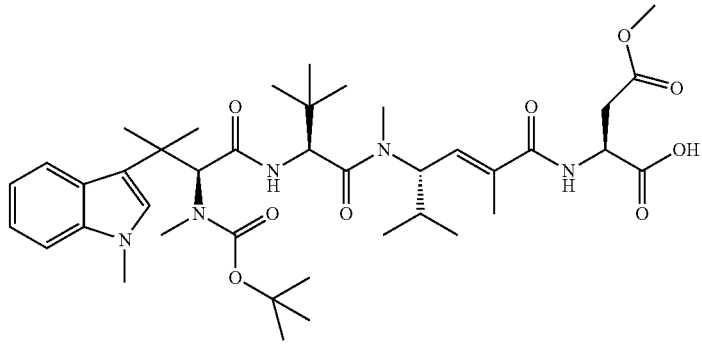 [SMILES: COC(=O)C[C@H](NC(=O)/C(C)=C/[C@H](C(C)C)N(C)C(=O)[C@@H](NC(=O)[C@@H](N(C)C(=O)OC(C)(C)C)C(C)(C)c1cn(C)c2ccccc12)C(C)(C)C)C(=O)O] | 756 (M + H)+/ 1.518 | J |
Reference Examples 46 to 49
The compounds shown in the following table were obtained through the same reaction and treatment as b) step of Reference Example 2, using corresponding raw material compounds.
TABLE 7
| Reference Example | Structural Formula | LC-MS/Rt (min) | LC-MS Measurement Condition |
|---|---|---|---|
| 46 | 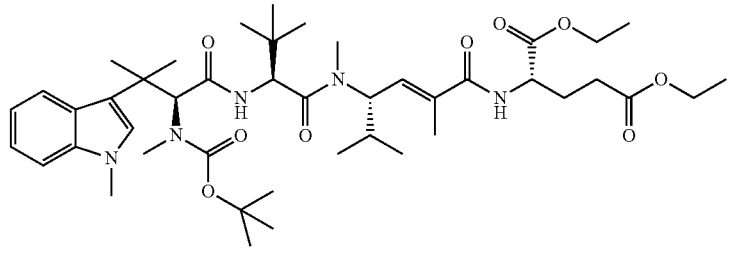 [SMILES: CCOC(=O)CC[C@H](NC(=O)/C(C)=C/[C@H](C(C)C)N(C)C(=O)[C@@H](NC(=O)[C@@H](N(C)C(=O)OC(C)(C)C)C(C)(C)c1cn(C)c2ccccc12)C(C)(C)C)C(=O)OCC] | 812(M + H)+/ 1.518 | J |
| 47 | 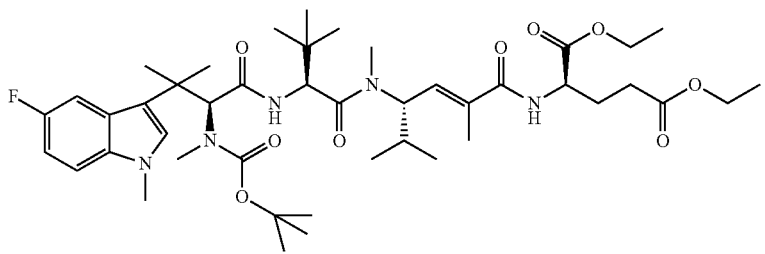 [SMILES: CCOC(=O)CC[C@@H](NC(=O)/C(C)=C/[C@H](C(C)C)N(C)C(=O)[C@@H](NC(=O)[C@@H](N(C)C(=O)OC(C)(C)C)C(C)(C)c1cn(C)c2ccc(F)cc12)C(C)(C)C)C(=O)OCC] | 852(M + Na)+/ 1.677 | J |

TABLE 7-continued

| Reference Example | Structural Formula | LC-MS/Rt (min) | LC-MS Measurement Condition |
|---|---|---|---|
| 48 | | 1186(M + Na)+/ 1.302 | J |
| 49 | | 943(M + Na)+/ 1.468 | J |

Reference Examples 50 to 56

The compounds shown in the following tables were obtained through the same reaction and treatment as b) step of Reference Example 2, using corresponding raw material compounds.

TABLE 8-1

| Reference Example | Structural Formula | LC-MS/ Rt (min) | LC-MS Measurement Condition |
|---|---|---|---|
| 50 | | 798(M + H)+/ 1.33 | E |
| 51 | | 969(M + H)+/ 1.693 | J |

TABLE 8-1-continued

| Reference Example | Structural Formula | LC-MS/ Rt (min) | LC-MS Measurement Condition |
|---|---|---|---|
| 52 | | 1068(M + H)+/ 1.751 | J |
| 53 | | 1358(M − H)−/ 1.404 | J |

TABLE 8-2

| 54 | | 1397 (M + Na)+/ 1.489 | J |
| 55 | | 1319 (M + Na)+/ 1.33 | E |

TABLE 8-2-continued

| 56 | 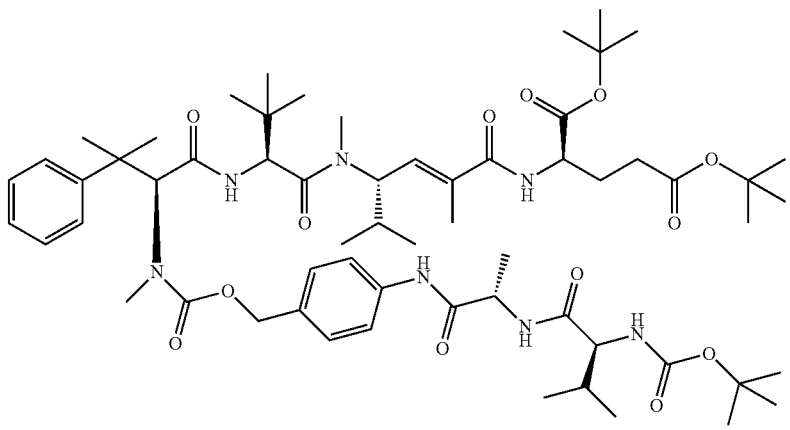 [SMILES: C/C(=C\[C@H](C(C)C)N(C)C(=O)[C@@H](NC(=O)[C@@H](N(C)C(=O)OCc1ccc(NC(=O)[C@H](C)NC(=O)[C@@H](NC(=O)OC(C)(C)C)C(C)C)cc1)C(C)(C)c1ccccc1)C(C)(C)C)C(=O)N[C@H](CCC(=O)OC(C)(C)C)C(=O)OC(C)(C)C] | 1134 (M + H)+/ 1.512 | J |

Reference Example 59

The compound shown in the following table was obtained through the same reaction and treatment as f) step of Reference Example 9, using a corresponding raw material compound.

TABLE 9

| Reference Example | Structural Formula | LC-MS/Rt (min) | LC-MS Measurement Condition |
|---|---|---|---|
| 59 |  | 812(M + H)+/ 1.509 | J |

Reference Examples 60 to 69

The compounds shown in the following tables were obtained through the same reaction and treatment as Example 2, using corresponding raw material compounds.

TABLE 10-1

| Reference Example | Structural Formula | LC-MS /Rt (min) | LC-MS Measurement Condition |
|---|---|---|---|
| 60 |  | 629(M + 2H)²⁺ /1.079 | J |

TABLE 10-1-continued

| Reference Example | Structural Formula | LC-MS /Rt (min) | LC-MS Measurement Condition |
|---|---|---|---|
| 61 | | 774(M + H)+ /1.276 | J |
| 62 | | 1038(M − H)− /1.746 | J |
| 63 | | 1012(M − H)− /1441 | J |
| 64 | | 1190(M + H)+ /0.920 | J |

TABLE 10-2
| 65 | 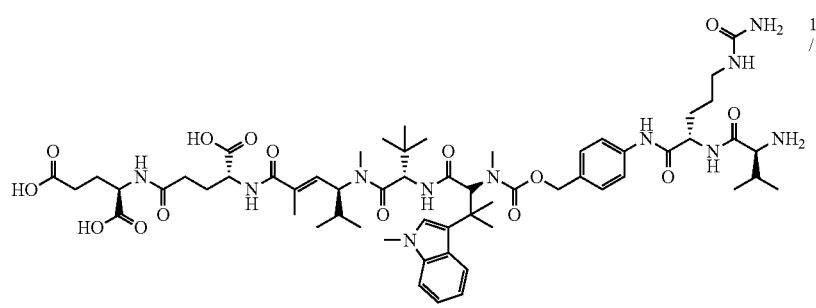 | 1188(M − H)⁻ /1.066 | J |
| 66 | 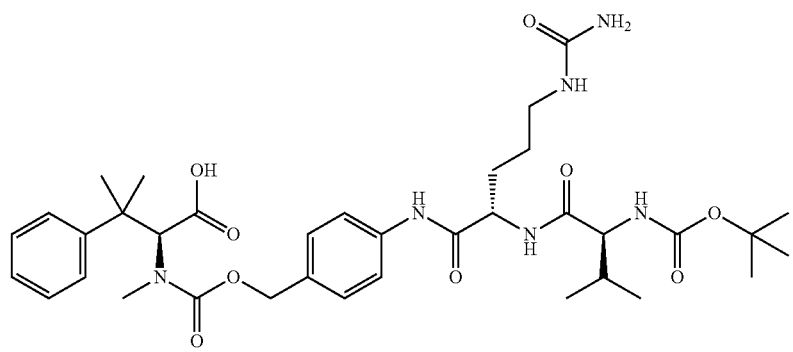 [SMILES: CC(C)[C@H](NC(=O)OC(C)(C)C)C(=O)N[C@@H](CCCNC(N)=O)C(=O)Nc1ccc(COC(=O)N(C)[C@H](C(=O)O)C(C)(C)c2ccccc2)cc1] | 713(M + H)⁺ /1.120 | J |
| 67 | 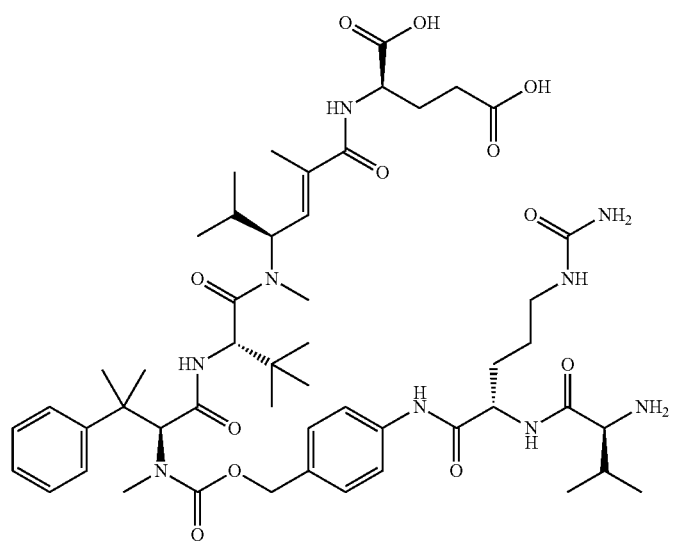 [SMILES: C/C(=C\[C@H](C(C)C)N(C)C(=O)[C@@H](NC(=O)[C@@H](N(C)C(=O)OCc1ccc(NC(=O)[C@H](CCCNC(N)=O)NC(=O)[C@@H](N)C(C)C)cc1)C(C)(C)c1ccccc1)C(C)(C)C)C(=O)N[C@H](CCC(=O)O)C(=O)O] | 1008(M + H)⁺ /0.921 | J |
| 68 | 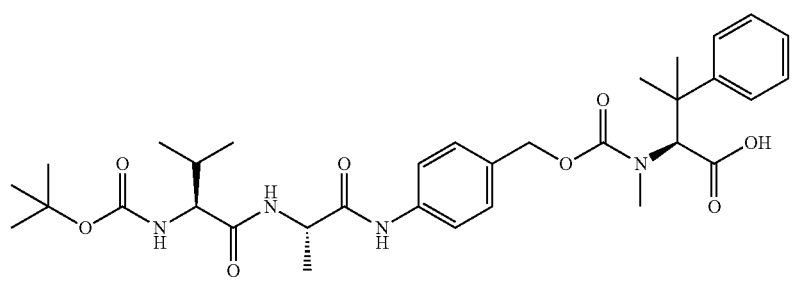 [SMILES: CC(C)[C@H](NC(=O)OC(C)(C)C)C(=O)N[C@@H](C)C(=O)Nc1ccc(COC(=O)N(C)[C@H](C(=O)O)C(C)(C)c2ccccc2)cc1] | 625(M − H)⁻ /1.182 | J |

TABLE 10-2-continued

| 69 | [structure] | 893(M + H)⁺ /1.315 | J |

Synthesis of Reference Examples 70 to 76

The compounds shown in the following tables were obtained through the same reaction and treatment as Example 1, using corresponding raw material compounds.

TABLE 11-1

| Reference Example | Structural Formula | LC-MS /Rt (min) | LC-MS Measurement Condition |
|---|---|---|---|
| 70 | [structure] | 380(M + H)⁺ /0.391 | E |
| 71 | [structure] | 643(M + 2H)²⁺ /1.044 | J |
| 72 | [structure] | 1260(M + H)⁺ /1.089 | J |

TABLE 11-1-continued
| Reference Example | Structural Formula | LC-MS /Rt (min) | LC-MS Measurement Condition |
|---|---|---|---|
| 73 | 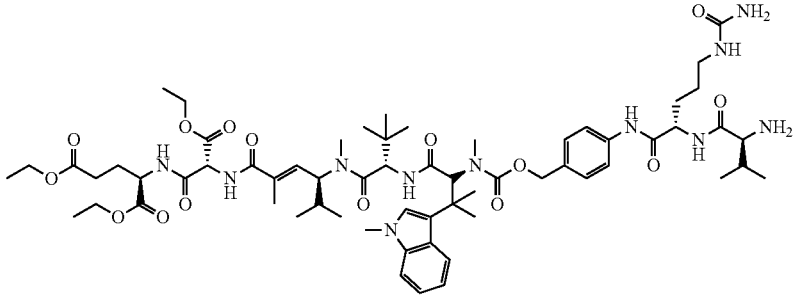 | 1274(M + H)+ /1.244 | J |
| 74 | 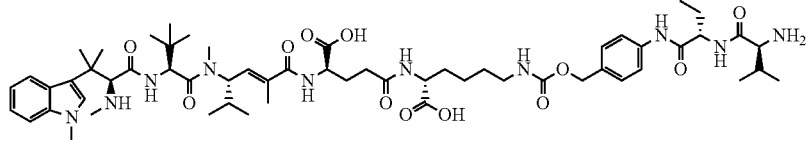 | 1187(M + H)+ /0.961 | J |
TABLE 11-2
| 75 | 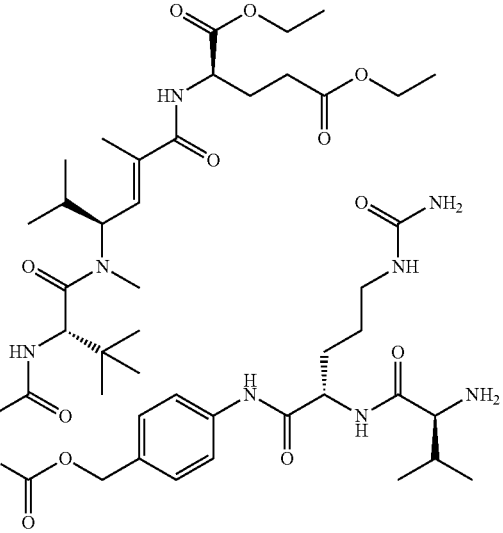 | 1086(M + Na)+ /1.083 | J |
| 76 | 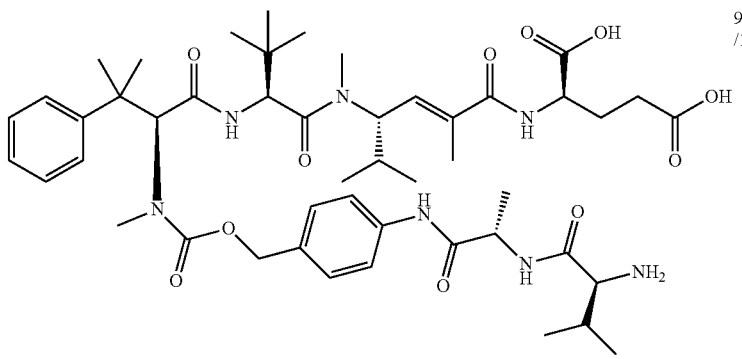 | 922(M + H)+ /1.224 | J |

Reference Example 77

The compound shown in the following table was obtained through the same reaction and treatment as Reference Example 101, using E11 described in Reference Example 101 and a corresponding raw material compound.

TABLE 12

| Reference Example | Structural Formula | LC-MS /Rt (min) | LC-MS Measurement Condition |
|---|---|---|---|
| 77 | 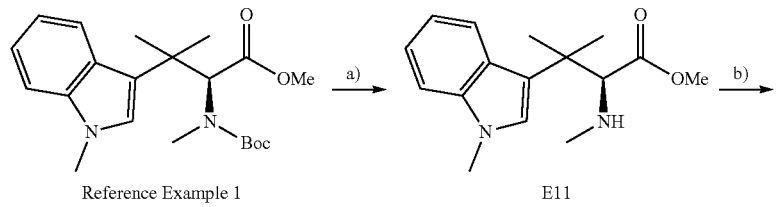 | 1089(M + H)+ /1.006 | J |

Reference Example 101

Diethyl (2R)-2-{[(5 S,8S,11 S,12E)-1-(4-{[(2S)-2-{[(2S)-2-amino-3-methylbutanoyl]amino}-5-(carbamoylamino)pentanoyl]amino}phenyl)-8-tert-butyl-4,10,13-trimethyl-5-[2-(1-methyl-1H-indol-3-yl)propan-2-yl]-3,6,9,14-tetraoxo-11-(propan-2-yl)-2-oxa-4,7,10-triazatetradec-12-en-14-yl]amino}pentanedioate

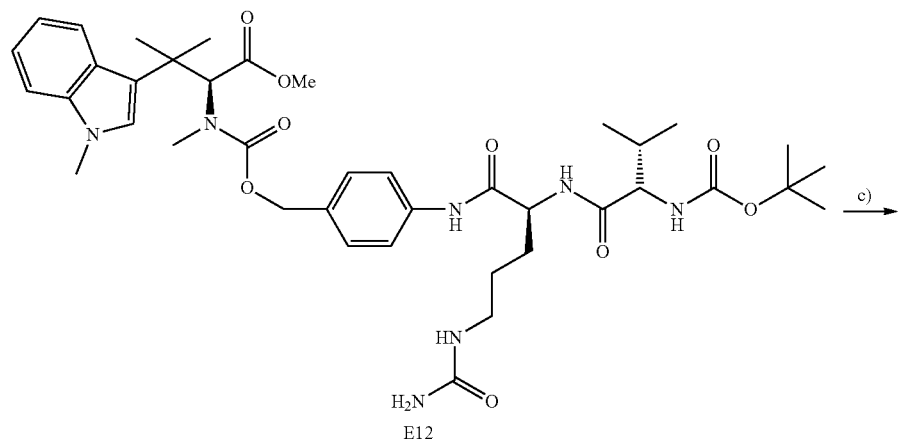

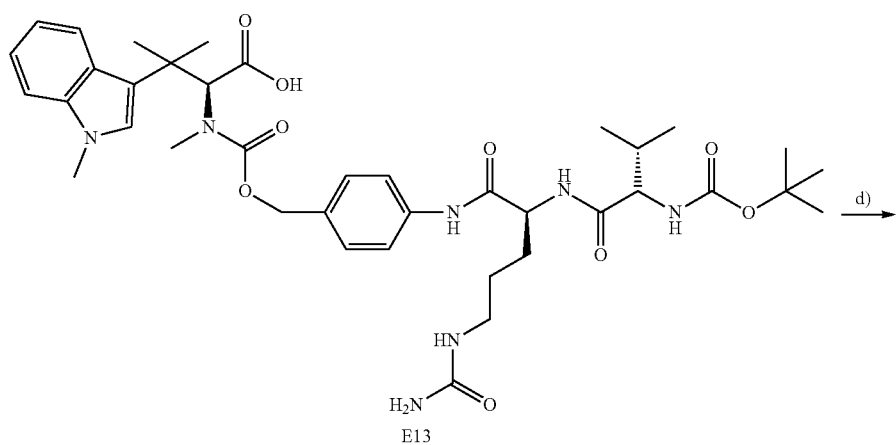
E13
d)
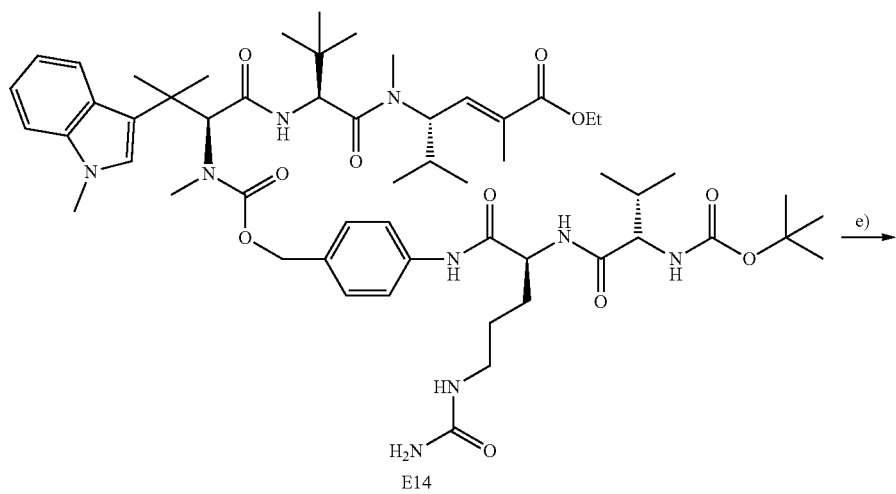
E14
e)
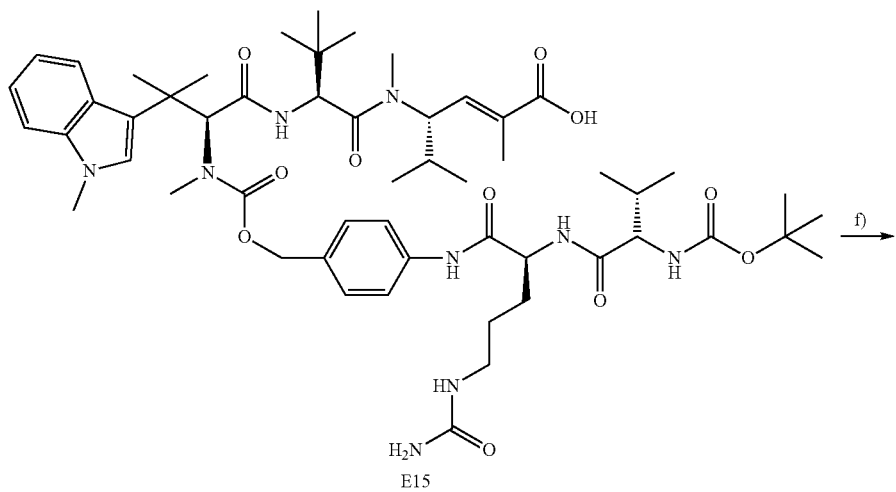
E15
f)

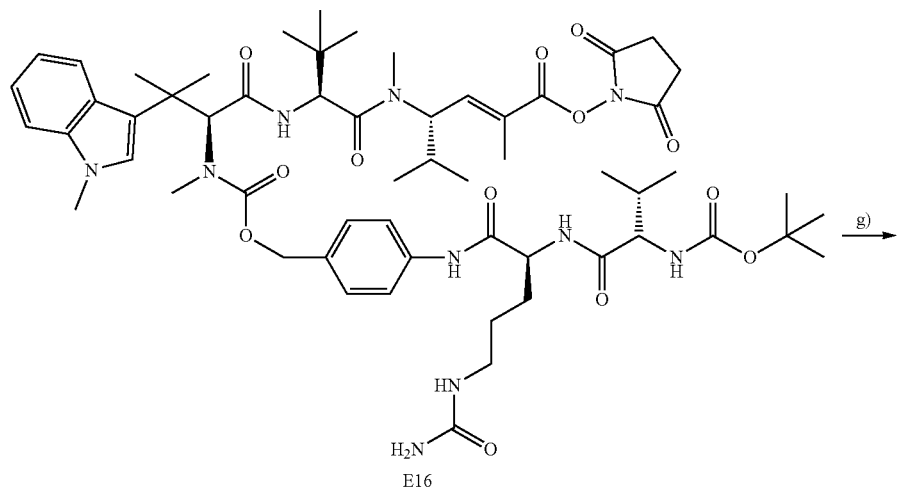
E16
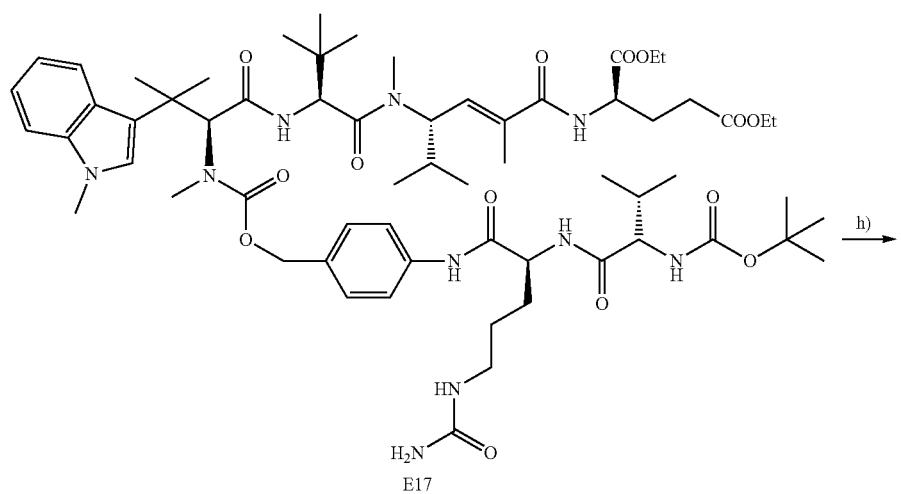
E17
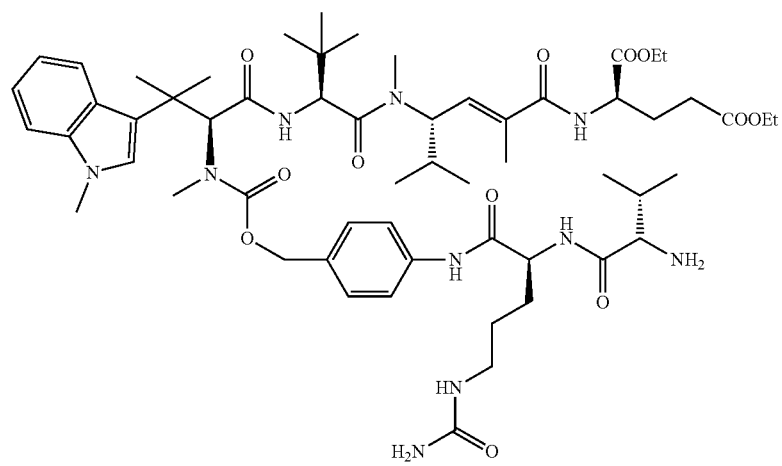
Reference Example 101 a) Production of N,β,β,1-tetramethyl-L-tryptophan methyl ester (compound E11)

To a solution of Reference Example 1 (402 mg) in chloroform (5 mL), trifluoroacetic acid (1 mL) was added, and the resultant mixture was stirred at 25° C. for 45 minutes. After the reaction ended, the reaction solution was purified by silica gel column chromatography (eluting solvent; methanol:chloroform) to give compound E11 (306 mg).

$^1$H-NMR (400 MHz, CDCl$_3$):1.47-1.48 (6H, m), 2.21 (3H, d, J=1.8 Hz), 3.61 (3H, d, J=2.3 Hz), 3.71 (1H, d, J=1.8 Hz), 3.72 (3H, d, J=1.8 Hz), 6.83 (1H, d, J=1.8 Hz), 7.08 (1H, t, J=8.2 Hz), 7.19 (1H, t, J=8.2 Hz), 7.27 (1H, d, J=8.2 Hz), 7.81 (1H, d, J=8.2 Hz).

LC-MS: 275 (M+H)$^+$ (0.856 min, Measurement Condition D)

b) Production of N-(tert-butoxycarbonyl)-L-valyl-N$^5$-carbamoyl-N-{4-[({[(2S)-1-methoxy-3-methyl-3-(1-methyl-1H-indol-3-yl)-1-oxobutan-2-yl](methyl)carbamoyl}oxy)methyl]phenyl}-L-ornithine amide (Compound E12)

A mixed solution of compound E11 (306 mg), N-(tert-butoxycarbonyl)-L-valyl-N$^5$-carbamoyl-N-[4-({[(4-nitrophenoxy)carbonyl]oxy}methyl)phenyl]-L-ornithine amide (791 mg), 1-hydroxy-7-benzotriazole (101 mg), 2,6-lutidine (663 mg) and N,N-dimethylformamide (5.5 mL) was stirred at 45° C. for 8 hours. After the reaction ended, water was added and the resultant mixture was extracted with chloroform. The organic layer was washed with water and saturated sodium bicarbonate and then dried over anhydrous sodium sulfate, and the solvent was distilled off under reduced pressure. The residue was purified by silica gel column chromatography (eluting solvent; chloroform:methanol) to give compound E12 (516 mg).

LC-MS: 780 (M+H)$^+$ (1.369 min, Measurement Condition D)

c) Production of N-(tert-butoxycarbonyl)-L-valyl-N$^5$-carbamoyl-N-{4-[({[(1S)-1-carboxy-2-methyl-2-(1-methyl-1H-indol-3-yl)propyl](methyl)carbamoyl}oxy)methyl]phenyl}-L-ornithine amide (Compound E13)

By the same approach as Reference Example 2-a), from compound 12 (516 mg), compound E13 (175 mg) was obtained.

LC-MS: 766 (M+H)$^+$, 764 (M−H)$^−$ (1.285 min, Measurement Condition D)

d) Production of N-(tert-butoxycarbonyl)-L-valyl-N-{4-[(5S,8S,11S,12E)-8-tert-butyl-4,10,13-trimethyl-5-[2-(1-methyl-1H-indol-3-yl)propan-2-yl]-3,6,9,14-tetraoxo-11-(propan-2-yl)-2,15-dioxa-4,7,10-triazaheptadec-12-en-1-yl]phenyl}-N$^5$-carbamoyl-L-ornithine amide (Compound E14)

By the same approach as Reference Example 2-b), from compound E13 (130 mg), compound E14 (146 mg) was obtained.

LC-MS: 1060 (M+H)$^+$ (1.380 min, Measurement Condition D)

e) Production of N-(tert-butoxycarbonyl)-L-valyl-N-{4-[(5S,8S,11S,12E)-8-tert-butyl-13-carboxy-4,10-dimethyl-5-[2-(1-methyl-1H-indol-3-yl)propan-2-yl]-3,6,9-trioxo-11-(propan-2-yl)-2-oxa-4,7,10-triazatetradec-12-en-1-yl]phenyl}-N$^5$-carbamoyl-L-ornithine amide (Compound E15)

By the same approach as Reference Example 2-c), from compound E14 (148 mg), compound E15 (145 mg) was obtained.

LC-MS: 1032 (M+H)$^+$ (1.231 min, Measurement Condition D)

f) Production of N-(tert-butoxycarbonyl)-L-valyl-N-{4-[(5S,8S,11S,12E)-8-tert-butyl-14-[(2,5-dioxopyrrolidin-1-yl)oxy]-4,10,13-trimethyl-5-[2-(1-methyl-1H-indol-3-yl)propan-2-yl]-3,6,9,14-tetraoxo-11-(propan-2-yl)-2-oxa-4,7,10-triazatetradec-12-en-1-yl]phenyl}-N$^5$-carbamoyl-L-ornithine amide (Compound E16)

By the same approach as Reference Example 2-d), from compound E15 (145 mg), compound E16 (139 mg) was obtained.

LC-MS: 1129 (M+H)$^+$ (1.271 min, Measurement Condition D)

g) Production of diethyl (2R)-2-{[(5S,8S,11S,12E)-1-(4-{[(2S)-2-({(2S)-2-[(tert-butoxycarbonyl)amino]-3-methylbutanoyl}amino)-5-(carbamoylamino)pentanoyl]amino}phenyl)-8-tert-butyl-4,10,13-trimethyl-5-[2-(1-methyl-1H-indol-3-yl)propan-2-yl]-3,6,9,14-tetraoxo-11-(propan-2-yl)-2-oxa-4,7,10-triazatetradec-12-en-14-yl]amino}pentanedioate (Compound E17)

By the same approach as Reference Example 3, from compound E16 (139 mg), compound E17 (154 mg) was obtained.

LC-MS: 1217 (M+H)$^+$ (1.533 min, Measurement Condition D)

h) Production of diethyl (2R)-2-{[(5S,8S,11S,12E)-1-(4-{[(2S)-2-{[(2S)-2-amino-3-methylbutanoyl]amino}-5-(carbamoylamino)pentanoyl]amino}phenyl)-8-tert-butyl-4,10,13-trimethyl-5-[2-(1-methyl-1H-indol-3-yl)propan-2-yl]-3,6,9,14-tetraoxo-11-(propan-2-yl)-2-oxa-4,7,10-triazatetradec-12-en-14-yl]amino}pentanedioate (Reference Example 101)

By the same approach as Reference Example 101-a), from compound E17 (92 mg), Reference Example 101 (87 mg) was obtained.

LC-MS: 1117 (M+H)$^+$ (1.279 min, Measurement Condition D)

Reference Example 102

L-Valyl-N-{4-[(5S,8S,11S,12E,16R)-8-tert-butyl-16,18-dicarboxy-4,10,13-trimethyl-5-[2-(1-methyl-1H-indol-3-yl)propan-2-yl]-3,6,9,14-tetraoxo-11-(propan-2-yl)-2-oxa-4,7,10,15-tetraazaoctadec-12-en-1-yl]phenyl}-$N^5$-carbamoyl-L-ornithine amide

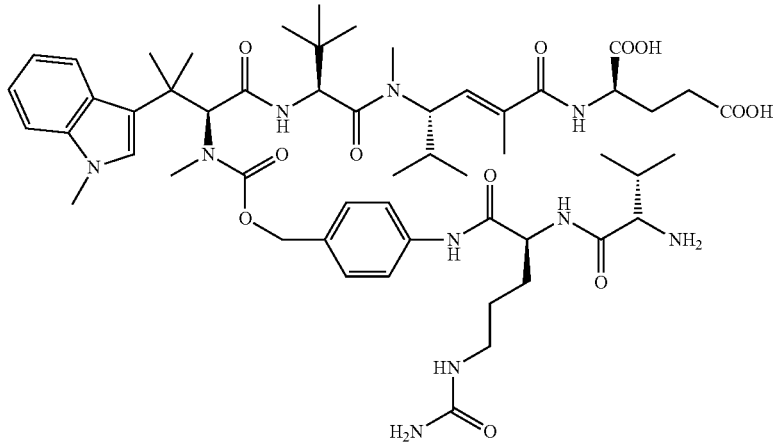

Reference Example 102

By carrying out synthesis by the same approach as Reference Example 2-c), and through purification by reversed phase column chromatography (eluting solvent; acetonitrile with 0.1% TFA:water), from Reference Example 101 (87 mg), Reference Example 102 (79 mg) was obtained.

LC-MS: 1061 (M+H)$^+$ (1.124 min, Measurement Condition D)

Reference Example 103

L-Prolyl-L-alanyl-$N^1$-(4-{[(N-{(2E,4S)-2,5-dimethyl-4-[methyl(N,β,β,1-tetramethyl-L-tryptophyl-3-methyl-L-valyl)amino]hex-2-enoyl}-L-α-glutamyl)oxy]methyl}phenyl)-L-aspartamide

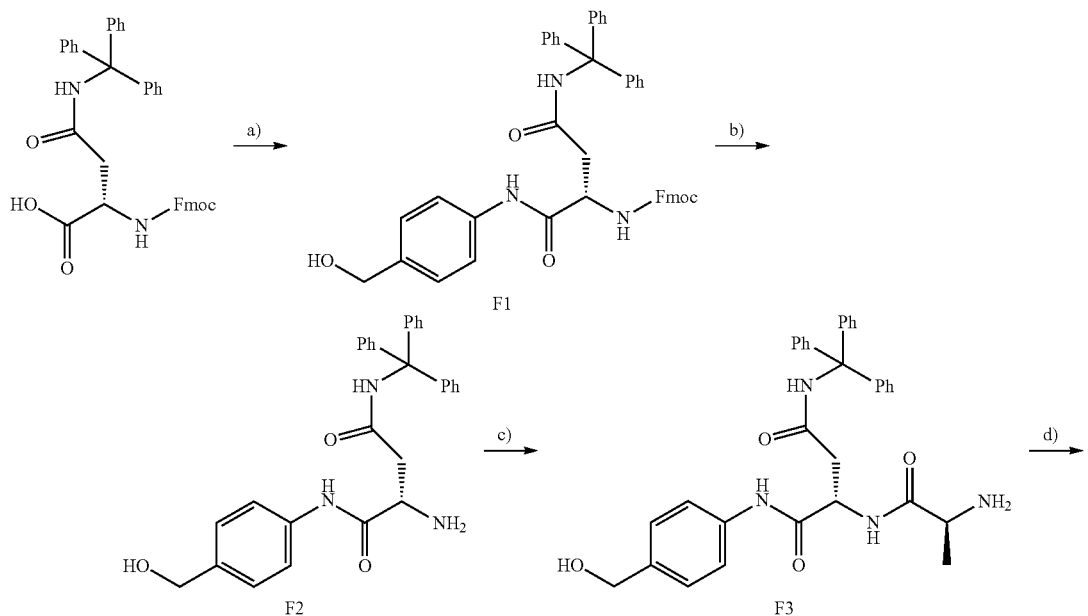

-continued
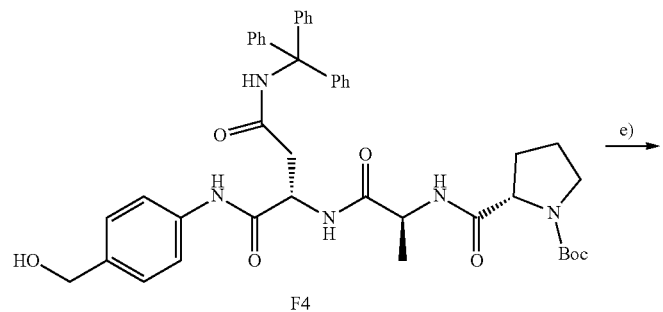
F4
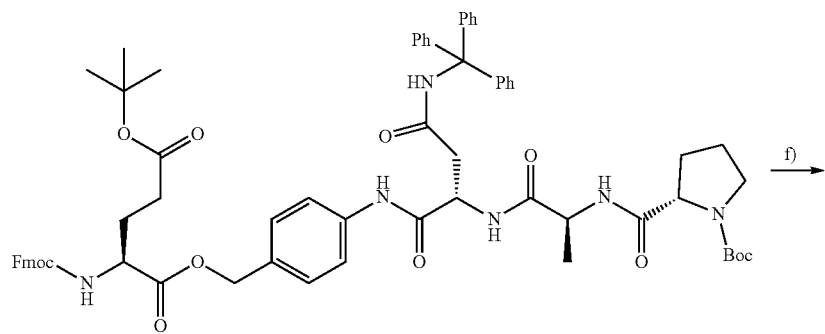
F5
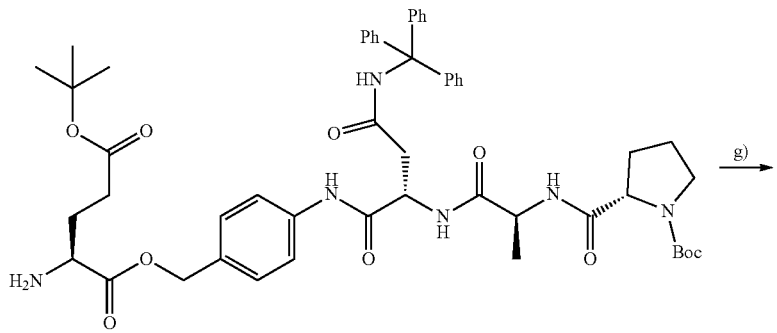
F6
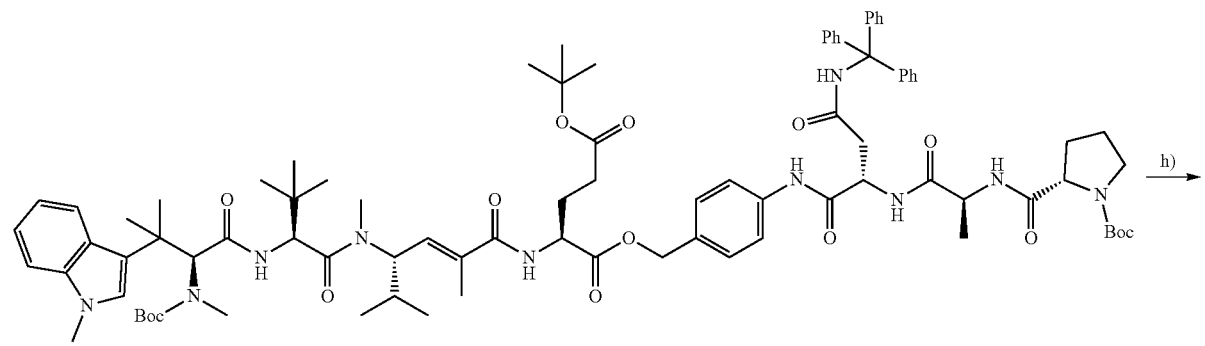
F7

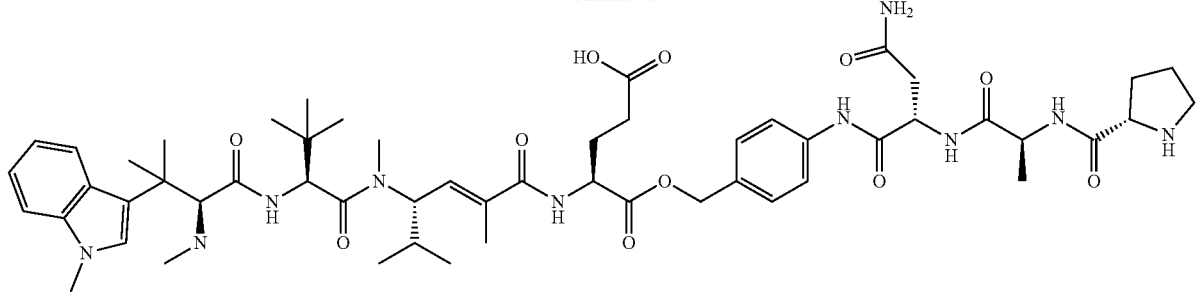

Reference Example 103 a) Production of 9H-fluoren-9-ylmethyl[(2S)-1-{[4-(hydroxymethyl)phenyl]amino}-1,4-dioxo-4-(trithylamino)butan-2-yl]carbamate (Compound F1)

To a solution of $N^2$-[(9H-fluoren-9-ylmethoxy)carbonyl]-N-trimethyl-L-asparagine (Fmoc-Asn(Trt)-OH, 18 g) and p-aminobenzyl alcohol (3.9 g) in THF (150 mL), 1-ethoxycarbonyl-2-ethoxy-1,2-dihydroquinoline (EEDQ) (8.6 g) was added, and the resultant mixture was stirred at room temperature overnight. To the residue obtained by distilling off the solvent under reduced pressure, ethyl acetate was added, and the resultant mixture was stirred at room temperature. The solid thus obtained was collected by filtration, washed with ethyl acetate and dried under reduced pressure. The same washing was carried out once again to give compound F1 (19.2 g).
LC-MS: 702 (M+H)$^+$ (3.36 min, Measurement Condition G)

b) Production of $N^1$-[4-(hydroxymethyl)phenyl]-$N^4$-trityl-L-aspartamide (Compound F2)

To compound F1 (3.0 g), a 30% piperidine-THF solution was added, and the resultant mixture was stirred at room temperature for 5 hours. To the residue obtained by concentrating the mixture under reduced pressure, diethyl ether was added, and the resultant mixture was washed and the solid was collected by filtration. The solid thus obtained was washed with diethyl ether and dried. The same washing step was carried out again to give compound F2 (1.82 g).
LC-MS: 480 (M+H)$^+$ (3.00 min, Measurement Condition F)

c) Production of L-alanyl-$N^1$-[4-(hydroxymethyl)phenyl]-$N^4$-trityl-L-aspartamide (Compound F3)

A solution of compound F2 (1.5 g), N-[(9H-fluoren-9-ylmethoxy)carbonyl]-L-alanine (Fmoc-Ala-OH, 1.23 g), 1-ethyl-3-(3-dimethylaminopropyl)carbodiimide hydrochloride (714 mg), 1-hydroxy-1H-benzotriazole monohydrate (505 mg) in N,N-dimethylformamide (15 mL) was stirred at room temperature overnight. After adding ethyl acetate, the resultant mixture was washed with a saturated aqueous ammonium chloride solution and saturated brine, and the organic solvent layer was collected and dried over sodium sulfate. After removing sodium sulfate, the amorphous product obtained through concentration was purified by short column chromatography (eluting solvent; methanol:chloroform). To the amorphous product thus obtained, a 30% piperidine-THF solution was added, and the resultant mixture was stirred at room temperature for 5 hours. The residue obtained by concentrating the mixture under reduced pressure was purified by column chromatography (eluting solvent; methanol:chloroform) to give compound F3 (562 mg).
LC-MS: 551 (M+H)$^+$ (2.89 min, Measurement Condition F)

d) Production of 1-(tert-butoxycarbonyl)-L-prolyl-L-alanyl-$N^1$-[4-(hydroxymethyl)phenyl]-$N^4$-trityl-L-aspartamide (Compound F4)

A solution of compound F3 (275 mg), 1-(tert-butoxycarbonyl)-L-proline (Boc-Pro-OH, 118 mg), 1-ethyl-3-(3-dimethylaminopropyl)carbodiimide hydrochloride (714 mg), 1-hydroxy-1H-benzotriazole monohydrate (505 mg) in N,N-dimethylformamide (15 mL) was stirred at room temperature overnight. After adding ethyl acetate, the resultant mixture was washed with a saturated aqueous ammonium chloride solution and saturated brine, and the organic solvent layer was collected and dried over sodium sulfate. After removing sodium sulfate, the amorphous product obtained through concentration was purified by column chromatography (eluting solvent; methanol:chloroform) to give compound F4 (321 mg).
LC-MS: 748 (M+H)$^+$ (2.42 min, Measurement Condition G)

e) Production of 1-(4-{[(2S)-2-{[(2S)-2-({[(2S)-1-(tert-butoxycarbonyl)pyrrolidin-2-yl]carbonyl}amino)propanoyl]amino}-4-oxo-4-(tritylamino)butanoyl]amino}benzyl)5-tert-butyl (2S)-2-{[(9H-fluoren-9-ylmethoxy)carbonyl]amino}pentanedioate (Compound F5)

Compound F4 (242 mg), (2S)-5-tert-butoxy-2-{[(9H-fluoren-9-ylmethoxy)carbonyl]amino}-5-oxopentanoic acid monohydrate (Fmoc-Glu(OtBu)-OH·H$_2$O, 150 mg), p-toluenesulfonyl chloride (TsCl) (65 mg) were dissolved in acetonitrile (5.0 mL), and the solution was cooled to 0° C. To that acetonitrile solution, I-methylimidazole (0.06 mL) was added, and the solution was stirred overnight while bringing it back to room temperature. After adding ethyl acetate, the resultant mixture was washed with a saturated aqueous ammonium chloride solution and saturated brine, and the organic solvent layer was collected and dried over sodium sulfate. After removing sodium sulfate, the amorphous product obtained through concentration was purified by column chromatography (eluting solvent; methanol:chloroform) to give compound F5 (342 mg).
LC-MS: 1155 (M+H)$^+$ (4.60 min, Measurement Condition G)

f) Production of 1-(4-{[(2S)-2-{[(2S)-2-({[(2S)-1-(tert-butoxycarbonyl)pyrrolidin-2-yl]carbonyl}amino)propanoyl]amino}-4-oxo-4-(tritylamino)butanoyl]amino}benzyl)5-tert-butyl (2S)-2-aminopentanedioate (Compound F6)

By the same approach as Reference Example 103-b), from compound F5 (342 mg), compound F6 (110 mg) was obtained.
LC-MS: 933 (M+H)$^+$ (2.23 min, Measurement Condition G)

g) Production of 1-(4-{[(2S)-2-{[(2S)-2-({[(2S)-1-(tert-butoxycarbonyl)pyrrolidin-2-yl]carbonyl}amino)propanoyl]amino}-4-oxo-4-(tritylamino)butanoyl]amino}benzyl)5-tert-butyl (2S)-2-{[(6S,9S,12S,13E)-9-tert-butyl-2,2,5,11,14-pentamethyl-6-[2-(1-methyl-1H-indol-3-yl)propan-2-yl]-4,7,10,15-tetraoxo-12-(propan-2-yl)-3-oxa-5,8,11-triazapentadec-13-en-15-yl]amino}pentanedioate (Compound F7)

Compound F6 (30 mg), compound A13 (22 mg), bromotripyrrolidinophosphonium hexafluorophosphate (20 mg), 4-dimethylaminopyridine (5 mg) were dissolved in N,N-dimethylformamide (5.0 mL), and the solution was cooled to 0° C. To that mixed solution, N-diisopropylethylamine (0.017 mL) was added dropwise, and the solution was stirred overnight while bringing it back to room temperature. Ethyl acetate was added, and the resultant mixture was washed with a saturated aqueous ammonium chloride solution and saturated brine, and dried over sodium sulfate. After removing sodium sulfate, the amorphous product obtained through concentration was purified by silica gel column chromatography (eluting solvent; methanol:chloroform) to give compound F7 (42 mg).
LC-MS: 1541 (M+H)$^+$ (5.23 min, Measurement Condition G)

h) Production of L-prolyl-L-alanyl-N$^1$-(4-{[(N-{(2E,4S)-2,5-dimethyl-4-[methyl(N,β,β,1-tetramethyl-L-tryptophyl-3-methyl-L-valyl)amino]hex-2-enoyl}-L-α-glutamyl)oxy]methyl}phenyl)-L-aspartamide (Reference Example 103)

By carrying out synthesis by the same approach as Reference Example 101-a), and through purification by reversed phase column chromatography (eluting solvent; acetonitrile with 0.1% TFA:water), from compound F7 (42 mg), Reference Example 103 (10.3 mg) was obtained.
LC-MS: 1043 (M+H)$^+$ (2.79 min, Measurement Condition F)

Reference Examples 104 to 106

The compounds shown in the following table were obtained through the same reaction and treatment as Example 1 and Reference Example 12, using corresponding raw material compounds.

TABLE 13

| Reference Example | Structural Formula | LC-MS /Rt (min) | LC-MS Measurement Condition |
|---|---|---|---|
| 104 | 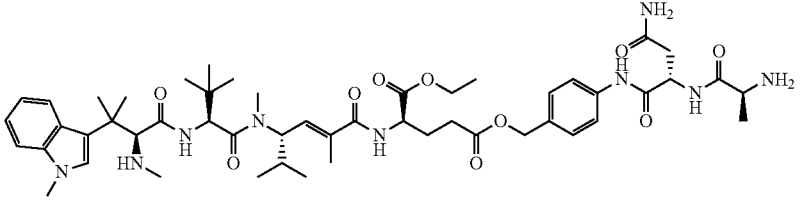 [SMILES: CCOC(=O)[C@@H](CCC(=O)OCc1ccc(NC(=O)[C@H](CC(N)=O)NC(=O)[C@H](C)N)cc1)NC(=O)/C(C)=C/[C@H](C(C)C)N(C)C(=O)[C@@H](NC(=O)[C@@H](NC)C(C)(C)c1cn(C)c2ccccc12)C(C)(C)C] | 974(M + H)$^+$ /0.81 | J |
| 105 | 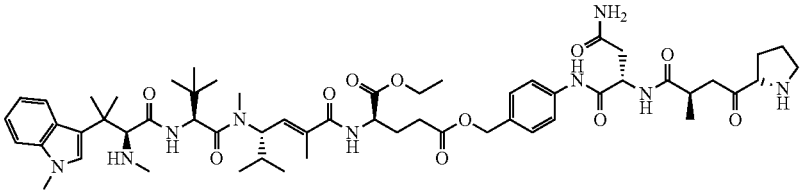 | 1071(M + H)$^+$ /0.865 | J |
| 106 | 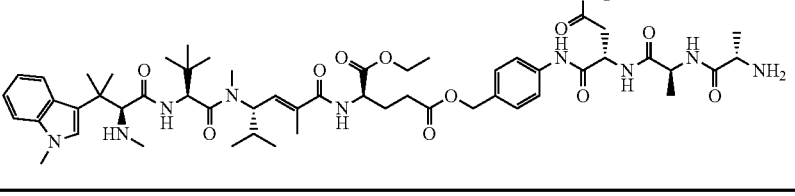 | 1045(M + H)$^+$ /0.909 | J |

Reference Examples 108 to 110

The compounds shown in the following table were obtained through the same reaction and treatment as b) step of Reference Example 101, using corresponding raw material compounds.

TABLE 14

| Reference Example | Structural Formula | LC-MS /Rt (min) | LC-MS Measurement Condition |
|---|---|---|---|
| 108 | | 1287(M − H)⁻ /1.168 | J |
| 109 | | 727(M + H)⁺ /1.419 | J |
| 110 | | 663(M + Na)⁺ /1.280 | J |

Reference Examples 111 to 121

In Accordance with the methods described in Bioorg. Med. Chem. Lett. 2004 Nov. 1; 14(21): 5317-22, J. Med. Chem. 2004 Sep. 9; 47(19): 4774-86, International Publication No. WO 2003/082268, International Publication No. WO 2016/123582 and the like, the compounds shown in the following tables were obtained.

TABLE 15-1

| Reference Example | Structural Formula | LC-MS /Rt (min) | LC-MS Measurement Condition |
|---|---|---|---|
| 111 | | 438(M + H)⁺ /0.886 | E |

TABLE 15-1-continued

| Reference Example | Structural Formula | LC-MS /Rt (min) | LC-MS Measurement Condition |
|---|---|---|---|
| 112 | | 552(M + H)+ /0.76 | J |
| 113 | | 552(M + H)+ /0.76 | J |
| 114 | | 542(M + H)+ /1.46 | D |
| 115 | | 492(M + H)+ /1.26 | D |
| 116 | | 480(M + H)+ /1.25 | D |
| 117 | | 480.(M + H)+ /1.30 | D |
| 118 | | 502.(M − H)− /1.18 | D |

TABLE 15-2

| # | Structure | Data |
|---|---|---|
| 119 | 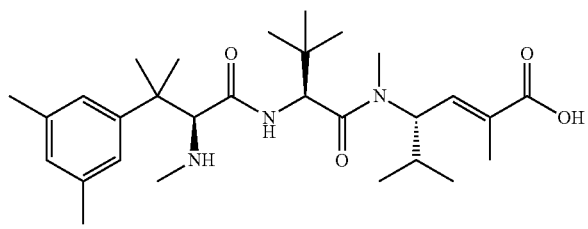 [SMILES: CN[C@H](C(=O)N[C@H](C(=O)N(C)[C@H](/C=C(\C)C(=O)O)C(C)C)C(C)(C)C)C(C)(C)c1cc(C)cc(C)c1] | 502(M + H)+ J /1.044 |
| 120 | 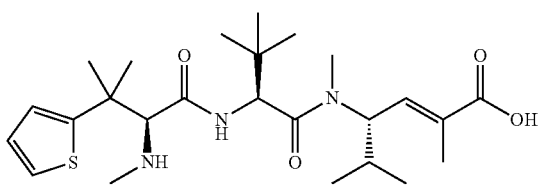 [SMILES: CN[C@H](C(=O)N[C@H](C(=O)N(C)[C@H](/C=C(\C)C(=O)O)C(C)C)C(C)(C)C)C(C)(C)c1cccs1] | 480(M + H)+ J /1.13 |
| 121 | 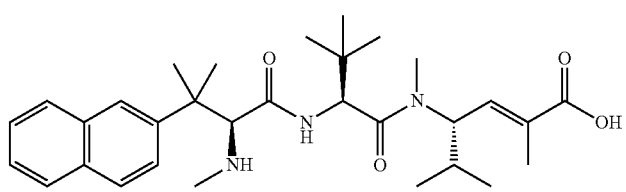 [SMILES: CN[C@H](C(=O)N[C@H](C(=O)N(C)[C@H](/C=C(\C)C(=O)O)C(C)C)C(C)(C)C)C(C)(C)c1ccc2ccccc2c1] | 524(M + H)+ D /1.304 |

Reference Example 122

N,3,3-Trimethyl-2-(((S)-3-methyl-2-(methylamino)-3-(m-tolyl)butanamido)butanamido)hex-2-enoic acid Reference Example 122

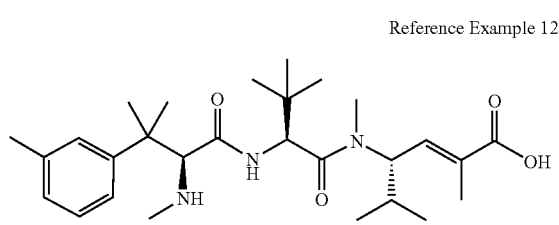

A mixed solution of (S,E)-4-((S)-2-((S)-3-(3-bromophenyl)-3-methyl-2-(methylamino)butanamido)-N,3, 3-trimethylbutanamido)-2,5-dimethylhex-2-enoic acid (62.5 mg), tetrakis(triphenylphosphine)palladium(0) (13.07 mg), dimethylzinc (0.113 mL) and tetrahydrofuran (5 mL) was stirred at 60° C. for 2.5 hours. After the reaction ended, the solvent was distilled off under reduced pressure. The residue was purified by silica gel chromatography (eluting solvent; chloroform:methanol) to give Reference Example 122 (29.7 mg).

LC-MS: 488 (M+H)+/0.68 min, Measurement Condition E

Reference Example 123

(S,E)-4-((S)-2-((S)-3-(3-Cyanophenyl)-3-methyl-2-(methylamino)butanamido)-N,3, 3-trimethylbutanamido)-2,5-dimethylhex-2-enoic acid Reference Example 123

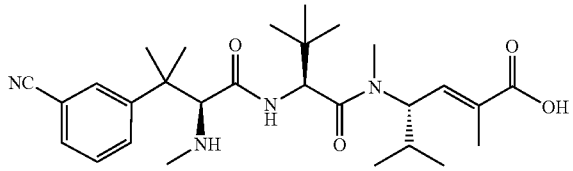

A mixed solution of (S,E)-4-((S)-2-((S)-3-(3-bromophenyl)-3-methyl-2-(methylamino)butanamido)-N,3, 3-trimethylbutanamido)-2,5-dimethylhex-2-enoic acid (76.1 mg), tetrakis(triphenylphosphine)palladium(0) (15.92 mg), zinc (18.01 mg), zinc cyanide (32.3 mg) and N,N-dimethylformamide (1 mL) was stirred at 120° C. for 1 hour under microwave irradiation. After the reaction ended, the solvent was distilled off under reduced pressure. After partially purifying the residue by silica gel chromatography (eluting solvent; chloroform:methanol), through reversed phase HPLC (the mobile phase was water with 0.1% TFA/acetonitrile with 0.035% TFA solvent), Reference Example 123 (53.5 mg) was obtained.

LC-MS: 499 (M+H)+/0.99 min, Measurement Condition E

Reference Example 124

(S,E)-4-((S)-2-((S)-3-([1,1'-Biphenyl]-3-yl)-3-methyl-2-(methylamino)butanamido)-N,3,3-trimethylbutanamido)-2,5-dimethylhex-2-enoic acid

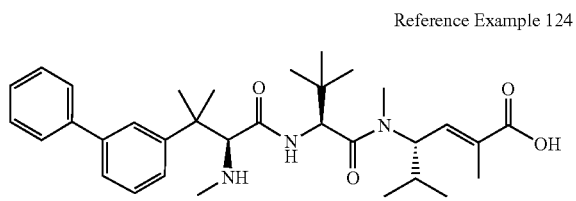 [SMILES: CN[C@H](C(=O)N[C@H](C(=O)N(C)[C@H](/C=C(\C)C(=O)O)C(C)C)C(C)(C)C)C(C)(C)c1cccc(-c2ccccc2)c1]

Reference Example 124

A mixed solution of (S,E)-4-((S)-2-((S)-3-(3-bromophenyl)-3-methyl-2-(methylamino)butanamido)-N,3,3-trimethylbutanamido)-2,5-dimethylhex-2-enoic acid (64.3 mg), tetrakis(triphenylphosphine)palladium(0) (13.45 mg), phenylboranic acid (28.4 mg), sodium carbonate (24.67 mg) and tetrahydrofuran (5 mL) was stirred at 80° C. for 3.5 hours. The solvent was distilled off under reduced pressure. Through reversed phase HPLC (the mobile phase was water with 0.1% TFA/acetonitrile with 0.035% TFA solvent), Reference Example 124 (10.7 mg) was obtained. LC-MS: 550 (M+H)$^+$/0.88 min, Measurement Condition E

Reference Example 125

(S,E)-4-((S)-2-((S)-3-(4-(tert-Butoxycarbonyl)phenyl)-3-methyl-2-(methoxyamino) butanamido)-N,3,3-trimethylbutanamido)-2,5-dimethylhex-2-enoic acid

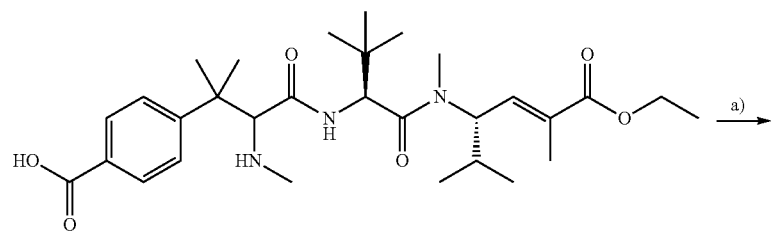

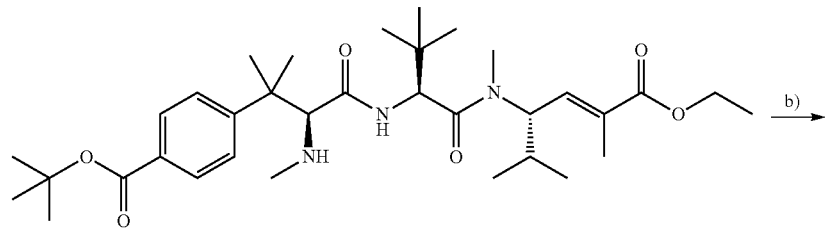

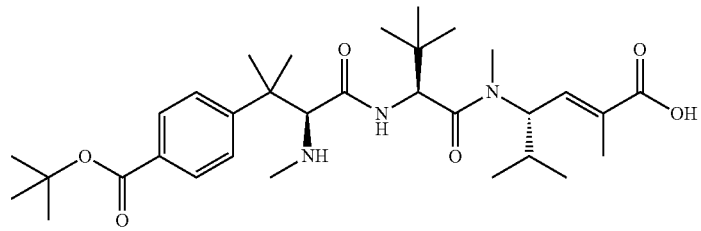

Reference Example 125 a) Production of tert-butyl 4-((S)-4-(((S)-1-(((S,E)-6-ethoxy-2,5-dimethyl-6-oxohex-4-en-3-yl)(methyl)amino)-3,3-dimethyl-1-oxobutan-2-yl)amino)-2-methyl-3-(methylamino)-4-oxobutan-2-yl)benzoate To a mixed solution of 4-(4-(((S)-1-(((S,E)-6-ethoxy-2,5-dimethyl-6-oxohex-4-en-3-yl)(methyl)amino)-3,3-dimethyl-1-oxobutan-2-yl)amino)-2-methyl-3-(methylamino)-4-oxobutan-2-yl)benz oic acid (104.0 mg) and toluene (1 mL), N,N-dimethylfluoroamido-di-tert-butyl acetate (0.456 mL) was added, and the resultant mixture was subjected to heating reflux for 14 hours. After distilling off the solvent under reduced pressure, the residue was purified by silica gel chromatography to give tert-butyl 4-((S)-4-(((S)-1-(((S,E)-6-ethoxy-2,5-dimethyl-6-oxohex-4-en-3-yl)(methyl)amino)-3,3-dimethyl-1-oxobutan-2-yl)amino)-2-methyl-3-(methylamino)-4-oxobutan-2-yl)benzoate (21.0 mg).

LC-MS: 602 (M+H)$^+$/1.47 min, Measurement Condition E b) Production of (S,E)-4-((S)-2-((S)-3-(4-(tert-butoxycarbonyl) phenyl)-3-methyl-2-(methoxyamino)butanamido)-N,3,3-trimethylbutanamido)-2,5-dimethylhex-2-enoic acid (Reference Example 125)

To a mixed solution of tert-butyl 4-((S)-4-(((S)-1-(((S,E)-6-ethoxy-2,5-dimethyl-6-oxohex-4-en-3-yl)(methyl)amino)-3,3-dimethyl-1-oxobutan-2-yl)amino)-2-methyl-3-(methylamino)-4-oxobutan-2-yl)benzoate (10.5 mg), methanol (3 mL) and water (1 mL), lithium hydroxide (4.39 mg) was added, and the resultant mixture was stirred at room temperature for 2 days. The solvent was distilled off under reduced pressure, and the residue was purified by reversed phase HPLC (the mobile phase was water with 0.1% TFA/acetonitrile with 0.035% TFA solvent) to give Reference Example 125 (7.0 mg).

LC-MS: 574 (M+H)$^+$/1.49 min, Measurement Condition E

Reference Example 126

4-((S)-4-(((S)-1-(((S,E)-5-Carboxy-2-methylhex-4-en-3-yl)(methyl)amino)-3,3-dimethyl-1-oxobutan-2-yl)amino)-2-methyl-3-(methylamino)-4-oxobutan-2-yl)benzoic acid

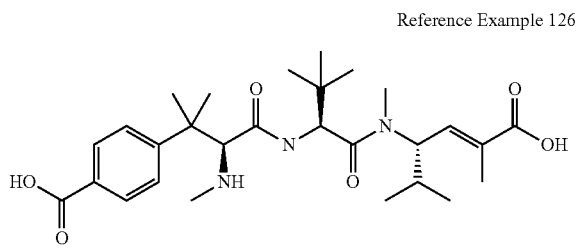 [SMILES: CN[C@H](C(=O)N[C@H](C(=O)N(C)[C@H](/C=C(\C)C(=O)O)C(C)C)C(C)(C)C)C(C)(C)c1ccc(C(=O)O)cc1]

Reference Example 126

To a mixed solution of tert-butyl 4-((S)-4-(((S)-1-(((S,E)-6-ethoxy-2,5-dimethyl-6-oxohex-4-en-3-yl)(methyl)amino)-3,3-dimethyl-1-oxobutan-2-yl)amino)-2-methyl-3-(methylamino)-4-oxobutan-2-yl)benzoate (10.5 mg), methanol (3 mL) and water (1 mL), lithium hydroxide (4.39 mg) was added, and the resultant mixture was stirred at room temperature for 5 days. After distilling off the solvent under reduced pressure, the residue was dissolved in chloroform (4 mL), trifluoroacetic acid (1 mL) was added, and the resultant mixture was stirred at room temperature for 17 hours. After distilling off the solvent under reduced pressure, the residue was purified by reversed phase HPLC (the mobile phase was water with 0.1% TFA/acetonitrile with 0.035% TFA solvent) to give Reference Example 126 (7.40 mg).

LC-MS: 518 (M+H)$^+$/1.08 min, Measurement Condition E

Reference Example 127

(4S,E)-4-((2S)-2-(3-(4-Hydroxyphenyl)-3-methyl-2-(methylamino)butyl)-N,3,3-trim ethylbutanamido)-2,5-dimethylhex-2-enoic acid

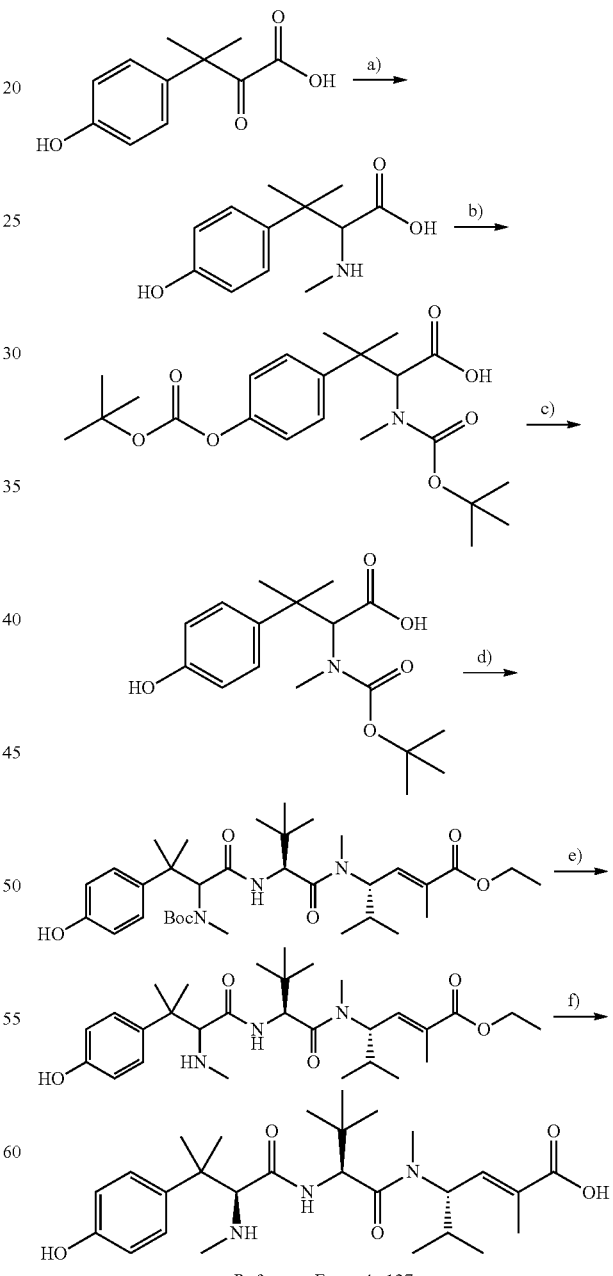

Reference Example 127 a) Production of 3-(4-hydroxyphenyl)-3-methyl-2-(methylamino)butanoic acid

Under nitrogen atmosphere, a solution of 3-(4-hydroxyphenyl)-3-methyl-2-oxobutanoic acid (54.9 g) in anhydrous tetrahydrofuran (480 mL) was ice-cooled, and methylamine (280 mL) (2 mol/L tetrahydrofuran solution) was added dropwise. After stirring the mixture at room temperature for 1 hour, borane-pyridine complex (27.5 mL) was added dropwise, and the resultant mixture was stirred at 55° C. for 2.5 hours. Under ice cooling, methanol (240 mL) was added dropwise, and the mixture was stirred at room temperature for 2 hours. After distilling off the solvent under reduced pressure, tetrahydrofuran was added, and the suspension was subjected to suction filtration. The powder was washed with tetrahydrofuran to give 3-(4-hydroxyphenyl)-3-methyl-2-(methylamino)butanoic acid (40.7 g).

b) Production of 2-((tert-butoxycarbonyl)(methyl)amino)-3-(4-((tert-butoxycarbonyl)oxy)phenyl)-3-methylbutanoic acid Under nitrogen atmosphere, to a suspension of 3-(4-hydroxyphenyl)-3-methyl-2-(methylamino)butanoic acid (10.2 g) in 1,4-dioxane/water (1:1) (160 mL), di-tert-butyl carbonate (39.9 g) and potassium carbonate (25.4 g) were added, and the resultant mixture was stirred at 40° C. overnight. Ethyl acetate and water were added to the reaction solution, and after changing the pH to 2 to 3 with a 1 mol/L aqueous potassium bisulfate solution, the mixture was extracted with ethyl acetate. The organic layer was washed with saturated brine, followed by drying over anhydrous magnesium sulfate, and the solvent was then distilled off under reduced pressure. The residue was purified by silica gel chromatography (eluting solvent; chloroform:methanol) to give 2-((tert-butoxycarbonyl)(methyl)amino)-3-(4-((tert-butoxycarbonyl)oxy)phenyl)-3-methylbutanoic acid.

c) Production of (S)-2-((tert-butoxycarbonyl)(methyl)amino)-3-(4-hydroxyphenyl)-3-methylbutanoic acid (153.7 mg), ethyl (S,E)-4-((S)-2-amino-N,3,3-trimethylbutanamido)-2,5-dimethylhex-2-enoate hydrochloride Under nitrogen atmosphere, 2-((tert-butoxycarbonyl)(methyl)amino)-3-(4-((tert-butoxycarbonyl)oxy)phenyl)-3-methylbutanoic acid (15.7 g) was dissolved in dichloromethane (370 mL), a 28% sodium methoxide methanol solution (15.8 g) and methanol (14 mL) were added, and the resultant mixture was stirred at room temperature for 1.5 hours. Ethyl acetate and a 4% aqueous potassium bisulfate solution were added to the reaction solution, and the mixture was extracted. The organic layer was washed with saturated brine, followed by drying over anhydrous magnesium sulfate, and the solvent was distilled off under reduced pressure. The residue was purified by silica gel chromatography (eluting solvent; chloroform:methanol) to give (S)-2-((tert-butoxycarbonyl)(methyl)amino)-3-(4-hydroxyphenyl)-3-methylbutanoic acid (153.7 mg) and ethyl (S,E)-4-((S)-2-amino-N,3,3-trimethylbutanamido)-2,5-dimethylhex-2-enoate hydrochloride (9.73 g).

d) Production of ethyl (9S,12S,E)-9-(tert-butyl)-6-(2-(4-hydroxyphenyl)propan-2-yl)-12-isopropyl-2,2,5,11,14-pentamethyl-4,7,10-trioxo-3-oxa-5,8,11-triazapentadec-13-en-15-oate A suspension of (S)-2-((tert-butoxycarbonyl)(methyl)amino)-3-(4-hydroxyphenyl)-3-methylbutanoic acid (153.7 mg), ethyl (S,E)-4-((S)-2-amino-N,3,3-trimethylbutanamido)-2,5-dimethylhex-2-enoate hydrochloride (117.6 mg), N-ethyl-N-isopropylpropan-2-amine (0.172 mL), 1-ethyl-3-(3-dimethylaminopropyl)carbodiimide hydrochloride (129 mg), 1-hydroxybenzotriazole (103 mg) and DMF (5 mL) was stirred at room temperature for 17 hours. After distilling off the solvent under reduced pressure, chloroform was added, the organic layer was washed with a saturated aqueous sodium bicarbonate solution and then dried over anhydrous sodium sulfate, and the solvent was distilled off under reduced pressure. The residue was purified by silica gel chromatography (eluting solvent; hexane:ethyl acetate) to give ethyl (9S,12S,E)-9-(tert-butyl)-6-(2-(4-hydroxyphenyl)propan-2-yl)-12-isopropyl-2,2,5,11,14-pentamethyl-4,7,10-trioxo-3-oxa-5,8,11-triazapentadec-13-en-15-oate (206.3 mg).

LC-MS: 618 (M+H)$^+$/1.69 min, Measurement Condition E e) Production of ethyl (4S,E)-4-((2S)-2-(3-(4-hydroxyphenyl)-3-methyl-2-(methylamino)butanamido)-N,3,3-trimethylbutanamido)-2,5-dimethylhex-2-enoate To a mixed solution of ethyl (9S,12S,E)-9-(tert-butyl)-6-(2-(4-hydroxyphenyl)propan-2-yl)-12-isopropyl-2,2,5,11,14-pentamethyl-4,7,10-trioxo-3-oxa-5,8,11-triazapentadec-13-en-15-oate (189.2 mg) and chloroform (4 mL), TFA (1 mL) was added, and the resultant mixture was stirred at room temperature for 1 hour. The solvent was distilled off under reduced pressure. Chloroform was added, and the organic layer was washed with a saturated aqueous sodium bicarbonate solution and then dried over anhydrous sodium sulfate, and the solvent was distilled off under reduced pressure. The residue was purified by silica gel chromatography (eluting solvent; hexane:ethyl acetate) to give ethyl (4S,E)-4-((2S)-2-(3-(4-hydroxyphenyl)-3-methyl-2-(methylamino)butanamido)-N,3, 3-trimethylbutanamido)-2,5-dimethylhex-2-enoate (110.1 mg).

LC-MS: 518 (M+H)$^+$/1.09 min, Measurement Condition E f) Production of (4S,E)-4-((2S)-2-(3-(4-hydroxyphenyl)-3-methyl-2-(methylamino)butyl)-N,3,3-trimethylbutanamido)-2,5-dimethylhex-2-enoi c acid (Reference Example 127)

To a mixed solution of ethyl (4S,E)-4-((2S)-2-(3-(4-hydroxyphenyl)-3-methyl-2-(methylamino)butanamido)-N,3,3-trimethylbutanamido)-2,5-dimethylhex-2-enoate (110.1 mg), methanol (3 mL) and water (1 mL), lithium hydroxide (35.7 mg) was added under ice cooling, and the resultant mixture was stirred at room temperature for 2 days. The solvent was distilled off under reduced pressure, and the residue was purified by reversed phase HPLC (the mobile phase was water with 0.1% TFA/acetonitrile with 0.035% TFA solvent) to give Reference Example 127 (113.2 mg).

LC-MS: 490 (M+H)$^+$/1.03 min, Measurement Condition E

Reference Examples 128 to 131

The compounds shown in the following table were obtained through the same reaction and treatment as d) step of Reference Example 2, using corresponding raw material compounds.

TABLE 16

| Reference Example | Structural Formula | LC-MS /Rt (min) | LC-MS Measurement Condition |
|---|---|---|---|
| 128 | | 878(M + Na)+ /1.426 | J |
| 129 | | 647(M + H)+ /0.89 | J |
| 130 | | 585(M + H)+ /0.67 | J |
| 131 | | 649(M + H)+ /0.81 | J |

Reference Examples 132 to 143

The compounds shown in the following tables were obtained through the same reaction and treatment as b) step of Reference Example 2, using corresponding raw material compounds.

TABLE 17-1

| Reference Example | Structural Formula | LC-MS /Rt (min) | LC-MS Measurement Condition |
|---|---|---|---|
| 132 | | 699(M + H)+ /1.24 | J |

TABLE 17-1-continued

| Reference Example | Structural Formula | LC-MS /Rt (min) | LC-MS Measurement Condition |
|---|---|---|---|
| 133 | | 648(M + H)+ /1.21 | J |
| 134 | | 595(M + H)+ /1.00 | J |
| 135 | | 637(M + H)+ /1.34 | J |
| 136 | | 647(M + H)+ 136 | J |
| 137 | | 656(M + H)+ /1.27 | J |
| 138 | | 661(M + H)+ /1.187 | J |
| 139 | | 659(M + H)+ /1.089 | J |

TABLE 17-2
| | | |
|---|---|---|
| 140 | (structure) | 637(M + H)⁺ J /1.127 |
| 141 | (structure) | 681(M + H)⁺ J /1.232 |
| 142 | (structure) | 709(M + H)⁺ J /0.77 |
| 143 | (structure) | 731(M + H)⁺ J /1.33 |
Example 1
(2R)-2-{[(2E,4S)-4-{[(2S)-2-{[(2S)-2-Amino-3-methyl-3-(1-methyl-1H-indol-3-yl)butanoyl]amino}-3,3-dimethylbutanoyl](methyl)amino}-2,5-dimethyl-hex-2-enoyl]amino}pentane diethyl diester
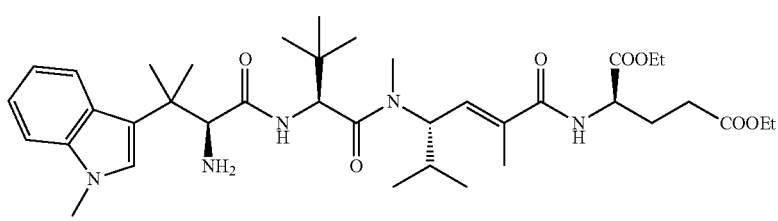 [SMILES: CCOC(=O)CC[C@@H](NC(=O)/C(C)=C/[C@H](C(C)C)N(C)C(=O)[C@@H](NC(=O)[C@@H](N)C(C)(C)c1cn(C)c2ccccc12)C(C)(C)C)C(=O)OCC]

To a solution of Reference Example 8 (70 mg) in chloroform (1.0 mL), trifluoroacetic acid (0.2 mL) was added, and the resultant mixture was stirred at 25° C. for 2 hours. After the reaction ended, the reaction solution was purified by silica gel column chromatography (eluting solvent; methanol:chloroform) to give Example 1 (47 mg).

LC-MS: 698 (M+H)⁺ (1.205 min, Measurement Condition D)

Example 2

β,β,1-Trimethyl-L-tryptophyl-N-[(3S,4E)-6-{[(1R)-1,3-dicarboxypropyl]amino}-2,5-dimethyl-6-oxo-hex-4-en-3-yl]-N,3-dimethyl-L-valinamide

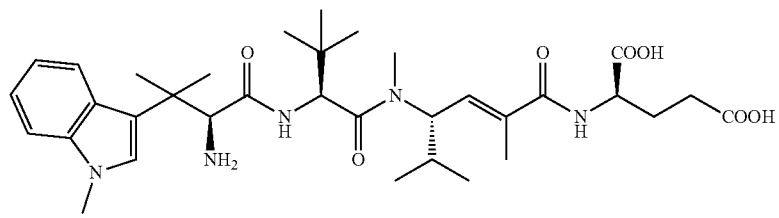 [SMILES: C/C(=C\[C@H](C(C)C)N(C)C(=O)[C@@H](NC(=O)[C@@H](N)C(C)(C)c1cn(C)c2ccccc12)C(C)(C)C)C(=O)N[C@H](CCC(=O)O)C(=O)O]

To a solution of Example 1 (42 mg) in methanol (1.0 mL), 1 mol/L lithium hydroxide (0.36 mL) was added, and the resultant mixture was stirred at 25° C. for 12 hours. After the reaction ended, through purification by silica gel column chromatography (eluting solvent; chloroform:methanol), Example 2 (28 mg) was obtained.

LC-MS: 642 (M+H)⁺ 640 (M−H)⁻ (1.056 min, Measurement Condition D)

Example 3

N-{(2E,4S)-2,5-Dimethyl-4-[methyl(N,β,β,1-tetramethyl-L-tryptophyl-3-m ethyl-L-valyl)amino]hex-2-enoyl}-L-α-aspartyl-L-t-aspartyl-L-α-aspartyl-L-α-aspartyl-L-α-aspartic acid

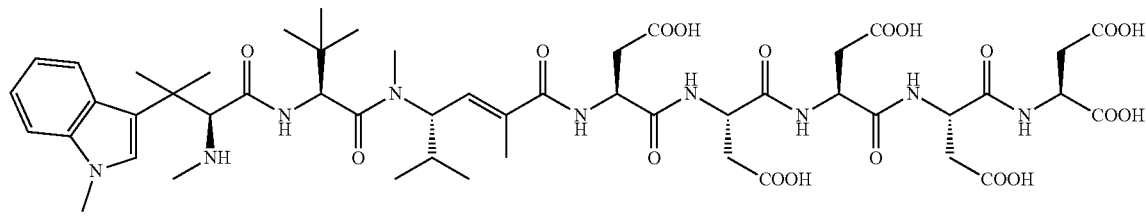 [SMILES: CN[C@H](C(=O)N[C@H](C(=O)N(C)[C@H](/C=C(\C)C(=O)N[C@@H](CC(=O)O)C(=O)N[C@@H](CC(=O)O)C(=O)N[C@@H](CC(=O)O)C(=O)N[C@@H](CC(=O)O)C(=O)N[C@@H](CC(=O)O)C(=O)O)C(C)C)C(C)(C)C)C(C)(C)c1cn(C)c2ccccc12]

To a solution of Reference Example 5 (16 mg) in chloroform (0.8 mL), trifluoroacetic acid (0.2 mL) was added, and the resultant mixture was stirred at 25° C. for 2 hours. After the reaction ended, the reaction solution was purified by reversed phase column chromatography (eluting solvent; acetonitrile with 0.1% TFA:water) to give Example 3 (8.9 mg).

LC-MS: 1102 (M+H)$^+$, 1100 (M−H)$^−$ (0.986 min, Measurement Condition D)

Examples 4 to 51

The compounds shown in the following Table 18 to Table 20 were obtained through the same reaction and treatment as Example 1, 2 or 3, using corresponding raw material compounds.

TABLE 18-1

| Example | Q | (AA)$_1$ | LC-MS /Rt(min) | LC-MS Measurement Condition |
|---|---|---|---|---|
| 4 | 1-methylindol-3-yl | NH-CH(COOH)-CH$_2$CH$_2$-COOH | 656 (M + H)$^+$ /1.036 | C |
| 5 | 1-methylindol-3-yl | NH-CH(COOH)-(CH$_2$)$_4$-NH$_2$ | 655 (M + H)$^+$ /0.933 | D |
| 6 | 1-methylindol-3-yl | NH-CH(COOH)-CH$_2$CH$_2$-COOH | 656 (M + H)$^+$ /1.038 | D |
| 7 | 1-methylindol-3-yl | NH-CH(COOtBu)-(CH$_2$)$_4$-NH$_2$ | 711 (M + H)$^+$ /1.034 | D |
| 8 | 1-methylindol-3-yl | NH-CH(COOEt)-CH$_2$CH$_2$-COOEt | 712 (M + H)$^+$ /3.17 | F |

TABLE 18-1-continued

| Example | Q | (AA)₁ | LC-MS /Rt(min) | LC-MS Measurement Condition |
|---|---|---|---|---|
| 9 | N-methylindol-3-yl | CH(COOEt)CH₂CH₂COOEt | 712 (M + H)⁺ /1.091 | C |
| 10 | N-methylindol-3-yl | CH(COOEt)CH₂COOEt | 698 (M + H)⁺ /3.21 | F |
| 11 | N-methylindol-3-yl | CH(COOH)CH₂COOH | 642 (M + H)⁺ /0.998 | D |
| 12 | N-methylindol-3-yl | CH(COOH)CH₂CH₂COOEt | 684 (M + H)⁺ /2.99 | F |
| 13 | N-methylindol-3-yl | CH(COOEt)CH₂CH₂COOH | 684 (M + H)⁺ /2.95 | F |
| 14 | N-methylindol-3-yl | CH(COOEt)CH₂CH₂COOH | 684 (M + H)⁺ /1.045 | A |

TABLE 18-2

| 15 | N-methylindol-3-yl | CH(COOH)CH₂CH₂COOEt | 684 (M + H)⁺ /2.99 | F |

TABLE 18-2-continued

| | R1 | R2 | MS | Method |
|---|---|---|---|---|
| 16 | 1-methylindol-3-yl | -NH-CH(COOEt)-CH2-COOEt | 698 (M + H)+ /0.991 | E |
| 17 | 1-methylindol-3-yl | -NH-CH(COOH)-CH2-COOEt | 670 (M + H)+ /0.842 | E |
| 18 | 1-methylindol-3-yl | -NH-CH(COOEt)-CH2-COOH | 670 (M + H)+ /0.840 | E |
| 19 | 1-methylindol-3-yl | -NH-CH(COOEt)-CH2-COOH | 670 (M + H)+ /0.843 | E |
| 20 | 1-methylindol-3-yl | -NH-CH(COOH)-CH2-COOEt | 670 (M + H)+ /0.843 | E |
| 21 | 1-methylindol-3-yl | -NH-CH(COOH)-CH2-COOH | 642 (M + H)+ /1.054 | D |
| 22 | 1-methylindol-3-yl | -NH-CH(COOMe)-CH2-SH | 644 (M + H)+ /1.119 | A |
| 23 | 1-methylindol-3-yl | -NH-CH(COOH)-CH2-SH | 630 (M + H)+ /1.060 | A |
| 24 | 5-fluoro-1-methylindol-3-yl | -NH-CH(COOEt)-CH2-CH2-COOH | 702 (M + H)+ /0.971 | B |

TABLE 18-2-continued

| 25 | 5-F, N-Me indol-3-yl | (S)-CH(COOEt)-NH-/-CH2CH2-COOEt | 730 (M + H)+/1.254 | D |
| 26 | 5-F, N-Me indol-3-yl | (S)-CH(COOH)-NH-/-CH2CH2-COOH | 674 (M + H)+/1.068 | D |
| 27 | 5-OMe, N-Me indol-3-yl | (S)-CH(COOEt)-NH-/-CH2CH2-COOH | 714 (M + H)+/0.964 | B |

TABLE 18-3

| 28 | 6-F, N-Me indol-3-yl | (S)-CH(COOH)-NH-/-CH2CH2-COOH | 674 (M + H)+/0.963 | B |
| 29 | phenyl | (R)-CH(COOEt)-NH-/-CH2CH2-COOEt | 659 (M + H)+/1.208 | D |
| 30 | phenyl | (S)-CH(COOH)-NH-/-CH2CH2-COOH | 603 (M + H)+/1.131 | C |
| 31 | phenyl | (S)-CH(COO-tBu)-NH-/-CH2CH2-COOH | 659 (M + H)+/1.099 | C |
| 32 | phenyl | (S)-CH(COOH)-NH-/-CH2CH2-COOH | 603 (M + H)+/0.870 | D |

TABLE 18-3-continued

| 33 | [indole structure with N-Me] | [lysine-like structure with COOH and NH2] | 655 (M + H)+/ 0.854 | D |

TABLE 19

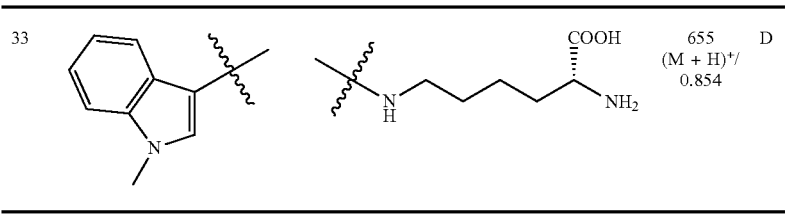

| Example | Q | (AA)₁ | (AA)₂ | LC-MS/ Rt(min) | LC-MS Measurement Condition |
|---|---|---|---|---|---|
| 34 | [N-Me indole] | [COOEt branch] | [COOEt] | 869 (M + H)+/ 3.28 | F |
| 35 | [N-Me indole] | [COOH branch] | [COOH] | 785 (M + H)+/ 2.69 | F |
| 36 | [N-Me indole] | [COOEt branch] | [COOEt] | 869 (M + H)+/ 3.28 | F |
| 37 | [N-Me indole] | [COOMe branch] | [COOEt] | 855 (M + H)+/ 1.216 | D |
| 38 | [N-Me indole] | [COOH branch] | [COOH] | 785 (M + H)+ 783 (M − H)−/ 1.029 | D |
| 39 | [N-Me indole] | [COOEt branch] | [COOEt] | 869 (M + H)+/ 3.27 | F |

TABLE 19-continued

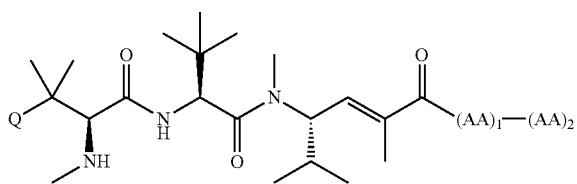

| Example | Q | (AA)₁ | (AA)₂ | LC-MS/ Rt(min) | LC-MS Measurement Condition |
|---|---|---|---|---|---|
| 40 | 1-methylindol-3-yl | NH-CH(CH₂CH₂COOH)-C(=O) | NH-CH(COOH)-CH₂CH₂COOH | 785 (M + H)⁺/ 2.66 | F |
| 41 | 1-methylindol-3-yl | NH-CH(CH₂CH₂COOEt)-C(=O) | NH-CH(COOEt)-CH₂CH₂COOEt | 869 (M + H)⁺/ 3.26 | F |
| 42 | 1-methylindol-3-yl | NH-CH(CH₂CH₂COOH)-C(=O) | NH-CH(COOH)-CH₂CH₂COOH | 785 (M + H)⁺/ 2.66 | F |
| 43 | 1-methylindol-3-yl | NH-CH(COOEt)-CH₂CH₂-C(=O) | NH-CH(COOEt)-CH₂CH₂COOEt | 869 (M + H)⁺/ 1.274 | D |
| 44 | 1-methylindol-3-yl | NH-CH(COOH)-CH₂CH₂-C(=O) | NH-CH(COOH)-CH₂CH₂COOH | 785 (M + H)⁺ 783 (M − H)⁻/ 1.056 | D |
| 45 | 1-methylindol-3-yl | NH-CH(COOH)-CH₂CH₂-C(=O) | NH-CH(COOH)-(CH₂)₄NH₂ | 784 (M + H)⁺ 782 (M − H)⁻/ 0.984 | D |
| 46 | phenyl | NH-CH(COOH)-CH₂CH₂-C(=O) | NH-CH(COOH)-CH₂CH₂COOH | 732 (M + H)⁺/ 0.892 | C |

TABLE 20

| Example | (AA)$_m$ | LC-MS/ Rt(min) | LC-MS Measurement Condition |
|---|---|---|---|
| 47 | | 914 (M + H$^+$) 912 (M − H)$^−$/ 1.023 | D |
| 48 | | 1172 (M + H)$^+$ 1170 (M − H)$^−$/ 0.976 | D |
| 49 | | 909 (M + 2H)$^{2+}$ 907 (M − 2H)$^{2−}$/ 0.957 | D |

TABLE 20-continued

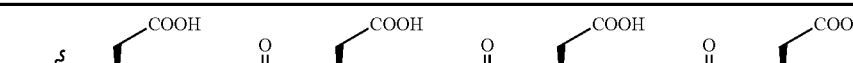

| Example | (AA)$_m$ | LC-MS/ Rt(min) | LC-MS Measurement Condition |
|---|---|---|---|
| 50 | | 839 (M + 2H)$^{2+}$ 837 (M − 2H)$^{2−}$/ 0.966 | D |
| 51 | | 1172 (M + H$^+$) 1170 (M − H)$^−$/ 0.902 | D |

Another Synthesis Method of Examples 22 to 23

The compounds shown in the following table were obtained by treating the raw material compound, Reference Example 31 or 60, with an aqueous dithiothreitol phosphate solution and an aqueous triethylamine tetraacetate phosphate solution, in a mixed solvent of methanol and ethyl acetate, in accordance with the synthesis method described in J. Med. Chem. 2006, 49, 4392-4408.

TABLE 21

| Example | Structural Formula | LC-MS/ Rt (min) | LC-MS Measurement Condition |
|---|---|---|---|
| 22 | 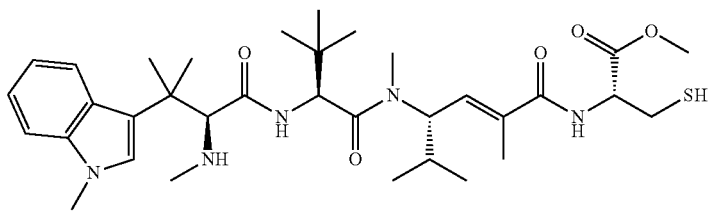 [SMILES: CN[C@H](C(=O)N[C@H](C(=O)N(C)[C@H](/C=C(\C)C(=O)N[C@@H](CS)C(=O)OC)C(C)C)C(C)(C)C)C(C)(C)c1cn(C)c2ccccc12] | 644 (M + H)$^+$/ 1.118 | J |

TABLE 21-continued

| Example | Structural Formula | LC-MS/ Rt (min) | LC-MS Measurement Condition |
|---|---|---|---|
| 23 | 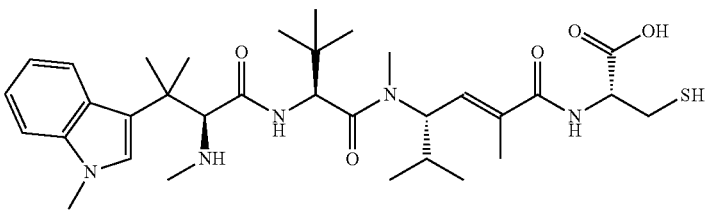 [SMILES: CN[C@H](C(=O)N[C@H](C(=O)N(C)[C@H](/C=C(\C)C(=O)N[C@@H](CS)C(=O)O)C(C)C)C(C)(C)C)C(C)(C)c1cn(C)c2ccccc12] | 630 (M + H)+/ 1.057 | C |

Example 52

The compound shown in the following table was obtained through the same reaction and treatment as Reference Example 3 and Example 1, using Reference Example 19.

TABLE 22

| Example | Structural Formula | LC-MS/ Rt (min) | LC-MS Measurement Condition |
|---|---|---|---|
| 52 | 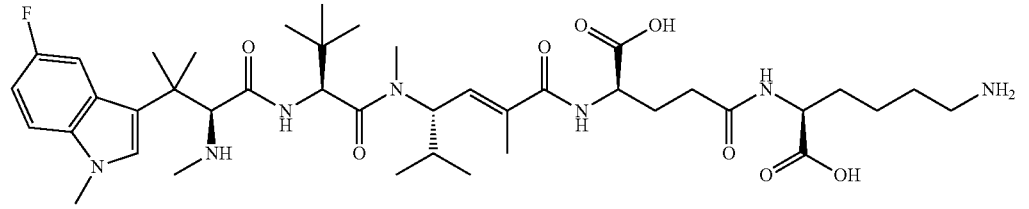 [SMILES: CN[C@H](C(=O)N[C@H](C(=O)N(C)[C@H](/C=C(\C)C(=O)N[C@H](CCC(=O)N[C@@H](CCCCN)C(=O)O)C(=O)O)C(C)C)C(C)(C)C)C(C)(C)c1cn(C)c2ccc(F)cc12] | 800 (M − H)−/ 0.923 | J |

Examples 53 to 54

The compounds shown in the following table were obtained through the same reaction and treatment as Reference Example 9, using J11 of Reference Example 9 and a corresponding raw material compound.

TABLE 23

| Example | Structural Formula | LC-MS/ Rt (min) | LC-MS Measurement Condition |
|---|---|---|---|
| 53 | 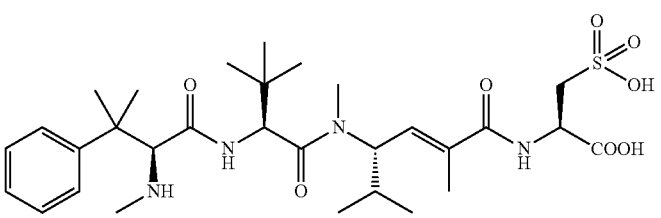 [SMILES: CN[C@H](C(=O)N[C@H](C(=O)N(C)[C@H](/C=C(\C)C(=O)N[C@@H](CS(=O)(=O)O)C(=O)O)C(C)C)C(C)(C)C)C(C)(C)c1ccccc1] | 623 (M − H)−/ 0.81 | J |

TABLE 23-continued

| Example | Structural Formula | LC-MS/ Rt (min) | LC-MS Measurement Condition |
|---|---|---|---|
| 54 | (structure) | 321 (M + 2H)+2/ 0.539 | J |

Examples 55 to 66

The compounds shown in the following tables were obtained through the same reaction and treatment as a) step of Reference Example 2, using corresponding raw material compounds.

TABLE 24-1

| Example | Structural Formula | LC-MS/ Rt (min) | LC-MS Measurement Condition |
|---|---|---|---|
| 55 | (structure) | 871 (M + H)+/ 1.15 | J |
| 56 | (structure) | 621 (M + H)+/ 1.04 | J |
| 57 | (structure) | 567 (M + H)+/ 0.80 | J |
| 58 | (structure) | 609 (M + H)+/ 0.99 | J |
| 59 | (structure) | 619 (M + H)+/ 0.96 | J |

TABLE 24-1-continued

| Example | Structural Formula | LC-MS/ Rt (min) | LC-MS Measurement Condition |
|---|---|---|---|
| 60 | | 628 (M + H)+/ 0.98 | J |
| 61 | | 633 (M + H)+/ 0.887 | J |
| 62 | | 631 (M + H)+/ 0.986 | J |

TABLE 24-2

| | | | |
|---|---|---|---|
| 63 | | 609 (M + H)+/ 0.828 | J |
| 64 | | 653 (M + H)+/ 1.099 | J |
| 65 | | 681 (M + H)+/ 1.02 | J |
| 66 | | 703 (M + H)+/ 1.06 | J |

Examples 67 to 69

The compounds shown in the following table were obtained through the same reaction and treatment as Reference Example 3, using corresponding raw material compounds.

TABLE 25

| Example | Structural Formula | LC-MS/ Rt (min) | LC-MS Measurement Condition |
|---|---|---|---|
| 67 | | 679 (M + H)+/ 1.06 | J |
| 68 | | 617 (M + H)+/ 0.90 | J |
| 69 | | 681 (M + H)+/ 0.92 | J |

Example 70

The compound shown in the following table was obtained through the same reaction and treatment as a) step of Reference Example 2 and a) step of Reference Example 101, using Reference Example 125.

TABLE 26

| Example | Structural Formula | LC-MS/ Rt (min) | LC-MS Measurement Condition |
|---|---|---|---|
| 70 | | 647 (M + H)+/ 0.90 | J |

Example 71

The compound shown in the following table was obtained through the same reaction and treatment as Example 1, using Example 66.

TABLE 27

| Example | Structural Formula | LC-MS/ Rt (min) | LC-MS Measurement Condition |
|---|---|---|---|
| 71 | (structure) | 647 (M + H)+/ 0.83 | J |

Examples 72 to 73

The compounds shown in the following table were obtained from Reference Example 2 through the same reaction and treatment as Reference Example 3.

TABLE 28

| Example | Structural Formula | LC-MS/ Rt (min) | LC-MS Measurement Condition |
|---|---|---|---|
| 72 | (structure) | 684 (M + H)+/ 1.153 | J |
| 73 | (structure) | 656 (M + H)+/ 1.105 | J |

Example M1

Diethyl (2R)-2-{[(5S,8S,11S,12E)-8-tert-butyl-1-(4-{[(2S)-5-(carbamoylamino)-2-{[(2S)-2-{[6-(2,5-dioxo-2,5-dihydro-1H-pyrrol-1-yl)hexanoyl]amino}-3-methylbutanoyl]amino}pentanoyl]amino}phenyl)-4,10,13-trimethyl-5-[2-(1-methyl-1H-indol-3-yl)propan-2-yl]-3,6,9,14-tetraoxo-11-(propan-2-yl)-2-oxa-4,7,10-triazatetradec-12-en-14-yl]amino}pentanedioate

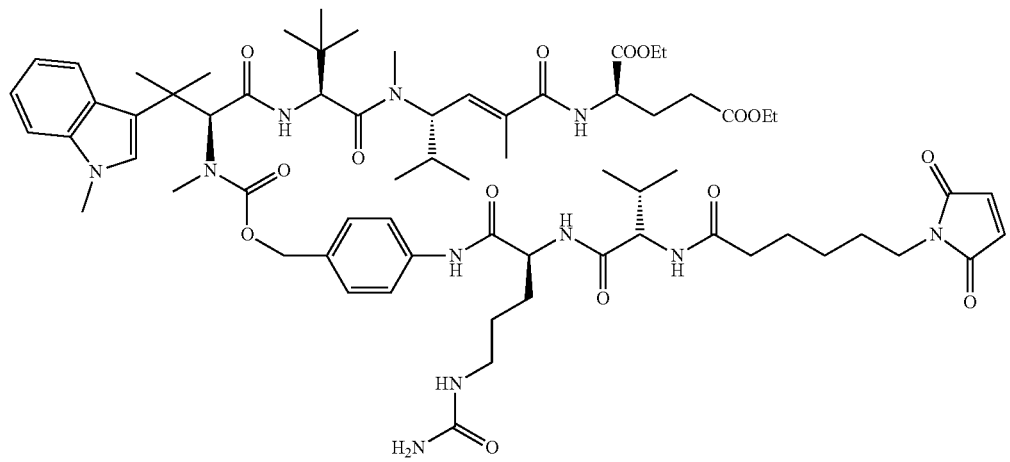

A mixed solution of Reference Example 101 (14 mg), N-succinimidyl 6-maleimidohexanoate (4.7 mg) and N,N-dimethylformamide (1 mL) was stirred at 25° C. for 48 hours. After the reaction ended, the reaction solution was purified by reversed phase column chromatography (eluting solvent; acetonitrile with 0.1% TFA:water) to give Example M1 (5.8 mg).

LC-MS: 1310 (M+H)$^+$ (1.398 min, Measurement Condition D)

Examples M2 to M12

The compounds shown in the following Table 29 and Table 30 were obtained through the same reaction and treatment as Example 1, 3 or M1, using corresponding raw material compounds.

TABLE 29

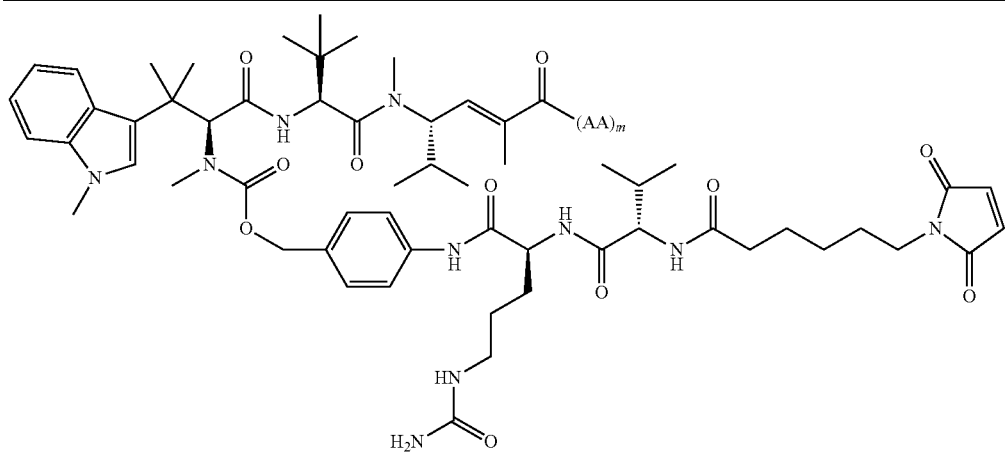

| Example | (AA)$_m$ | LC-MS/ Rt (min) | LC-MS Measurement Condition |
|---|---|---|---|
| M 2 | ⸺NH—CH(COOH)—CH$_2$CH$_2$—COOH | 1254 (M + H)$^+$/ 1.290 | D |

TABLE 29-continued
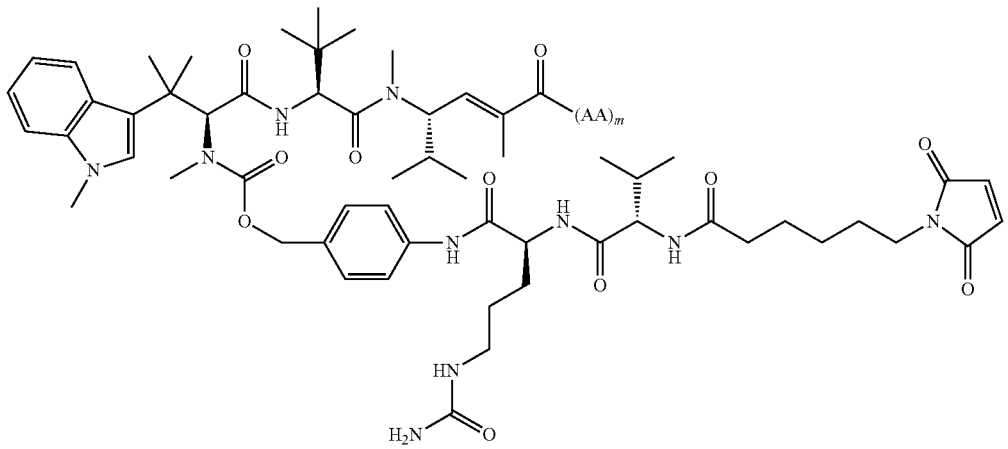
| Example | (AA)$_m$ | LC-MS/ Rt (min) | LC-MS Measurement Condition |
|---|---|---|---|
| M 3 | [structure with COOEt, NH, COOH] | 1282 (M + H)$^+$/ 1.291 | D |
| M 4 | [structure with COOH, NH, COOH, COOH] | 1383 (M + H)$^+$/ 1.073 | D |
| M 5 | [structure with COOH, NH, COOH, COOH] | 1383 (M + H)$^+$/ 1.197 | D |

TABLE 30

| Example | (AA)n | Y | G¹ | G² | G³ | LC-MS/Rt (min) | LC-MS Measurement Condition |
|---|---|---|---|---|---|---|---|
| M6 | [structure: COOEt-bearing residue] | [structure: -O-CH2-C6H4-NH-] | L-Cit | L-Val | — | 1238 (M+H)⁺/1.183 | B |
| M7 | [structure: COOEt-bearing residue] | [structure: -O-CH2-C6H4-NH-] | L-Asn | L-Ala | — | 1167 (M+H)⁺/1.126 | B |
| M8 | [structure: COOEt-bearing residue] | [structure: -O-CH2-C6H4-NH-] | L-Asn | L-Ala | L-Pro | 1264 (M+H)⁺/1.143 | B |
| M9 | [structure: COOEt-bearing residue] | [structure: -O-CH2-C6H4-NH-] | L-Asn | L-Ala | L-Ala | 1238 (M+H)⁺/1.090 | B |
| M10 | [structure: di-COOEt bearing dipeptide] | [structure: -O-CH2-C6H4-NH-] | L-Asn | L-Ala | L-Pro | 1421 (M+H)⁺/3.34 | F |
| M11 | [structure: COOH-bearing residue] | [structure: -O-CH2-C6H4-NH-] | L-Asn | L-Ala | L-Pro | 1236 (M+H)⁺/3.08 | F |

TABLE 30-continued

| Example | (AA)ₙ | Y | G¹ | G² | G³ | LC-MS/ Rt (min) | LC-MS Measurement Condition |
|---|---|---|---|---|---|---|---|
| M12 | (structure with COOH groups) | (structure with benzyl ester-NH) | L-Cit | L-Val | — | 1380 (M − H)⁻/ 1.005 | D |

Example M13

The compound shown below was obtained through the same reaction and treatment as Example M1, using a corresponding raw material compound.

N-[6-(2,5-dioxo-2,5-dihydro-1H-pyrrol-1-yl) hexanoyl]-L-valyl-N-{4-[(5S, 8S,11S,12E,16R)-8-tert-butyl-16,18-dicarboxy-4,10,13-trimethyl-3,6,9,14-tetraoxo-5-(2-phenylpropan-2-yl)-11-(propan-2-yl)-2-oxa-4,7,10,15-tetraazaoctadec-12-en-1-yl] phenyl}-N⁵-carbamoyl-L-ornithine amide

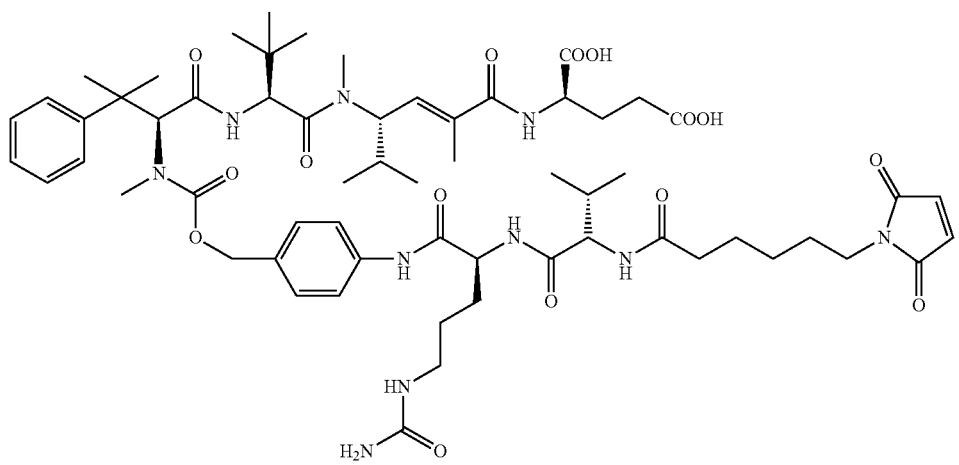

LC-MS: 1201 (M+H)⁺ (1.110 min, Measurement Condition D)

Example M14

The compound shown in the following table was obtained through the same reaction and treatment as Example M1, using a corresponding raw material compound.

TABLE 31

| Example | Structural Formula | LC-MS/ Rt (min) | LC-MS Measurement Condition |
|---|---|---|---|
| M14 | | 1113 (M − H)⁻/ 1.224 | J |

The NMR data of Examples 4, 32, 53 to 60, 65 to 69 and 71 are shown in the following tables.

TABLE 32-1

| Example No. | NMR Data |
|---|---|
| 4 | ¹H-NMR (DMSO-D6) δ: 0.68 (3H, s), 0.79 (3H, s), 0.91 (9H, s), 1.36 (3H, s), 1.40 (3H, s), 1.70-2.15 (11H, m), 2.94 (3H, s), 3.16 (3H, s), 3.39 (1H, s), 3.71 (3H, s), 4.09 (1H, s), 4.77 (1H, d, J = 9.6 Hz), 4.91 (1H, d, J = 9.6 Hz), 6.30 (1H, s), 6.99 (1H, t, J = 7.3 Hz), 7.09-7.13 (1H, m), 7.37 (1H, d, J = 7.8 Hz), 7.74 (1H, d, J = 9.1 Hz), 7.81 (1H, d, J = 7.8 Hz). |
| 32 | ¹H-NMR (CD₃OD) δ: 0.88 (3H, d, J = 6.9 Hz), 0.93 (3H, d, J = 6.9 Hz), 1.06 (9H, s), 1.37 (3H, s), 1.47 (3H, s), 1.96 (3H, d, J = 1.4 Hz), 1.99-2.10 (2H, m), 2.19-2.28 (1H, m), 2.43 (2H, t, J = 7.8 Hz), 2.49 (3H, s), 3.14 (3H, s), 4.33 (1H, s), 4.47 (1H, dd, J = 9.1, 5.0 Hz), 4.93 (1H, s), 5.07 (1H, t, J = 10.1 Hz), 6.40 (1H, dd, J = 9.6, 1.4 Hz), 7.35 (1H, t, J = 7.3 Hz), 7.45 (2H, t, J = 7.8 Hz), 7.54 (2H, d, J = 7.3 Hz). |
| 53 | ¹H-NMR (CD₃OD) δ: 0.95-1.05 (15H, m), 1.17 (3H, d, J = 3.7 Hz), 1.28-1.38 (3H, m), 1.46 (1H, s), 1.54 (4H, s), 1.97 (1H, dd, J = 11.3, 4.0 Hz), 2.40 (1H, bs), 2.57 (1H, d, J = 4.3 Hz), 2.60 (2H, d, J = 4.9 Hz), 3.59 (3H, d, J = 3.7 Hz), 4.46 (1H, d, J = 4.3 Hz), 4.62 (1H, s), 5.20 (1H, d, J = 4.3 Hz), 5.40 (1H, d, J = 5.5 Hz), 7.35 (1H, t, J = 3.7 Hz), 7.45 (2H, d, J = 7.3 Hz), 7.56 (1H, t, J = 9.8 Hz). |
| 54 | ¹H-NMR (CD₃OD) δ: 0.93-1.00 (6H, m), 1.07 (9H, dd, J = 13.4, 11.6 Hz), 1.27 (3H, tt, J = 13.7, 4.6 Hz), 1.37 (2H, t, J = 14.0 Hz), 1.43 (1H, t, J = 11.9 Hz), 2.24-2.34 (1H, m), 2.41-2.44 (1H, m), 2.49 (2H, d, J = 1.8 Hz), 2.79-2.89 (1H, m), 3.51 (2H, d, J = 1.8 Hz), 4.12-4.17 (1H, m), 4.21-4.30 (1H, m), 4.39 (1H, dd, J = 10.4, 7.3 Hz), 4.45 (1H, s), 5.14 (1H, d, J = 1.8 Hz), 5.21-5.31 (1H, m), 7.25 (1H, t, J = 6.4 Hz), 7.36 (2H, t, J = 6.7 Hz), 7.47 (2H, dd, J = 18.9, 8.5 Hz). |
| 55 | ¹H-NMR (CD₃OD) δ: 0.88 (3H, d, J = 6.1 Hz), 0.92 (3H, d, J = 6.1 Hz), 1.07 (9H, s), 1.39 (3H, s), 1.52 (3H, s), 1.97 (3H, d, J = 8.5 Hz), 1.99-2.09 (2H, m), 2.18-2.29 (1H, m), 2.43 (2H, t, J = 7.3 Hz), 2.51 (3H, s), 3.14 (3H, s), 4.37 (1H, s), 4.43-4.51 (1H, m), 4.93 (1H, d, J = 4.3 Hz), 5.07 (1H, t, J = 9.4 Hz), 6.40 (1H, d, J = 9.8 Hz), 7.65 (2H, d, J = 8.5 Hz), 7.79 (1H, d, J = 6.7 Hz), 7.88 (1H, s), 8.50-8.57 (1H, m). |
| 56 | ¹H-NMR (CD₃OD) δ: 0.87 (3H, d, J = 6.1 Hz), 0.92 (3H, d, J = 6.1 Hz), 1.06 (9H, s), 1.37 (3H, s), 1.46 (3H, s), 1.96 (3H, s), 1.97-2.09 (2H, m), 2.18-2.28 (1H, m), 2.43 (2H, t, J = 7.0 Hz), 2.51 (3H, d, J = 1.8 Hz), 3.13 (3H, s), 4.31 (1H, s), 4.44-4.51 (1H, m), 4.91 (1H, s), 5.06 (1H, t, J = 10.1 Hz), 6.39 (1H, d, J = 7.9 Hz), 7.09 (1H, t, J = 8.2 Hz), 7.32 (2H, dd, J = 20.4, 9.4 Hz), 7.46 (1H, t, J = 7.0 Hz). |
| 57 | ¹H-NMR (CD₃OD) δ: 0.73 (3H, d, J = 5.1 Hz), 0.83 (3H, d, J = 6.7 Hz), 0.93 (9H, s), 1.17 (3H, d, J = 3.8 Hz), 1.21 (3H, d, J = 5.1 Hz), 1.44-1.54 (1H, m), 1.67-1.78 (1H, m), 1.82-2.07 (9H, m), 2.10-2.21 (1H, m), 2.34 (2H, t, J = 5.4 Hz), 2.88 (1H, dt, J = 22.5, 10.2 Hz), 3.00 (3H, s), 3.33-3.41 (2H, m), 3.99 (1H, d, J = 9.8 Hz), 4.38 (1H, dd, J = 9.1, 4.9 Hz), 4.62 (1H, t, J = 4.0 Hz), 4.94 (1H, dd, J = 18.9, 8.5 Hz). |
| 58 | ¹H-NMR (CD₃OD) δ: 0.71-0.78 (5H, m), 0.81 (3H, t, J = 5.5 Hz), 0.93 (9H, d, J = 4.9 Hz), 0.96-1.26 (6H, m), 1.60-1.75 (4H, m), 1.84 (3H, d, J = 3.0 Hz), 1.87-2.02 (2H, m), 2.08-2.19 (1H, m), 2.29-2.36 (2H, m), 2.52 (3H, d, J = 6.1 Hz), 3.00 (3H, d, J = 4.9 Hz), 3.88 (1H, d, J = 4.3 Hz), 4.38 (1H, t, J = 4.6 Hz), 4.80 (1H, d, J = 4.9 Hz), 4.90-4.96 (1H, m), 6.28 (1H, d, J = 7.9 Hz). |

TABLE 32-2

59 $^1$H-NMR (CD$_3$OD) δ: 0.76-0.82 (6H, m), 0.96 (9H, s), 1.24 (3H, s), 1.31 (3H, s), 1.86 (3H, s), 1.89-2.03 (2H, m), 2.15 (1H, m), 2.34 (2H, t, J = 7.3 Hz), 2.39 (3H, s), 3.03 (3H, d, J = 5.5 Hz), 4.15 (1H, s), 4.38 (1H, dd, J = 9.1, 4.9 Hz), 4.83 (1H, t, J = 4.0 Hz), 4.90-5.00 (1H, m), 6.30 (1H, d, J = 9.1 Hz), 6.73 (2H, dd, J = 17.1, 8.5 Hz), 7.23 (2H, dd, J = 12.5, 8.8 Hz).

60 $^1$H-NMR (CD$_3$OD) δ: 0.79 (3H, d, J = 6.1 Hz), 0.83 (3H, d, J = 6.7 Hz), 0.97 (9H, s), 1.30 (3H, s), 1.41 (3H, s), 1.86 (3H, s), 1.95 (2H, tt, J = 13.7, 5.2 Hz), 2.10-2.19 (1H, m), 2.34 (2H, t, J = 7.3 Hz), 2.43 (3H, s), 3.04 (3H, s), 4.23 (1H, s), 4.38 (1H, dd, J = 9.1, 4.9 Hz), 4.81 (2H, t, J = 4.0 Hz), 4.97 (1H, t, J = 10.1 Hz), 6.30 (1H, d, J = 9.1 Hz), 7.53 (1H, t, J = 7.9 Hz), 7.63 (1H, d, J = 7.9 Hz), 7.75 (1H, d, J = 7.9 Hz), 7.80 (1H, s).

65 $^1$H-NMR (CD$_3$OD) δ: 0.78 (3H, d, J = 6.7 Hz), 0.82 (3H, d, J = 7.9 Hz), 0.83 (9H, s), 1.38 (3H, s), 1.44 (3H, s), 1.84 (3H, s), 1.87-2.01 (2H, m), 2.14 (1H, td, J = 13.3, 7.3 Hz), 2.33 (2H, t, J = 7.0 Hz), 2.38 (3H, s), 3.02 (3H, s), 4.17 (1H, s), 4.38 (1H, dd, J = 9.1, 4.9 Hz), 4.45 (1H, s), 4.92 (1H, t, J = 10.1 Hz), 6.29 (1H, d, J = 9.1 Hz), 7.26 (1H, t, J = 7.9 Hz), 7.40 (2H, d, J = 5.8 Hz), 7.59 (1H, s).

66 $^1$H-NMR (CD$_3$OD) δ: 0.79 (3H, d, J = 6.1 Hz), 0.83 (3H, d, J = 6.1 Hz), 0.97 (9H, s), 1.31 (3H, s), 1.41 (3H, s), 1.50 (9H, s), 1.87 (3H, s), 1.89-2.00 (2H, m), 2.17 (1H, tt, J = 13.4, 6.8 Hz), 2.35 (2H, t, J = 5.4 Hz), 2.41 (3H, s), 3.04 (3H, s), 4.28 (1H, s), 4.36-4.41 (1H, m), 4.82 (1H, t, J = 4.0 Hz), 4.97 (1H, t, J = 9.8 Hz), 6.31 (1H, dd, J = 9.8, 1.2 Hz), 7.51 (2H, d, J = 6.3), 7.92 (2H, d, J = 6.6 Hz).

67 $^1$H-NMR (CD$_3$OD) δ: 0.78 (3H, d, J = 6.1 Hz), 0.82 (3H, d, J = 6.1 Hz), 0.97 (9H, s), 1.34 (3H, s), 1.43 (3H, s), 1.87 (3H, s), 1.89-2.00 (2H, m) 2.10-2.19 (1H, m), 2.34 (2H, t, J = 7.0 Hz), 2.42 (3H, s), 3.05 (3H, s), 4.34 (1H, s), 4.39 (1H, dd, J = 9.4, 5.2 Hz), 4.85 (1H, t, J = 4.3 Hz), 4.98 (1H, t, J = 9.8 Hz), 6.30 (1H, d, J = 9.8 Hz), 7.28 (1H, t, J = 7.3 Hz), 7.41 (4H, dt, J = 26.0, 7.6 Hz), 7.52 (1H, d, J = 6.7 Hz), 7.57 (2H, d, J = 7.3 Hz), 7.72 (1H, s), 8.39 (1H, d, J = 8.5 Hz).

68 $^1$H-NMR (CD$_3$OD) δ: 0.78 (3H, d, J = 6.1 Hz), 0.83 (3H, d, J = 6.7 Hz), 0.96 (9H, d, J = 4.9 Hz), 1.26 (3H, s), 1.35 (3H, s), 1.86 (3H, d, J = 4.3 Hz), 1.88-1.99 (2H, m), 2.09-2.19 (1H, m), 2.29 (3H, d, J = 5.5 Hz), 2.33 (2H, d, J = 6.7 Hz), 2.39 (3H, d, J = 5.5 Hz), 3.03 (3H, d, J = 5.5 Hz), 4.25 (1H, s), 4.38 (1H, t, J = 4.6 Hz), 4.82 (1H, d, J = 5.5 Hz), 4.96 (1H, d, J = 9.8 Hz), 6.29 (1H, brs), 7.07 (1H, brs), 7.22 (2H, brs), 7.27 (1H, brs).

69 $^1$H-NMR (CD$_3$OD) δ: 0.80 (3H, d, J = 6.7 Hz), 0.84 (3H, d, J = 6.8 Hz), 0.98 (9H, d, J = 6.1 Hz), 1.28 (3H, d, J = 6.1 Hz), 1.37 (3H, d, J = 6.1 Hz), 1.87 (3H, d, J = 6.1 Hz), 1.92-1.98 (2H, m), 2.14-2.19 (1H, m), 2.35 (2H, d, J = 6.7 Hz), 2.43 (3H, d, J = 6.1 Hz), 3.05 (3H, d, J = 6.7 Hz), 4.23 (1H, d, J = 6.7 Hz), 4.39 (1H, d, J = 4.3 Hz), 4.83 (1H, d, J = 4.3 Hz), 4.99 (1H, t, J = 8.2 Hz), 6.31 (1H, brs), 7.29 (1H, t, J = 7.6 Hz), 7.44 (2H, t, J = 7.3 Hz), 7.66 (1H, d, J = 4.9 Hz).

71 $^1$H-NMR (CD$_3$OD) δ: 0.79 (3H, d, J = 5.6 Hz), 0.82 (3H, d, J = 5.2 Hz), 0.97 (9H, d, J = 4.9 Hz), 1.31 (3H, d, J = 3.7 Hz), 1.41 (3H, d, J = 3.7 Hz), 1.86 (3H, d, J = 4.3 Hz), 1.90-1.98 (2H, m), 2.12-2.16 (1H, m), 2.34 (2H, t, J = 6.1 Hz), 2.41 (3H, d, J = 4.9 Hz), 3.04 (3H, d, J = 4.9 Hz), 4.28 (1H, d, J = 4.0 Hz), 4.39 (1H, dd, J = 9.1, 4.9 Hz), 4.78-4.82 (1H, m), 4.95-5.00 (1H, m), 6.30 (1H, d, J = 5.5 Hz), 7.55 (2H, dd, J = 7.6, 4.6 Hz), 7.99 (2H, dd, J = 7.6, 4.6 Hz).

Antibodies used for Example ADCs are commercially available, or may be produced in accordance with the literatures shown in the following table.

TABLE 33

| Antibody Name | Reference Literature |
|---|---|
| Brentuximab | Japanese Patent No. 4303964 |
| Labetuzumab | Cancer Res., 1995, 55, 5935s-5945s |
| Coltuximab | Proc. Natl. Acad. Sci. U.S.A. 1994, 91, 969-973 |
| Anetumab | Mol. Cancer Ther., 2014, 13, 1537-1548 |
| Polatuzumab | Blood, 2007, 110, 616-623 |
| Vadastuximab | Japanese Unexamined Patent Publication No. 2015-520758 |
| Glembatumumab | Japanese Patent No. 5716151 |
| Indatuximab | Japanese Unexamined Patent Publication No. 2016-053053 |
| Depatuxizumab | Mol. Cancer Ther., 2015, 14, 1141-1151 |
| Antibody of AMG 595 | Mol. Cancer Ther., 2015, 14, 1614-1624 |
| Inotuzumab | Japanese Patent No. 04486494 |

Example ADC1

Brentuximab-Example M2 conjugate (average DAR: 7.41)

Example ADC1

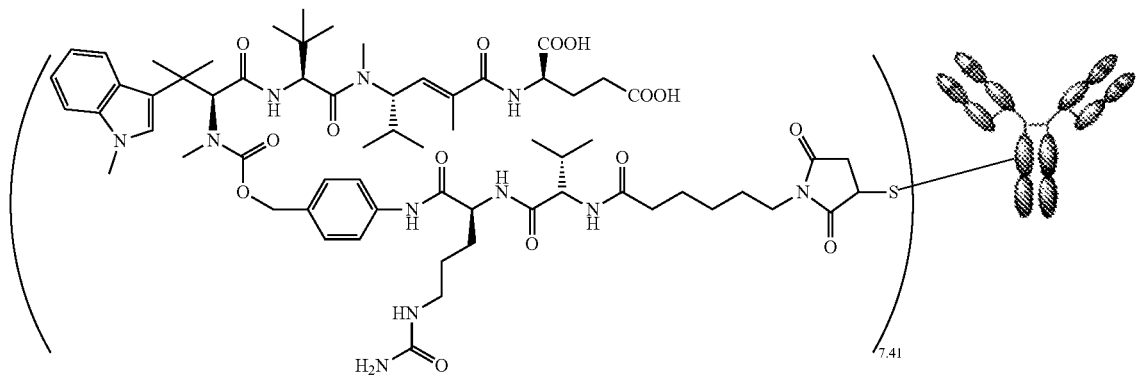

To a phosphate buffered saline solution (3.77 mL, pH 7.4) of brentuximab (91 mg), a trishydroxymethylaminomethane hydrochloride buffered solution (12.2 mL, pH 7.5) of 1 mmol/L tris(2-carboxyethyl)phosphine (TCEP) was added, and the resultant solution was incubated at 37° C. for 45 minutes. After cooling the antibody solution to 0° C., through treatment with a PD-10 desalination column pre-equilibrated with a phosphate buffered saline solution (pH 7.4), a phosphate buffered saline solution (pH 7.4) of the reduced anti-CD30 antibody (brentuximab) was obtained. After cooling this to 0° C., a 1 mmol/L DMSO solution of Example M2 (12.2 mL) 10 times diluted with a phosphate buffered saline solution (pH 7.4) was added as a modifying agent and completely mixed, and the resultant solution was incubated at 4° C. for 16 hours. Thereafter, through purification by a PD-10 desalination column pre-equilibrated with a phosphate buffered saline solution (pH 7.4) and subsequent centrifugal concentration, Example ADC1 (78.2 mg) was obtained.

The average DAR of the ADC thus obtained was measured by reducing or non-reducing SDS-PAGE, or HPLC-HIC. Alternatively, the average DAR may be measured qualitatively or quantitatively by ultraviolet-visible absorption spectroscopy (UV-Vis), reducing or non-reducing SDS-PAGE, HPLC-HIC, SEC, RP-HPLC, LC-MS or the like. These methods are described in Antibody Drug Conjugates, Methods in Molecular Biology vol. 1045, 2013. pp 267-284. L. Ducry, Ed.

When the average drug antibody ratio of an ADC produced with a human $IgG_1$ antibody is 8, production of the ADC may also be assumed from the results of reducing and non-reducing SDS-PAGE. Specifically, when bands are strongly detected in the vicinity of a molecular weight of 50 kDa and a molecular weight of 25 kDa as a result of SDS-PAGE analysis for Example ADC under disulfide non-reducing conditions, using See Blue (R) Plus2 (Thermo Fisher Scientific K.K.) as a marker, this indicates that the modifying agent conjugates to the cysteine residues involved in the disulfide bonds between the light chains and heave chains and of the hinge of the antibody, which means that an ADC with an average drug antibody ratio of 8 is obtained.

The average DAR of Example ADC1, determined from HPLC-HIC analysis, was 7.41.

Example ADC2

Brentuximab-Example M2 Conjugate (Average DAR: 3.76)

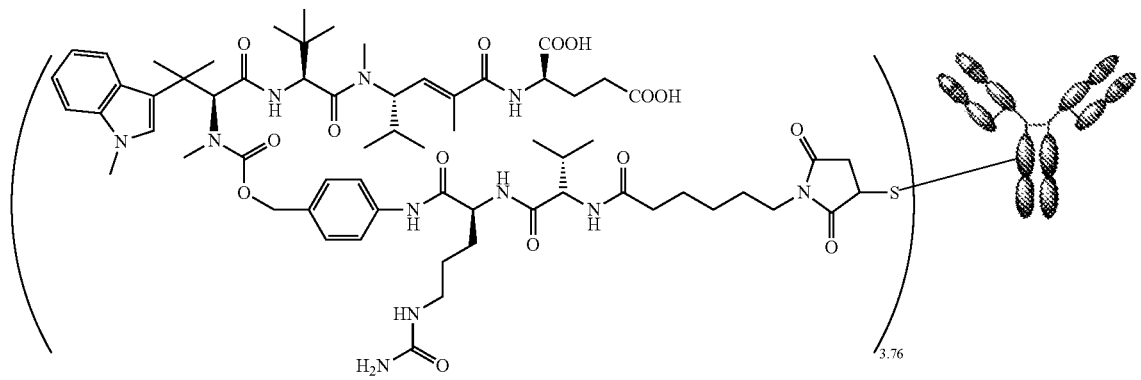

Example ADC2

In the protocol of Example ADC 1, by changing the amount of TCEP or the modifying agent to be added, the DAR of the ADC may be adjusted. In accordance with the protocol of Example ADC1, Example ADC 2 was obtained by using TCEP in an amount of 4 molar equivalent.

Examples ADC3 to 22

The ADCs shown in the following Table 34 were obtained through the same reaction and treatment as Example ADC1, using corresponding antibodies and modifying agents. In addition, the average DARs of these ADCs were calculated or assumed from UV-Vis, HPLC-HIC or SDS-PAGE analysis in the same manner as Example ADC1.

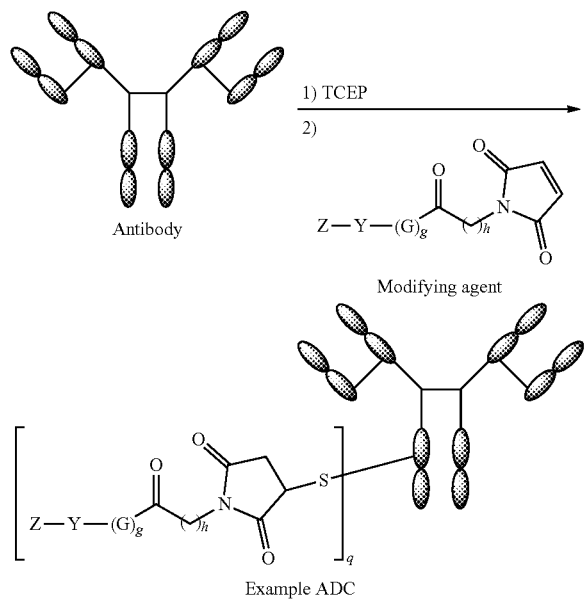

Example ADC

TABLE 34

| Example | Antibody | Modifying agent | Average DAR | Analysis |
|---|---|---|---|---|
| ADC 3 | Brentuximab | Example M1 | 8 | SDS-PAGE |
| ADC 4 | Brentuximab | Example M3 | 8 | SDS-PAGE |
| ADC 5 | Brentuximab | Example M4 | 8 | SDS-PAGE |
| ADC 6 | Brentuximab | Example M5 | 8 | SDS-PAGE |
| ADC 7 | Brentuximab | Example M6 | 8 | SDS-PAGE |
| ADC 8 | Brentuximab | Example M6 | 3.75 | HPLC-HIC |
| ADC 9 | Brentuximab | Example M12 | 8 | SDS-PAGE |
| ADC 10 | Brentuximab | Example M13 | 8 | SDS-PAGE |
| ADC 11 | Trastuzumab | Example M6 | 8 | SDS-PAGE |
| ADC 12 | Trastuzumab | Example M7 | 8 | SDS-PAGE |
| ADC 13 | Trastuzumab | Example M8 | 8 | SDS-PAGE |
| ADC 14 | Trastuzumab | Example M9 | 8 | SDS-PAGE |
| ADC 15 | Rituximab | Example M6 | 8 | SDS-PAGE |
| ADC 16 | Rituximab | Example M7 | 8 | SDS-PAGE |
| ADC 17 | Rituximab | Example M8 | 8 | SDS-PAGE |
| ADC 18 | Rituximab | Example M9 | 8 | SDS-PAGE |
| ADC 19 | Anti-embigin antibody | Example M6 | 8 | SDS-PAGE |
| ADC 20 | Anti-embigin antibody | Example M7 | 8 | SDS-PAGE |
| ADC 21 | Anti-embigin antibody | Example M8 | 8 | SDS-PAGE |
| ADC 22 | Anti-embigin antibody | Example M9 | 8 | SDS-PAGE |

Examples ADC23 to 39

The Example ADCs shown in the following table were obtained through the same reaction and treatment as Example ADC1, using corresponding antibodies and modifying agents (compounds of Examples).

TABLE 35

| Example | Antibody | Modifying agent | HIC retention time (min) | HIC condition | Average DAR |
|---|---|---|---|---|---|
| ADC23 | Trastuzumab | M2 | 6.32 | A | 7.67 |
| ADC24 | Gemtuzumab | M2 | 6.88 | A | 7.32 |
| ADC25 | Labetuzumab | M2 | 6.85 | A | 7.7 |
| ADC26 | Rituximab | M2 | 6.56 | A | 7.58 |
| ADC27 | Coltuximab | M2 | 6.36 | A | 7.8 |
| ADC28 | Denintuzumab | M2 | 6.86 | A | 8 |
| ADC29 | Alemtuzumab | M2 | 6.23 | A | 7.66 |
| ADC30 | Anetumab | M2 | 6.73 | A | 7..57 |
| ADC31 | Polatuzumab | M2 | 6.22 | A | 7.61 |
| ADC32 | Vadastuximab | M2 | 6.28 | A | 7.55 |
| ADC33 | Glembatumumab | M2 | 7.55 | A | 8 |
| ADC34 | Indatuximab | M2 | 6.58 | A | 7.79 |
| ADC35 | Depatuxizumab | M2 | 6.71 | A | 7.71 |
| ADC36 | Laprituximab | M2 | 6.31 | A | 7.63 |
| ADC37 | Cetuximab | M2 | 6.42 | A | 7.63 |
| ADC38 | Antibody of AMG 595 | M2 | 6.52 | A | 7.52 |
| ADC39 | Inotuzumab | M2 | 6.16 | A | 5.39 |

The Rt (min) of the Example ADCs in the above table is that of the peak of ADCs with a DAR of 8, observed by HPLC-HIC analysis (measurement condition H).

TEST EXAMPLES

Hereinafter, results of pharmacological tests with respect to particular Examples of the hemiasterlin derivative, antibody-drug conjugate and ADC intermediate according to the present invention will be shown and their pharmacological actions will be explained, but the present invention is not limited to compounds or antibody-drug conjugates shown in these Test Examples.

Test Example 1: Evaluation of Activity for Inhibiting Microtubule Polymerization Using Porcine Tubulins (1)

Using a tubulin polymerization inhibition assay kit (catalog number: BK006P) purchased from Cytoskeleton Inc., the polymerization inhibitory activity of compounds of Examples with a concentration of 0.91 μM was evaluated in accordance with the protocol appended to the kit. In summary of the protocol, to a 96 well microplate, 80 mM PIPES pH 6.9, 2 mM MgCl, 0.5 mM EGTA and 5% DMSO buffered solution of the compound to be evaluated was added in an amount of 10 μL for each well, and to these wells, 3 mg/mL porcine tubulin 80 mM PIPES pH 6.9, 2 mM MgCl, 0.5 mM EGTA, 1 mM GTP and 10.2% glycerol solution was added in an amount of 100 μL for each well. In order to examine a state in which tubulins polymerize over time, the absorbance at 340 nm was measured at 37° C., using a microplate reader. As the polymerization of tubulins progresses, the absorbance at 340 nm rises. The results are shown in FIG. 1 and FIG. 2.

As shown in FIG. 1, Examples 4, 9, 23, 28, 43 and 44 exhibited activities for inhibiting microtubule polymerization in the microtubule polymerization inhibition evaluation test. In particular, Example 4 exhibited a stronger polymerization inhibitory activity.

Figure 2:
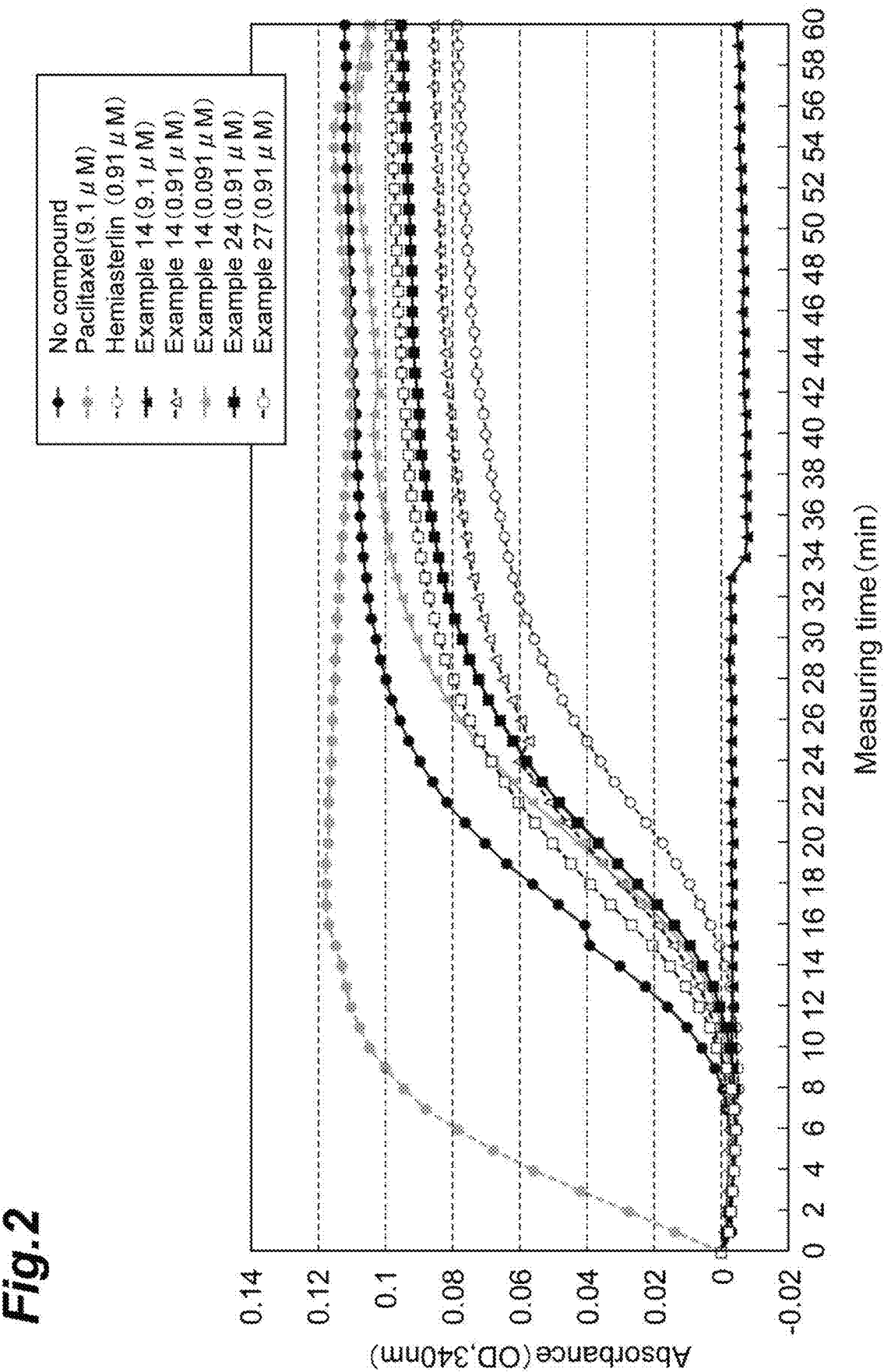
FIG. 2 shows activities of Examples 14, 24 and 27 to inhibit polymerization of porcine tubulins.

As shown in FIG. 2, Examples 14, 24 and 27 exhibited activities for inhibiting microtubule polymerization in the microtubule polymerization inhibition evaluation test. Example 14 exhibited polymerization inhibitory activity concentration-dependently.

Test Example 2: Evaluation of Activity for Inhibiting Microtubule Polymerization Using Porcine Tubulins (2)

Using a tubulin polymerization inhibition assay kit (catalog number: BK006P) purchased from Cytoskeleton Inc., the polymerization inhibitory activity of compounds of Examples was evaluated in accordance with the protocol appended to the kit. To a 96 well microplate, 80 mM PIPES pH 6.9, 2 mM MgCl, 0.5 mM EGTA and 5% DMSO buffered solution of the compound to be evaluated was added in an amount of 10 μL for each well, and to these wells, 3 mg/mL porcine tubulin 80 mM PIPES pH 6.9, 2 mM MgCl, 0.5 mM EGTA, 1 mM GTP and 10.2% glycerol solution was added in an amount of 100 μL for each well. In order to examine a state in which tubulins polymerize over time, the absorbance at 340 nm was measured at 37° C., using a microplate reader. As the polymerization of tubulins progresses, the absorbance at 340 nm rises.

The tubulin polymerization inhibitory activity was evaluated based on the proportion of polymerized tubulins 60 minutes after the assay initiation. Specifically, the microtubule polymerization rate (%) was calculated by dividing the absorbance of tubulins that had polymerized at wells to which the compound had been added by the absorbance of tubulins that had polymerized at wells to which the compound had not been added, and multiplying the obtained value by 100.

TABLE 36

| Compound | Microtubule polymerization rate (%) |
|---|---|
| Hemiasterlin | 3 |
| Example 2 | 4 |
| Example 3 | 3 |
| Example 11 | 5 |
| Example 13 | 21 |
| Example 17 | 4 |
| Example 18 | 3 |
| Example 19 | 7 |
| Example 20 | 5 |
| Example 21 | 2 |
| Example 30 | 5 |
| Example 31 | 5 |
| Example 32 | 2 |
| Example 38 | 5 |
| Example 45 | 1 |
| Example 46 | 1 |
| Example 47 | 3 |
| Example 48 | 4 |
| Example 49 | 5 |
| Example 50 | 3 |
| Example 51 | 33 |
| Example 55 | 16 |
| Example 56 | 7 |
| Example 57 | 5 |
| Example 58 | 5 |
| Example 59 | 2 |
| Example 60 | 6 |
| Example 62 | 6 |
| Example 66 | 9 |
| Example 67 | 42 |
| Example 68 | 4 |

TABLE 36-continued

| Compound | Microtubule polymerization rate (%) |
|---|---|
| Example 69 | 5 |
| Example 71 | 4 |
| Example 72 | 1 |

It is indicated that the lower value the microtubule polymerization rate is, the more strongly the compound inhibits polymerization of microtubules.

As shown from the results of Test Example 1 and Test Example 2, it was revealed that the hemiasterlin derivatives according to the present invention exhibit tubulin polymerization inhibitory activity.

Test Examples 3: Cellular Toxicity Test (1)

SU-DHL-1 cells (American Type Culture Collection, hereinafter, ATCC) and Karpas-299 cells (European Collection of Authenticated Cell Cultures, hereinafter, ECACC), which are human lymphoma cell lines, were cultured in RPMI 1640 (GIBCO) containing 10% fetal bovine serum (MP Biomedicals) (hereinafter, referred to as the "culture medium" in this test). SU-DHL-1 cells and Karpas-299 cells were prepared to be $2 \times 10^6$ cells/mL in the culture medium, and were added to a 96 well microplate for cell culturing in an amount of 50 μL for each well. Compounds of Examples or hemiasterlin 4 times diluted with the culture medium in 8 stages were added to the microplate in an amount of 50 μL for each well. To wells to which the test substance was not added, the culture medium was added in an amount of 50 μL for each well. These were cultured at 37 degree under 5% $CO_2$ for 4 days. After culturing, the microplate was taken out from the incubator, and was left at rest at room temperature for 10 minutes. To each well, 50 μL of CellTiter-Glo Luminescent Cell Viability Assay (Promega) was added, and the resultant mixture was stirred. This mixture was incubated at a dark place for 20 minutes. Using a microplate luminometer, luminescence at each well was measured, thereby calculating the cell viability for each concentration of the test substance. From the cell viability, the $IC_{50}$ value of the test substance was determined. The results are shown in Table 37 and Table 38.

The $IC_{50}$ value was calculated by the following formula:

$$IC_{50}(nM) = \text{antilog}(LOG_{10}(a/b) \times (e-d)/(c-d) + LOG_{10}b)$$

a: concentration a of test substance
b: concentration b of test substance
c: cell viability upon adding test substance with concentration a
d: cell viability upon adding test substance with concentration b
e: intermediate value between maximum and minimum among cell viabilities upon
adding test substances with different concentrations
(a and b are concentrations crossing the cell viability e, and a>b is indicated).

The cell viability at each concentration was calculated by the following formula:

$$\text{Cell Viability (\%)} = a'/b' \times 100$$

a': mean value of luminescence amount of wells to which test substance was added (n=6)
b': mean value of luminescence amount of wells to which test substance was not added (n=6)
(n represents the number of evaluations performed per test substance concentration).

TABLE 37

| Cell | Compound | IC$_{50}$ (nM) |
|---|---|---|
| SU-DHL-1 | Example 4 | 250 |
| | Example 14 | 0.24 |
| | Example 11 | 158 |
| | Example 22 | 1.22 |
| | Example 23 | >50 |
| | Example 28 | 115 |
| | Example 38 | 755 |
| | Example 44 | 631 |
| Karpas-299 | Hemiasterlin | 0.032 |
| | Example 1 | 93.9 |
| | Example 2 | >125 |
| | Example 3 | >5000 |
| | Example 4 | 291 |
| | Example 5 | 87.2 |
| | Example 6 | 34 |
| | Example 7 | 1.21 |
| | Example 11 | 220 |
| | Example 14 | 0.12 |
| | Example 29 | <0.015 |
| | Example 30 | 458 |
| | Example 38 | 1112 |
| | Example 44 | 503 |
| | Example 45 | >500 |
| | Example 48 | 1719 |
| | Example 49 | 3182 |
| | Example 50 | 1998 |
| | Example 51 | 1314 |

TABLE 38

| Cell | Compound | IC$_{50}$ (nM) |
|---|---|---|
| Karpas-299 | Example 17 | 0.528 |
| | Example 18 | 0.065 |
| | Example 19 | 0.628 |
| | Example 20 | 1.54 |
| | Example 32 | 101 |
| | Example 47 | 773 |
| | Example 52 | 230 |
| | Example 53 | 122 |
| | Example 54 | 22.2 |
| | Example 55 | 34.6 |
| | Example 56 | 275 |
| | Example 57 | >1000 |
| | Example 58 | >1000 |
| | Example 59 | 412 |
| | Example 60 | 406 |
| | Example 64 | 30 |
| | Example 65 | >1000 |
| | Example 66 | >1000 |
| | Example 67 | 149 |
| | Example 68 | 26.5 |
| | Example 69 | 97.1 |
| | Example 70 | 721 |
| | Example 71 | 701 |
| | Example 72 | 106 |

Test Examples 4: Cellular Toxicity Test (2)

SK-BR-3 cells (ATCC), which are a human breast cancer cell line, were cultured in McCoy's 5A (GIBCO) containing 10% fetal bovine serum (MP Biomedicals) (hereinafter, referred to as the "culture medium" in this test). SK-BR-3 cells were prepared to be 2×10$^6$ cells/mL in the culture medium, added to a 96 well microplate for cell culturing in an amount of 50 µL for each well, and cultured at 37 degree under 5% CO$_2$ overnight, and then, compounds of Examples or hemiasterlin 4 times diluted with the culture medium in 8 stages were added to the microplate in an amount of 50 µL for each well. To wells to which the test substance was not added, the culture medium was added in an amount of 50 µL for each well. These were cultured at 37 degree under 5% CO$_2$ for 3 days. After culturing, the microplate was taken out from the incubator, and was left at rest at room temperature for 10 minutes. 50 µL of CellTiter-Glo Luminescent Cell Viability Assay (Promega) was added, and the resultant mixture was stirred. This mixture was incubated at a dark place for 20 minutes. Using a microplate luminometer, luminescence at each well was measured, thereby calculating the cell viability for each concentration of the test substance. The IC$_{50}$ value was calculated in accordance with the method described in Test Example 3. The results are shown in Table 39.

TABLE 39

| Cell | Compound | IC$_{50}$ (nM) |
|---|---|---|
| SK-BR-3 | Hemiasterlin | 0.088 |
| | Example 4 | 192.9 |
| | Example 11 | 157 |
| | Example 14 | 1.03 |
| | Example 22 | 1.92 |
| | Example 23 | 143 |
| | Example 24 | 25 |
| | Example 27 | 50.2 |
| | Example 28 | 154 |
| | Example 38 | 719 |
| | Example 44 | 892 |

As shown in the above Table 37 to Table 39, the compounds shown to exhibit activities for inhibiting microtubule polymerization equivalent to that of hemiasterlin in Test Example 1 and Test Example 2 exhibited activities different from that of hemiasterlin in the cellular toxicity tests.

Test Example 5: Membrane Permeability Test

By the parallel artificial membrane permeability assay (PAMPA), the membrane permeability of compounds of Examples was examined as follows: To the donor plate, System solution (pION inc.) and GIT Lipid-0 (pION inc.) were added in an amount of 200 µL and 4 µL for each well, respectively. To the acceptor plate, Acceptor Sink Buffer (pION inc.) was added in an amount of 200 µL. Both plates were superposed and incubated at 37° C. for 4 hours, and then, UVs in the solutions on the side of acceptor and on the side of donor were measured with an UV plate reader (190 to 500 nm). Compounds with poor UV absorption were measured by LC-MS. The permeability coefficient P$_e$ (10$^{-6}$ cm/sec) of the drug was calculated by the following formula. The results are shown in Table 40 and Table 41.

[Expression 1]

$$P_e = -\frac{2.303 V_D}{A(t - \tau_{SS})}\left(\frac{1}{1+r_s}\right) \cdot \log_{10}\left[-r_a + \left(\frac{1+r_a}{1-R}\right) \cdot \frac{C_D(t)}{C_D(0)}\right]$$

$$r_a = (V_D/V_A) P_e^{(A-D)}/P_e^{(D-A)} = r_V P_e^{(A-D)}/P_e^{(D-A)}$$

$$r_v = (V_D/V_A)$$

$V_D$ = volume of donor well $V_A$ = volume of acceptor well $t$ = permeation time -continued $\tau^{SS}$ = steady state time R = retention $C_D$ and $C_A$ = concentration in donor and acceptor well

TABLE 40

| Compound | $P_e(10^{-6}$ cm/sec) (pH7.4) |
|---|---|
| Hemiasterlin | 25.6 |
| Example 3 | <0.1 |
| Example 4 | <0.1 |
| Example 6 | <0.1 |
| Example 14 | 4.5 |
| Example 38 | <0.1 |
| Example 44 | <0.1 |

TABLE 41

| Compound | $P_e(10^{-6}$ cm/sec) (pH7.4) |
|---|---|
| Example 2 | 0.2 |
| Example 5 | 0.8 |
| Example 17 | <0.1 |
| Example 18 | 2.6 |
| Example 19 | 2.1 |
| Example 20 | <0.1 |
| Example 21 | <0.1 |
| Example 24 | 12.1 |
| Example 30 | <0.1 |
| Example 32 | <0.1 |
| Example 47 | <0.1 |
| Example 48 | <0.1 |
| Example 52 | <0.1 |
| Example 53 | <0.1 |
| Example 55 | <0.1 |
| Example 56 | 0.7 |
| Example 57 | <0.1 |
| Example 58 | 9.0 |
| Example 59 | 0.5 |
| Example 60 | <0.1 |
| Example 65 | <0.1 |
| Example 66 | <0.1 |
| Example 67 | <0.1 |
| Example 68 | <0.1 |
| Example 69 | <0.1 |
| Example 70 | 0.9 |
| Example 71 | <0.1 |
| Example 72 | <0.1 |

From the results of Test Examples 3 to 5, it is inferred that the reason why the compounds of Examples having activities for inhibiting microtubule polymerization equivalent to that of hemiasterlin consequently exhibited lower activities compared to that of hemiasterlin in the cellular toxicity tests is based on the difference between cell permeabilities of these compounds. That is, it is believed that the reason why the activities in the cellular toxicity tests were reduced compared to the activities in the evaluation of polymerization inhibitory activity is because the compounds of Examples have low cell membrane permeability and transfer of the Example compounds into cells was suppressed.

Test Examples 6: Cellular Toxicity Test (1) for ADCs

SU-DHL-1 cells (ATCC), which are CD30 antigen-positive cells, and Karpas-299 cells (ECACC), which are CD30 antigen-positive cells, were cultured in RPMI 1640 (GIBCO) containing 10% fetal bovine serum (MP Biomedicals) (hereinafter, referred to as "culture medium A" in this test). In addition, SK-BR-3 cells (ATCC), which are CD30 antigen-negative cells, were cultured in McCoy's 5A (GIBCO) containing 10% fetal bovine serum (MP Biomedicals) (hereinafter, referred to as "culture medium B" in this test). SU-DHL-1 cells, Karpas-299 cells and SK-BR-3 cells were prepared to be $2\times10^6$ cells/mL in culture medium A or culture medium B, and were added to a 96 well microplate for cell culturing in an amount of 50 µL for each well. After the addition, SK-BR-3 cells were cultured at 37 degree under 5% $CO_2$ overnight. ADCs 4 times diluted with culture medium A or culture medium B in 8 stages were added to the microplate in an amount of 50 µL for each well. To wells to which no ADC was added, culture medium A or culture medium B was added in an amount of 50 µL for each well, and SU-DHL-1 cells and Karpas-299 cells, and SK-BR-3 cells were cultured at 37 degree under 5% $CO_2$ for 4 days or 3 days, respectively. After culturing, the microplate was taken out from the incubator, and was left at rest at room temperature for 10 minutes. To each well, 50 µL of CellTiter-Glo Luminescent Cell Viability Assay (Promega) was added, and the resultant mixture was stirred. This mixture was incubated at a dark place for 20 minutes. Using a microplate luminometer, luminescence was measured, thereby calculating the cell viability for each concentration of the ADC. The $IC_{50}$ value was calculated in accordance with the method described in Test Example 3. The results are shown in Table 42.

TABLE 42

| Cell | ADC | Corresponding compound | $IC_{50}$ (nM) |
|---|---|---|---|
| SK-BR-3 | Example ADC1 | Example 4 | >6.6 |
| (CD30 | Example ADC3 | Example 9 | >6.6 |
| antigen-negative) | Example ADC4 | Example 14 | >6.6 |
| SU-DHL-1 | Example ADC1 | Example 4 | 0.04 |
| (CD30 | Example ADC3 | Example 9 | 0.18 |
| antigen-positive) | Example ADC4 | Example 14 | 0.12 |
|  | Example ADC7 | Example 14 | 0.14 |
|  | Example ADC8 | Example 14 | 0.097 |
| Kapas-299 | Brentuximab | — | >6.6 |
| (CD30 | Example ADC1 | Example 4 | 0.035 |
| antigen-positive) | Example ADC3 | Example 9 | 0.13 |
|  | Example ADC4 | Example 14 | 0.21 |
|  | Example ADC5 | Example 38 | 0.031 |
|  | Example ADC6 | Example 44 | 0.023 |
|  | Example ADC9 | Example 45 | 0.017 |
|  | Example ADC10 | Example 32 | 0.022 |

As shown in the above Table 42, Examples ADC1, ADC3 and ADC4, which are antibody-drug conjugates of Examples 4, 9 and 14 with brentuximab, respectively, exhibited cytotoxic activities selectively to the CD30 antigen-positive cells. These results represent that even compounds with weak cellular toxicity due to low membrane permeability exhibit strong cytotoxic activities by forming conjugates with the antibody. Furthermore, antibody-drug conjugates other than Examples ADC1, ADC3 and ADC4 similarly exhibited strong cytotoxic activities.

Test Example 7: Pharmacokinetic Evaluation Test Using Mice

A pharmacokinetic evaluation test was performed by single intravenous administration of Example 4 at a dose of 1.0 mg/kg to mice. A calibration curve was made from measurements of Example 4 with known concentration, and by interpolating measurements of each specimen to this, the amount of the compound contained in unit volume of each plasma was calculated using LC-MS. Pharmacokinetics of compound 14 and hemiasterlin were similarly evaluated. The results are shown in Table 43 and Table 44.

TABLE 43

| Time | Example 4 (Blood concentration: ng/mL) | | | | | Hemiasterlin (Blood concentration: ng/mL) | | | | |
|---|---|---|---|---|---|---|---|---|---|---|
| (hr) | 1 | 2 | 3 | Mean value | S.D. | 1 | 2 | 3 | Mean value | S.D. |
| 0.5 | 10.3 | 10.2 | 20.6 | 13.7 | 5.9 | 54.5 | 99.8 | 40.6 | 65.0 | 31.0 |
| 2 | 0.7 | 1.0 | 0.7 | 0.8 | 0.1 | 25.1 | 22.2 | 30.20 | 25.8 | 4.1 |
| 6 | n.d. | n.d. | n.d. | n.d. | — | 18.9 | 18.2 | 30.2 | 22.4 | 6.7 |
| 24 | n.d. | n.d. | n.d. | n.d. | — | 2.4 | 12.8 | 9.5 | 8.3 | 5.3 |

TABLE 44

| Time | Example 14 (Blood concentration: ng/mL) | | | | | Example 4 detected as metabolite of Example 14 (Blood concentration: ng/mL) | | | | |
|---|---|---|---|---|---|---|---|---|---|---|
| (hr) | 1 | 2 | 3 | mean | S.D. | 1 | 2 | 3 | mean | S.D. |
| 0.5 | n.d. | n.d. | n.d. | n.d. | — | 50.2 | 36.4 | 53.5 | 46.7 | 9.0 |
| 2 | n.d. | n.d. | n.d. | n.d. | — | 2.7 | 3.1 | 1.7 | 2.5 | 0.7 |
| 6 | n.d. | n.d. | n.d. | n.d. | — | n.d. | n.d. | n.d. | n.d. | — |
| 24 | n.d. | n.d. | n.d. | n.d. | — | n.d. | n.d. | n.d. | n.d. | — |

(n.d. in the tables means less than the detection limit value (0.5 ng/mL).)

Upon determining the half life of each compound, the half life of Example 4 was less than 0.5 hour, the half life of Example 14 was less than 0.5 hour, and the half life of hemiasterlin was less than 13.1 hours. Example 14 is considered to be subjected to hydrolysis in the body, mainly producing Example 4, and eliminated. From these results, it was shown that the hemiasterlin derivative according to the present invention is quickly eliminated when it is liberated in the blood.

Test Example 8: Efficacy Test for Antibody-Drug Conjugates in Karpas-299 Tumor Type Using CB-17SCID Mice This test is a representative test for evaluating antitumor actions of drugs. Karpas human anaplastic giant cell lymphoma models were made by subcutaneously transplanting $5\times10^6$ cells to CB-17SCID mice. In such tumor models, treatment was initiated after the tumor reached a mean volume of 90 to 110 mm$^3$. To mice, a solution formed by dissolving Example ADC1 in phosphate buffered saline was injected intravenously once. The tumor volume was calculated using the formula: 0.5 (longest dimension×vertical dimension$^2$). When the tumor reached about 2000 mm$^3$, the mouse was excluded from the test and the mean tumor size was no longer plotted. The efficacies of Example ADC2 and a mixture of Example 4 and brentuximab were also tested in the same manner. Note that the method of this test is described in Hamblett K. J. et al., Clin. Cancer Res., 2004, 10, 7063-7070 and the like.

Figure 3:
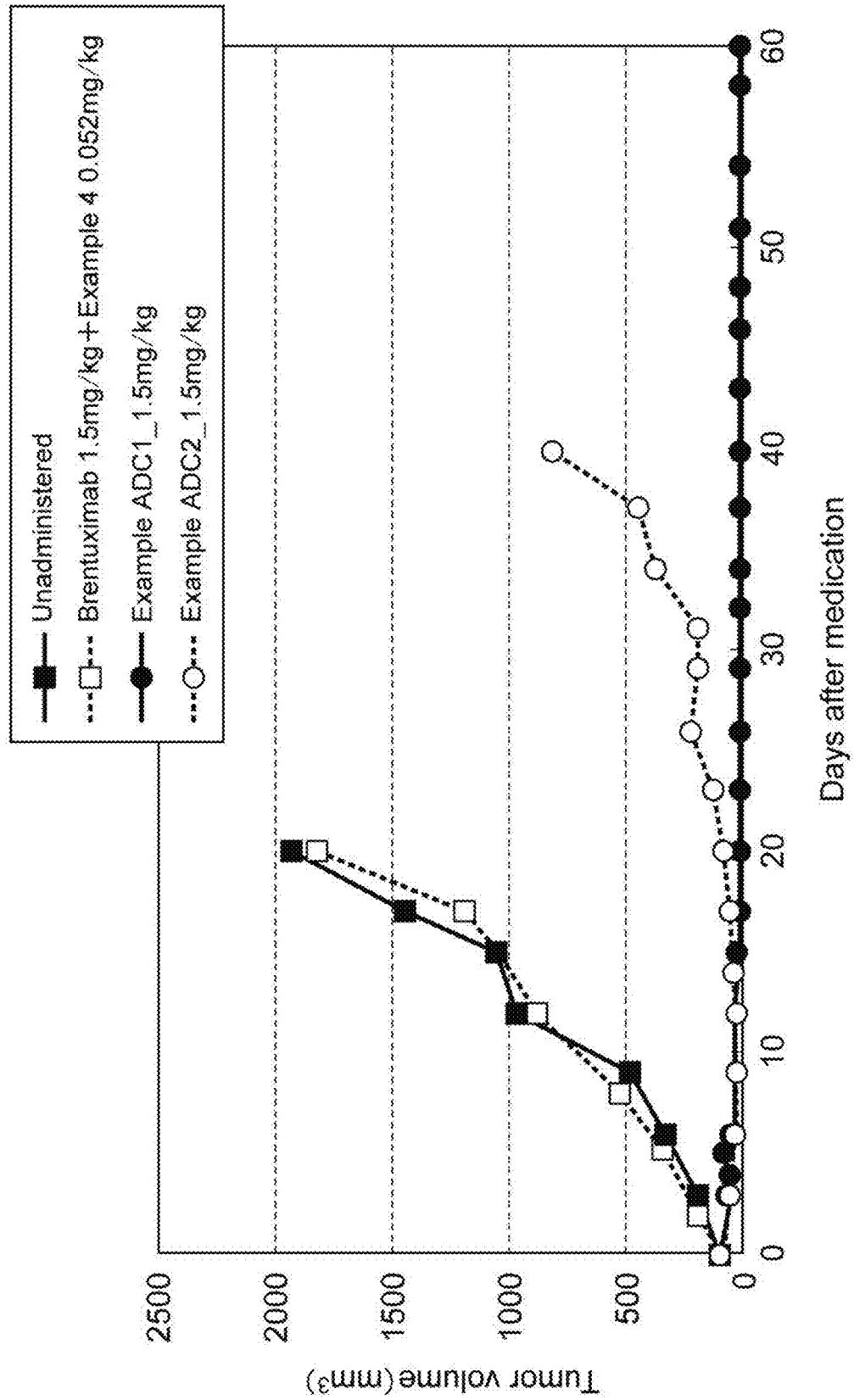
FIG. 3 shows therapeutic efficacies of Example ADC1 and Example ADC2 to Karpas-299 xenograft tumors (CD30 antigen-positive) transplanted to SCID mice.

The results are shown in FIG. 3. In the mice to which Example ADC1 or Example ADC2 was administered, satisfactory regression of the tumor was seen. On the other hand, in the mice to which the mixture of Example 4 and brentuximab in substantially the same amount was given, the tumor progressed.

Test Example 9: Toxicity (Safety) Test of Drug or Antibody-Drug Conjugate Using Sprague-Dawley Rats This test is a representative test for evaluating toxicity (safety) of drugs or antibody-drug conjugates. The toxicity may be confirmed by single or repetitive tail intravenous administration of a drug or antibody-drug conjugate and by performing general symptom observation, hematologic test, blood chemistry study, bone marrow examination, autopsy, organ weight, histopathologic examination and the like. Note that this test is described in New Edition Toxicology, edited by Board of Education in The Japanese Society of Toxicology, Asakura Publishing Co., Ltd., (2009); Summary Technical Documentation for Brentuximab Vedotin, Pharmaceuticals and Medical Devices Agency; and the like.

Test Examples 10: Cellular Toxicity Test (2) for ADCs

In accordance with the method described in Test Example 6, the cell viabilities upon using Example ADCs were measured. However, the cell viability was determined as the percentage of the mean value of luminescence amounts of wells to which Example ADCs were added at a certain concentration (n=3) relative to the luminescence amount of the well to which the antibody was added at the same concentration (n=1). The results are shown in the following table.

TABLE 45

| ADC or antibody | Compound contained | Concentration upon evaluation (nM) | Cell type | Cell viability (%) |
|---|---|---|---|---|
| Example ADC23 | Example M2 | 333 | SK-BR-3 | 10 |
| Example ADC24 | Example M2 | 6.6 | HL-60 | 84 |
| Example ADC25 | Example M2 | 200 | LS174T | 38 |
| Example ADC26 | Example M2 | 106 | Raji | 1 |
| Example ADC29 | Example M2 | 26.6 | Raji | 68 |
| Example ADC30 | Example M2 | 333 | OVCAR-3 | 8 |
| Example ADC31 | Example M2 | 333 | SU-DHL-16 | 91 |
| Example ADC32 | Example M2 | 333 | HL-60 | 16 |
| Example ADC33 | Example M2 | 333 | SK-MEL-2 | 23 |
| Example ADC34 | Example M2 | 333 | SK-BR-3 | 7 |
| Example ADC35 | Example M2 | 333 | MDA-MB-468 | 99.3 |
| Example ADC36 | Example M2 | 333 | MDA-MB-468 | 90 |
| Example ADC37 | Example M2 | 333 | MDA-MB-468 | 94 |
| Example ADC39 | Example M2 | 106 | Raji | 1 |

As shown in Test Example 10, when Example ADCs were used, more remarkable reduction in the number of cells was confirmed than when their antibody moieties were used. From this, it was revealed that the ADCs according to the present invention exhibit stronger cellular toxicities, compared to the antibodies themselves.

From the above results, it was found that the compounds of Examples exhibit lower activities in the cellular toxicity tests, compared to the Comparative Example compounds. On the other hand, the Example compounds did not lose tubulin polymerization inhibitory activity originating from the hemiasterlin structure. In addition, the antibody-drug conjugates obtained by bonding the Example compounds to antibodies exhibited high activity in the cellular toxicity tests. From these results, it is inferred that the difference between cellular toxicities of the Comparative Example compounds and the Example compounds is based on the difference between cell permeabilities. That is, it is believed that the compounds of Examples have low cell membrane permeability and transfer of the Example compounds into cells was suppressed, and therefore, they exhibited weaker cellular toxicities compared to the Comparative Example compounds. As such, according to antibody-drug conjugates containing the compounds of Examples, it is suggested that, even if reversible dissociation of the antibody moiety and the drug moiety is brought about in the systemic blood, transfer of the compounds of Examples with low cell membrane permeability into normal cells can be suppressed, thereby reducing side effects.

INDUSTRIAL APPLICABILITY

As explained above, the antibody-drug conjugates according to the present invention exhibits cytotoxic activity selectively in antigen-expressing cells and has low cytotoxicity in normal cells, and therefore, is expected to be an anticancer agent excellent in safety.

The invention claimed is:

1. A compound represented by formula (1):

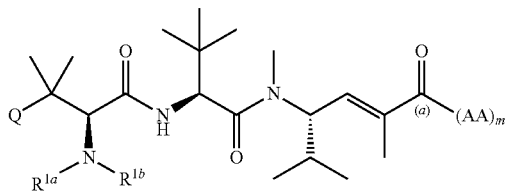

(1)

wherein
AA represents a glutamic acid residue (Glu), an aspartic acid residue (Asp), a cysteine residue (Cys), or a $C_{1-3}$ alkyl ester thereof, and when there is a plurality of AAs, each AA may be the same as or different from each other and AAs are bonded to each other via an amide bond;
an N-terminal nitrogen atom of $(AA)_m$ forms an amide bond together with carbonyl (a);
Q represents a group represented by formula (Q-1), formula (Qa-2), or formula (Qa-7):

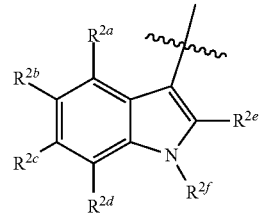

(Q-1)

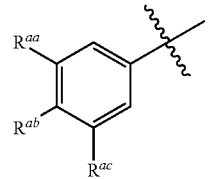

(Qa-2)

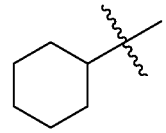

(Qa-7)

where
$R^{2a}$ and $R^{2e}$ represent a hydrogen atom;
$R^{2b}$, $R^{2c}$, and $R^{2d}$ each independently represent a hydrogen atom, a halogen atom, or a $C_{1-3}$ alkoxy group;
$R^{2f}$ represents a methyl group or an ethyl group; and
$R^{aa}$, $R^{ab}$ and $R^{ac}$ each independently represent a hydrogen atom, a halogen atom, a hydroxy group, a cyano group, a carboxyl group, or a $C_{1-3}$ alkyl group, $C_{1-3}$ alkoxy group or $C_{1-4}$ alkyl ester group optionally substituted with 1 to 3 fluorine atoms;
$R^{1a}$ and $R^{1b}$ each independently represent a hydrogen atom or a $C_{1-3}$ alkyl group; and
m represents an integer of 1 to 10,
or a salt thereof;
wherein the compound excludes a compound in which AA represents an aspartic acid residue (Asp), Q represents an unsubstituted phenyl group, one of R1a and R1b represents a methyl group and the other represents a hydrogen atom, and m represents an integer of 1.

2. The compound according to claim 1, represented by formula (1):

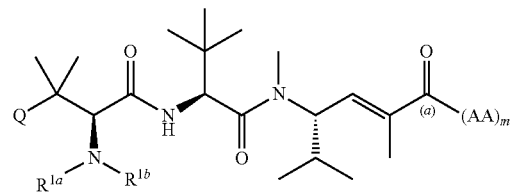

(1)

wherein
AA represents a glutamic acid residue (Glu), an aspartic acid residue (Asp) or a cysteine residue (Cys), or a $C_{1-3}$ alkyl ester thereof, and when there is a plurality of AAs, each AA may be the same as or different from each other and AAs are bonded to each other via an amide bond;

an N-terminal nitrogen atom of $(AA)_m$ forms an amide bond together with carbonyl (a);

Q represents an unsubstituted phenyl group or a group represented by formula (Q-1):

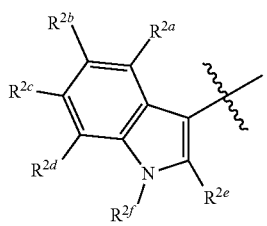

(Q-1)

where
$R^{2a}$ and $R^{2e}$ represent a hydrogen atom;
$R^{2b}$, $R^{2c}$, and $R^{2d}$ each independently represent a hydrogen atom, a halogen atom, or a methoxy group; and
$R^{2f}$ represents a methyl group;
$R^{1a}$ and $R^{1b}$ each independently represent a hydrogen atom, a methyl group, or an ethyl group; and
m represents an integer of 1 to 10, or a salt thereof.

3. The compound according to claim 1, wherein Q is a group represented by formula (Q-2):

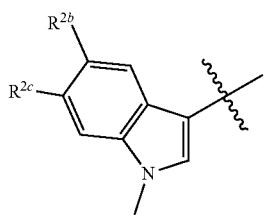

(Q-2)

where $R^{2b}$ and $R^{2c}$ each independently represent a hydrogen atom, a halogen atom, or a $C_{1-3}$ alkoxy group, or a salt thereof.

4. The compound according to claim 1, wherein Q is a group represented by formula (Q-2):

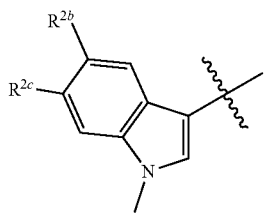

(Q-2)

where $R^{2b}$ and $R^{2c}$ each independently represent a hydrogen atom, a fluorine atom or a methoxy group, or a salt thereof.

5. The compound according to claim 3, wherein $R^{2b}$ and $R^{2c}$ are each a hydrogen atom, or a salt thereof.

6. The compound according to claim 1, wherein $R^{1a}$ is a methyl group and $R^{1b}$ is a hydrogen atom, or a salt thereof.

7. The compound according to claim 1, wherein m is an integer of 1 to 5, or a salt thereof.

8. The compound according to claim 1, wherein m is an integer of 2 to 10; and $(AA)_m$ is a linear peptide residue, or a salt thereof.

9. The compound according to claim 1, wherein m is an integer of 3 to 10; and $(AA)_m$ is a branched peptide residue having 1 or 2 branching points, or a salt thereof.

10. The compound according to claim 1, wherein $(AA)_m$ is a group represented by formula (A-1):

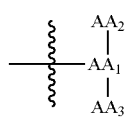

(A-1)

where $AA_1$, $AA_2$ and $AA_3$ each independently represent Glu or Asp, or a salt thereof.

11. The compound according to claim 1, wherein AA is D-Glu, L-Glu, D-Asp or L-Asp, and when there is a plurality of AAs, each AA may be the same as or different from each other, or a salt thereof.

12. The compound according to claim 1, wherein

AA is D-Glu, L-Glu, D-Asp or L-Asp, and when there is a plurality of AAs, each AA may be the same as or different from each other, and AAs are bonded to each other via an amide bond;

an N-terminal nitrogen atom of $(AA)_m$ forms an amide bond together with carbonyl (a);

Q represents an unsubstituted phenyl group or a group represented by formula (Q-1):

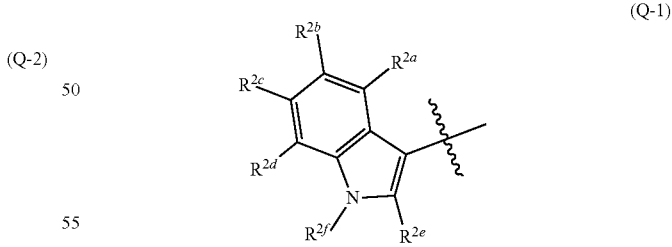

(Q-1)

where
$R^{2a}$ and $R^{2e}$ represent a hydrogen atom;
$R^{2b}$, $R^{2c}$ and $R^{2d}$ each independently represent a hydrogen atom, a halogen atom or methoxy group; and
$R^{2f}$ represents a methyl group;
$R^{1a}$ is a methyl group and $R^{1b}$ is a hydrogen atom; and
m represents an integer of 1 to 5, or a salt thereof.

13. The compound according to claim 1, selected from the following compounds:
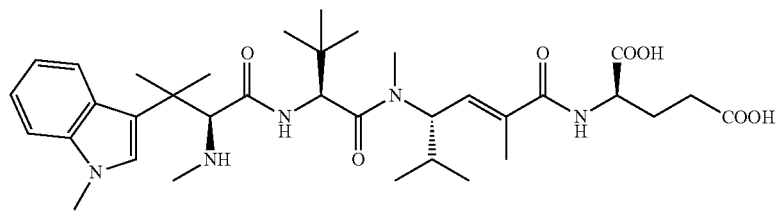
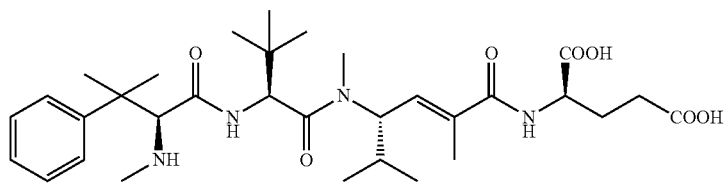
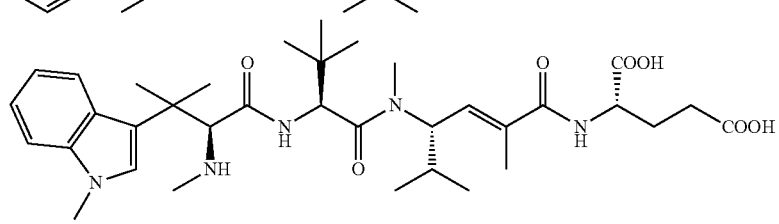
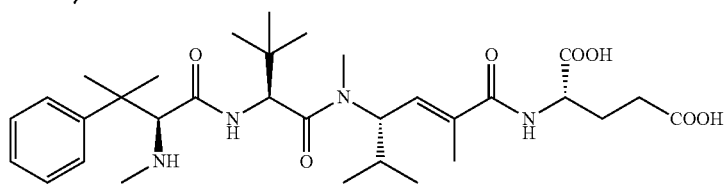
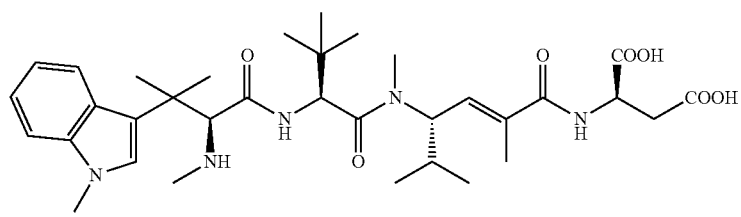
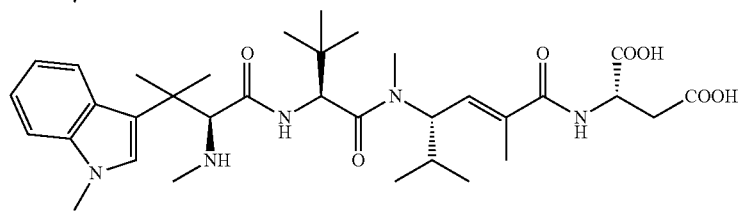
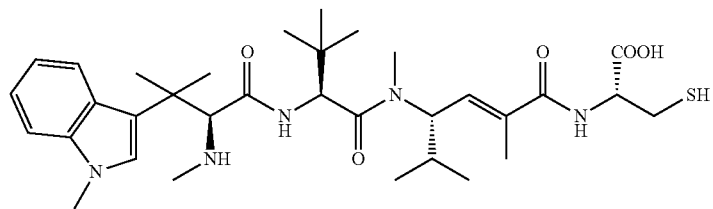
or a salt thereof.

14. The compound according to claim 1, represented by a formula selected from the following compounds:

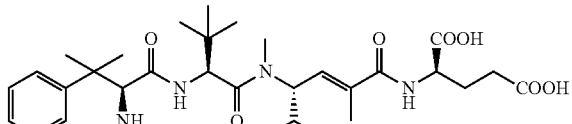

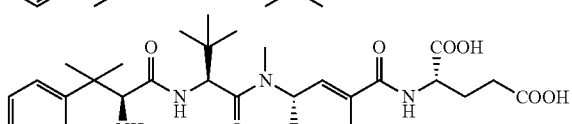

or a salt thereof.

15. The compound according to claim 1 represented by the following formula:

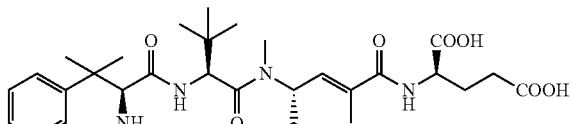

or a salt thereof.

16. A compound represented by formula (1):

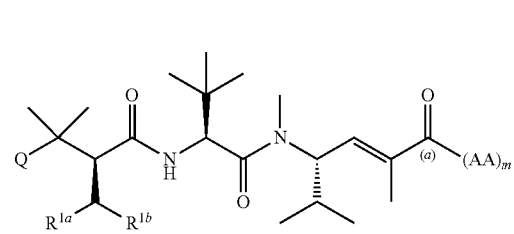

(1)

wherein
AA represents a glutamic acid residue (Glu), an aspartic acid residue (Asp), a cysteine residue (Cys), or a $C_{1-3}$ alkyl ester thereof, and when there is a plurality of AAs, each AA may be the same as or different from each other and AAs are bonded to each other via an amide bond;

an N-terminal nitrogen atom of $(AA)_m$ forms an amide bond together with carbonyl (a);

Q represents a group represented by formula (Q-1) or formula (Qa-2):

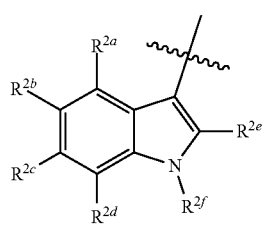
(Q-1)

-continued

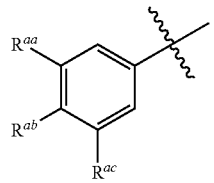
(Qa-2)

where
$R^{2a}$ and $R^{2e}$ represent a hydrogen atom,
$R^{2b}$, $R^{2c}$ and $R^{2d}$ each independently represent a hydrogen atom, a halogen atom, or a $C_{1-3}$ alkoxy group;
$R^{2f}$ represents a methyl group or an ethyl group; and
$R^{aa}$, $R^{ab}$ and $R^{ac}$ each independently represent a hydrogen atom, a halogen atom, a hydroxy group, a cyano group, a carboxyl group, or a $C_{1-3}$ alkyl group, $C_{1-3}$ alkoxy group or $C_{1-4}$ alkyl ester group optionally substituted with 1 to 3 fluorine atoms;
$R^{1a}$ and $R^{1b}$ each independently represent a hydrogen atom or a $C_{1-3}$ alkyl group; and
m represents an integer of 2 to 10,
or a salt thereof.

17. The compound according to claim 16, wherein
Q represents an unsubstituted phenyl group or a group represented by formula (Q-1):

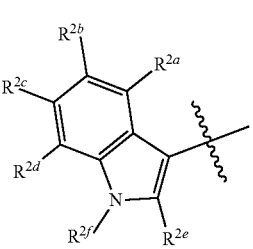
(Q-1)

where
$R^{2a}$ and $R^{2e}$ represent a hydrogen atom;
$R^{2b}$, $R^{2c}$ and $R^{2d}$ each independently represent a hydrogen atom, a halogen atom or a methoxy group; and
$R^{2f}$ represents a methyl group;
$R^{1a}$ and $R^{1b}$ each independently represent a hydrogen atom, a methyl group or an ethyl group; and
m represents an integer of 2 to 10,
or a salt thereof.

18. The compound according to claim 16, wherein $R^{1a}$ is a methyl group and $R^{1b}$ is a hydrogen atom,
or a salt thereof.

19. The compound according to claim 16, wherein AA is D-Glu, L-Glu, D-Asp or L-Asp, and when there is a plurality of AAs, each AA may be the same as or different from each other, or a salt thereof.

20. A compound represented by formula (1a):

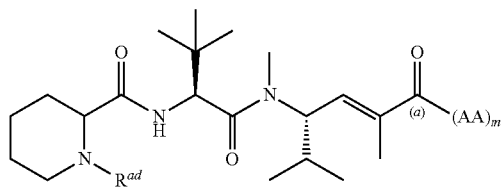

wherein
AA represents a glutamic acid residue (Glu), an aspartic acid residue (Asp), a cysteine residue (Cys), or a $C_{1-6}$alkyl ester thereof, and when there is a plurality of AAs, each AA may be the same as or different from each other and AAs are bonded to each other via an amide bond;
an N-terminal nitrogen atom of $(AA)_m$ forms an amide bond together with carbonyl (a);
$R^{ad}$ represents a hydrogen atom or a $C_{1-6}$alkyl group; and
m represents an integer of 1 to 10,
or a salt thereof.

21. The compound according to claim 20, wherein m is an integer of 1 to 5, or a salt thereof.

22. The compound according to claim 20, wherein m is an integer of 2 to 10; and
$(AA)_m$ is a linear peptide residue,
or a salt thereof.

23. The compound according to claim 20, wherein m is an integer of 3 to 10; and
$(AA)_m$ is a branched peptide residue having 1 or 2 branching points, or a salt thereof.

24. The compound according to claim 20, wherein $(AA)_m$ is a group represented by formula (A-1):

where $AA_1$, $AA_2$ and $AA_3$ each independently represent Glu or Asp,
or a salt thereof.

25. The compound according to claim 20, wherein AA is D-Glu, L-Glu, D-Asp or L-Asp, and when there is a plurality of AAs, each AA may be the same as or different from each other, or a salt thereof.

* * * * *